(12) United States Patent
Kuwahara et al.

(10) Patent No.: US 11,214,771 B2
(45) Date of Patent: *Jan. 4, 2022

(54) PRODUCTION METHOD FOR NERVE TISSUE

(71) Applicants: SUMITOMO DAINIPPON PHARMA CO., LTD., Osaka (JP); RIKEN, Wako (JP); SUMITOMO CHEMICAL COMPANY, LIMITED, Tokyo (JP)

(72) Inventors: Atsushi Kuwahara, Kobe (JP); Suguru Yamasaki, Kobe (JP); Yasushi Hiramine, Kobe (JP); Yoshiki Sasai, Wako (JP); Masayo Takahashi, Wako (JP)

(73) Assignees: SUMITOMO DAINIPPON PHARMA CO., LTD., Osaka (JP); RIKEN, Wako (JP); SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/521,334

(22) PCT Filed: Oct. 23, 2015

(86) PCT No.: PCT/JP2015/080016
§ 371 (c)(1),
(2) Date: Apr. 24, 2017

(87) PCT Pub. No.: WO2016/063985
PCT Pub. Date: Apr. 28, 2016

(65) Prior Publication Data
US 2017/0313976 A1 Nov. 2, 2017

(30) Foreign Application Priority Data
Oct. 24, 2014 (JP) .............................. JP2014-217867

(51) Int. Cl.
| | | |
|---|---|---|
| *C12N 5/0793* | (2010.01) | |
| *C12N 5/0797* | (2010.01) | |
| *A61K 35/30* | (2015.01) | |
| *A61L 27/00* | (2006.01) | |
| *A61K 35/12* | (2015.01) | |
| *C12Q 1/02* | (2006.01) | |
| *C12N 5/079* | (2010.01) | |
| *A61L 27/38* | (2006.01) | |
| *G01N 33/50* | (2006.01) | |

(52) U.S. Cl.
CPC .............. *C12N 5/062* (2013.01); *A61K 35/12* (2013.01); *A61K 35/30* (2013.01); *A61L 27/00* (2013.01); *A61L 27/383* (2013.01); *A61L 27/3895* (2013.01); *C12N 5/0618* (2013.01); *C12N 5/0619* (2013.01); *C12N 5/0621* (2013.01); *C12N 5/0623* (2013.01); *C12Q 1/02* (2013.01); *G01N 33/5014* (2013.01); *C12N 2500/99* (2013.01); *C12N 2501/115* (2013.01); *C12N 2501/15* (2013.01); *C12N 2501/155* (2013.01); *C12N 2501/16* (2013.01); *C12N 2501/40* (2013.01); *C12N 2501/41* (2013.01); *C12N 2501/415* (2013.01); *C12N 2501/727* (2013.01); *C12N 2506/45* (2013.01); *C12N 2533/52* (2013.01)

(58) Field of Classification Search
CPC .... C12N 5/0606; C12N 5/062; C12N 5/0621; C12N 5/0623; C12N 5/0618
See application file for complete search history.

(56) References Cited

U.S. PATENT DOCUMENTS

| | | |
|---|---|---|
| 8,287,854 B2 | 10/2012 | Phan |
| 8,956,866 B2 | 2/2015 | Idelson et al. |
| 9,850,465 B2 | 12/2017 | Parent et al. |
| 10,066,209 B2 | 9/2018 | Phan |
| 10,220,117 B2 | 3/2019 | Zhang et al. |
| 10,266,807 B2 | 4/2019 | Rajesh et al. |
| 10,724,000 B2 | 7/2020 | Graf et al. |
| 11,066,645 B2 | 7/2021 | Phan |
| 2003/0059868 A1 | 3/2003 | Greenwood et al. |
| 2003/0180947 A1 | 9/2003 | Wu et al. |

(Continued)

FOREIGN PATENT DOCUMENTS

| | | |
|---|---|---|
| CN | 1630714 A | 6/2005 |
| CN | 101330935 A | 12/2008 |

(Continued)

OTHER PUBLICATIONS

Davis-Dusenbery et al., "How to make spinal motor neurons," *Development*, 141(3): 491-501 (2014).
Hu et al., "Neural differentiation of human induced pluripotent stem cells follows developmental principles but with variable potency," *Proc. Natl. Acad. Sci. U.S.A.*, 107(9): 4335-4340 (2010).
European Patent Office, Extended European Search Report in European Patent Application No. 15852504.8 (dated Sep. 6, 2018).

(Continued)

Primary Examiner — Robert C Hayes
(74) Attorney, Agent, or Firm — Leydig, Voit & Mayer, Ltd.

(57) ABSTRACT

The present invention provides a method for producing neural cells or a neural tissue, including the following steps (1)-(3):
(1) a first step of culturing pluripotent stem cells in the absence of feeder cells and in a medium containing 1) a TGFβ family signal transduction pathway inhibiting substance and/or a Sonic hedgehog signal transduction pathway activating substance, and 2) a factor for maintaining undifferentiated state,
(2) a second step of culturing the cells obtained in the first step in suspension to form a cell aggregate, and
(3) a third step of culturing the aggregate obtained in the second step in suspension in the presence or absence of a differentiation-inducing factor to obtain an aggregate containing neural cells or a neural tissue.

27 Claims, 35 Drawing Sheets

(56) References Cited

U.S. PATENT DOCUMENTS

| | | |
|---|---|---|
| 2006/0122111 A1 | 6/2006 | Furukawa |
| 2007/0122903 A1 | 5/2007 | Rezania et al. |
| 2008/0044901 A1 | 2/2008 | Sasai et al. |
| 2008/0248005 A1 | 10/2008 | Phan |
| 2009/0053809 A1 | 2/2009 | Zander et al. |
| 2010/0009442 A1 | 1/2010 | Sasai et al. |
| 2010/0119492 A1 | 5/2010 | Hans et al. |
| 2011/0027333 A1 | 2/2011 | Idelson et al. |
| 2011/0091869 A1 | 4/2011 | Sasai et al. |
| 2011/0223140 A1 | 9/2011 | Park et al. |
| 2011/0274662 A1 | 11/2011 | Malcuit et al. |
| 2012/0129211 A1 | 5/2012 | Kattman et al. |
| 2013/0040330 A1 | 2/2013 | Sasai et al. |
| 2014/0308743 A1 | 10/2014 | Sasai et al. |
| 2014/0329321 A1 | 11/2014 | Rajesh et al. |
| 2014/0341864 A1 | 11/2014 | Nakano et al. |
| 2015/0118749 A1 | 4/2015 | Idelson et al. |
| 2015/0125506 A1 | 5/2015 | Idelson et al. |
| 2015/0132787 A1 | 5/2015 | Sasai et al. |
| 2016/0010055 A1 | 1/2016 | Parent et al. |
| 2016/0102292 A1 | 4/2016 | Phan |
| 2016/0186134 A1 | 6/2016 | Keller et al. |
| 2016/0186136 A1 | 6/2016 | Sasai et al. |
| 2016/0237403 A1 | 8/2016 | Sawada et al. |
| 2016/0243285 A1 | 8/2016 | Zhang et al. |
| 2016/0244721 A1 | 8/2016 | Sawada et al. |
| 2016/0251616 A1 | 9/2016 | Nakano et al. |
| 2016/0264936 A1 | 9/2016 | Nakano et al. |
| 2016/0369233 A1 | 12/2016 | Graf et al. |
| 2016/0376554 A1 | 12/2016 | Kuwahara et al. |
| 2017/0067017 A1 | 3/2017 | Meyer et al. |
| 2017/0253853 A1 | 9/2017 | Sasai et al. |
| 2017/0275593 A1 | 9/2017 | Hanna et al. |
| 2017/0313976 A1 | 11/2017 | Kuwahara et al. |
| 2017/0313981 A1 | 11/2017 | Kuwahara et al. |
| 2017/0319748 A1 | 11/2017 | Kuwahara et al. |
| 2018/0119103 A1 | 5/2018 | Phan |
| 2018/0245039 A1 | 8/2018 | Ando et al. |
| 2018/0258388 A1 | 9/2018 | Ando et al. |
| 2019/0127690 A1 | 5/2019 | Kuwahara et al. |
| 2020/0206387 A1 | 7/2020 | Takahashi et al. |
| 2020/0208103 A1 | 7/2020 | Sakaguchi et al. |
| 2021/0154370 A1 | 5/2021 | Nukaya et al. |
| 2021/0308188 A1 | 10/2021 | Nakano et al. |

FOREIGN PATENT DOCUMENTS

| | | |
|---|---|---|
| CN | 101688178 A | 3/2010 |
| CN | 102361970 A | 2/2012 |
| CN | 105358680 A | 2/2016 |
| CN | 105814192 A | 7/2016 |
| CN | 105829526 A | 8/2016 |
| CN | 107109367 A | 8/2017 |
| CN | 107326009 A | 11/2017 |
| CN | 108064274 A | 5/2018 |
| CN | 108291206 A | 7/2018 |
| CN | 110945119 A | 3/2020 |
| CN | 111094554 A | 5/2020 |
| CN | 111164205 A | 5/2020 |
| EP | 2128244 A1 | 12/2009 |
| EP | 2302036 A2 | 3/2011 |
| EP | 3211072 A1 | 8/2017 |
| JP | 2012-070731 A | 4/2012 |
| JP | 2012-245007 A | 12/2012 |
| JP | 2013-099345 A | 5/2013 |
| WO | 1995/013364 A1 | 5/1995 |
| WO | WO 2006/053629 A1 | 5/2006 |
| WO | WO 2009/148170 A1 | 12/2009 |
| WO | 2010/053472 A1 | 5/2010 |
| WO | WO 2011/043591 A2 | 4/2011 |
| WO | WO 2011/055855 A1 | 5/2011 |
| WO | WO 2012/135621 A2 | 10/2012 |
| WO | WO 2013/065763 A1 | 5/2013 |
| WO | WO 2013/077425 A1 | 5/2013 |
| WO | 2014/134213 A1 | 9/2014 |
| WO | 2015/011031 A1 | 1/2015 |
| WO | WO 2015/025967 A1 | 2/2015 |
| WO | WO 2015/053375 A1 | 4/2015 |
| WO | WO 2015/054526 A2 | 4/2015 |
| WO | WO 2015/068505 A1 | 5/2015 |
| WO | WO 2015/107738 A1 | 7/2015 |
| WO | WO 2016/032263 A1 | 3/2016 |
| WO | WO 2016/039317 A1 | 3/2016 |
| WO | WO 2016/063985 A1 | 4/2016 |
| WO | WO 2016/063986 A1 | 4/2016 |
| WO | WO 2017/043604 A1 | 3/2017 |
| WO | WO 2017/043605 A1 | 3/2017 |

OTHER PUBLICATIONS

Amoroso et al., "Accelerated High-Yield Generation of Limb-Innervating Motor Neurons from Human Stem Cells," *J. Neurosci.*, 33(2): 574-586 (2013).

Faravelli et al., "Motor neuron derivation from human embryonic and induced pluripotent stem cells: experimental approaches and clinical perspectives," *Stem Cell Res. Ther.*, 5(4): 87 (2014).

Osakada et al., "In vitro differentiation of retinal cells from human pluripotent stem cells by small-molecule induction," *J. Cell Sci.*, 122(17): 3169-3179 (2009).

European Patent Office, Communication Pursuant to Rule 164(1) EPC in European Patent Application No. 15852504.8 (dated May 14, 2018).

Akopian et al., "Comparison of defined culture systems for feeder cell free propagation of human embryonic stem cells," *In Vitro Cell. Dev. Biol. Anim.*, 46(3-4): 247-258 (2010).

Boucherie et al., "Brief Report: Self-Organizing Neuroepithelium from Human Pluripotent Stem Cells Facilitates Derivation of Photoreceptors," *Stem Cells*, 31(2): 408-414 (2013).

Chambers et al., "Highly efficient neural conversion of human ES and iPS cells by dual inhibition of SMAD signaling," *Nat. Biotechnol.*, 27(3): 275-280 (2009).

Chen, "Chemically defined conditions for human iPSC derivation and culture," *Nat. Methods*, 8(5): 424-429 (2011).

Denayer et al., "Canonical Wnt Signaling Controls Proliferation of Retinal Stem/Progenitor Cells in Postembryonic *Xenopus* Eyes," *Stem Cells*, 26(28): 2063-2074 (2008).

Eiraku, "Self-Organized Formation of Polarized Cortical Tissues from ESCs and Its Active Manipulation by Extrinsic Signals," *Cell Stem Cell*, 3(5): 519-532 (2008).

Eiraku et al., "Relaxation-expansion model for self-driven retinal morphogenesis," *Bioessays*, 34(1): 17-25 (2011).

Eiraku et al., "Self-organizing optic-cup morphogenesis in three-dimensional culture," *Nature*, 472(7341): 51-56 (2011).

Fuhrmann, "Wnt signaling in eye organogenesis," *Organogenesis*, 4(2): 60-67 (2008).

Furuta et al., "BMP4 is essential for lens induction in the mouse embryo," *Genes Dev.*, 12(23): 3764-3775 (1998).

Kadoshima et al., "Self-organization of axial polarity, inside-out layer pattern, and species-specific progenitor dynamics in human ES cell-derived neocortex," *Proc. Natl. Acad. Sci. U.S.A.*, 110(50): 20284-20289 (2013).

Kubo et al., "Wnt2b controls retinal cell differentiation at the ciliary marginal zone," *Development*, 130(3): 587-598 (2003).

Kubo et al., "Hairy1 acts as a node downstream of Wnt signaling to maintain retinal stem cell-like progenitor cells in the chick ciliary marginal zone," *Development*, 136(11): 1823-1833 (2009).

Lamba et al., "Efficient generation of retinal progenitor cells from human embryonic stem cells," *Pro Natl., Acad. Sci. U.S.A.*, 103(34): 12769-12774 (2006).

Lancaster et al., "Cerebral organoids model human brain development and microcephaly," *Nature*, 501(7467): 373-379 (2013).

Lang, "Pathways regulating lens induction in the mouse," *Int. J. Dev. Biol.*, 48(8-9): 783-791 (2004).

La Torre et al., "Production and Transplantation of Retinal Cells from Human and Mouse Embryonic Stem Cells," *Retinal Development: Methods and Protocols, Methods in Molecular Biology*, 884: 229-246 (2012).

(56) References Cited

OTHER PUBLICATIONS

Muguruma et al., "Ontogeny-recapitulating generation and tissue integration of ES cell-derived Purkinje cells," *Nat. Neurosci.*, 13(10): 1171-1180 (2010).
Nakagawa et al., "A novel efficient feeder-free culture system for the derivation of human induced pluripotent stem cells," *Sci. Rep.*, 4: 3594 (2014).
Nakano et al., "Self-Formation of Optic Cups and Storable Stratified Neural Retina from Human ESCs," *Cell Stem Cell*, 10(6): 771-785 (2012).
Osakada et al., "Control of neural differentiation from pluripotent stem cells," *Inflammation and Regeneration*, 28(3): 166-173 (2008).
Osakada et al., "Toward the generation of rod and cone photoreceptors from mouse, monkey and human embryonic stem cells," *Nat. Biotechnol.*, 26(2): 215-224 (2008).
Osakada et al., "Neural Induction and Patterning in Mammalian Pluripotent Stem Cells," *CNS & Neurological Disorders—Drug Targets*, 10(4): 419-432 (2011).
Ozair, "Neural induction and early patterning in vertebrates," *WIREs Dev. Biol.*, 2(4): 479-498 (2013).
Seiler et al., "Visual restoration and transplant connectivity in degenerate rats implanted with retinal progenitor sheets," *Eur. J. Neurosci.*, 31: 508-520 (2010).
Stephens et al., "Loss of *adenomatous polyposis coli* (*apc*) Results in an Expanded Ciliary Marginal Zone in the Zebrafish Eye," *Dev. Dyn.*, 239(7): 2066-2077 (2010).
Suga et al., "Self-formation of functional adenohypophysis in three-dimensional culture," *Nature*, 480(7375): 57-62 (2011).
Trousse et al., "BMP4 Mediates Apoptotic Cell Death in the Developing Chick Eye," *J. Neurosci.*, 21(4): 1292-1301 (2001).
Vugler et al., "Embryonic stem cells and retinal repair," *Mech. Dev.*, 124(11-12): 807-829 (2007).
Watanabe et al., "Directed differentiation of telencephalic precursors from embryonic stem cells," *Nat. Neurosci.*, 8(3): 288-296 (2005).
Wei et al., "Isolation and identification of retinal stem cells in mouse eye," *Journal of Third Military Medical University*, 25(24): 2161-2164 (2003).
Yang et al., "Efficient generation of lens progenitor cells and lentoid bodies from human embryonic stem cells in chemically defined conditions," *FASEB J.*, 24(9): 3274-3283 (2017).
Doi et al., "Isolation of Human Induced Pluripotent Stem Cell-Derived Dopaminergic Progenitors by Cell Sorting for Successful Transplantation," *Stem Cell Reports*, 2(3): 337-350 (2014).
Morizane et al., "Neural Induction with a Dopaminergic Phenotype from Human Pluripotent Stem Cells Through a Feeder-Free Floating Aggregation Culture," *Methods Mol. Biol.*, 1018: 11-19 (2013).
Yang et al., "Directed Differentiation into Neural Lineages and Therapeutic Potential of Porcine Embryonic Stem Cells in Rat Parkinson's Disease Model," *Cell Reprogram.*, 12(4): 447-461 (2010).
Ikeda et al., "In vitro neuronal differentiation induction using ES cells—telencephalic precursors and neural retinal precursors," *Experimental Medicine*, 24(2): 188-194 (2006).
Sasai, "Self-organization as seen in pattern formation of neural tissue: Challenge to Emergent Biology," *Brain Science Review*, 99-112 (2014).
Kuwahara et al., "Generation of a ciliary margin-like stem cell niche from self-organizing human retinal tissue," *Nat. Commun.*, 6: 6286 (2015).
Messina et al., "Noggin-Mediated Retinal Induction Reveals a Novel Interplay Between Bone Morphogenetic Protein Inhibition, Transforming Growth Factor β, and Sonic Hedgehog Signaling," *Stem Cells*, 33(8): 2496-2508 (2015).
Zhou et al., "Differentiation of human embryonic stem cells into cone photoreceptors through simultaneous inhibition of BMP, TGFβ and Wnt signaling," *Development*, 142(19): 3294-3306 (2015).
Japanese Patent Office, International Search Report in International Patent Application No. PCT/JP2017/016120 (dated Jul. 11, 2017).
Du et al., "Regulation of Retinal Progenitor Cell Differentiation by Bone Morphogenetic Protein 4 Is Mediated by the Smad/Id Cascade," *Invest. Ophthalmol. Vis. Sci.*, 51(7): 3764-3773 (2010).
Loebel et al., "Lineage choice and differentiation in mouse embryos and embryonic stem cells," *Dev. Biol.*, 264(1): 1-14 (2003).
Miyazawa et al., "Two major Smad pathways in TGF-β superfamily signaling," *Genes to Cell*, 7(12): 1191-1204 (2002).
European Patent Office, Supplementary European Search Report in European Patent Application No. 15852025 (dated Apr. 20, 2018).
Stanton et al., "Small-molecule modulators of the *Sonic Hedgehog* signaling pathway," *Mol. Biosyst.*, 6(1): 44-54 (2010).
U.S. Appl. No. 15/521,387, filed Apr. 24, 2017.
U.S. Appl. No. 16/095,339, filed Oct. 19, 2018.
European Patent Office, Extended European Search Report in European Patent Application No. 17786064.0 (dated Oct. 17, 2019).
Zhang et al., "Rapid and Efficient Generation of Neurons from Human Pluripotent Stem Cells in a Multititre Plate Format," *J. Vis. Exp.*, 73: e4335 (2013).
European Patent Office, Extended European Search Report in European Patent Application No. 21166628.4 (dated Jul. 19, 2021).
Shafaie et al., "In Vitro Cell Models for Ophthalmic Drug Development Applications," *BioRes. Open Access*, 5(1): 94-108 (2016).
Zacharias et al., "In Vitro Evidence for Mycophenolic Acid Dose-Related Cytotoxicity in Human Retinal Cells," *Retina*, 33(10): 2155-2161 (2013).

FIG. 4
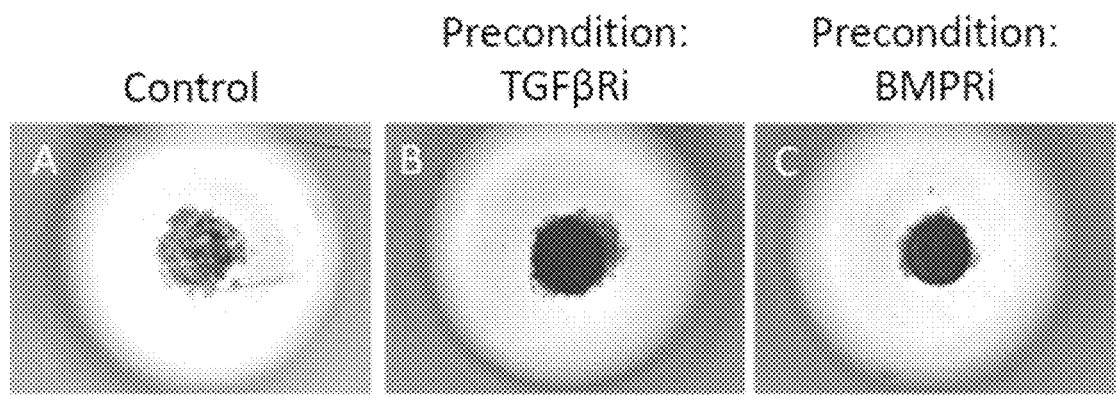
FIG. 5
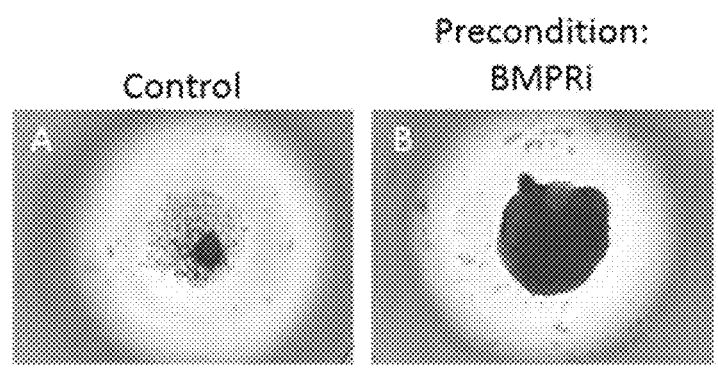
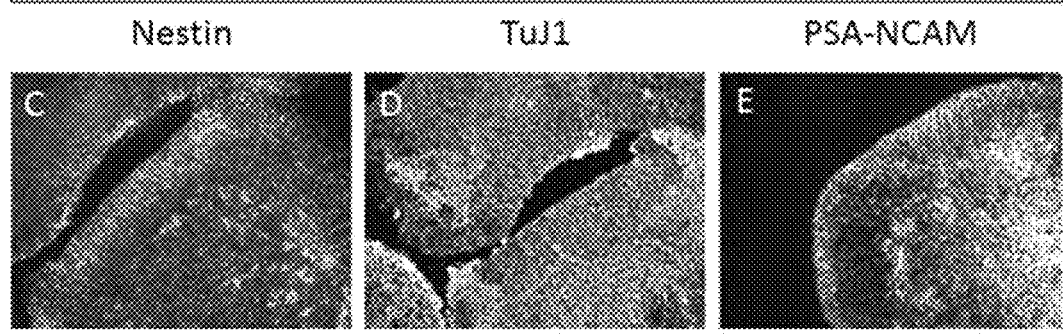

PRODUCTION METHOD FOR NERVE TISSUE

CROSS-REFERENCE TO RELATED APPLICATIONS

This patent application is the U.S. national phase of International Patent Application No. PCT/JP2015/080016, filed on Oct. 23, 2015, which claims the benefit of Japanese Patent Application No. 2014-217867, filed on Oct. 24, 2014, the disclosures of which are incorporated herein by reference in their entireties for all purposes.

TECHNICAL FIELD

The present invention relates to a method for producing neural tissues such as retinal tissue and the like from pluripotent stem cells.

BACKGROUND ART

As a method for producing neural tissues such as retinal tissue and the like from pluripotent stem cells, a method for producing neural tissue which comprises forming uniformed aggregates of pluripotent stem cells in a serum-free medium, culturing them in suspension, culturing them in suspension in a culture medium for differentiation induction in the presence of a differentiation-inducing factor and the like as appropriate to induce differentiation of pluripotent stem cells into the intended neural cells has been reported (patent document 1 and non-patent document 1). For example, a method for obtaining a multi-layered retinal tissue from pluripotent stem cells (non-patent document 2 and patent document 2), and a method for obtaining multi-layered retinal tissue which comprises forming uniformed aggregates of pluripotent stem cells in a serum-free medium containing a Wnt signal transduction pathway inhibiting substance, culturing them in suspension in the presence of a basement membrane preparation, and culturing them in suspension in a serum-containing medium (non-patent document 3 and patent document 3) are known. In addition, a method for inducing differentiation of pluripotent stem cells into a hypothalamic tissue (patent document 4 and non-patent document 4), and a method inducing differentiation of pluripotent stem cells into neural precursor cells (non-patent document 5 and 6) have also been reported.

The pluripotent stem cells as a starting material of these production methods, particularly in the case of primate pluripotent stem cells, were cultured to maintain undifferentiated state in the presence of feeder cells and with the addition of a factor for maintaining undifferentiated state. In recent years, improvement has been made in the culturing to maintain undifferentiated state, and a method of culturing primate pluripotent stem cells in the absence of feeder cells (feeder-free) with the addition of a factor for maintaining undifferentiated state has been reported (non-patent documents 7, 8 and 9). A stable method for producing neural cells or a neural tissue, which uses pluripotent stem cells subjected to feeder-free culture by this method as a starting material has been desired.

DOCUMENT LIST

Patent Documents

[patent document 1] WO 2009/148170
[patent document 2] WO 2011/055855
[patent document 3] WO 2013/077425
[patent document 4] WO 2013/065763

Non-Patent Documents

[non-patent document 1] Cell Stem Cell, 3, 519-32 (2008)
[non-patent document 2] Nature, 472, 51-56 (2011)
[non-patent document 3] Cell Stem Cell, 10(6), 771-775 (2012)
[non-patent document 4] Nature, 480, 57-62 (2011)
[non-patent document 5] Nature Biotechnology, 27(3), 275-80 (2009)
[non-patent document 6] Proc Natl Acad Sci USA, 110(50), 20284-9 (2013)
[non-patent document 7] Nature Methods, 8, 424-429 (2011)
[non-patent document 8] Scientific Reports, 4, 3594 (2014)
[non-patent document 9] In Vitro Cell Dev Biol Anim., 46, 247-58 (2010)

SUMMARY OF THE INVENTION

Problems to be Solved by the Invention

The problem to be solved by the present invention is provision of a method for producing neural tissues such as retinal tissue and the like and neural cells from pluripotent stem cells prepared or cultured to maintain undifferentiated state in the absence of feeder cells.

Means of Solving the Problems

The present inventors have conducted intensive studies in an attempt to solve the aforementioned problems and found that a spherical cell aggregate having a smooth surface and a dense inside, and maintaining an undifferentiated state can be formed with high efficiency by culturing pluripotent stem cells in the absence of feeder cells (under feeder-free condition) in a medium containing a TGFβ family signal transduction pathway inhibiting substance and/or a Sonic hedgehog signal transduction pathway activating substance, and then subjecting the cells to suspension culturing. In addition, the present inventors have found that by using this high quality cell aggregate, neural tissues such as retinal tissue and the like and neural cells can be induced with high efficiency, which resulted in the completion of the present invention.

That is, the present invention relates to the following.
[1] A method for producing neural cells or a neural tissue, comprising the following steps (1)-(3):
(1) a first step of culturing pluripotent stem cells in the absence of feeder cells and in a medium comprising 1) a TGFβ family signal transduction pathway inhibiting substance and/or a Sonic hedgehog signal transduction pathway activating substance, and 2) a factor for maintaining undifferentiated state,
(2) a second step of culturing the cells obtained in the first step in suspension to form a cell aggregate, and
(3) a third step of culturing the aggregate obtained in the second step in suspension in the presence or absence of a differentiation-inducing factor to obtain an aggregate containing neural cells or a neural tissue.
[2] The production method of [1], wherein, in the second step, the cells obtained in the first step are dispersed, and the dispersed cells are cultured in suspension.
[3] The production method of [1] or [2], wherein the factor for maintaining undifferentiated state is an FGF signal transduction pathway activating substance.

[4] The production method of [3], wherein the FGF signal transduction pathway activating substance is bFGF.

[5] The production method of any of [1]-[4], wherein, in the second step, the cells are cultured in suspension in a serum-free medium containing a Sonic hedgehog signal transduction pathway activating substance.

[6] The production method of any of [1]-[5], wherein, in the third step, the aggregate is cultured in suspension in the presence of a differentiation-inducing factor.

[7] The production method of any of [1]-[6], wherein the TGFβ family signal transduction pathway inhibiting substance is a Nodal/Activin signal transduction pathway inhibiting substance, a TGFβ signal transduction pathway inhibiting substance, or a BMP signal transduction pathway inhibiting substance.

[8] The production method of any of [1]-[7], wherein the TGFβ family signal transduction pathway inhibiting substance is Lefty, SB431542, A-83-01 or LDN193189.

[9] The production method of any of [1]-[8], wherein the Sonic hedgehog signal transduction pathway activating substance is Shh, SAG or Purmorphamine.

[10] The production method of any of [1]-[9], wherein the differentiation-inducing factor in the third step is a BMP signal transduction pathway activating substance.

[11] The production method of [10], wherein the BMP signal transduction pathway activating substance is one or more proteins selected from the group consisting of BMP2, BMP4, BMP7 and GDF7.

[12] The production method of [10], wherein the BMP signal transduction pathway activating substance is BMP4.

[13] The production method of any of [1]-[12], wherein the aggregate obtained in the third step comprises a retinal tissue.

[14] The production method of any of [1]-[13], wherein the aggregate obtained in the third step comprises one or more cells selected from the group consisting of retinal progenitor cell, neural retinal progenitor cell, photoreceptor precursor cell, photoreceptor cell, rod photoreceptor cell, cone photoreceptor cell, horizontal cell, amacrine cell, interneuron, ganglion cell, retinal pigment epithelial cell, and ciliary marginal zone cell.

[15] The production method of [13] or [14], wherein the differentiation-inducing factor in the third step is a BMP signal transduction pathway activating substance, and the medium in the second step contains a Sonic hedgehog signal transduction pathway activating substance.

[16] The production method of [15], wherein the pluripotent stem cells are human pluripotent stem cells, the Sonic hedgehog signal transduction pathway activating substance in the medium in the second step has a concentration corresponding to Sonic hedgehog signal transduction activity of SAG at 10 nM-700 nM, and the retinal tissue is a human retinal tissue.

[17] The production method of [15] or [16], wherein, in the third step, the BMP signal transduction pathway activating substance is added to the medium between day 1 and day 9 after the start of the second step.

[18] The production method of [13] or [14], wherein, in the third step, the aggregate is cultured in a medium containing a Sonic hedgehog signal transduction pathway activating substance at a concentration not more than a concentration corresponding to Sonic hedgehog signal transduction activity of SAG at 700 nM.

[19] The production method of any of [1]-[9], wherein the differentiation-inducing factor in the third step is a TGFβ family signal transduction pathway inhibiting substance and/or a Wnt signal transduction pathway inhibiting substance.

[20] The production method of [19], wherein the TGFβ family signal transduction pathway inhibiting substance is Lefty, SB431542, A-83-01 or LDN193189.

[21] The production method of [19] or [20], wherein the Wnt signal transduction pathway inhibiting substance is IWR-1-endo.

[22] The production method of any of [1]-[9] or [19]-[21], wherein the aggregate obtained in the third step contains a cerebral tissue.

[23] The production method of any of [1]-[22], wherein a period for the culturing in the first step is 0.5 hr-144 hr.

[24] The production method of any of [1]-[23], wherein the first step is performed by an adhesion culturing method.

[25] The production method of any of [1]-[24], wherein, in the third step, the differentiation-inducing factor is added to the medium between day 3 and day 6 after the start of the second step.

[26] The production method of any of [1]-[15] and [17]-[25], wherein the pluripotent stem cells are primate pluripotent stem cells.

[27] The production method of any of [1]-[26], wherein the pluripotent stem cells are human pluripotent stem cells.

[28] The production method of any of [1]-[27], wherein the pluripotent stem cells are induced pluripotent stem cells.

[29] The production method of any of [1]-[28], wherein uniformed aggregates are formed in the second step.

[30] The production method of any of [1]-[29], wherein the suspension culturing is performed in the absence of a basement membrane preparation.

[31] A reagent for evaluating toxicity or efficacy of a test substance, comprising neural cells or a neural tissue produced by the method of any of [1]-[30].

[32] A method for evaluating toxicity or efficacy of a test substance, comprising bringing the substance into contact with neural cells or a neural tissue produced by the method of any of [1]-[30], and detecting an influence of the substance on the cells or tissue.

[33] A medicament for treating a disease due to a disorder of a neural cell or a neural tissue, comprising neural cells or a neural tissue produced by the method of any of [1]-[30].

[34] The medicament of [33], wherein the neural cells or neural tissue is retinal progenitor cells, retinal layer-specific neurons, retinal tissue, cerebral neural precursor cells, cerebral layer-specific neurons, or cerebral tissue.

[35] A method of treating a disease due to a disorder of a neural cell or a neural tissue, comprising transplanting an effective amount of neural cells or a neural tissue produced by the method of any of [1]-[30] to a subject in need of the transplantation.

[36] Neural cells or a neural tissue produced by the method of any of [1]-[30] for use in the treatment of a disease due to a disorder of a neural cell or a neural tissue.

[37] A pharmaceutical composition comprising neural cells or a neural tissue produced by the method of any of [1]-[30] as an active ingredient.

Effect of the Invention

According to the present invention, a high quality cell aggregate, as well as neural tissues such as retinal tissue and the like, and neural cells can be produced with high efficiency from pluripotent stem cells cultured in the absence of feeder cells.

BRIEF DESCRIPTION OF THE DRAWINGS

FIG. 4 shows bright field images of aggregates.

FIG. 5 shows bright field images of aggregates (A and B), and immunohistochemical staining images of aggregates for neural tissue markers (Nestin, TuJ1, PSA-NCAM) (C-E).

DESCRIPTION OF EMBODIMENTS

1. Definition

Figure 1:
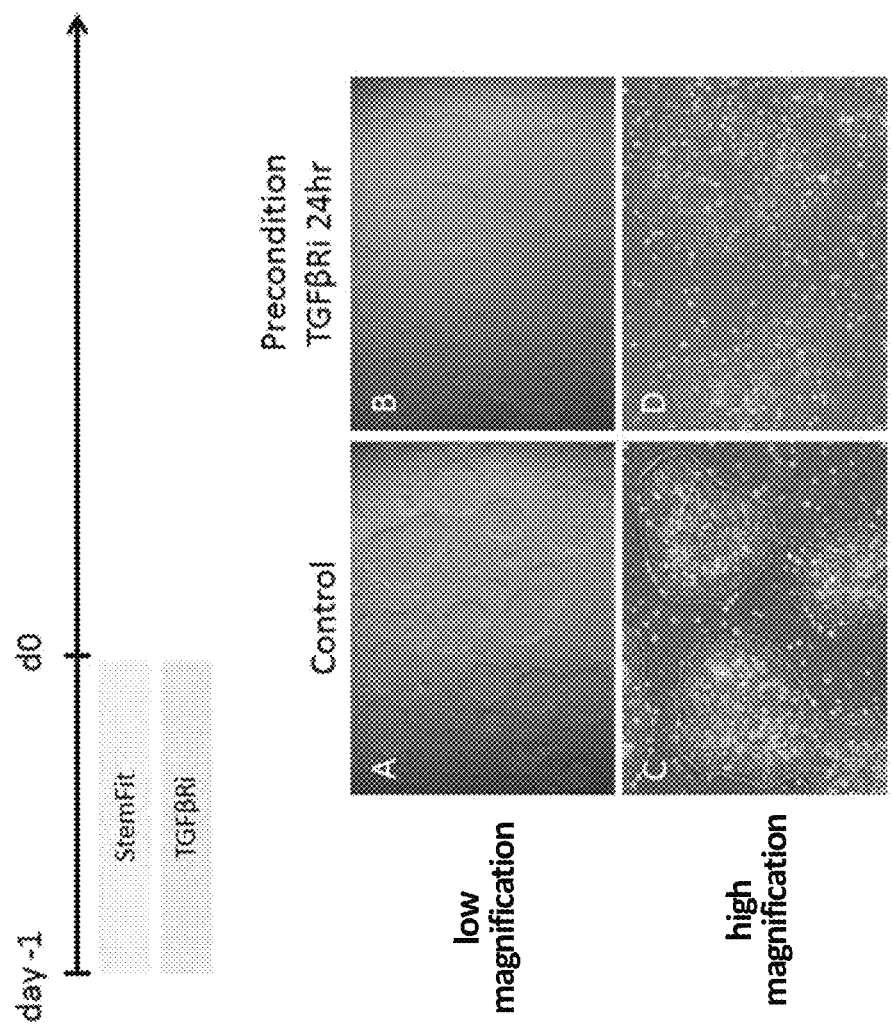
FIG. 1 shows culture conditions of Example 1, and the morphology of human iPS cells after culture.

In the present invention, "stem cell" means an undifferentiated cell having differentiation potency and proliferative capacity (particularly self-renewal competence) maintaining differentiation potency. The stem cell includes subpopulations such as pluripotent stem cell, multipotent stem cell, unipotent stem cell and the like according to the differentiation potency. Pluripotent stem cell refers to a stem cell capable of being cultured in vitro and having a potency to differentiate into any cell lineage belonging to three germ layers (ectoderm, mesoderm, endoderm) and/or extraembryonic tissue (pluripotency). The multipotent stem cell means a stem cell having a potency to differentiate into plural types of tissues or cells, though not all kinds. The unipotent stem cell means a stem cell having a potency to differentiate into a particular tissue or cell.

Pluripotent stem cell can be induced from fertilized egg, clone embryo, germ stem cell, stem cell in a tissue, somatic cell and the like. Examples of the pluripotent stem cell include embryonic stem cell (ES cell), EG cell (embryonic germ cell), induced pluripotent stem cell (iPS cell) and the like. Muse cell (Multi-lineage differentiating stress enduring cell) obtained from mesenchymal stem cell (MSC), and GS cell produced from reproductive cell (e.g., testis) are also encompassed in the pluripotent stem cell. Embryonic stem cell was first established in 1981, and has also been applied to the generation of knockout mouse since 1989. In 1998, human embryonic stem cell was established, which is also being utilized for regenerative medicine. ES cell can be produced by culturing an inner cell mass on a feeder cell or in a medium containing LIF. The production methods of ES cell are described in, for example, WO 96/22362, WO 02/101057, U.S. Pat. Nos. 5,843,780, 6,200,806, 6,280,718 and the like. Embryonic stem cells are available from given organizations, or a commercially available product can be purchased. For example, human embryonic stem cells, KhES-1, KhES-2 and KhES-3, are available from Kyoto University's Institute for Frontier Medical Sciences. The Rx::GFP cell line (derived from KhES-1), which is a human embryonic stem cell, is available from RIKEN. EB5 cell, which is a mouse embryonic stem cell, is available from Incorporated Administrative Agency RIKEN, and D3 cell line, which is a mouse embryonic stem cell, is available from ATCC.

Nuclear transfer ES cell (ntES cell), which is one of the ES cells, can be established from a clone embryo produced by transplanting the nucleus of a somatic cell into an enucleated egg.

EG cell can be produced by culturing a primordial germ cell in a medium containing mSCF, LIF and bFGF (Cell, 70: 841-847, 1992).

The "induced pluripotent stem cell" in the present invention is a cell induced to have pluripotency by reprogramming a somatic cell by a known method and the like. Specifically, a cell induced to have pluripotency by reprogramming differentiated somatic cells such as fibroblast, peripheral blood mononuclear cell and the like by the expression of a combination of a plurality of genes selected from the group consisting of reprogramming genes including Oct3/4, Sox2, Klf4, Myc (c-Myc, N-Myc, L-Myc), Glis1, Nanog, Sal14, lin28, Esrrb and the like can be mentioned. Examples of preferable combination of reprogramming factors include (1) Oct3/4, Sox2, Klf4, and Myc (c-Myc or L-Myc), and (2) Oct3/4, Sox2, Klf4, Lin28 and L-Myc (Stem Cells, 2013; 31:458-466).

Induced pluripotent stem cell was established by Yamanaka et al. in mouse cell in 2006 (Cell, 2006, 126(4), pp. 663-676). In 2007, induced pluripotent stem cell was also established from human fibroblast, and has pluripotency and self-renewal competence similar to those of embryonic stem cells (Cell, 2007, 131(5), pp. 861-872; Science, 2007, 318(5858), pp. 1917-1920; Nat. Biotechnol., 2008, 26(1), pp. 101-106).

Besides the production method based on direct reprogramming by gene expression, induced pluripotent stem cell can also be obtained from somatic cell by the addition of a compound and the like (Science, 2013, 341, pp. 651-654).

It is also possible to obtain established induced pluripotent stem cell and, for example, human induced pluripotent cell lines established by Kyoto University such as 201B7 cell, 201B7-Ff cell, 253G1 cell, 253G4 cell, 1201C1 cell, 1205D1 cell, 1210B2 cell or, 1231A3 cell and the like are available from Kyoto University and iPS Academia Japan, Inc. As the established induced pluripotent stem cell, for example, Ff-I01 cell and Ff-I14 cell established by Kyoto University are available from Kyoto University.

While the somatic cell used for obtaining induced pluripotent stem cell is not particularly limited, tissue-derived fibroblast, blood-lineage cells (e.g., peripheral blood mononuclear cell, T cell), hepatocyte, pancreatic cell, intestinal epithelial cell, smooth muscle cell and the like can be mentioned.

When induced pluripotent stem cell is produced by reprogramming by the expression of several kinds of genes, the means for gene expression is not particularly limited. Examples of the aforementioned means include an infection method using a virus vector (e.g., retrovirus vector, lentivirus vector, Sendaivirus vector, adenovirus vector, adeno-associated virus vector), a gene transfer method using a plasmid vector (e.g., plasmid vector, episomal vector) (e.g., calcium phosphate method, lipofection method, RetroNectin method, electroporation method), a gene transfer method using an RNA vector (e.g., calcium phosphate method, lipofection method, electroporation method), a method with direct injection of protein and the like.

When an induced pluripotent stem cell is produced, it can be produced in the presence of a feeder cell or in the absence of feeder cells (feeder-free). When an induced pluripotent stem cell is produced in the presence of a feeder cell, the induced pluripotent stem cell can be produced by a known method in the presence of a factor for maintaining undifferentiated state. While a medium to be used for producing an induced pluripotent stem cell in the absence of feeder cells is not particularly limited, a known maintenance medium for embryonic stem cells and/or induced pluripotent stem cells, and a medium for establishing induced pluripotent stem cell under feeder-free can be used. Examples of the medium for feeder-free establishment for establishing an induced pluripotent stem cell under feeder-free conditions include feeder-free media such as Essential 8 medium, TeSR medium, mTeSR medium, mTeSR-E8 medium, StemFit medium and the like. When an induced pluripotent stem cell is produced, for example, it can be produced by gene transfer of 4 factors of Oct3/4, Sox2, Klf4, and Myc into somatic cell by using a Sendaivirus vector in the absence of feeder cells.

The pluripotent stem cell to be used in the present invention is preferably ES cell or induced pluripotent stem cell, more preferably induced pluripotent stem cell.

As the multipotent stem cell, tissue stem cells (also called stem cell in tissue, tissue-specific stem cell or somatic stem cell) such as hematopoietic stem cell, neural stem cell, retinal stem cell, mesenchymal stem cell and the like can be mentioned.

Genetically-modified pluripotent stem cells can be produced by using, for example, a homologous recombination technique. Examples of the gene on the chromosome to be modified include a cell marker gene, a histocompatibility antigen gene, a gene related to a disease due to a disorder of neural cell and so on. A target gene on the chromosome can be modified using the methods described in Manipulating the Mouse Embryo, A Laboratory Manual, Second Edition, Cold Spring Harbor Laboratory Press (1994); Gene Targeting, A Practical Approach, IRL Press at Oxford University Press (1993); Biomanual Series 8, Gene Targeting, Making of Mutant Mouse using ES cell, YODOSHA CO., LTD. (1995); and so on.

To be specific, for example, the genomic DNA comprising the target gene to be modified (e.g., cell marker gene, histocompatibility antigen gene, disease-related gene and so on) is isolated, and a targeting vector used for homologous recombination of the target gene is produced using the isolated genomic DNA. The produced targeting vector is introduced into stem cells and the cells that showed homologous recombination between the target gene and the targeting vector are selected, whereby stem cells having the modified gene on the chromosome can be produced.

Examples of the method for isolating genomic DNA comprising the target gene include known methods described in Molecular Cloning, A Laboratory Manual, Second Edition, Cold Spring Harbor Laboratory Press (1989), Current Protocols in Molecular Biology, John Wiley & Sons (1987-1997) and so on. The genomic gene comprising the target gene can also be isolated using genomic DNA library screening system (manufactured by Genome Systems), Universal GenomeWalker Kits (manufactured by CLONTECH) and so on. A polynucleotide encoding the target protein can also be used instead of genome DNA. The polynucleotide can be obtained by amplifying the corresponding polynucleotide by the PCR method.

Production of targeting vector used for homologous recombination of the target gene, and efficient selection of a homologous recombinant can be performed according to the methods described in Gene Targeting, A Practical Approach, IRL Press at Oxford University Press (1993); Biomanual Series 8, Gene Targeting, Making of Mutant Mouse using ES cell, YODOSHA CO., LTD. (1995); and so on. As the targeting vector, any of replacement type or insertion type can be used. As the selection method, methods such as positive selection, promoter selection, negative selection, polyA selection and so on can be used.

Examples of a method for selecting the desired homologous recombinant from the selected cell lines include Southern hybridization method, PCR method and so on for the genomic DNA.

The "mammal" in the present invention encompasses rodents, ungulata, carnivora, primates and the like. The rodents encompass mouse, rat, hamster, guinea pig and the like. Ungulata encompass swine, bovine, goat, horse, sheep and the like. Carnivora encompasses dog, cat and the like. The "primates" in the present invention refers to mammals belonging to the primate, and the primates include prosimian such as lemur, loris, tupai and the like, and anthropoidea such as monkey, ape, human and the like.

The pluripotent stem cell to be used in the present invention is a pluripotent stem cell of a mammal, preferably a pluripotent stem cell of rodents (e.g., mouse, rat) or primates (e.g., human, monkey), more preferably a human pluripotent stem cell, more preferably a human induced pluripotent stem cell (iPS cell) or human embryonic stem cell (ES cell).

The "suspension culturing" or "suspension culture method" in the present invention refers to culturing while maintaining a state in which cells or cell aggregates are suspended in a culture medium and a method of performing the culture. That is, suspension culturing is performed under conditions in which cells or cell aggregates are not adhered to a culture vessel and the like, and culturing performed under conditions permitting adhesion to a culture vessel and the like (adhesion culturing or adhesion culture method) is not included in the category of suspension culturing. In this case, adhesion of cell means that a strong cell-substratum junction is formed between a cell or cell aggregate and a culture vessel. More particularly, suspension culturing refers to culturing under conditions in which a strong cell-substratum junction is not formed between a cell or cell aggregate and a culture vessel, and adhesion culturing refers to culturing under conditions in which a strong cell-substratum junction is formed between a cell or cell aggregate and a culture vessel and the like.

In a cell aggregate in suspension culture, a planar cell-cell adhesion is formed. In cell aggregates in suspension culture, a cell-substratum junction is hardly formed with a culture vessel and the like and, even if it is formed, its contribution is small. In some embodiment, an endogenous cell-substratum junction is present inside the aggregate, but a cell-substratum junction is hardly formed with a culture vessel and the like and, even if it is formed, its contribution is small.

The planar cell-cell adhesion (plane attachment) means that a cell attaches to another cell via planes. More particularly, the planar cell-cell adhesion means that, for example, not less than 1%, preferably not less than 3%, more preferably not less than 5%, of the surface area of a cell adheres to the surface of another cell. A surface of a cell can be observed by staining with a reagent (e.g., DiI) that stains membranes, immunostaining of cell adhesion molecules (e.g., E-cadherin and N-cadherin).

The cell culture vessel to be used when performing suspension culturing is not particularly limited as long as it enables "culturing in suspension" and those of ordinary skill in the art can appropriately determine same. Examples of such cell culture vessel include flask, tissue culture flask, culture dish (dish), petri dish, tissue culture dish, multidish, microplate, microwell plate, micropore, multiplate, multi-well plate, chamber slide, schale, tube, tray, culture bag, spinner flask, Erlenmeyer flask, roller bottle and so on. To enable suspension culturing, these culture vessels are preferably non-cell-adherent. Useful non-cell-adherent culture vessels include culture vessels whose surfaces have not undergone an artificial treatment for improving the cell adhesiveness (e.g., surface treatment with extracellular matrix such as basement membrane preparation, laminin, entactin, collagen, gelatin etc., and the like, or coating treatment with polymer such as polylysine, polyornithine and the like or positive electric charge treatment and the like), and the like. As a non-cell-adherent culture vessel, culture vessels whose surfaces have been artificially treated to decrease adhesiveness to the cells (e.g., superhydrophilic treatment with MPC polymer and the like, protein low adsorption treatment etc.) and the like can be used. Roller culture using spinner flask, roller bottle and the like may be performed. The culture surface of the culture vessel may be a flat bottom or may have concaves and convexes.

A culture vessel used for adhesion culturing is not particularly limited as long as "adhesion culturing" can be performed, and those of ordinary skill in the art can appropriately select a culture vessel suitable according to the culture scale, culture conditions and period for the culturing. Examples of such culture vessel include flasks, tissue culture flasks, culture dishes (dishes), tissue culture dishes, multi-dishes, microplates, micro-well plates, multi-plates, multi-well plates, chamber slides, schale, tubes, trays, culture bags, microcarrier, bead, stack plate, spinner flask and roller bottles. To enable adhesion culturing, these culture vessels are preferably cell-adherent. Cell-adherent culture vessels include culture vessels whose surfaces have been artificially treated to improve cell adhesiveness, and specifically, a surface-processed culture vessel, or, a culture vessel whose inside is coated with a coating agent can be mentioned. Examples of the coating agent include extracellular matrix such as laminin [including laminin $\alpha 5\beta 1\gamma 1$ (hereinafter laminin 511), laminin $\alpha 1\beta 1\gamma 1$ (hereinafter laminin 111) and the like and laminin fragment (laminin 511E8 etc.)], entactin, collagen, gelatin, vitronectin, Synthemax (Corning Incorporated), Matrigel and the like, or polymers such as polylysine, polyornithine and the like. Examples of the surface-processed culture vessel include culture vessels surface-processed by a positive electric charge treatment and the like.

The medium to be used for culturing cells in the present invention can be prepared from a medium generally used for culturing animal cells as a basal medium. Examples of the basal medium include media that can be used for culturing animal cells such as BME medium, BGJb medium, CMRL1066 medium, Glasgow MEM (GMEM) medium, Improved MEM Zinc Option medium, IMDM medium, Medium199 medium, Eagle MEM medium, $\alpha$MEM medium, DMEM medium, F-12 medium, DMEM/F-12 medium, IMDM/F12 medium, Ham medium, RPMI1640 medium, Fischer's medium, and mixed medium thereof etc.

The "serum-free medium" in the present invention means a medium free of unadjusted or unpurified serum. In the present invention, a medium containing purified blood-derived components and animal tissue-derived components (e.g., growth factor) is also included in a serum-free medium unless unadjusted or unpurified serum is contained therein.

The serum-free medium may contain a serum alternative. Examples of the serum alternative include one appropriately containing albumin, transferrin, fatty acid, collagen precursor, trace element, 2-mercaptoethanol or 3' thiolglycerol, or equivalents of these etc., and so on. Such serum alternative may be prepared by, for example, the method described in WO98/30679. In addition, the serum alternative may be a commercially available product. Examples of such commercially available serum alternative include Knockout™ Serum Replacement (Life Technologies, now ThermoFisher: hereinafter sometimes to be indicated as KSR), Chemically Defined Lipid Concentrated (manufactured by Life Technologies) and Glutamax™ (manufactured by Life Technologies), B27 (manufactured by Life Technologies), N2 supplement (manufactured by Life Technologies).

The serum-free medium to be used for suspension culturing may appropriately contain a fatty acid or lipid, amino acid (e.g., non-essential amino acids), vitamin, growth factor, cytokine, antioxidant, 2-mercaptoethanol, pyruvic acid, buffering agent, inorganic salts and so on.

To avoid complicated preparation, a serum-free medium supplemented with an appropriate amount (e.g., about 0.5% to about 30%, preferably about 1% to about 20%) of commercially available KSR (manufactured by Life Technologies) may be used as such serum-free medium (e.g., medium of 1:1 mixture of F-12 medium and IMDM medium supplemented with 10% KSR, Chemically-defined Lipid concentrated, and 450 µM 1-monothioglycerol). As a product equivalent to KSR, the medium disclosed in JP-A-2001-508302 can be mentioned.

The "serum-containing medium" in the present invention means a medium containing unadjusted or unpurified serum. The medium may contain a fatty acid, lipid, amino acid (e.g., non-essential amino acids), vitamin, growth factor, cytokine, antioxidant, 2-mercaptoethanol, 1-monothioglycerol, pyruvic acid, buffering agent, inorganic salts and so on. For example, when a pluripotent stem cell is induced to differentiate into a retinal tissue and the like by using a basement membrane preparation such as Matrigel and the like, a serum medium can be used (Cell Stem Cell, 10(6), 771-775 (2012)). In addition, a serum medium can be used in the step of maintaining the neural tissue (e.g., retinal tissue, cerebral tissue) produced by the present invention (to be also referred to as mature culture).

In the present invention, the culturing is preferably performed under xeno-free conditions. The "xeno-free" means conditions eliminating components derived from species different from that of the cell to be cultured.

In the present invention, the "medium containing substance X" and "in the presence of substance X" refer to a medium supplemented with an exogenous substance X or a medium containing an exogenous substance X, or in the presence of an exogenous substance X. That is, when the cells or tissues present in the medium endogenously express, secrete or produce substance X, the endogenous substance X is distinguished from the exogenous substance X, and a medium free of exogenous substance X is understood to fall outside the category of the "medium containing substance X", even when it contains endogenous substance X.

For example, a "medium containing a TGFβ family signal transduction pathway inhibiting substance" is a medium supplemented with an exogenous TGFβ family signal transduction pathway inhibiting substance or a medium containing an exogenous TGFβ family signal transduction pathway inhibiting substance.

In the present invention, a feeder cell refers to a cell other than a stem cell co-exist when culturing the stem cell. Examples of the feeder cells used for culturing pluripotent stem cells while maintaining undifferentiated state include mouse fibroblasts (MEF etc.), human fibroblasts, SNL cells and the like. As the feeder cells, feeder cells that underwent a growth suppression treatment is preferable. Examples of the growth suppression treatment include treatment with a growth inhibitor (e.g., mitomycin C), gamma radiation, UV irradiation and the like. Feeder cells used for culturing pluripotent stem cells while maintaining undifferentiated state contributes to the maintenance of undifferentiation of pluripotent stem cell by secretion of a humoral factor (preferably factor for maintaining undifferentiated state), or production of a scaffold for cell adhesion (extracellular substrate).

In the present invention, the absence of feeder cells (feeder-free) means culturing in the absence of feeder cells. The absence of feeder cells means, for example, conditions free of addition of feeder cells, or conditions substantially free of feeder cells (e.g., the ratio of the number of feeder cells relative to the total number of cells is not more than 3%).

In the present invention, an "aggregate" of cells refers to a clump formed by assembly of cells dispersed in a medium, wherein the cells are adhered to each other. Cell clumps, embryoid bodies, spheres, spheroids are also encompassed in the cell aggregates. Preferably, a planar cell-cell adhesion is formed in the aggregate of cells. In some embodiments, cells sometimes form a cell-cell junction and/or a cell adhesion, for example, adherence junction, in some or all of the aggregates. The "aggregate" in the present invention specifically includes an aggregate produced in the second step of the above-mentioned present invention [1], which is formed by cells dispersed at the time of the start of the suspension culturing, and an aggregate produced in the third step of the above-mentioned present invention [1], which contains induced neural cells differentiated from pluripotent stem cell, and the "aggregate" also includes an aggregate already formed at the time of the start of the second step in the above-mentioned present invention [1] (i.e., at the time of the start of suspension culture). The cell aggregate formed in the second step encompasses "embryoid body (EB)".

In the present invention, "uniformed aggregates" means that the size of each aggregate is constant when a plurality of aggregates are cultured, and that the variance in the length of the maximum diameter is small when the size of the aggregates are evaluated by the length of the maximum diameter. More specifically, it means that not less than 75% of aggregates in the whole aggregate population are within mean±100%, preferably mean±50%, more preferably mean±20%, of the maximum diameter in the population of the aggregates.

In the present invention, to "form uniformed cell aggregates" means to "rapidly aggregate a given number of dispersed cells" to form cell aggregates uniform in size, when gathering the cells to form cell aggregates and culturing the aggregates in suspension.

Dispersion refers to dividing cells or a tissue into small cell clots (not less than 2 cells and not more than 100 cells, preferably not more than 50 cells) or single cells by a dispersion treatment such as enzymatic treatment, physical treatment and the like. A given number of dispersed cells is a collection of a certain number of cell clots or single cells.

Examples of the method of dispersing pluripotent stem cells include a mechanical dispersion treatment, a cell dispersion solution treatment, and a cell protecting agent addition treatment. These treatments may be performed in combination. Preferably, a cell dispersion treatment is performed and then a mechanical dispersion treatment is performed.

As a method of mechanical dispersion treatment, a pipetting treatment or a scraping operation by a scraper can be mentioned.

As a cell dispersion solution to be used for the cell dispersion solution treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TrypLE Select (manufactured by Life Technologies) and TrypLE Express (manufactured by Life Technologies) can also be used.

When pluripotent stem cells are dispersed, cell death of the pluripotent stem cells may be suppressed by treating with a cell protecting agent. As a cell protecting agent to be used for the cell protecting agent treatment, a FGF signal transduction pathway activating substance, heparin, an IGF signal transduction pathway activating substance, serum, and serum alternative can be mentioned. To suppress cell death induced by dispersion (particularly, cell death of human pluripotent stem cells), a Rho-associated coiled-coil kinase (ROCK) inhibiting substance or a Myosin inhibiting substance may be added at the time of dispersion. As a ROCK inhibiting substance, Y-27632, Fasudil (HA1077), H-1152 and the like can be mentioned. As a Myosin inhibiting substance, Blebbistatin can be mentioned. As a preferable cell protecting agent, a ROCK inhibiting substance can be mentioned.

For example, a method for dispersing pluripotent stem cells includes, for example, a method involving treating a colony of pluripotent stem cells with a cell dispersion solution (TrypLE Select) in the presence of a ROCK inhibiting substance as a cell protecting agent, and further dispersing them by pipetting.

In the production method of the present invention, it is preferable to form an aggregate of pluripotent stem cells by rapidly gathering the pluripotent stem cells. When an aggregate of pluripotent stem cells is formed in such a manner, an epithelium-like structure can be formed with good reproducibility in the cells induced and differentiated from the formed aggregate. Examples of the experimental operation to form an aggregate include a method involving keeping cells in a small space by using a plate with small wells (e.g., plate with wells having a base area of about 0.1-2.0 cm$^2$ when calculated in terms of flat bottom), micropore and so on, a method involving aggregating cells by centrifugation for a short time using a small centrifugation tube. As a plate with small wells, for example, 24 well plate (area of about 1.88 cm$^2$ when calculated in terms of flat bottom), 48 well plate (area of about 1.0 cm$^2$ when calculated in terms of flat bottom), 96 well plate (area of about 0.35 cm$^2$ when calculated in terms of flat bottom, inner diameter about 6-8 mm), and 384 well plate can be mentioned. Preferred is 96 well plate. As a shape of the plate with small wells, the shape of the bottom surface when the well is seen from above is, for example, polygon, rectangle, ellipse, true circle, preferably true circle. As a shape of the plate with small wells when the well is seen from the side well, the shape of the bottom surface may be a flat bottom structure or a structure having high outer circumference and low inner concave. The shape of the bottom surface includes, for example, U-bottom, V-bottom, M-bottom, preferably U-bottom or V-bottom, more preferably V-bottom. As a plate with small wells, a cell culture dish (e.g., 60 mm-150 mm dish, culture flask) with a concave convex, or dent on the bottom surface may also be used. The bottom surface of a plate with small wells is preferably a non-cell-adhesive bottom surface, preferably the aforementioned non-cell-adhesive-coated bottom surface.

Formation of aggregates comprising pluripotent stem cells, or a cell population containing pluripotent stem cells, and uniformity thereof can be determined based on the size of the aggregate mass and the number of cells therein, macroscopic morphology, microscopic morphology by tissue staining analysis and homogeneity thereof, and the like. In addition, formation of an epithelial-like structure in the aggregate, and uniformity thereof can be determined based on the macroscopic morphology of the aggregate, microscopic morphology by tissue staining analysis and uniformity thereof, expression of differentiation and undifferentiation markers and uniformity thereof, control of expression of differentiation marker and synchronism thereof, reproducibility of differentiation efficiency between aggregates, and so on.

The "tissue" in the present invention refers to a structure of a cell population having a structure in which one kind of cells having a uniformed morphology or property, or plural types of cells having different morphologies and properties are sterically arranged in a given pattern.

In the present invention, the "neural tissue" refers to a tissue constituted of neural cells including cerebrum, midbrain, cerebellum, spinal cord, retina, peripheral nerve, forebrain, hindbrain, telencephalon, diencephalon and the like in the developing stage or adult stage. A neural tissue sometimes forms an epithelial structure (neuroepithelium) having a layer structure, and the amount of neuroepithelium in cell aggregates can be evaluated by bright field observation using an optical microscope.

In the present invention, the "neural cell" refers to a cell other than epidermal lineage cell in a tissue derived from ectoderm. That is, it includes cells such as neural precursor cell, neuron (neuronal cell), glia, neural stem cell, neuron precursor cell, glial precursor cell and the like. The neural cell also encompasses cell constituting the below-mentioned retinal tissue (retinal cell), retinal progenitor cell, retinal layer-specific neuron, neural retinal cell, and retinal pigment epithelial cell. The neural cell can be identified by using Nestin, TuJ1, PSA-NCAM, N-cadherin and the like as a marker. Neuron (or neuronal cell) is a functional cell that forms a neural circuit and contributes to signal transduction, and can be identified by using the expression of immature neuronal markers such as TuJ1, Dcx, HuC/D and the like and/or mature neuronal cell markers such as Map2, NeuN and the like as an index.

As glia, astrocyte, oligodendrocyte, Müller glia and the like can be mentioned. As an astrocyte marker, GFAP can be mentioned; as an oligodendrocyte marker, O4 can be mentioned, and as a Müller glia marker, CRALBP and the like can be mentioned.

The neural stem cell is a cell having differentiation potency (multipotency) into neuron and glial cell, and proliferative capacity (sometimes to be referred to as self-renewal competence) maintaining multipotency. As the neural stem cell marker, Nestin, Sox2, Musashi, Hes family, CD133 and the like can be mentioned; however, these markers are markers for progenitor/precursor cells in general and are not considered neural stem cell-specific markers. The number of neural stem cells can be evaluated by neurosphere assay, clonal assay and the like.

The neuronal precursor cell is a cell having proliferative capacity, which produces neuron and does not produce glial cell. As a neuronal precursor cell marker, Tbr2, Tα1 and the like can be mentioned. Alternatively, an immature neuronal marker (TuJ1, Dcx, HuC/D)-positive and growth marker (Ki67, pH3, MCM)-positive cell can also be identified as a neuronal precursor cell.

The glial precursor cell is a cell having proliferative capacity, which produces glial cell and does not produce neuron.

The neural precursor cell is an assembly of precursor cells including neural stem cell, neuronal precursor cell and glial precursor cell, and has proliferative capacity and neuron- and glia-productivity. The neural precursor cell can be identified using Nestin, GLAST, Sox2, Sox1, Musashi, Pax6 and the like as markers. Alternatively, a neural cell marker-positive and growth marker (Ki67, pH3, MCM)-positive cell can also be identified as a neural precursor cell.

In the present invention, the "retinal tissue" means a tissue in which one type or at least two or more types of cells such as photoreceptor cells, photoreceptor precursor cells, rod photoreceptor cells, cone photoreceptor cells, interneurons, horizontal cells, bipolar cells, amacrin cells, retinal ganglion cells (ganglion cells), retinal pigment epithelial cell (RPE), ciliary marginal zone cell, their progenitor/precursor cells and retinal progenitor cells and so on, which constitute respective retinal layers in retina in vivo, are sterically arranged in layers. The retinal layer which is constituted by each cell can be confirmed by a known method, for example, presence or absence of the expression of a cell marker or the level thereof, etc.

The "retinal layer" in the present invention means each layer constituting the retina. Specific examples thereof include retinal pigment epithelial layer, photoreceptor layer, external limiting membrane, outer nuclear layer, outer plexiform layer, inner nuclear layer, inner plexiform layer, ganglion cell layer, nerve fiber layer and inner limiting membrane.

The "retinal progenitor cell" in the present invention refers to a progenitor cell capable of differentiating into any mature retinal cell including photoreceptor cell, horizontal cell, bipolar cell, amacrine cell, retinal ganglion cell, retinal pigment epithelial cell and the like.

In the present invention, the "neural retinal progenitor cell" refers to a progenitor cell capable of differentiating into any one of or plural mature retinal cells including photoreceptor cell, horizontal cell, bipolar cell, amacrine cell, retinal ganglion cells, and the like. In general, a neural retinal progenitor cell does not differentiate into a retinal pigment epithelial cell.

The photoreceptor precursor cell, horizontal cell precursor cell, bipolar cell precursor cell, amacrine cell precursor cell, retinal ganglion cell precursor cell, and retinal pigment epithelial precursor cell refer to precursor cells committed to differentiate into photoreceptor cell, horizontal cell, bipolar cell, amacrine cell, retinal ganglion cells, and retinal pigment epithelial cell, respectively.

In the present invention, the "retinal layer-specific neuron" is a cell constituting a retina layer and is a neuron specific to the retinal layer. Examples of the retinal layer-specific neuron include bipolar cell, retinal ganglion cells, amacrine cell, horizontal cell, photoreceptor cell, retinal pigment epithelial cell, rod cell and cone cell.

Examples of the retinal cell marker include Rx (also referred to as Rax), PAX6 and Chx10 expressed in retinal progenitor cell, Nkx2.1 expressed in precursor cell of hypothalamus neuron but not expressed in retinal progenitor cell, Sox1 expressed in hypothalamus neuroepithelium but not expressed in retina, Crx, Blimp1 and the like expressed in precursor cell of photoreceptor cell, and the like. Examples of the marker of the retinal layer-specific neuron include Chx10, PKCα and L7 expressed in bipolar cell, TUJI and Brn3 expressed in retinal ganglion cells, Calretinin expressed in amacrine cell, Calbindin expressed in horizontal cell, Rhodopsin and Recoverin expressed in mature photoreceptor cell, Nrl and Rhodopsin expressed in rod cell, Rxr-gamma and S-Opsin expressed in cone cell, RPE65 and Mitf expressed in retinal pigment epithelium cell, Rdh10 and SSEA1 expressed in ciliary marginal zone and the like.

In the present invention, the "cerebral tissue" is a tissue in which one type or at least plural types of cells constituting cerebrum in the fetal stage or of adult (e.g., cortical neural precursor cell, dorsal cerebral neural precursor cell, ventral cerebral neural precursor cell, cerebral layer structure specific neuron, layer 1 neuron, layer 2 neuron, layer 3 neuron, layer 4 neuron, layer 5 neuron, layer 6 neuron, glial cell (astrocyte and oligodendrocyte), these precursor cell and the like) are sterically arranged in layers. The cerebrum in the fetal stage is also called forebrain or telencephalon. The presence of each cell can be confirmed by a known method, for example, presence or absence of expression of cell marker or the level thereof and the like.

In the present invention, the "cerebral layer" means each layer constituting adult cerebrum or fetal stage cerebrum, and specifically includes molecule layer, external granular layer, external pyramidal layer, internal granular layer, ganglionic layer (internal pyramidal layer), multiform layer, layer 1, layer 2, layer 3, layer 4, layer 5, layer 6, cortex zone, intermediate zone, subventricular zone, and ventricular zone.

Examples of the "cerebral neural precursor cell" in the present invention include neuronal precursor cell, layer 1 neuronal precursor cell, layer 2 neuronal precursor cell, layer 3 neuronal precursor cell, layer 4 neuronal precursor cell, layer 5 neuronal precursor cell, layer 6 neuronal precursor cell, astrocyte precursor cell, oligodendrocyte precursor cell and the like. They are precursor cells committed to differentiate into layer 1 neuron, layer 2 neuron, layer 3 neuron, layer 4 ganglionic layer 5 neuron, layer 6 neuron, astrocyte, and oligodendrocyte, respectively.

In the present invention, the "cerebral neural precursor cell" includes a multipotent stem cell (multipotent neural stem cell) having differentiation potency (multipotency) into at least plural differentiation lineages from layer 1 neuron, layer 2 neuron, layer 3 neuron, layer 4 neuron, layer 5 neuron, layer 6 neuron, astrocyte, and oligodendrocyte.

In the present invention, the "cerebral layer-specific neuron" is a cell constituting a cerebral layer and is a neuron specific to the cerebral layer. As the cerebral layer-specific neuron, layer 1 neuron, layer 2 neuron, layer 3 neuron, layer 4 ganglionic layer 5 neuron, layer 6 neuron, cerebral excitatory neuron, cerebral inhibitory neuron and the like can be mentioned.

Examples of the cerebral cell marker include FoxG1 (alias Bf1) expressed in cerebral cell, Sox2 and Nestin expressed in cerebral neural precursor cell, Pax6 and Emx2 expressed in dorsal cerebral neural precursor cell, Dlx1, Dlx2 and Nkx2.1 expressed in ventral cerebral neural precursor cell, Tbr2, Nex, Svet1 expressed in neuronal precursor cell, Tbr1 expressed in layer 6 neuron, Ctip2 expressed in layer 5 neuron, RORβ expressed in layer 4 neuron, Cux1 or Brn2 expressed in layer 3 neuron or layer 2 neuron, Reelen expressed in layer 1 neuron and the like.

2. Method for Producing Neural Cells or Neural Tissue

The production method 1 of the present invention is a method for producing neural cells or neural tissue, comprising m the following steps (1)-(3):
(1) a first step of culturing pluripotent stem cells in the absence of feeder cells and in a medium comprising 1) a TGFβ family signal transduction pathway inhibiting substance and/or a Sonic hedgehog signal transduction pathway activating substance, and 2) a factor for maintaining undifferentiated state,
(2) a second step of culturing the cells obtained in the first step in suspension to form a cell aggregate, and
(3) a third step of culturing the aggregate obtained in the second step in suspension in the presence or absence of a differentiation-inducing factor to obtain an aggregate containing neural cells or neural tissue.

In step (1), pluripotent stem cells are cultured in the absence of feeder cells and in a medium containing 1) a TGFβ family signal transduction pathway inhibiting substance and/or a Sonic hedgehog signal transduction pathway activating substance, and 2) a factor for maintaining undifferentiated state.

As a preferable pluripotent stem cell in step (1), induced pluripotent stem cell or embryonic stem cell (ES cell), more preferably human induced pluripotent stem cell or human embryonic stem cell (ES cell) can be mentioned.

The production method of induced pluripotent stem cells is not particularly limited, and it can be produced by a method well known to those of ordinary skill in the art as mentioned above. It is also desirable to perform a step for preparing induced pluripotent stem cells (that is, a step of reprogramming somatic cells to establish pluripotent stem cells) under feeder-free condition.

While the production method of embryonic stem cells (ES cells) is not particularly limited, and can be produced by a method well known to those of ordinary skill in the art as mentioned above, it is also desirable to perform a step for preparing embryonic stem cells (ES cells) under feeder-free condition.

The maintenance culturing or expansion culturing of pluripotent stem cells to be used in step (1) can be performed by a method well known to those of ordinary skill in the art as mentioned above. While the maintenance culturing and expansion culturing of pluripotent stem cells can be performed by adhesion culturing or suspension culturing, it is preferably performed by adhesion culturing. While the maintenance culturing and expansion culturing of pluripotent stem cells may be performed in the presence of feeders or under feeder-free condition, it is preferably performed under feeder-free condition. The absence of feeder cells (feeder-free) in the maintenance culturing and expansion culturing of pluripotent stem cells means a condition substantially free of feeder cell (e.g., the ratio of the number of feeder cells relative to the total number of cells is not more than 3%). Preferably, the maintenance culturing and expansion culturing of pluripotent stem cells is performed under a condition free of feeder cells.

The absence of feeder cells (feeder-free) in step (1) means a condition substantially free of feeder cells (e.g., the ratio of the number of feeder cells relative to the total number of cells is not more than 3%). Preferably, step (1) is performed under a condition free of feeder cells. The medium to be used in step (1) is not particularly limited as long as it is a medium enabling culturing of pluripotent stem cells to maintain undifferentiated state under feeder-free conditions (feeder-free medium). Preferably, to enable culturing to maintain undifferentiated state, it contains a factor for maintaining undifferentiated state.

The factor for maintaining undifferentiated state is not particularly limited as long as it is a substance having an action to suppress differentiation of pluripotent stem cells. Examples of the factor for maintaining undifferentiated state widely used by those of ordinary skill in the art include a FGF signal transduction pathway activating substance, a TGFβ family signal transduction pathway activating substance, insulin and the like in the case of primed pluripotent stem cells (e.g., human ES cells, human iPS cells). As the FGF signal transduction pathway activating substance, fibroblast growth factors (e.g., bFGF, FGF4, FGF8) can be specifically mentioned. As the TGFβ family signal transduction pathway activating substance, a TGFβ signal transduction pathway activating substance, a Nodal/Activin signal transduction pathway activating substance can be mentioned. As the TGFβ signal transduction pathway activating substance, TGFβ1, TGFβ2 can be mentioned. As the Nodal/Activin signal transduction pathway activating substance, Nodal, Activin A, Activin B can be mentioned. When human pluripotent stem cells (human ES cells, human iPS cells) are cultured, the medium in step (1) preferably contains bFGF as a factor for maintaining undifferentiated state.

The factor for maintaining undifferentiated state to be used in the present invention is generally a factor for maintaining undifferentiated state of mammals. The mammals are, for example, those mentioned above. Since the factor for maintaining undifferentiated state may have cross-reactivity among mammal species, a factor for maintaining undifferentiated state of any mammal may also be used as long as the undifferentiated state of the pluripotent stem cells to be cultured can be maintained. Preferably, a factor for maintaining undifferentiated state of a mammal of the same species as the cells to be cultured is used. For example, for the culturing of human pluripotent stem cells, human factor for maintaining undifferentiated states (e.g., bFGF, FGF4, FGF8, EGF, Nodal, Activin A, Activin B, TGFβ 1, TGFβ 2 etc.) are used. Here, the "human protein X" means that protein X has the amino acid sequence of protein X naturally expressed in human in vivo.

The factor for maintaining undifferentiated state to be used in the present invention is preferably isolated. Being "isolated" means that an operation to remove factors other than the intended component or cell has been performed, and the component or cell is no longer in a naturally occurring state. Therefore, "isolated protein X" does not include an endogenous protein X produced from the cells or tissue to be cultured, and contained in a cell or tissue or in the medium. The purity of the "isolated protein X" (percentage of the weight of protein X to the total protein weight) is generally not less than 70%, preferably not less than 80%, more preferably not less than 90%, further preferably not less than 99%, further preferably 100%. Therefore, in one embodiment, the present invention comprises a step of providing an isolated factor for maintaining undifferentiated state. In one embodiment, it includes a step of exogenously adding an isolated factor for maintaining undifferentiated state to a medium used in step (1). Alternatively, a factor for maintaining undifferentiated state may be added in advance to a medium to be used in step (1).

The concentration of the factor for maintaining undifferentiated state in the medium to be used in step (1) is a concentration capable of maintaining the undifferentiated state of the pluripotent stem cells to be cultured, and can be appropriately determined by those of ordinary skill in the art. For example, specifically, when bFGF is used as a factor for maintaining undifferentiated state in the absence of feeder cells, the concentration thereof is generally about 4 ng-500 ng/mL, preferably about 10 ng-200 ng/mL, more preferably m about 30 ng-150 ng/mL.

As the feeder-free medium, many synthetic media have been developed and are commercially available and, for example, Essential 8 medium can be mentioned. Essential 8 medium is DMEM/F12 medium containing L-ascorbic acid-2-phosphate magnesium (64 mg/l), sodium selenium (14 μg/l), insulin (19.4 mg/l), NaHCO$_3$ (543 mg/l), transferrin (10.7 mg/l), bFGF (100 ng/mL), and a TGFβ family signal transduction pathway activating substance (TGFβ 1 (2 ng/mL) or Nodal (100 ng/mL)) as additives (Nature Methods, 8, 424-429 (2011)). Examples of the commercially available feeder-free medium include Essential 8 (manufactured by Life Technologies), S-medium (manufactured by DS Pharma Biomedical), StemPro (manufactured by Life Technologies), hESF9 (Proc Natl Acad Sci USA. 2008 Sep. 9; 105(36):13409-14), mTeSR1 (manufactured by STEMCELL Technologies), mTeSR2 (manufactured by STEMCELL Technologies), and TeSR-E8 (manufactured by STEMCELL Technologies). In addition to these, StemFit (manufactured by Ajinomoto Co., Inc.) can be mentioned as the feeder-free medium. The present invention can be performed conveniently by using these in the above-mentioned step (1).

In step (1), the pluripotent stem cells may be cultured under any conditions of suspension culturing and adhesion culturing, preferably adhesion culturing.

While a culture vessel used for adhesion culturing is not particularly limited as long as "adhesion culturing" can be performed, a cell adhesive culture vessel is preferable. Cell-adhesive culture vessels include culture vessels whose surfaces have been artificially treated to improve cell adhesiveness, and specifically, the above-mentioned surface-processed culture vessel, a culture vessel whose inside is coated with a coating agent can be mentioned. Examples of the coating agent include extracellular matrix such as laminin [including laminin α5β1γ1 (hereinafter laminin 511), laminin allyl (hereinafter laminin 111) and the like and laminin fragment (laminin 511E8 etc.)], entactin, collagen, gelatin, vitronectin, Synthemax (Corning Incorporated), Matrigel and the like, or polymer such as polylysine, polyornithine and the like, and the like. It is also possible to use a culture container whose surface is processed by a positive electric charge treatment and the like. Preferred is laminin and more preferred is laminin 511E-8. Laminin 511E-8 can be a commercially available product (e.g., iMatrix-511, Nippi).

The medium to be used in step (1) contains a TGFβ family signal transduction pathway inhibiting substance and/or a Sonic hedgehog signal transduction pathway activating substance. In the first step, pluripotent stem cells are treated with a TGFβ family signal transduction pathway inhibiting substance and/or a Sonic hedgehog signal transduction pathway activating substance, and subjected to suspension culturing in the second step, as a result of which the state of the pluripotent stem cells change, the quality of aggregate is improved, and a spherical cell aggregate having a smooth surface and a dense inside, and maintaining an undifferentiated state can be produced with high efficiency.

The TGFβ family signal transduction pathway (i.e., TGFβ superfamily signal transduction pathway) is a signal transduction pathway intracellularly transmitted by the Smad family with TGFβ, Nodal/Activin or BMP as a ligand.

The TGFβ family signal transduction pathway inhibiting substance refers to a substance that inhibits the TGFβ family signal transduction pathway, i.e., signal transduction pathway transmitted by the Smad family, and specific examples include a TGFβ signal transduction pathway inhibiting substance, a Nodal/Activin signal transduction pathway inhibiting substance and a BMP signal transduction pathway inhibiting substance. A TGFβ signal transduction pathway inhibiting substance is not particularly limited as long as it inhibits the signal transduction pathway caused by TGFβ, and may be any of nucleic acid, protein, and low-molecular-weight organic compound. Examples of the substance include a substance that directly acts on TGFβ (e.g., protein, antibody, aptamer etc.), a substance that suppresses expression of a gene encoding TGFβ (e.g., antisense oligonucleotide, siRNA etc.), a substance that inhibits the binding of a TGFβ, receptor and TGFβ, and a substance that inhibits a physiological activity caused by signal transduction by TGFβ receptor (e.g., TGFβ receptor inhibitor, Smad inhibitor etc.). A protein known as a TGFβ signal transduction pathway inhibiting substance, Lefty and the like can be mentioned. As a TGFβ, signal transduction pathway inhibiting substance, a compound well known to those of ordinary skill in the art can be used and, specifically, SB431542, LY-364947, SB-505124, A-83-01 and the like can be mentioned. Here, SB431542 (4-(5-benzol[1,3]dioxol-5-yl-4-pyridin-2-yl-1H-imidazol-2-yl)-benzamide) and A-83-01(3-(6-methyl-2-pyridinyl)-N-phenyl-4-(4-quinolinyl)-1H-pyrazole-1-carbothioamide) are compounds known as inhibitors of TGFβ receptor (ALK5) and Activin receptor (ALK4/7) (i.e., TGFβR inhibitor). The TGFβ signal transduction pathway inhibiting substance is preferably SB431542 or A-83-01.

The Nodal/Activin signal transduction pathway inhibiting substance is not particularly limited as long as it inhibits a signal transduction pathway caused by Nodal or Activin, and may be any of nucleic acid, protein, and low-molecular-weight organic compound. Examples of the substance include a substance that directly acts on Nodal or Activin (e.g., antibody, aptamer etc.), a substance that suppresses expression of a gene encoding Nodal or Activin (e.g., antisense oligonucleotide, siRNA etc.), a substance that inhibits the binding of a Nodal/Activin receptor and Nodal/Activin, and a substance that inhibits a physiological activity caused by signal transduction by Nodal/Activin receptor. As a Nodal/Activin signal transduction pathway inhibiting substance, a compound well known to those of ordinary skill in the art can be used and, specifically, SB431542, A-83-01 and the like can be mentioned. Also, a protein (Lefty, Cerberus etc.) known as a Nodal/Activin signal transduction pathway inhibiting substance may be used. A Nodal/Activin signal transduction pathway inhibiting substance is preferably SB431542, A-83-01 or Lefty.

The BMP signal transduction pathway inhibiting substance is not particularly limited as long as it inhibits a signal transduction pathway caused by BMP, and may be any of nucleic acid, protein, and low-molecular-weight organic compound. Here, as BMP, BMP2, BMP4, BMP7 and GDF7 can be mentioned. Examples of the substance include a substance that directly acts on BMP (e.g., antibody, aptamer etc.), a substance that suppresses expression of a gene encoding BMP (e.g., antisense oligonucleotide, siRNA etc.), a substance that inhibits the binding of a BMP receptor (BMPR) and BMP, and a substance that inhibits a physiological activity caused by signal transduction by BMP receptor. As BMPR, ALK2 and ALK3 can be mentioned. As a BMP signal transduction pathway inhibiting substance, a compound well known to those of ordinary skill in the art can be used and, specifically, LDN193189, Dorsomorphin and the like can be mentioned. Here, LDN193189 (4-[6-(4-piperazin-1-ylphenyl)pyrazolo[1,5-a]pyrimidin-3-yl]quinoline) is a known BMPR (ALK2/3) inhibitor (hereinafter BMPR inhibitor), and is generally commercially available in the form of hydrochloride. Also, a protein (Chordin, Noggin etc.) known as a BMP signal transduction pathway inhibiting substance may be used. A BMP signal transduction pathway inhibiting substance is preferably LDN193189.

A TGFβ family signal transduction pathway inhibiting substance is preferably Lefty, SB431542, A-83-01 or LDN193189.

Plural kinds of TGFβ family signal transduction pathway inhibiting substances having different points of action may be used in combination. By combining them, the aggregate quality improving effect is expected to be enhanced. For example, a combination of a TGFβ signal transduction pathway inhibiting substance and a BMP signal transduction pathway inhibiting substance, a combination of a TGFβ signal transduction pathway inhibiting substance and a Nodal/Activin signal transduction pathway inhibiting substance, a combination of a BMP signal transduction pathway inhibiting substance and a Nodal/Activin signal transduction pathway inhibiting substance can be mentioned. Preferably, a TGFβ signal transduction pathway inhibiting substance is used in combination with a BMP signal transduction pathway inhibiting substance. A specific preferable combination is, for example, a combination of SB431542 and LDN193189.

The Sonic hedgehog (hereinafter sometimes to be indicated as Shh) signal transduction pathway activating substance is a substance capable of enhancing signal transduction mediated by Shh. Examples of the Shh signal transduction pathway activating substance include proteins belonging to the Hedgehog family (e.g., Shh and Ihh), Shh receptor, Shh receptor agonist, PMA (Purmorphamine; 9-cyclohexyl-N-[4-(4-morpholinyl)phenyl]-2-(1-naphthalenyloxy)-9H-purin-6-amine), SAG (Smoothened Agonist; N-methyl-N'-(3-pyridinylbenzyl)-N'-(3-chlorobenzo[b]thiophene-2-carbonyl)-1,4-diaminocyclohexane) and the like. The Shh signal transduction pathway activating substance is preferably Shh protein (Genbank accession numbers: NM_000193, NP_000184), SAG or PMA.

A TGFβ family signal transduction pathway inhibiting substance and a Shh signal transduction pathway activating substance may be used in combination. By combining them, the aggregate quality improving effect is expected to be enhanced. As a specific combination, a combination of any TGFβ family signal transduction pathway inhibiting substance selected from the group consisting of Lefty, 5B431542, A-83-01 and LDN193189, and a Shh signal transduction pathway activating substance selected from the group consisting of Shh protein, SAG and PMA can be mentioned. When a TGFβ family signal transduction pathway inhibiting substance and a Shh signal transduction pathway activating substance are used in combination, cells may be cultured in a medium containing both a TGFβ family signal transduction pathway inhibiting substance and a Shh signal transduction pathway activating substance, or cells may be treated with either of a TGFβ family signal transduction pathway inhibiting substance and a Shh signal transduction pathway activating substance, and continuously treated with either or both of them.

The concentrations of the TGFβ family signal transduction pathway inhibiting substance and the Sonic hedgehog signal transduction pathway activating substance can be appropriately determined to fall within a range capable of affording the aforementioned effects. For example, SB431542 is generally used at a concentration of 0.1-200 µM, preferably 2-50 µM. A-83-01 is generally used at a concentration of 0.05-50 µM, preferably 0.5-5 µM. LDN193189 is generally used at a concentration of 1-2000 nM, preferably 10-300 nM. Lefty is generally used at a concentration of 5-200 ng/ml, preferably 10-50 ng/ml. Shh protein is generally used at a concentration of 20-1000 ng/ml, preferably 50-300 ng/ml. SAG is generally used at a concentration of 1-2000 nM, preferably 10-700 nM, more preferably 30-600 nM. PMA is generally used at a concentration of 0.002-20 µM, preferably 0.02-2 µM. In one embodiment, a TGFβ family signal transduction pathway inhibiting substance can be appropriately used in an amount conferring TGFβ family signal transduction pathway inhibiting activity equivalent to that of SB43154 at the aforementioned concentration. In one embodiment, a Sonic hedgehog signal transduction pathway activating substance can be appropriately used in an amount conferring Shh signal transduction promoting activity equivalent to that of SAG at the aforementioned concentration.

The TGFβ family signal transduction pathway inhibiting activity of SB431542, LDN193189 and the like can be determined by a method well known to those of ordinary skill in the art by, for example, detecting phosphorylation of Smad by Western blotting method (Mol Cancer Ther. (2004) 3, 737-45). The Sonic hedgehog signal transduction promoting activity of SAG and the like can be determined by a method well known to those of ordinary skill in the art by, for example, reporter gene assay focusing on the expression of Gli1 gene (Oncogene (2007) 26, 5163-5168).

While the medium used for step (1) may be a serum-containing medium or a serum-free medium, it is preferably a serum-free medium, to avoid contamination with chemically-undefined components.

To avoid contamination with a chemically-undefined component, a medium to be used for step (1) may be a medium whose components are chemically-defined.

In step (1), the pluripotent stem cells may be cultured under any conditions of suspension culturing and adhesion culturing, preferably adhesion culturing.

For culturing pluripotent stem cells under feeder-free conditions in step (1), the aforementioned feeder-free medium can be used as a medium. As the feeder-free medium, Essential 8, S-medium, StemPro, hESF9, mTeSR1, mTeSR2, TeSR-E8, or StemFit and the like can be mentioned, and Essential 8 or StemFit is preferably used.

For culturing pluripotent stem cells under feeder-free conditions in step (1), an appropriate matrix may be used as a scaffold to provide a scaffold in stead of the feeder cells to the pluripotent stem cell. The pluripotent stem cells are subjected to adhesion culturing in a cell container whose surface is coated with a matrix as a scaffold.

As a matrix available as a scaffold, laminin (Nat Biotechnol 28, 611-615 (2010)), laminin fragment (Nat Commun 3, 1236 (2012)), basement membrane preparation (Nat Biotechnol 19, 971-974 (2001)), gelatin, collagen, heparan sulfate proteoglycan, entactin, vitronectin and the like can be mentioned.

"Laminin" is a heterotrimer molecule consisting of α, β, γ chains and an extracellular matrix protein containing isoforms having different subunit chain compositions. Specifically, laminin has about 15 kinds of isoforms based on the combinations of heterotrimers with 5 kinds of α chains, 4 kinds of β chains and 3 kinds of γ chains. The name of laminin is determined by combining respective numbers of α chain (α1-α5), β chain (β1-β4) and γ chain (γ1-γ3). For example, a laminin having a combination of α5 chain, β1 chain, γ1 chain is named laminin 511. In the present invention, laminin 511 is preferably used (Nat Biotechnol 28, 611-615 (2010)).

Laminin to be used in the present invention is generally a mammalian laminin. As the mammal, those mentioned above can be recited. To achieve xeno-free conditions, laminin of a mammal of the same species as the cell to be cultured is preferably used. For example, human laminin (preferably, human laminin 511) is used for culturing human pluripotent stem cells.

A laminin fragment to be used in the present invention is not particularly limited as long as it has adhesiveness to pluripotent stem cells and enables maintenance culturing of pluripotent stem cell under feeder-free conditions, and is preferably E8 fragment. Laminin E8 fragment was identified as a fragment with strong cell adhesion activity among the fragments obtained by digestion of laminin 511 with elastase (EMBO J., 3:1463-1468, 1984, J. Cell Biol., 105:589-598, 1987). In the present invention, E8 fragment of laminin 511 is preferably used (Nat Commun 3, 1236 (2012), Scientific Reports 4, 3549 (2014)). The laminin E8 fragment to be used in the present invention is not required to be an elastase digestion product of laminin and may be a recombinant. To avoid contamination of unidentified components, a recombinant laminin fragment is preferably used in the present invention. A E8 fragment of laminin 511 is commercially available and can be purchased from, for example, Nippi, Inc. and the like.

The laminin or laminin fragment to be used in the present invention is preferably isolated.

The "basement membrane preparation" in the present invention refers to one containing basement membrane-constituting components having a function to control cell morphology, differentiation, growth, motility, expression of function and so on which are similar to those of epithelial cell, when intended cells capable of forming a basement membrane are plated thereon and cultured. For example, neural cells and neural tissues produced by the present invention may be dispersed, and cultured in the presence of a basement membrane preparation when further adhesion culturing is performed. Here, the "basement membrane constituting components" refers to extracellular matrix molecules in the form of a thin membrane present between epithelial cell layer and interstitial cell layer and so on in animal tissues. A basement membrane preparation can be produced by, for example, removing cells capable of forming a basement membrane, which adhere onto a support via a basement membrane, from a support with a solution capable of dissolving the lipid of the cells, an alkali solution and so on. Examples of the basement membrane preparation include products commercially available as basement membrane preparation (e.g., Matrigel™ (manufactured by Corning Incorporated: hereinafter sometimes referred to as Matrigel)), Geltrex™ (manufactured by Life Technologies), and extracellular matrix molecules known as basement membrane components (e.g., laminin, type IV collagen, heparan sulfate proteoglycan, entactin and so on).

Matrigel™ is a basement membrane preparation extracted from Engelbreth Holm Swarn (EHS) mouse sarcoma. The main component of Matrigel™ is type IV collagen, laminin, heparan sulfate proteoglycan, and entactin. In addition to these, TGF-β, FGF, tissue plasminogen activator, and a growth factor naturally produced by EHS tumor are contained. The "growth factor reduced product" of Matrigel™ has a lower growth factor concentration than common Matrigel™, and the standard concentration thereof is <0.5 ng/ml for EGF, <0.2 ng/ml for NGF, <5 pg/ml for PDGF, 5 ng/ml for IGF1, and 1.7 ng/ml for TGFβ.

To avoid contamination of unidentified components, an isolated laminin or laminin fragment is preferably used in the present invention.

Preferably, in the culturing of pluripotent stem cells under feeder-free conditions in step (1), the pluripotent stem cells are cultured in an adhered state in a cell container with surface coated with isolated laminin 511 or E8 fragment of laminin 511 (more preferably, E8 fragment of laminin 511).

While the period for the culturing of pluripotent stem cells in step (1) is not particularly limited as long as the effect of improving the quality of the aggregate formed in step (2) can be achieved, it is generally 0.5-144 hr. The period for the culturing of the pluripotent stem cells in step (1) is preferably not less than 1 hr, not less than 2 hr, not less than 6 hr, not less than 12 hr, not less than 18 hr, or not less than 24 hr. The period for the culturing of the pluripotent stem cells in step (1) is preferably within 96 hr or 72 hr. In one embodiment, the period for the culturing of pluripotent stem cells in step (1) is preferably 2-96 hr, more preferably 6-48 hr, further preferably 12-48 hr, further more preferably 18-28 hr (e.g., 24 hr). That is, the first step is started 0.5-144 hr (preferably, 18-28 hr) before the start of step (2), and step (2) is continuously performed on completion of step (1). In a further embodiment, the period for the culturing of pluripotent stem cells in step (1) is preferably 18-144 hr, 24-144 hr, 24-96 hr, or 24-72 hr. When the cells are treated with either of a TGFβ family signal transduction pathway inhibiting substance and a Shh signal transduction pathway activating substance, and continuously treated with the other, the treatment time of each can be set to fall within the range of the aforementioned period for the culturing.

The culture conditions such as culture temperature, and $CO_2$ concentration in step (1) can be appropriately determined. While the culture temperature is, for example, about 30° C. to about 40° C., preferably about 37° C. The $CO_2$ concentration is, for example, about 1% to about 10%, preferably about 5%.

In one preferable embodiment, human pluripotent stem cells (e.g., human iPS cells) are cultured in an adhered state in the absence of feeder cells and in a serum-free medium containing bFGF. The adhesion culturing is preferably performed in a cell container with surface coated with laminin 511, E8 fragment of laminin 511 or vitronectin. The adhesion culturing is preferably performed using Essential 8, TeSR medium, mTeSR medium, mTeSR-E8 medium, or StemFit medium, more preferably Essential 8 or StemFit medium, as a feeder-free medium.

In one preferable embodiment, human pluripotent stem cells (e.g., human iPS cells) are cultured in suspension in the absence of feeder cells and in a serum-free medium containing bFGF. In the suspension culturing, human pluripotent stem cells may form an aggregate of human pluripotent stem cells.

In a preferable embodiment, the cells obtained in step (1) maintain a pluripotent-like state, and the pluripotent-like state is maintained throughout step (1). The pluripotent-like state means a state maintaining at least a part of the characteristics unique to pluripotent stem cells and common to pluripotent stem cells, including pluripotency. The pluripotent-like state does not require strict pluripotency. Specifically, the state expressing all or a part of the markers to be an index of pluripotent state is included in the "pluripotent-like state". As the marker of the pluripotent-like state, Oct3/4 positive, alkaline phosphatase positive and the like can be mentioned. In one embodiment, a cell maintaining the pluripotent-like state is Oct3/4 positive. It is included in a "cell showing a pluripotent-like state" even when the expression level of Nanog is low as compared to ES cell or iPS cell.

In one embodiment, the cells obtained in step (1) are stem cells having a potency to differentiate into at least a neural cell or neural tissue (preferably, retinal tissue, retinal cell, retinal progenitor cell, or retinal layer-specific neuron). In one embodiment, the cells obtained in step (1) is Oct3/4 positive stem cells having a potency to differentiate into at least a neural cell or neural tissue (preferably, retinal tissue, retinal cell, retinal progenitor cell, or retinal layer-specific neuron).

In a preferable embodiment, human pluripotent stem cells (e.g., iPS cells) are cultured in an adhered state in the absence of feeder cells and in a serum-free medium containing a TGFβ family signal transduction pathway inhibiting substance and/or a Sonic hedgehog signal transduction pathway activating substance, and bFGF.

The above-mentioned adhesion culturing is preferably performed in a cell container whose surface is coated with laminin 511 or E8 fragment of laminin 511. The TGFβ family signal transduction pathway inhibiting substance is preferably a TGFβ signal transduction pathway inhibiting substance (e.g., SB431542, A-83-01, Lefty), a Nodal/Activin signal transduction pathway inhibiting substance (e.g., Lefty, SB431542, A-83-01), a BMP signal transduction pathway inhibiting substance (e.g., LDN193189, Chordin, Noggin), or a combination thereof (e.g., SB431542 and LDN193189). The TGFβ family signal transduction pathway inhibiting substance is more preferably Lefty, SB431542, A-83-01, or LDN193189, or a combination thereof (e.g., SB431542 and LDN193189). The Sonic hedgehog signal transduction pathway activating substance is preferably Shh protein, SAG or Purmorphamine (PMA), more preferably SAG. A TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) may be used in combination. The period for the culturing is 0.5-144 hr (preferably, 18-144 hr, 24-144 hr, 24-96 hr, or 24-72 hr (e.g., 18-28 hr)).

Step (1) is performed by, for example, culturing the pluripotent stem cells to maintain undifferentiated state in the absence of feeder cells and in a medium containing a factor for maintaining undifferentiated state in advance, adding a TGFβ family signal transduction pathway inhibiting substance and/or a Sonic hedgehog signal transduction pathway activating substance to the culture, and continuing the culturing.

For example, human pluripotent stem cells (e.g., human iPS cells) are cultured to maintain undifferentiated state in the absence of feeder cells and in a serum-free medium containing bFGF. The maintenance culturing is preferably performed by adhesion culturing. The adhesion culturing is preferably performed in a cell container whose surface is coated with vitronectin, laminin 511 or E8 fragment of laminin 511. Then, a TGFβ family signal transduction pathway inhibiting substance and/or a Sonic hedgehog signal transduction pathway activating substance are/is added to the culture, and the culturing is continued. The TGFβ, family signal transduction pathway inhibiting substance is preferably a TGFβ signal transduction pathway inhibiting substance (e.g., SB431542, A-83-01, Lefty), a Nodal/Activin signal transduction pathway inhibiting substance (e.g., SB431542, A-83-01, Lefty), a BMP signal transduction pathway inhibiting substance (e.g., LDN193189), or a combination thereof (e.g., SB431542 and LDN193189). The TGFβ family signal transduction pathway inhibiting substance is more preferably Lefty, SB431542, A-83-01, or LDN193189, or a combination thereof (e.g., SB431542 and LDN193189). The Sonic hedgehog signal transduction pathway activating substance is preferably Shh protein, SAG or PMA. A TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) may be used in combination. After the addition, the culturing is continued for 0.5-144 hr (preferably, 18-144 hr, 24-144 hr, 24-96 hr, or 24-72 hr (e.g., 18-28 hr)).

Step (2) wherein the cells obtained in step (1) are cultured in suspension in a medium to form a cell aggregate is explained.

The medium to be used in step (2) is not particularly limited as long as it is as described in the above-mentioned section of definition. The medium to be used in step (2) may be a serum-containing medium or serum-free medium. To avoid contamination of chemically-undefined components, a serum-free medium is preferably used in the present invention. For example, a serum-free medium free of both a BMP signal transduction pathway activating substance and a Wnt signal transduction pathway inhibiting substance can be used. To avoid complicated preparation, for example, a serum-free medium supplemented with an appropriate amount of a commercially available serum alternative such as KSR and so on (e.g., medium of 1:1 mixture of IMDM and F-12, which is supplemented with 10% KSR, 450 μM 1-monothioglycerol and 1× Chemically Defined Lipid Concentrate, or medium of GMEM supplemented with 5%-20% KSR, NEAA, pyruvic acid, 2-mercaptoethanol) is preferably used. The amount of KSR to be added to a serum-free medium in the case of human pluripotent stem cells is generally about 1% to about 30%, preferably about 2% to about 20%.

For formation of an aggregate, dispersed cells are first prepared by a dispersing operation of the cells obtained in step (1). The "dispersed cells" obtained by the dispersing operation refers to a state where, for example, not less than 70% of cells are single cells and not more than 30% of cells are clumps of 2-50 cells. Preferably, as the dispersed cells, a state where not less than 80% of cells are single cells, and not more than 20% of cells are clumps of 2-50 cells can be mentioned. The dispersed cells refer to a state almost free of mutual adhesion of cells (e.g., plane attachment). In a part of the embodiment, dispersed cells refer to a state almost free of cell-cell junction (e.g., adhesive bond).

A dispersion operation of the cells obtained in step (1) may contain the above-mentioned mechanical dispersion treatment, cell dispersion solution treatment, and cell protecting agent treatment. These treatments may be performed in combination. Preferably, a cell dispersion solution treatment is performed simultaneously with a cell protecting agent treatment and then a mechanical dispersion treatment is performed.

As a cell protecting agent to be used for the cell protecting agent treatment, a FGF signal transduction pathway activating substance, heparin, an IGF signal transduction pathway activating substance, serum, and serum alternative can be mentioned. As a cell protecting agent for suppressing cell death of pluripotent stem cells (particularly, cell death of human pluripotent stem cells) induced by dispersion, a Rho-associated coiled-coilkinase (ROCK) inhibitor or a Myosin inhibitor may be added. To suppress cell death of pluripotent stem cells (particularly, human pluripotent stem cells) induced by dispersion, and protect the cells, a Rho-associated coiled-coilkinase (ROCK) inhibitor or a Myosin inhibitor may be added from the start of the second step culture. As a ROCK inhibitor, Y-27632, Fasudil (HA1077), H-1152 and the like can be mentioned.

As a Myosin inhibitor, Blebbistatin can be mentioned. As a cell dispersion solution to be used for the cell dispersion treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TrypLE Select (manufactured by Life Technologies) and TrypLE Express (manufactured by Life Technologies) can also be used.

As a method of mechanical dispersion treatment, a pipetting treatment or scraping by a scraper can be mentioned.

The dispersed cells are suspended in the above-mentioned medium.

Then, a suspension of the dispersed cells is seeded in the above-mentioned culture vessel, and the dispersed cells are cultured under a condition non-adhesive to the culture vessel, whereby plural cells are gathered to form an aggregate.

In this case, plural cell aggregates may be simultaneously formed in one culture vessel by seeding the dispersed cells in a comparatively large culture vessel such as a 10 cm dish. However, the size of the aggregates varies in this case. Thus, for example, a given amount of dispersed stem cells are placed in each well of a multiwell plate (U-bottom, V-bottom) such as a 96-well microplate, and static culture is performed, whereby the cells are rapidly coagulated to form one aggregate in each well. The aggregates are recovered from plural wells, whereby a population of uniformed aggregates can be obtained.

The concentration of the cells in step (2) can be appropriately set so that cell aggregates can be more uniformly and efficiently formed. For example, when human cells (e.g., cells obtained from human iPS cell in step (1)) are cultured in suspension using a 96-well microwell plate, a liquid prepared m to achieve about $1\times10^3$ to about $1\times10^5$ cells, preferably about $3\times10^3$ to about $5\times10^4$ cells, more preferably about $4\times10^3$ to about $2\times10^4$ cells, further preferably about $4\times10^3$ to about $1.6\times10^4$ cells, further more preferably about $8\times10^3$ to about $1.2\times10^4$ cells, per well is added to the wells, and the plate is stood to form aggregates.

The culture conditions such as culture temperature, $CO_2$ concentration and so on in step (2) can be appropriately determined. The culture temperature is, for example, about 30° C. to about 40° C., preferably about 37° C. The $CO_2$ concentration is, for example, about 1% to about 10%, preferably about 5%.

In step (2), when a medium change operation is performed, for example, an operation to add a fresh medium without discarding the existing medium (medium addition operation), an operation to discard about a half amount of the existing medium (about 30-90%, for example, 40-60% of the volume of the existing medium) and add about a half amount of a fresh medium (30-90%, for example, about 40-60% of the volume of the existing medium) (half-medium change operation), and an operation to discard about the whole amount of the existing medium (not less than 90% of the amount of the existing medium) and add about the whole amount of a fresh medium (not less than 90% of the amount of the existing medium) (full-medium change operation) can be mentioned.

When a particular component (e.g., differentiation-inducing factor) is added at a certain time point, for example, an operation to calculate the final concentration, to discard about a half amount of the existing medium, and to add about a half amount of a fresh medium containing a particular component at a concentration higher than the final concentration, specifically 1.5 times-3 times the final concentration, for example, about 2 times the final concentration, (half-medium change operation, half-medium change) may be performed.

When the concentration of a particular component contained in the existing medium is maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time pointed, for example, the medium change operation may be performed plural times per day, preferably plural times (e.g., 2-3 times) within 1 hr. Also, when the concentration of a component contained in the existing medium is to be decreased by dilution at a certain time point, the cells or aggregates may be transferred to another culture container.

While the tool used for the medium change operation is not particularly limited, for example, pipetter, micropipette, multichannel micropipette, continuous dispenser, and the like can be mentioned. For example, when a 96 well plate is used as a culture vessel, a multichannel micropipette may be used.

The period for suspension culturing necessary for forming a cell aggregate can be determined as appropriate according to the cell to be used, so that the cells can be aggregated uniformly. To form uniformed cell aggregates, it is desirably as short as possible. The steps for the dispersed cells to form cell aggregates can be divided into a step for gathering cells, and a step for forming cell aggregates from the gathered cells. In a step of seeding the dispersed cells (i.e., at the time of the start of suspension culture) to gathering of the cells, for example, in case of human cells (e.g., stem cells obtained from human iPS cells in step (1)), the gathered cells are formed preferably within about 24 hr, more preferably within about 12 hr. The period from the time point of seeding the dispersed cells (i.e., at the time of the start of suspension culture) to form an aggregate in case of human pluripotent stem cells (e.g., human iPS cells) is, for example, preferably within about 72 hr, more preferably within about 48 hr. The period for cell aggregate formation can be appropriately adjusted by controlling the tools for aggregating the cells, centrifugation conditions and so on.

Formation of cell aggregates and uniformity thereof can be determined based on the size and cell number of the aggregates, macroscopic morphology, microscopic morphology by tissue staining analysis and uniformity thereof, expression of differentiation- and undifferentiation-markers and uniformity thereof, control of expression of differentiation marker and synchronism thereof, reproducibility of differentiation efficiency between the aggregates, and so on.

After aggregate formation, the aggregate may be continuously cultured as it is. The period for suspension culturing in step (2) is generally 12 hr-6 days, preferably about 12 hr-48 hr.

In one embodiment, the medium used in step (2) contains a Sonic hedgehog signal transduction pathway activating substance. In step (1), pluripotent stem cells are treated with a TGFβ family signal transduction pathway inhibiting substance and/or a Sonic hedgehog signal transduction pathway activating substance; and in the second step, the cells obtained in the first step are cultured in suspension in a medium (preferably serum-free medium) containing a Sonic hedgehog signal transduction pathway activating substance to further improve quality of the aggregate, and a spherical, smooth surfaced, uncollapsed, and dense inside aggregate of cells maintaining undifferentiated properties can be formed at a high efficiency.

As the Sonic hedgehog signal transduction pathway activating substance, those mentioned above can be used. Preferably, the Sonic hedgehog signal transduction pathway activating substance is SAG, Purmorphamine (PMA) or Shh protein. The concentration of the Sonic hedgehog signal transduction pathway activating substance in the medium can be appropriately determined to fall within a range capable of achieving the aforementioned effects. SAG is generally used at a concentration of 1-2000 nM, preferably 10 nM-1000 nM, more preferably 10 nM-700 nM, further preferably 50 nM-700 nM, further preferably 100 nM-600 nM, further preferably 100 nM-500 nM. PMA is generally used at a concentration of 0.002-20 µM, preferably 0.02-2 µM. Shh protein is generally used at a concentration of 20-1000 ng/ml, preferably 50-300 ng/ml. When a Sonic hedgehog signal transduction pathway activating substance other than SAG, PMA, and Shh protein is used, it is desirably used at a concentration conferring Sonic hedgehog signal transduction promoting activity equivalent to that of SAG at the above-mentioned concentration.

The timing of addition of a Sonic hedgehog signal transduction pathway activating substance to the medium is not particularly limited as long as the above-mentioned effects can be afforded, but a higher effect can be obtained when it is added earlier. A Sonic hedgehog signal transduction pathway activating substance is added to the medium generally within 6 days, preferably within 3 days, more preferably within 1 day, from the start of step (2), and further preferably at the time of the start of step (2).

In a preferable embodiment, in step (2), the human cells obtained in step (1) (e.g., cells obtained from human iPS cells in step (1)) are subjected to suspension culturing in a serum-free medium containing a Sonic hedgehog signal transduction pathway activating substance (e.g., SAG, PMA, Shh protein) to form aggregates. A Sonic hedgehog signal transduction pathway activating substance is preferably contained in the medium from the time of the start of suspension culture. A ROCK inhibitor (e.g., Y-27632) may also be added to the medium. The period for the culturing is 12 hr-6 days, preferably 12 hr-48 hr. The aggregates formed are preferably uniformed aggregates.

For example, the human cells obtained in step (1) (e.g., cells obtained from human iPS cells in step (1)) are recovered, dispersed into single cells or a state close thereto in a serum-free medium containing a Sonic hedgehog signal transduction pathway activating substance (e.g., SAG, PMA, Shh protein), and subjected to suspension culturing. The serum-free medium may contain a ROCK inhibitor (e.g., Y-27632). A suspension of human pluripotent stem cells (e.g., human iPS cells) is seeded in the above-mentioned culture vessel and the dispersed pluripotent stem cells are cultured under conditions where they are non-adhesive to the culture vessel, whereby plural pluripotent stem cells are assembled to form an aggregate. The period for the culturing is 12 hr-6 days, preferably 12 hr-48 hr. The aggregates formed are preferably uniformed aggregates.

In one preferable embodiment, in step (1), pluripotent stem cells are treated with a TGFβ signal transduction pathway inhibiting substance, and in step (2), the cells obtained in step (1) are subjected to suspension culturing in a medium containing a Sonic hedgehog signal transduction pathway activating substance (e.g., SAG, PMA, Shh protein). Preferably, SB431542 or A-83-01 may be used here as a TGFβ signal transduction pathway inhibiting substance.

In one preferable embodiment, in step (1), pluripotent stem cells are treated with a BMP signal transduction pathway inhibiting substance, and in step (2), the cells obtained in step (1) are subjected to suspension culturing in a medium free of a Sonic hedgehog signal transduction pathway activating substance (e.g., SAG, PMA, Shh protein). Preferably, LDN193189 may be used here as a BMP signal transduction pathway inhibiting substance.

In one preferable embodiment, in step (1), pluripotent stem cells (e.g., human pluripotent stem cell) are treated with a TGFβ family signal transduction pathway inhibiting substance (e.g., a TGFβ signal transduction pathway inhibiting substance (e.g., Lefty, SB431542, A-83-01), a Nodal/Activin signal transduction pathway inhibiting substance (e.g., Lefty, SB431542, A-83-01), a BMP signal transduction pathway inhibiting substance (e.g., LDN193189), or a combination thereof (e.g., SB431542 and LDN193189) etc.); a Sonic hedgehog signal transduction pathway activating substance (e.g., Shh protein, SAG, PMA); or a combination of a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) and, in step (2), suspension culturing of the cells obtained in step (1) is performed in a medium containing a Sonic hedgehog signal transduction pathway activating substance (e.g., SAG, PMA, Shh protein).

In another embodiment, in step (1), pluripotent stem cells (e.g., human pluripotent stem cells) are treated with a TGFβ family signal transduction pathway inhibiting substance (e.g., a TGFβ signal transduction pathway inhibiting substance (e.g., a Lefty, SB431542, A-83-01), a Nodal/Activin signal transduction pathway inhibiting substance (e.g., Lefty, SB431542, A-83-01), a BMP signal transduction pathway inhibiting substance (e.g., LDN193189), or a combination thereof (e.g., SB431542 and LDN193189) etc.); a Sonic hedgehog signal transduction pathway activating substance (e.g., Shh protein, SAG, PMA); or a combination of a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA) and, in step (2), suspension culturing of the cells obtained in step (1) is performed in a medium free of a Sonic hedgehog signal transduction pathway activating substance (e.g., SAG, PMA, Shh protein).

In any embodiment, the medium in step (2) preferably contains a ROCK inhibitor (e.g., Y-27632).

By performing step (2) in this manner, an aggregate of the cells obtained in step (1), or the cells derived therefrom are formed. The present invention also provides a method for producing such aggregate. The aggregate obtained in step (2) has higher quality than the one formed by a treatment with a TGFβ family signal transduction pathway inhibiting substance and/or a Sonic hedgehog signal transduction pathway activating substance is not performed in step (1). To be specific, a population of aggregates having a high ratio of spherical cell aggregates having a smooth surface, a dense inside, and uncollapsed shape can be obtained. In one embodiment, when aggregates (e.g., not less than 100 aggregates) are randomly selected on day 6 from the start of the second step, the sum of the ratios of uncollapsed aggregates and/or non-cystic aggregates is, for example, not less than 70%, preferably not less than 80%.

The aggregate obtained in step (2) has a potency to differentiate into various differentiated cells and differentiated tissues. In one embodiment, the aggregate obtained in step (2) has a potency to differentiate into a neural cell or a neural tissue (preferably, retinal tissue, retinal cell, retinal progenitor cell, or retinal layer-specific neuron).

In one embodiment, by using the stem cells obtained in step (1) and having a potency to differentiate into at least a neural cell or a neural tissue (preferably, retinal tissue, retinal cell, retinal progenitor cell, or retinal layer-specific neuron) (preferably, Oct3/4 positive stem cells having a potency to differentiate into at least a neural cell or a neural tissue (preferably, retinal tissue, retinal cell, retinal progenitor cell, or retinal layer-specific neuron)) in step (2), an aggregate containing stem cells having a potency to differentiate into at least a neural cell or a neural tissue (preferably, retinal tissue, retinal cell, retinal progenitor cell, or retinal layer-specific neuron) (preferably Oct3/4 positive stem cells) can be obtained. Various differentiated cells and differentiated tissues can be induced with high efficiency by culturing the aggregate obtained in step (2) under appropriate differentiation conditions.

In one embodiment, the aggregate obtained in step (2) contains cells corresponding to the cells in an intermediate stage between the cells obtained at the completion of step (1) which maintains a pluripotent-like state (specifically, expressing Oct3/4), and a neural cell or a neural tissue. These cells express any of pluripotent state marker Oct3/4, ectoderm marker (Sox1, Sox2, N-cadherin, TP63), neuroectoderm marker (Sox1, Sox2, Nestin, N-cadherin, Otx2), and the aforementioned neural cell marker. That is, in one embodiment, the aggregate obtained in step (2) contains a mixture of cells expressing any of pluripotent state marker Oct3/4, ectoderm marker (Sox1, Sox2, N-cadherin, TP63), neuroectoderm marker (Sox1, Sox2, Nestin, N-cadherin, Otx2), and the aforementioned neural cell marker. That is, the aggregate obtained in step (2) contains stem cells having a potency to differentiate into at least a neural cell or neural tissue, and/or progenitor/precursor cells of a neural cell or neural tissue. The progenitor/precursor cells are characterized in that they show an ability (competence) to express the aforementioned neural cell markers when they are cultured under known appropriate culture conditions. Therefore, in one embodiment, the aggregate obtained in step (2) contains Oct3/4 positive stem cells having a potency to differentiate into at least a neural cell or neural tissue, and/or progenitor/precursor cells of a neural cell or neural tissue. A part of the cells contained in the aggregate obtained in step (2) may express the aforementioned neural tissue markers. In one embodiment, the aggregate obtained in step (2) may contain Oct3/4 positive cells at a proportion of not less than 50%, for example, not less than 70%, of the total cells.

In step (2), when a medium change operation is performed, for example, an operation to add a fresh medium without discarding the existing medium (medium addition operation), an operation to discard about a half amount of the existing medium (about 30-90%, for example, about 40-60% of the volume of the existing medium) and add about a half amount of a fresh medium (about 30-90%, for example, about 40-60% of the volume of the existing medium) (half-medium change operation), and an operation to discard about the whole amount of the existing medium (not less than 90% of the amount of the existing medium) and add about the whole amount of a fresh medium (not less than 90% of the amount of the existing medium) (full-medium change operation) can be mentioned.

When a particular component (e.g., differentiation-inducing factor) is added at a certain time point, for example, an operation to calculate the final concentration, to discard about a half amount of the existing medium, and to add about a half amount of a fresh medium containing a particular component at a concentration higher than the final concentration (specifically 1.5 times-3.0 times the final concentration, for example, about 2 times the final concentration) (half-medium change operation, half-medium change) may be performed.

When the concentration of a particular component contained in the existing medium is maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time pointed, for example, the medium change operation may be performed plural times per day, preferably plural times (e.g., 2-3 times) within 1 hr. Also, when the concentration of a component contained in the existing medium is to be decreased by dilution at a certain time point, the cell or aggregate may be transferred to another culture vessel.

While the tool used for the medium change operation is not particularly limited, for example, pipetter, micropipette, multichannel micropipette, continuous dispenser, and the like can be mentioned. For example, when a 96 well plate is used as a culture container, a multichannel micropipette may be used.

Step (3) where an aggregate containing neural cells or a neural tissue are induced from the aggregate obtained in step (2) is explained.

As a method for inducing an aggregate of pluripotent stem cells into neural cells or a neural tissue by suspension culturing, many methods have been reported. For example, the methods described in WO 2005/123902, WO 2009/148170, WO 2008/035110, WO 2011/055855, Cell Stem Cell, 3, 519-32 (2008), Nature, 472, 51-56 (2011), Cell Stem Cell, 10(6), 771-775 (2012), Nature Biotechnology, 27(3), 275-80 (2009), Proc Natl Acad Sci USA, 110(50), 20284-9 (2013) and the like are known, though the method is not limited thereto. By applying such various induction methods of neural cells or neural tissues to the aggregate obtained in step (2) and culturing the aggregate obtained in step (2) under appropriate neuronal differentiation induction conditions, aggregates containing neural cells or a neural tissue can be produced.

For example, the aggregate obtained in step (2) is cultured in suspension in the presence or absence (preferably in the presence) of a differentiation-inducing factor to give an aggregate containing neural cells or a neural tissue.

The differentiation-inducing factor is a factor having an activity to induce differentiation into a cell or tissue, which is, for example, a factor having an activity to differentiate (or determine the fate of) a stem cell or a progenitor/precursor cell into a particular differentiation lineage. Examples of the differentiation-inducing factor include, but are not particularly limited to, in vivo gene product such as growth factor and the like, low-molecular-weight compound regulating the action of gene product in vivo, hormones, physiologically active substances such as vitamins and the like, and the like. Examples of the differentiation-inducing factor widely used by those of ordinary skill in the art include a BMP signal transduction activating substance, a BMP signal transduction pathway inhibiting substance, a Shh signal transduction pathway activating substance, a Shh signal transduction pathway inhibiting substance, a FGF signal transduction pathway activating substance, a FGF signal transduction pathway inhibiting substance, a Wnt signal transduction pathway activating substance, and a Wnt signal transduction pathway inhibiting substance. Responses to a differentiation-inducing factor vary depending on the kind and differentiation state (differentiation potency, potential) of the cell, and the effect of the differentiation-inducing factor may vary even in the differentiation induction process, depending on the concentration and timing of addition of the differentiation-inducing factor. Also, it is known that the optimal concentration of a differentiation-inducing factor that exhibits similar effects varies depending on the animal species and, for example, it is known that, between mouse cell and human cell, the optimal concentration of human cell is generally higher (particularly in ectoderm, endoderm). There are many reports on the methods of differentiation induction of pluripotent stem cells into particular cells or tissues, and a differentiation-inducing factor or a differentiation induction method suitable for the intended cell or tissue can be selected.

The differentiation-inducing factor to be used in the present invention is generally a mammalian differentiation-inducing factor. Examples of the mammal include those mentioned above. Since differentiation-inducing factor may have cross-reactivity among mammalian species, differentiation-inducing factor of any mammal may also be used as long as differentiation induction of the cultured pluripotent stem cell can be achieved. Preferably, a mammalian differentiation-inducing factor of the same species as the cell to be cultured is used.

The differentiation-inducing factor used in the present invention is preferably isolated. Therefore, in one embodiment, the present invention comprises a step of providing an isolated differentiation-inducing factor. In one embodiment, moreover, the present invention comprises a step of exogenously adding the isolated differentiation-inducing factor to the medium to be used in step (3).

In one embodiment, a neuronal differentiation-inducing factor is used as a differentiation-inducing factor in the method of the present invention, whereby an aggregate containing neural cells or a neural tissue can be produced.

In one embodiment, the medium to be used in step (3) is, for example, a serum-free medium or a serum-containing medium (preferably serum-free medium) supplemented with a differentiation-inducing factor. Such medium may or may not contain a basement membrane preparation. As the basement membrane preparation, those mentioned above can be used. When a basement membrane preparation is added, the concentration thereof is, for example, 0.1 to 10%, more preferably 0.5% to 2%, in volume concentration when Matrigel is used. To avoid contamination with a chemically unidentified substance, a basement membrane preparation is not added.

A serum-free medium or serum-containing medium to be used for such medium is not particularly limited as long as it is as mentioned above. To avoid complicated preparation, for example, a serum-free medium supplemented with an appropriate amount of a commercially available serum alternative such as KSR and so on (e.g., medium of 1:1 mixture of IMDM and F-12 supplemented with 10% KSR, 450 µM 1-monothioglycerol and 1× Chemically Defined Lipid Concentrate or a medium of GMEM supplemented with 5%-20% KSR, NEAA, pyruvic acid, 2-mercaptoethanol) is preferably used. The amount of KSR to be added to a serum-free medium in the case of human ES cells is generally about 1% to about 20%, preferably about 2% to about 20%.

As the medium (preferably serum-free medium) to be used in step (3), the medium (preferably serum-free medium) used in step (2) may be directly used, or may be replaced with a fresh medium (preferably serum-free medium). When the serum-free medium used in step (2) free of differentiation-inducing factor is directly used for step (3), a differentiation-inducing factor may be added to the medium.

In step (3), when a medium change operation is performed, for example, an operation to add a fresh medium without discarding the existing medium (medium addition operation), an operation to discard about a half amount of the existing medium (about 40-80% of the volume of the existing medium) and add about a half amount of a fresh medium (about 40-80% of the volume of the existing medium) (half-medium change operation), and an operation to discard about the whole amount of the existing medium (not less than 90% of the amount of the existing medium) and add about the whole amount of a fresh medium (not less than 90% of the amount of the existing medium) (full-medium change operation) can be mentioned.

When a particular component (e.g., differentiation-inducing factor) is added at a certain time point, for example, an operation to calculate the final concentration, to discard about a half amount of the existing medium, and to add about a half amount of a fresh medium containing a particular component at a concentration higher than the final concentration (specifically 1.5 times-3.0 times the final concentration, for example, about 2 times the final concentration) (half-medium change operation, half-medium change) may be performed.

When the concentration of a particular component contained in the existing medium is maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time pointed, for example, the medium change operation may be performed plural times per day, preferably plural times (e.g., 2-3 times) within 1 hr. Also, when the concentration of a component contained in the existing medium is to be decreased by dilution at a certain time point, the cell or aggregate may be transferred to another culture container.

While the tool used for the medium change operation is not particularly limited, for example, pipetter, micropipette, multichannel micropipette, continuous dispenser, and the like can be mentioned. For example, when a 96 well plate is used as a culture container, a multichannel micropipette may be used.

A differentiation-inducing factor may be added after about 24 hr or later from the start of the suspension culturing in step (2), and may also be added to the medium within several days from the start of the suspension culturing (e.g., within 15 days or 18 days). Preferably, a differentiation-inducing factor is added to the medium within day 1 to day 18, or day 1 to day 15, more preferably day 1 to day 9, further preferably day 3 to day 8 or day 2 to day 9, still more preferably, day 3 to day 6, from the start of the suspension culturing.

In a further embodiment, a differentiation-inducing factor (e.g., a Wnt signal transduction pathway inhibiting substance, a TGFβ family signal transduction pathway inhibiting substance and the like) may be added simultaneously with or within about 24 hr from the start of the suspension culturing in step (2).

After the addition of a differentiation-inducing factor to the medium and the start of the differentiation induction of aggregate into neural cells, addition of the differentiation-inducing factor to the medium is not necessary, and the medium may be exchanged with a serum-free medium or serum-containing medium each free of a differentiation-inducing factor. In one embodiment, after the start of the differentiation induction of the aggregate into neural cells, the concentration of the differentiation-inducing factor in the medium is gradually or stepwisely decreased at a ratio of 40-60% per 2-4 days by exchanging the medium with a serum-free medium or a serum-containing medium, each free of a differentiation-inducing factor.

In a specific embodiment, the medium is partly or entirely exchanged with a medium containing a differentiation-inducing factor on day 0-18, preferably day 1-9, more preferably day 2-8, further preferably day 3 or 4, after the start of suspension culturing (i.e., after the start of the aforementioned step (2)), and the cells can be cultured in the presence of a differentiation-inducing factor for about 1-100 days. To maintain the concentration of the differentiation-inducing factor at the same level, the medium may be partly or entirely exchanged with a medium containing a differentiation-inducing factor. Alternatively, as mentioned above, the concentration of the differentiation-inducing factor may also be stepwisely reduced.

The cells that have started differentiation induction into neural cells can be confirmed by, for example, detecting the expression of neural marker gene in the cells. As one embodiment of step (3), a step of culturing the aggregate formed in step (2) in a serum-free medium or serum medium containing a differentiation-inducing factor at a concentration m necessary for neuronal differentiation induction, in suspension, until emergence of a cell expressing a neural marker gene, thereby obtaining an aggregate containing neural cells can be mentioned.

In one embodiment, a BMP signal transduction pathway activating substance is used as a differentiation-inducing factor. That is, the aggregate obtained in the second step is cultured in suspension in the presence of a BMP signal transduction pathway activating substance to give an aggregate containing neural cells or a neural tissue.

The BMP signal transduction pathway activating substance is a substance capable of enhancing signal transduction mediated by BMP. Examples of the BMP signal transduction pathway activating substance include BMP proteins such as BMP2, BMP4, BMP7 etc., GDF proteins such as GDF7 etc., anti-BMP receptor antibody, BMP partial peptide and so on. BMP2 protein, BMP4 protein and BMP7 protein are available from, for example, R&D Systems, and GDF7 protein is available from, for example, Wako Pure Chemical Industries, Ltd.

The concentration of a BMP signal transduction pathway activating substance may be a concentration at which differentiation of an aggregate of pluripotent stem cells or stem cells derived therefrom into neural cells can be induced. For example, in the case of BMP4, it is added to the medium to a concentration of about 0.01 nM to about 1 μM, preferably about 0.1 nM to about 100 nM, more preferably about 1 nM to about 10 nM, further preferably about 1.5 nM (55 ng/mL).

In one embodiment, differentiation (spontaneous differentiation) into neural cells or neural tissues can also be induced by performing step (3) in a serum-free medium or serum-containing medium (preferably serum-free medium) each free of the aforementioned differentiation-inducing factor and a serum-free medium or serum-containing medium (preferably serum-free medium) each free of the aforementioned factor for maintaining undifferentiated state. For example, an aggregate containing neural cells or a neural tissue can also be obtained by culturing the aggregate obtained in step (2) in suspension in a serum-free medium or serum-containing medium (preferably serum-free medium) substantially free of (namely, not at all containing or containing at a concentration not more than physiological activity expressing concentration) a BMP signal transduction pathway activating substance (e.g., BMP4) and a Sonic hedgehog signal transduction pathway activating substance (e.g., SAG, PMA).

Such medium is not particularly limited as long as it is as mentioned above. To avoid complicated preparation, for example, a serum-free medium supplemented with an appropriate amount of a commercially available serum alternative such as KSR and the like (e.g., a medium of 1:1 mixture of IMDM and F-12 supplemented with 10% KSR, 450 μM 1-monothioglycerol and 1× Chemically Defined Lipid Concentrate) is preferably used. The amount of KSR to be added to the serum-free medium is, for example, generally about 1% to about 20%, preferably about 2% to about 20%, in the case of human ES cell.

As a medium (preferably serum-free medium) to be used in step (3), the medium (preferably serum-free medium) used in step (2) can also be used as it is, or the medium may be replaced with a fresh medium (preferably serum-free medium) can be used.

Other culturing conditions in step (3), such as culturing temperature, $CO_2$ concentration and the like, can be set as appropriate. The culturing temperature is, for example, about to 40° C., preferably about 37° C. The $CO_2$ concentration is, for example, about 1 to 10%, preferably about 5%.

The fact that an aggregate comprising neural cells is obtained can be confirmed by, for example, detecting the presence of a cell expressing a neural cells marker in the aggregate. Examples of the neural cells marker include, but are not limited to, Nestin, TuJ1, PSA-NCAM and the like. In one embodiment, the culturing of step (3) is performed until not less than 20% (preferably, not less than 30%, not less than 40%, not less than 50%, not less than 60%) of the cells contained in the aggregate express any neural cells marker selected from the group consisting of Nestin, TuJ1 and PSA-NCAM.

The obtained aggregate containing neural cells may be used as it is as a reagent for evaluating toxicity or drug efficacy. The aggregate containing neural cells may be subjected to a dispersion treatment (e.g., trypsin/EDTA treatment or papain treatment), and the obtained cells are subjected to a selection using FACS or MACS, whereby highly pure neural cells can also be obtained.

In one embodiment, the aggregate containing neural cells, which is obtained in step (3), contains a neuroepithelial structure and a neural tissue and/or neural cells are contained in the epithelial structure. While the neuroepithelial structure exists covering the surface of the aggregate, a part thereof may also be formed inside the aggregate. Using the aggregate obtained in step (2), an aggregate containing a neuroepithelial structure can be induced with high efficiency. The neuroepithelial structure can be identified as a neural marker gene (e.g., Nestin, TuJ1, PSA-NCAM)-positive epithelial structure. The neuroepithelial structure can be obtained as a neural tissue. In one embodiment, the culturing of step (3) is performed until a neuroepithelial structure is formed in the aggregate. As one embodiment of step (3), a step of culturing the aggregate formed in step (2) in suspension under a neuronal differentiation inducing conditions (e.g., in a serum-free medium or serum-containing medium containing a differentiation-inducing factor at a concentration necessary for neuronal differentiation induction) until emergence of a neuroepithelial structure, thereby obtaining an aggregate containing a neuroepithelial structure, can be mentioned.

In one embodiment, the aggregate obtained in step (2) or step (3) may be dispersed and seeded in a cell culture dish, and cultured in an adhered state to produce neural cells or a neural tissue. Alternatively, in one embodiment, the aggregate obtained in step (2) or step (3) may be dispersed, the obtained dispersed cells are seeded in a cell culture dish, and cultured in an adhered state to produce neural cells or a neural tissue. As the medium, the aforementioned medium can be used, and a differentiation-inducing factor may also be added to the medium. As a cell culture dish, the aforementioned dish for adhesion culturing can be used. The cell culture dish may be coated with a cell adhesion molecule and the like (e.g., laminin coat). Production of neural cells or a neural tissue can be confirmed by immunostaining for a neural cell or neural tissue marker.

In one embodiment, an aggregate free of neural cells, which is obtained during the suspension culturing in step (2) or step (3), may be seeded in a dish for adhesion culture, and cultured in an adhered state until differentiated into neural cells. While the medium to be used for adhesion culturing is not particularly limited, the medium used in the abovementioned step (3) may also be used.

In one embodiment, cells free of neural cells, which are obtained during the adhesion culturing in step (2) or step (3), may be detached from the dish for adhesion culturing, seeded in a dish for suspension culturing, and cultured in suspension until differentiated into neural cells. While the medium to be used for suspension culturing is not particularly limited, the medium used in step (3) may also be used.

The neuroepithelial structure existing on the surface of the aggregate can be physically cut out from the aggregate by using tweezers and the like under a microscope.

By the production method of the present invention, neural tissues such as neuroepithelial structure and the like can be obtained with high efficiency from pluripotent stem cells. Since a neuroepithelial structure obtained by the production method of the present invention contains various neural cells, various neurons and progenitor/precursor cells thereof can also be isolated by FACS and the like by using antibodies to the markers of various neural cells.

The obtained aggregate containing a neural tissue such as neuroepithelial structure and the like may be used as it is as a reagent for evaluating toxicity or drug efficacy. It is also possible to obtain highly pure neural cells by subjecting the aggregate containing a neural tissue such as neuroepithelial structure and the like to a dispersion treatment (e.g., trypsin/EDTA treatment or papain treatment), and the obtained cells are subjected to a selection by FACS or MACS.

3. Method for Producing Retinal Tissue

The production method 2 of the present invention is a method for producing a retinal tissue, comprising the following steps (1)-(3):
(1) a first step of culturing pluripotent stem cells in the absence of feeder cells and in a medium comprising 1) a TGFβ family signal transduction pathway inhibiting substance and/or a Sonic hedgehog signal transduction pathway activating substance, and 2) a factor for maintaining undifferentiated state,
(2) a second step of culturing the cells obtained in the first step in suspension to form a cell aggregate, and
(3) a third step of culturing the aggregate obtained in the second step in suspension in the presence of a BMP signal transduction pathway activating substance to obtain an aggregate containing a retinal tissue.

Step (1) of the production method 2 of the present invention can be performed in the same manner as in step (1) of the production method 1 of the present invention.

Preferably, the cell obtained in step (1) comprises stem cells having a potency to differentiate into at least retinal tissue, retinal cell, retinal progenitor cell, or retinal layer-specific neuron. In one embodiment, the cells obtained in step (1) include Oct3/4 positive stem cells having a potency to differentiate into at least retinal tissue, retinal cell, retinal progenitor cell, or retinal layer-specific neuron. In one embodiment, the cells obtained in step (1) contain Oct3/4 positive stem cells at a proportion of not less than 60%, for example, not less than 90%.

Step (2) of the production method 2 of the present invention can also be performed in the same manner as in step (2) of the production method 1 of the present invention.

The medium used in step (2) of production method 2 preferably contains a Sonic hedgehog signal transduction pathway activating substance. In step (1), pluripotent stem cells are treated with a TGFβ family signal transduction pathway inhibiting substance and/or a Sonic hedgehog signal transduction pathway activating substance; and in step (2), the cells obtained in step (1) are cultured in suspension in a medium (preferably serum-free medium) containing a Sonic hedgehog signal transduction pathway activating substance to form an aggregate, whereby the quality of the aggregate is further improved and the differentiation potency into retinal tissue is enhanced. Using the high quality aggregate, an aggregate containing a retinal tissue can be induced with high efficiency.

As the Sonic hedgehog signal transduction pathway activating substance, those mentioned above can be used. Preferably, the Sonic hedgehog signal transduction pathway activating substance is Shh protein, SAG or PMA. The concentration of the Sonic hedgehog signal transduction pathway activating substance in the medium can be appropriately determined to fall within a range capable of achieving the aforementioned effects. SAG is generally used at a concentration of 1-2000 nM, preferably 10 nM-700 nM, more preferably 30 nM-600 nM. PMA is generally used at a concentration of 0.002-20 µM, preferably 0.02-2 µM. Shh protein is generally used at a concentration of 20-1000 ng/ml, preferably 50-300 ng/ml. When a Sonic hedgehog signal transduction pathway activating substance other than Shh protein, SAG or PMA is used, it is desirably used at a concentration conferring Sonic hedgehog signal transduction promoting activity equivalent to that of SAG at the above-mentioned concentration.

The concentration of the Sonic hedgehog signal transduction pathway activating substance in the medium may be varied during the period of step (2). For example, the Sonic hedgehog signal transduction pathway activating substance is provided to fall within the above-mentioned range at the time of the start of step (2), and the concentration may be gradually or stepwisely decreased at a ratio of 40-60% per 2-4 days.

The timing of addition of a Sonic hedgehog signal transduction pathway activating substance to the medium is not particularly limited as long as the above-mentioned effects can be afforded, but a higher effect can be obtained when it is added earlier. A Sonic hedgehog signal transduction pathway activating substance is added to the medium generally within 6 days, preferably within 3 days, more preferably within 1 day, from the start of step (2), and further preferably at the time of the start of step (2).

In a preferable embodiment, the human cells obtained in step (1) (e.g., cells obtained from human iPS cells in step (1)) are cultured in suspension in a serum-free medium containing a Sonic hedgehog signal transduction pathway activating substance (e.g., SAG, PMA, Shh protein) to form an aggregate. A Sonic hedgehog signal transduction pathway activating substance is preferably contained in the medium from the time of the start of suspension culture. A ROCK inhibiting substance (e.g., Y-27632) may also be added to the medium. The period for the culturing is 12 hr-6 days, preferably 12 hr-48 hr. The aggregates formed are preferably uniformed aggregates.

For example, the human cells obtained in step (1) (e.g., cells obtained from human iPS cells in step (1)) are recovered, dispersed to single cells or a state close thereto, and subjected to suspension culturing in a serum-free medium containing a Sonic hedgehog signal transduction pathway activating substance (e.g., SAG, PMA). The serum-free medium may contain a ROCK inhibitor (e.g., Y-27632). A suspension of human stem cells (e.g., stem cells derived from human iPS cells) is seeded in the above-mentioned culture vessel and the dispersed cells are cultured under conditions non-adhesive to the culture vessel, whereby plural pluripotent stem cells are assembled to form an aggregate. The period for the culturing is 12 hr-6 days (preferably 12 hr-48 hr). The aggregates formed are preferably uniformed aggregates.

By performing step (2) in this manner, aggregates of the cells obtained in step (1), or the cells derived therefrom can be formed. The present invention also provides a production method of such aggregate. The aggregate obtained in step (2) have higher quality than the one formed by a treatment with a TGFβ family signal transduction pathway inhibiting substance and/or a Sonic hedgehog signal transduction pathway activating substance is not performed in step (1). To be specific, a population of spherical cell aggregates having a smooth surface and a dense inside, and having a high ratio of uncollapsed aggregates can be obtained. In one embodiment, when aggregates (e.g., not less than 100 aggregates) are randomly selected on day 6 from the start of the second step, the ratio of non-cystic aggregates is, for example, not less than 70%, preferably not less than 80%.

The aggregate obtained in step (2) has a potency to differentiate into a retinal tissue. By culturing the aggregate obtained in step (2) under the condition of the following step (3), an aggregate containing a retinal tissue can be produced with high efficiency.

In one embodiment, by using the stem cells obtained in step (1) and having a potency to differentiate into at least retinal tissue, retinal cell, retinal progenitor cell, or retinal layer-specific neuron (preferably, Oct3/4 positive stem cells having a potency to differentiate into at least retinal tissue, retinal cell, retinal progenitor cell, or retinal layer-specific neuron) in step (2), an aggregate containing stem cells having a potency to differentiate into at least retinal tissue, retinal cell, retinal progenitor cell, or retinal layer-specific neuron (e.g., Oct3/4 positive stem cells) can be obtained.

Step (3) wherein the aggregate obtained in step (2) is cultured in suspension in the presence of a BMP signal transduction pathway activating substance to obtain an aggregate containing a retinal tissue is explained.

The medium to be used in step (3) is, for example, a serum-free medium or a serum-containing medium (preferably serum-free medium) supplemented with a BMP signal transduction pathway activating substance.

The serum-free medium or serum-containing medium to be used for such medium is not particularly limited as long as it is as mentioned above. To avoid complicated preparation, for example, a serum-free medium supplemented with an appropriate amount of a commercially available serum alternative such as KSR and so on (e.g., medium of 1:1 mixture of IMDM and F-12 supplemented with 10% KSR, 450 µM 1-monothioglycerol and 1× Chemically Defined Lipid Concentrate) can be preferably used. The amount of KSR to be added to a serum-free medium in the case of human pluripotent stem cell (e.g., iPS cell) is generally about 1% to about 20%, preferably about 2% to about 20%.

The medium (preferably, serum-free medium) to be used in step (3) may also be the medium (preferably, serum-free medium) used in step (2), or may be replaced with a fresh medium (preferably, serum-free medium). When the medium used in step (2), which is free of a BMP signal transduction pathway substance, is directly used in step (3), a BMP signal transduction pathway activating substance may be added to the medium.

Examples of the BMP signal transduction pathway activating substance to be used in step (3) include BMP proteins such as BMP2, BMP4, BMP7 etc., GDF proteins such as GDF7 etc., anti-BMP receptor antibody, BMP partial peptide and so on. BMP2 protein, BMP4 protein and BMP7 protein are available from, for example, R&D Systems, and GDF7 protein is available from, for example, Wako Pure Chemical Industries, Ltd. As a preferable BMP signal transduction pathway activating substance, BMP4 can be mentioned.

The concentration of the BMP signal transduction pathway activating substance may be a concentration at which differentiation of the cells that form an aggregate of pluripotent stem cells, into retinal cells can be induced. For example, in the case of human BMP4, it is added to the medium to a concentration of about 0.01 nM to about 1 µM, preferably about 0.1 nM to about 100 nM, more preferably about 1 nM to about 10 nM, further preferably about 1.5 nM (55 ng/mL). When a BMP signal transduction pathway activating substance other than BMP4 is used, it is desirably used at a concentration at which a BMP signal transduction promoting activity equivalent to that of BMP4 at the above-mentioned concentration is shown.

The concentration of the BMP signal transduction pathway activating substance in the medium may be varied during the period of step (3). For example, the BMP signal transduction pathway activating substance is provided to fall within the above-mentioned range at the time of the start of step (3), and the concentration may be gradually or stepwisely decreased at a ratio of 40-60% per 2-4 days.

A BMP signal transduction pathway activating substance may be added after about 24 hr or later from the start of the suspension culturing in step (2), and may also be added to the medium within several days from the start of the suspension culturing (e.g., within 15 days). Preferably, a BMP signal transduction pathway activating substance is added to the medium within day 1 to day 15, more preferably day 1 to day 9, further preferably day 3 to day 8 or day 2 to day 9, still more preferably, day 3 to day 6, from the start of the suspension culture.

In a specific embodiment, the medium is partly or entirely exchanged with a medium containing BMP4 on day 1-9, preferably day 2-8, further preferably day 3 or 4, after the start of suspension culturing (i.e., after the start of the aforementioned step (2)) to adjust the final concentration of BMP4 to about 1-10 nM, and the cells can be cultured in the presence of BMP4 for about 1-12 days, preferably 2-9 days, more preferably 2-5 days. To maintain the concentration of BMP4 at the same level, the medium may be partly or entirely exchanged one or two times with a medium containing BMP4. Alternatively, as mentioned above, the concentration of BMP4 may also be reduced in stages.

After the addition of the BMP signal transduction pathway activating substance to the medium, and the start of the differentiation induction of the cells forming an aggregate into retinal cells, addition of the BMP signal transduction pathway activating substance to the medium is not necessary, and the medium may be exchanged with a serum-free medium or serum-containing medium each free of the BMP signal transduction pathway activating substance. In one embodiment, after the start of the differentiation induction into retinal cell, the concentration of the BMP signal transduction pathway activating substance in the medium is gradually or stepwisely decreased at a ratio of 40-60% per 2-4 days by exchanging the medium with a serum-free medium or a serum-containing medium, each free of a BMP signal transduction pathway activating substance. The cells that started differentiation induction into retinal cells can be confirmed by, for example, detecting the expression of retinal progenitor cell marker gene (e.g., Rx gene (alias Rax), Pax6 gene, Chx10 gene) in the cells. The aggregate formed in step (2) by using pluripotent stem cells in which a fluorescence reporter protein gene such as GFP and so on is knocked-in into the Rax gene locus is cultured in suspension in the presence of the BMP signal transduction pathway activating substance at a concentration necessary for differentiation induction into retinal cell, and fluorescence emitted from the expressed fluorescence reporter protein is detected, whereby the time period when differentiation induction into retinal cell was started can be confirmed. One embodiment of step (3) is a step culturing the aggregate formed in step (2) in suspension in a serum-free medium or serum-containing medium containing a BMP signal transduction pathway activating substance at a concentration necessary for differentiation induction into retinal cell, until a cell expressing retinal progenitor cell marker gene (e.g., Rx gene, Pax6 gene, Chx10 gene) begins appearing, thereby obtaining a cell aggregate comprising retinal progenitor cells.

In step (3), when a medium change operation is performed, for example, an operation to add a fresh medium without discarding the existing medium (medium addition operation), an operation to discard about a half amount of the existing medium (about 40-80% of the volume of the existing medium) and add about a half amount of a fresh medium (about 40-80% of the volume of the existing medium) (half-medium change operation), and an operation to discard about the whole amount of the existing medium (not less than 90% of the amount of the existing medium) and add about the whole amount of a fresh medium (not less than 90% of the amount of the existing medium) (full-medium change operation) can be mentioned.

When a particular component (e.g., BMP4) is added at a certain time point, for example, an operation to calculate the final concentration, to discard about a half amount of the existing medium, and to add about a half amount of a fresh medium containing a particular component at a concentration higher than the final concentration (specifically 1.5-3.0 times the final concentration, for example, about 2 times the final concentration) (half-medium change operation, half-medium change) may be performed.

When the concentration of a particular component contained in the existing medium is to be maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time pointed, for example, the medium change operation may be performed plural times per day, preferably plural times (e.g., 2-3 times) within 1 hr. Also, when the concentration of a component contained in the existing medium is to be decreased by dilution at a certain time point, the cell or aggregate may be transferred to another culture container.

While the tool used for the medium change operation is not particularly limited, for example, pipetter, micropipette, multichannel micropipette, continuous dispenser, and the like can be mentioned. For example, when a 96 well plate is used as a culture container, a multichannel micropipette may be used.

In one embodiment, when the concentration of the Shh signal transduction pathway activating substance added to the medium in step (2) is comparatively low (e.g., not more than 700 nM for SAG, and a concentration conferring Shh signal transduction promoting activity equivalent to or lower than that of SAG at the above-mentioned concentration, for other Shh signal transduction pathway activating substances), medium change is not necessary, and a differentiation-inducing factor (e.g., BMP4) may be added to the medium used in step (2). On the other hand, when the concentration of the Shh signal transduction pathway activating substance is comparatively high (e.g., exceeding 700 nM or not less than 1000 nM for SAG, and a concentration conferring a Shh signal transduction promoting activity equivalent to that of SAG at the above-mentioned concentration, for other Shh signal transduction pathway activating substances), it is desirable to change the medium to a fresh medium containing a differentiation-inducing factor (e.g., BMP4) to suppress an influence of the Shh signal transduction pathway activating substance remaining when a differentiation-inducing factor is added.

In a preferable embodiment, the concentration of a Shh signal transduction pathway activating substance in the medium to be used in step (3) is, when calculated in terms of Shh signal transduction promoting activity of SAG, not more than 700 nM, preferably not more than 300 nM, more preferably not more than 10 nM, further preferably not more than 0.1 nM, further preferably free of a Shh signal transduction pathway activating substance. The medium "free of a Shh signal transduction pathway activating substance" also includes a medium substantially free of a Shh signal transduction pathway activating substance, for example, a medium free of a Shh signal transduction pathway activating substance at a concentration imparting an adverse influence on selective differentiation into a retinal progenitor cell or a retinal tissue. The medium "free of a Shh signal transduction pathway activating substance" also includes a medium substantially not supplemented with a Shh signal transduction pathway activating substance, for example, a medium not supplemented with a Shh signal transduction pathway activating substance at a concentration imparting an adverse influence on selective differentiation into a retinal progenitor cell or a retinal tissue.

The culture conditions such as culture temperature, $CO_2$ concentration and so on in step (3) can be appropriately determined. The culture temperature is, for example, about 30° C. to about 40° C., preferably about 37° C. The $CO_2$ concentration is, for example, about 1% to about 10%, preferably about 5%.

By such culturing, differentiation of the cells forming the aggregate obtained in step (2) into retinal progenitor cells is induced, whereby an aggregate containing the retinal progenitor cells can be obtained. The present invention also provides a method for producing such aggregate containing retinal progenitor cell. That an aggregate comprising retinal progenitor cells was obtained can be confirmed by, for example, detecting the presence of cells expressing Rax, PAX6 or Chx10, which is a retinal progenitor cell marker, in the aggregate. One embodiment of step (3) is a step of culturing the aggregate formed in step (2) in suspension in a serum-free medium or serum-containing medium containing a BMP signal transduction pathway activating substance at a concentration necessary for differentiation induction into retinal cell, until a cell expressing Rx gene begins appearing, whereby obtaining an aggregate comprising retinal progenitor cells. In one embodiment, the culturing of step (3) is performed until not less than 20% (preferably, not less than 30%, not less than 40%, not less than 50%, not less than 60%) of the cells contained in the aggregate express Rx.

In a preferable embodiment of the production of retinal cells and/or a retinal tissue, in step (1), human pluripotent stem cells (e.g., human iPS cells) are cultured in an adhered state in the absence of feeder cells in a serum-free medium containing a TGFβ signal transduction pathway inhibiting substance (e.g., SB431542, A-83-01) and bFGF; in step (2), the cells are cultured in suspension in a serum-free medium containing a Sonic hedgehog signal transduction pathway activating substance (e.g., SAG, PMA, Shh protein); and in step (3), the aggregate is cultured in suspension in a serum-free medium containing a BMP signal transduction pathway activating substance (e.g., BMP4).

In addition, in a preferable embodiment of the production of retinal cells and/or a retinal tissue, in step (1), human pluripotent stem cells (e.g., human iPS cells) are cultured in an adhered state in the absence of feeder cells in a serum-free medium containing a BMP signal transduction pathway inhibiting substance (e.g., LDN193189) and bFGF; in step (2), the cells are cultured in suspension in a serum-free medium free of or containing a Sonic hedgehog signal transduction pathway activating substance (e.g., SAG, PMA); and in step (3), the aggregate is cultured in suspension in a serum-free medium containing a BMP signal transduction pathway activating substance (e.g., BMP4).

In a preferable embodiment of the production of retinal cells and/or a retinal tissue, in step (1), human pluripotent stem cells (e.g., human iPS cells) are cultured in an adhered state in the absence of feeder cells in a serum-free medium containing a Sonic hedgehog signal transduction pathway activating substance (e.g., SAG, PMA) and bFGF for preferably not less than 1 day and not more than 6 days, further preferably 2-4 days, in step (2), the cells are cultured in suspension in a serum-free medium containing a Sonic hedgehog signal transduction pathway activating substance (e.g., SAG, PMA), and in step (3), the aggregates are cultured in suspension in a serum-free medium containing a BMP signal transduction pathway activating substance (e.g., BMP4).

In a preferable embodiment of the production of retinal cells and/or a retinal tissue, in step (1), human pluripotent stem cells (e.g., human iPS cells) are cultured in an adhered state in the absence of feeder cells in a serum-free medium containing a TGFβ family signal transduction pathway inhibiting substance (e.g., a TGFβ signal transduction pathway inhibiting substance (e.g., Lefty, SB431542, A-83-01), a Nodal/Activin signal transduction pathway inhibiting substance (e.g., Lefty, SB431542, A-83-01), a BMP signal transduction pathway inhibiting substance (e.g., LDN193189), or a combination thereof (e.g., 5B431542 and LDN193189) etc.);

a Sonic hedgehog signal transduction pathway activating substance (e.g., Shh protein, SAG, PMA); or a combination of a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA); a bFGF, in step (2), the cells obtained step (1) are cultured in suspension in a serum-free medium containing a Sonic hedgehog signal transduction pathway activating substance (e.g., SAG, PMA, Shh protein) to form a cell aggregate, and in step (3), the aggregate is cultured in suspension in a serum-free medium containing a BMP signal transduction pathway activating substance (e.g., BMP4) to give an aggregate containing a retinal progenitor cell, retinal cell or retinal tissue.

The medium in step (2) preferably contains a ROCK inhibiting substance (e.g., Y-27632).

The obtained aggregate containing retinal progenitor cells may be used as it is as a reagent for evaluating toxicity or drug efficacy. An aggregate containing retinal progenitor cells is subjected to a dispersion treatment (e.g., trypsin/EDTA treatment or papain treatment), and the obtained cells are subjected to a selection using FACS or MACS, whereby highly pure retinal progenitor cells can also be obtained.

Furthermore, the aggregate containing retinal progenitor cells is continuously cultured in a serum-free medium or serum-containing medium to further differentiate the retinal progenitor cells, whereby a neuroepithelial structure-like retinal tissue can be produced.

A serum-free medium or serum-containing medium to be used for such medium is not particularly limited as long as it is as mentioned above. For example, a serum-containing medium which is a DMEM-F12 medium supplemented with 10% fetal bovine serum, N2 supplement, 100 μM taurine, and 500 nM retinoic acid, or a serum-free medium supplemented with an appropriate amount of a commercially available serum alternative such as KSR and so on (e.g., medium of 1:1 mixture of IMDM and F-12 supplemented with 10% KSR, 450 μM 1-monothioglycerol and 1× Chemically Defined Lipid Concentrate) and the like can be mentioned.

While the period for the culturing for inducing a retinal tissue from retinal progenitor cells varies depending on the intended retinal layer-specific neuron, it is, for example, about 7 days to about 200 days.

The retinal tissue exists covering the surface of the aggregate. After completion of the suspension culturing, the aggregate may be fixed with a fixative such as para-form-aldehyde solution and so on, and a cryosection is prepared, then formation of a retinal tissue having a layer structure may be confirmed by immunostaining and the like. Since respective layers of a retinal tissue are composed of different retinal progenitor cells (photoreceptor cell, horizontal cell, bipolar cell, amacrine cell, retinal ganglion cell), formation of a layer structure can be confirmed using antibodies against the aforementioned markers expressed in these cells by the immunostaining. In one embodiment, the retinal tissue is a Rx- or Chx10-positive neuroepithelial structure.

The retinal tissue existing on the surface of the aggregate can be physically cut out from the aggregate by using tweezers and the like. In this case, since a neural tissue other than the retinal tissue may be formed on the surface of each aggregate, a part of the neural tissue cut out from the aggregate may be subjected to confirmation by the below-mentioned immunostaining and the like, whereby the tissue can be confirmed to be a retinal tissue.

In one embodiment, the aggregate obtained in step (3) contains a retinal tissue and is substantially free of non-neural head ectoderm. In an aggregate containing a retinal tissue and substantially free of non-neural head ectoderm, for example, Rx-positive tissue is observed and an Rx-negative tissue is not observed on the outside thereof in the immunostaining images of the aforementioned aggregate frozen section.

One embodiment of step (3) is a step of culturing the aggregate formed in step (2) in suspension in a serum-free medium or serum-containing medium containing a BMP signal transduction pathway activating substance at a concentration necessary for differentiation induction into retinal cells, until a cell expressing Rx gene and/or Chx10 gene begins appearing to give an aggregate comprising retinal progenitor cells, and subsequently culturing the aggregate containing the retinal progenitor cells in suspension in a serum-free medium or serum-containing medium until a retinal tissue is formed, whereby obtaining an aggregate comprising a retinal tissue. When the aggregate containing the retinal progenitor cells is subsequently cultured in suspension in a serum-free medium or serum-containing medium until a retinal tissue is formed, the concentration of the BMP signal transduction pathway activating substance in the medium in order to induce retinal progenitor cells may be gradually or stepwisely decreased at a ratio of 40-60% per 2-4 days by exchanging the medium with a serum-free medium or a serum-containing medium, each free of a BMP signal transduction pathway activating substance. In one embodiment, suspension culturing of an aggregate containing retinal progenitor cells is performed until not less than 20% (preferably, not less than 30%, not less than 40%, not less than 50%, not less than 60%) of the cells contained in the aggregate expresses Chx10.

In one embodiment of step (3), the aggregate obtained in step (2), or an aggregate obtained by culturing the aggregate obtained in step (2) in suspension by the above-mentioned method may be subjected to adhesion culturing to form an adhered aggregate. The adhered aggregate is cultured in an adhered state in a serum-free medium or serum-containing medium containing a BMP signal transduction pathway activating substance at a concentration necessary for differentiation induction into a retinal cell, until a cell expressing Rx gene and/or a Chx10 gene begins appearing to give an aggregate containing retinal progenitor cells. The aggregate containing the retinal progenitor cells is cultured in an adhered state in a serum-free medium or serum-containing medium until a retinal tissue is formed, whereby an aggregate containing a retinal tissue is obtained. In one embodiment, adhesion culturing of the aggregate containing retinal progenitor cells is performed until not less than 10% (preferably, not less than 20%, not less than 30%, not less than 40%, not less than 50%) of the cells express Chx10.

By the production method 2 of the present invention, a retinal tissue can be obtained from pluripotent stem cells with high efficiency. The retinal tissue obtained by the production method 2 of the present invention contains specific neurons specific to each of the retinal layers, it is also possible to obtain a cell constituting a retinal tissue, such as photoreceptor cell, horizontal cell, bipolar cell, amacrine cell, retinal ganglion cell or a progenitor/precursor cell thereof and the like. Which cell was obtained from the obtained retinal tissue can be confirmed by a method known per se, for example, expression of a cell marker.

An aggregate containing the obtained retinal tissue may also be directly used as a reagent for evaluating toxicity or drug efficacy. An aggregate containing a retinal tissue is subjected to a dispersion treatment (e.g., trypsin/EDTA treatment), and the obtained cells are subjected to a selection using FACS or MACS, whereby highly pure retinal tissue-constituting cells, for example, highly pure photoreceptor cells, can also be obtained.

A ciliary marginal zone-like structure can be produced by the following step (A) and step (B) from the cell aggregate containing a retinal tissue, which is obtained by the production method 2 of the present invention and the like.

The ciliary marginal zone-like structure in the present invention refers to a structure similar to a ciliary marginal zone. Examples of the "ciliary marginal zone (CMZ)" include a tissue present in the boundary region of retinal tissue (specifically, neural retina) and retinal pigment epithelium in the retina in vivo, which is a region containing tissue stem cells of retina (retinal stem cells). Ciliary marginal zone is also called a ciliary margin or retinal margin, and the ciliary marginal zone, ciliary margin and retinal margin are equivalent tissues. It is known that the ciliary marginal zone plays an important role in the supply of retinal progenitor cells or differentiated cells to retinal tissues, maintenance of retinal tissue structure and so on. Examples of the marker gene of the ciliary marginal zone include Rdh10 gene (positive), Otx1 gene (positive), Zic1 (positive) and so on.

Step (A) comprises culturing a cell aggregate comprising a retinal tissue obtained by the production method 2 of the present invention in which Chx10 positive cells are present in a proportion of 20% or more and 100% or less of the retinal tissue, in a serum-free medium or serum-containing medium each containing a Wnt signal pathway activating substance and/or a FGF signal pathway inhibiting substance for only a period before the appearance of a RPE65 gene-expressing cell.

As a preferable culturing of step (A) here, suspension culturing can be mentioned.

As a serum-free medium to be used in step (A), a serum-free medium which is a basal medium supplemented with N2 or KSR can be mentioned. More specifically, a serum-free medium which is a DMEM/F-12 medium supplemented with N2 supplement (Life Technologies) can be mentioned. As the serum-containing medium, a serum-containing medium which is a basal medium supplemented with fetal bovine serum can be mentioned.

The culture conditions of step (A) such as culture temperature, $CO_2$ concentration can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

In step (A), the Wnt signal transduction pathway activating substance to be contained in a serum-free medium or serum-containing medium when the above-mentioned "cell aggregate comprising a retinal tissue" is cultured in the medium is not particularly limited as long as it can enhance signal transduction mediated by Wnt. Specific examples of the Wnt signal transduction pathway activating substance include a protein belonging to Wnt family (e.g., Wnt1, Wnt3a, Wnt7a), Wnt receptor, Wnt receptor agonist, GSK3β inhibitor (e.g., 6-Bromoindirubin-3'-oxime (BIO), CHIR99021, Kenpaullone) and so on.

The concentration of the Wnt signal transduction pathway activating substance to be contained in a serum-free medium or serum-containing medium in step (A) in the case of a common Wnt signal transduction pathway activating substance such as CHIR99021 is, for example, in the range of about 0.1 μM to about 100 μM, preferably, for example, in the range of about 1 μM to about 30 μM, more preferably, for example, around 3 μM.

The FGF signal transduction pathway inhibiting substance to be contained in a serum-free medium or serum-containing medium in step (A) when the above-mentioned "cell aggregate comprising a retinal tissue" is cultured in the medium is not particularly limited as long as it can inhibit signal transduction mediated by FGF. Examples of the FGF signal transduction pathway inhibiting substance include FGF receptor, FGF receptor inhibitor (e.g., SU-5402, AZD4547, BGJ398), MAP kinase cascade inhibiting substance (e.g., MEK inhibitor, MAPK inhibitor, ERK inhibitor), PI3 kinase inhibitor, Akt inhibitor and so on.

The concentration of the FGF signal transduction pathway inhibiting substance contained in a serum-free medium or serum-containing medium in step (A) only needs to be a concentration at which differentiation of an aggregate into ciliary marginal zone-like structure can be induced. For example, in the case of SU-5402, it is added to the medium to a concentration of about 0.1 μM to about 100 μM, preferably about 1 μM to about 30 μM, more preferably about 5 μM.

"Culturing for only a period before the appearance of a RPE65 gene-expressing cell" in step (A) means culturing in the whole or a part of the period before the appearance of a RPE65 gene-expressing cell. That is, culturing in the whole or a part of the period (any period) during which the aforementioned "cell aggregate comprising a retinal tissue" in the culture system is constituted by cells that do not substantially express RPE65 gene suffices. By employing such culturing, a cell aggregate in which a RPE65 gene-expressing cell does not appear can be obtained.

To determine such particular period, the aforementioned "cell aggregate comprising a retinal tissue" is used as a sample, and the presence or absence of expression of RPE65 gene contained in the sample or the level thereof may be measured by a general genetic engineering method or a biochemical method. Specifically, for example, the presence or absence of expression of RPE65 gene or the level thereof can be examined by subjecting a cryosection of the aforementioned "cell aggregate comprising a retinal tissue" to an immunostaining method using an antibody against RPE65 protein.

As a "period before the appearance of a RPE65 gene-expressing cell" in step (A), for example, a period during which the ratio of Chx10 positive cells present in the above-mentioned retinal tissue decreases than that at the time of start of the culturing of the aforementioned cell aggregate in a serum-free medium or serum-containing medium each containing a Wnt signal transduction pathway activating substance and/or a FGF signal transduction pathway inhibiting substance, and falls within the range of 30% to 0% can be mentioned. As the "cell aggregate in which a RPE65 gene-expressing cell does not appear", a cell aggregate in which Chx10 positive cells are present in the above-mentioned retinal tissue in a proportion of within 30% to 0% of the tissue can be mentioned.

While the number of days of the "period before the appearance of a RPE65 gene-expressing cell" in step (A) varies depending on the kind of the Wnt signal transduction pathway activating substance and/or the FGF signal transduction pathway inhibiting substance, the kind of the serum-free medium or serum-containing medium, other culture conditions and so on, it is, for example, within 14 days. More specifically, when a serum-free medium (e.g., serum-free medium which is a basal medium supplemented with N2) is used, the above-mentioned period is preferably, for example, within 10 days, more preferably, for example, 3 days to 6 days. When a serum-containing medium (e.g., serum-containing medium which is a basal medium supplemented with fetal bovine serum) is used, the aforementioned period is preferably, for example, within 12 days, more preferably, for example, 6 days to 9 days.

Then as step (B), the "cell aggregate in which a RPE65 gene-expressing cell does not appear" obtained by culturing as mentioned above is cultured in a serum-free medium or serum-containing medium each free of a Wnt signal transduction pathway activating substance.

As a preferable culturing in step (B), suspension culturing can be mentioned.

The serum-free medium of step (B) is preferably free of a FGF signal transduction pathway inhibiting substance.

As the serum-free medium in step (B), a medium which is a basal medium supplemented with N2 or KSR can be mentioned. As the serum-containing medium, a medium which is a basal medium supplemented with fetal bovine serum can be mentioned. More specifically, a serum-containing medium which is a DMEM/F-12 medium supplemented with fetal bovine serum can be mentioned.

The aforementioned serum-free medium or serum-containing medium in step (B) may contain a known growth factor, an additive and a chemical substance that promote the growth, and so on. Examples of the known growth factor include EGF, FGF, IGF, insulin and so on. Examples of the additive that promotes the growth include N2 supplement (Life Technologies), B27 supplement (Life Technologies), KSR (Life Technologies) and so on. Examples of the chemical substance that promotes the growth include retinoids (e.g., retinoic acid) and taurine.

A preferable period for the culturing in step (B) is, for example, a period for the culturing during which the ratio of Chx10 positive cells present in the above-mentioned retinal tissue increases than that at the time of start of the culturing of the aforementioned cell aggregate in a serum-free medium or serum-containing medium each free a Wnt signal transduction pathway activating substance, and reaches 30% or more.

The culture conditions such as culture temperature, $CO_2$ concentration and the like in step (B) can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

While the number of the above-mentioned culture days until "a cell aggregate comprising a ciliary marginal zone-like structure" is obtained in step (B) varies depending on the kind of the serum-free medium or serum-containing medium, other culture conditions and so on, it is, for example, within 100 days. The aforementioned number of culture days is preferably, for example, 20 days to 70 days, more preferably, for example, 30 days to 60 days.

In a "cell aggregate comprising a ciliary marginal zone-like structure" prepared by the aforementioned step (A), (B), a retinal pigment epithelium and a retinal tissue (specifically, neural retina) are present adjacent to the ciliary marginal zone-like structure in the same cell aggregate. The structure can be confirmed by microscopic observation and so on. Specifically, for example, the presence of a ciliary marginal zone-like structure as an epithelial structure having a thick retina side and a thin retinal pigment epithelium side, which is formed between a retinal tissue having high transparency and retinal pigment epithelium showing pigmentation, can be confirmed by microscopic observation. In addition, the presence of ciliary marginal zone-like structure can be confirmed by identifying Rdh10 positive, Otx1 positive, or Zic1 positive cells with immunostaining a frozen section of aggregate.

In a further embodiment, differentiation of a retinal tissue (neuroepithelial) contained in the aggregate proceeds by the aforementioned steps (A), (B), and a mature retinal tissue, and the aforementioned cell containing at least one, preferably plural, more preferably all cells selected from the group consisting of photoreceptor precursor cell, photoreceptor cell, cone photoreceptor cell, rod photoreceptor cell, horizontal cell, and interneuron (amacrine cell, ganglion cell etc.), can be produced.

A retinal pigment epithelial cell can be produced by the following step (C) from a cell aggregate containing a retinal tissue obtained by the production method 2 of the present invention and the like. A retinal pigment epithelial sheet can be produced by the following step (D) from a retinal pigment epithelial cell obtained by the following step (C).

The "retinal pigment epithelial cell" in the present invention means an epithelial cell present on the outside of the neural retinal tissue in retina in vivo. Whether it is a retinal pigment epithelial cell can be confirmed by those of ordinary skill in the art based on, for example, expression of a cell marker (RPE65 (matured retinal pigment epithelial cell), Mitf (juvenile or matured retinal pigment epithelial cell) and the like), the presence of melanin granule, characteristic cell morphology of polygon and the like.

First, in step (C), a cell aggregate containing a retinal tissue obtained by the production method 2 of the present invention is cultured in suspension in a serum-free medium or serum-containing medium free of a BMP signal transduction pathway activating substance but containing a Wnt signal transduction pathway activating substance to give an aggregate containing retinal pigment epithelial cells.

As a serum-free medium to be used in step (C), a serum-free medium which is a basal medium supplemented with N2 or KSR can be mentioned. More specifically, a serum-free medium which is a DMEM/F-12 medium supplemented with N2 supplement (Life Technologies) can be mentioned. As the serum-containing medium, a serum-containing medium which is a basal medium supplemented with fetal bovine serum can be mentioned.

The serum-free medium to be used in step (C) may contain, in addition to the aforementioned Wnt signal transduction pathway activating substance, the aforementioned Nodal/Activin signal transduction pathway activating substance, and/or the aforementioned FGF signal transduction pathway inhibiting substance.

A preferable culturing in step (C) is, for example, suspension culturing.

Step (D) in which the aggregate obtained in step (C) of the present invention is dispersed and the obtained cells are cultured in an adhered state is explained.

Step (D) is performed within 60 days, preferably within 30 days, more preferably 3 days, after the start of step (C).

As a serum-free medium or serum-containing medium to be used for adhesion culturing in step (D), the aforementioned medium can be mentioned. To avoid complicated preparation, a serum-free medium supplemented with an appropriate amount of a commercially available serum alternative such as KSR and the like (e.g., a medium of 1:1 mixture of DMEM/F-12 and Neurobasal supplemented with 1/2×N2 supplement, 1/2×B27 supplement and 100 μM 2-mercaptoethanol) is preferably used. The amount of KSR to be added to the serum-free medium is, for example, generally about 1% to about 20%, preferably about 2% to about 20%, in the case of a cell derived from human iPS cell.

In step (D), it is preferable to culture cells in the aforementioned serum-free medium or serum-containing medium containing a ROCK inhibiting substance.

In step (D), it is more preferable to culture cells in a serum-free medium or serum-containing medium further containing one or more substances selected from the group consisting of a Wnt signal transduction pathway activating substance, a FGF signal transduction pathway inhibiting substance, an Activin signal transduction pathway activating substance and a BMP signal transduction pathway activating substance.

The Activin signal transduction pathway activating substance is a substance capable of enhancing a signal mediated by Activin. Examples of the Activin signal transduction pathway activating substance include proteins belonging to the Activin family (e.g., Activin A, Activin B, Activin C, Activin AB and the like), Activin receptor, and Activin receptor agonist.

The concentration of the Activin signal transduction pathway activating substance to be used in step (D) may be any as long as a uniformed sheet of retinal pigment epithelial cells can be efficiently formed. For example, Recombinant Human/Mouse/Rat Activin A (R&D systems, #338-AC) is added to a concentration of about 1 ng/ml to about 10 μg/ml, preferably about 10 ng/ml to about 1 μg/ml, more preferably about 100 ng/ml.

An Activin signal transduction pathway activating substance is added, for example, within 18 days, preferably on day 6, from the start of step (D).

In step (D), adhesion culturing is preferably performed on a culture vessel whose surface is treated with a culture substrate. As a culture substrate to be used for treating culture vessel in step (D), a cell culture substrate enabling adhesion culturing of aggregate-derived cells and formation of a retinal pigment epithelial sheet can be mentioned.

4. Method for Producing Cerebral Tissue

The production method 3 of the present invention is a method for producing a cerebral tissue, comprising the following steps (1)-(3):

(1) a first step of culturing pluripotent stem cells in the absence of feeder cells and in a medium comprising 1) a TGFβ family signal transduction pathway inhibiting substance and/or a Sonic hedgehog signal transduction pathway activating substance, and 2) a factor for maintaining undifferentiated state,
(2) a second step of culturing the cells obtained in the first step in suspension to form a cell aggregate, and
(3) a third step of culturing the aggregate obtained in the second step in suspension in the presence of a TGFβ family signal transduction pathway inhibiting substance and/or a Wnt signal transduction pathway inhibiting substance to obtain an aggregate comprising a cerebral tissue.

Step (1) of the production method 3 of the present invention can be performed in the same manner as in step (1) of the production method 1 of the present invention.

Step (2) of the production method 3 of the present invention can also be performed in the same manner as in step (2) of the production method 1 of the present invention.

The medium to be used in step (2) of production method 3 may or may not contain a Sonic hedgehog signal transduction pathway activating substance.

The medium to be used in step (2) may contain a TGFβ family signal transduction pathway inhibiting substance and/or a Wnt signal transduction pathway inhibiting substance. In step (2), a TGFβ family signal transduction pathway inhibiting substance or a Wnt signal transduction pathway inhibiting substance may be added alone to the medium, and the both are preferably added in combination.

In step (3), as a differentiation-inducing factor, a TGFβ family signal transduction pathway inhibiting substance or a Wnt signal transduction pathway inhibiting substance may be added alone to the medium, and the both are preferably added in combination.

The medium to be used in step (3) is, for example, a serum-free medium or serum-containing medium (preferably, serum-free medium) supplemented with a TGFβ family signal transduction pathway inhibiting substance and/or a Wnt signal transduction pathway inhibiting substance.

A serum-free medium or serum-containing medium to be used for such medium is not particularly limited as long as it is as mentioned above. To avoid complicated preparation, for example, a serum-free medium supplemented with an appropriate amount of a commercially available serum alternative such as KSR and so on (e.g., GMEM medium supplemented with 20% KSR, 0.1 mM 2-mercaptoethanol, non-essential amino acid, 1 mM pyruvic acid) is preferably used. The amount of KSR to be added to a serum-free medium in the case of human pluripotent stem cells (e.g., iPS cells) is generally about 1% to about 30%, preferably about 2% to about 20%.

The medium (preferably, serum-free medium) to be used in step (3) may also be the medium (preferably, serum-free medium) used in step (2), or may be replaced with a fresh medium (preferably, serum-free medium). When the medium used in step (2), which is free of a TGFβ family signal transduction pathway inhibiting substance and/or a Wnt signal transduction pathway inhibiting substance, is directly used in step (3), a TGFβ family signal transduction pathway inhibiting substance and/or a Wnt signal transduction pathway inhibiting substance may be added to the medium. When the medium used in step (2), which contains a TGFβ family signal transduction pathway inhibiting substance and/or a Wnt signal transduction pathway inhibiting substance, is directly used in step (3), a half amount of the medium can be exchanged with the same medium.

Examples of the TGFβ family signal transduction pathway inhibiting substance to be used in steps (2) and (3) include a TGFβ signal transduction pathway inhibiting substance, a Nodal/Activin signal transduction pathway inhibiting substance and a BMP signal transduction pathway inhibiting substance.

The TGFβ signal transduction pathway inhibiting substance is not particularly limited as long as it inhibits the signal transduction pathway caused by TGFβ, and may be any of nucleic acid, protein, and low-molecular-weight organic compound. Examples of the substance include a substance that directly acts on TGFβ (e.g., protein, antibody, aptamer etc.), a substance that suppresses expression of a gene encoding TGFβ (e.g., antisense oligonucleotide, siRNA etc.), a substance that inhibits the binding of a TGFβ receptor and TGFβ, and a substance that inhibits a physiological activity caused by signal transduction by TGFβ receptor (e.g., TGFβ receptor inhibitor, Smad inhibitor etc.). A protein known as a TGFβ signal transduction pathway inhibiting substance, Lefty and the like can be mentioned. As a TGFβ signal transduction pathway inhibiting substance, a compound well known to those of ordinary skill in the art can be used and, specifically, SB431542, LY-364947, SB-505, A-83-01 and the like can be mentioned. Here, SB431542 (4-(5-benzole[1,3]dioxol-5-yl-4-pyridin-2-yl-1H-imidazol-2-yl)-benzamide) and A-83-01(3-(6-methyl-2-pyridinyl)-N-phenyl-4-(4-quinolinyl)-1H-pyrazole-1-carbothioamide) are compounds known as inhibitors of TGFβ receptor (ALK5) and Activin receptor (ALK4/7) (i.e., TGFβR inhibitor). The TGFβ signal transduction pathway inhibiting substance is preferably SB431542 or A-83-01.

The Nodal/Activin signal transduction pathway inhibiting substance is not particularly limited as long as it inhibits a signal transduction pathway caused by Nodal or Activin, and may be any of nucleic acid, protein, and low-molecular-weight organic compound. Examples of the substance include a substance that directly acts on Nodal or Activin (e.g., antibody, aptamer etc.), a substance that suppresses expression of a gene encoding Nodal or Activin (e.g., antisense oligonucleotide, siRNA etc.), a substance that inhibits the binding of a Nodal/Activin receptor and Nodal/Activin, and a substance that inhibits a physiological activity caused by signal transduction by Nodal/Activin receptor. As a Nodal/Activin signal transduction pathway inhibiting substance, a compound well known to those of ordinary skill in the art can be used and, specifically, SB431542, A-83-01 and the like can be mentioned. Also, a protein (Lefty, Cerberus etc.) known as a Nodal/Activin signal transduction pathway inhibiting substance may be used.

The BMP signal transduction pathway inhibiting substance is not particularly limited as long as it inhibits a signal transduction pathway caused by BMP, and may be any of nucleic acid, protein, and low-molecular-weight organic compound. Here, as BMP, BMP2, BMP4, BMP7 and GDF7 can be mentioned. Examples of the substance include a substance that directly acts on BMP (e.g., antibody, aptamer etc.), a substance that suppresses expression of a gene encoding BMP (e.g., antisense oligonucleotide, siRNA etc.), a substance that inhibits the binding of a BMP receptor (BMPR) and BMP, and a substance that inhibits a physiological activity caused by signal transduction by BMP receptor. As BMPR, ALK2 and ALK3 can be mentioned. As a BMP signal transduction pathway inhibiting substance, a compound well known to those of ordinary skill in the art can be used and, specifically, LDN193189, Dorsomorphin and the like can be mentioned. Here, LDN193189 (4-[6-(4-piperazin-1-ylphenyl)pyrazolo[1,5-a]pyrimidin-3-yl]quinoline) is a known BMPR (ALK2/3) inhibitor, and is generally commercially available in the form of hydrochloride. Also, a protein (Chordin, Noggin etc.) known as a BMP signal transduction pathway inhibiting substance may be used. A BMP signal transduction pathway inhibiting substance is preferably LDN193189.

A TGFβ family signal transduction pathway inhibiting substance is preferably SB431542, A-83-01 or LDN193189.

The Wnt signal transduction pathway inhibiting substance to be used in steps (2) and (3) is not particularly limited as long as it can suppress signal transduction mediated by Wnt, and may be any of protein, nucleic acid, low-molecular-weight compound and the like. The signal mediated by Wnt is transmitted via a Wnt receptor present as a heterodimer of Frizzled (Fz) and LRP5/6 (low-density lipoprotein receptor-related protein 5/6). Examples of the Wnt signal transduction pathway inhibiting substance include, but are not limited to, a substance that directly acts on Wnt or Wnt receptor (anti-Wnt antibody, anti-Wnt receptor antibody etc.), a substance that suppresses expression of gene encoding Wnt or Wnt receptor (e.g., antisense oligonucleotide, siRNA etc.), a substance that inhibits binding of Wnt receptor and Wnt (soluble Wnt receptor, dominant negative Wnt receptor etc., Wnt activating substance, Dkk1, Cerberus protein etc.), a substance that inhibits physiological activity caused by signal transduction by Wnt receptor [low-molecular-weight compounds such as CKI-7 (N-(2-aminoethyl)-5-chloroisoquinoline-8-sulfonamide), D4476 (4-[4-(2,3-dihydro-1,4-benzodioxin-6-yl)-5-(2-pyridinyl)-1H-imidazol-2-yl]benzamide), IWR-1-endo (IWR1e) (4-[(3aR,4S,7R,7aS)-1,3,3a, 4,7,7a-hexahydro-1,3-dioxo-4,7-methano-2H-isoindol-2-yl]-N-8-quinolinyl-benzamide), IWP-2 (N-(6-methyl-2-benzothiazolyl)-2-[(3,4,6,7-tetrahydro-4-oxo-3-phenylthieno[3,2-d]pyrimidin-2-yl)thio]acetamide) and the like, etc.] and the like. CKI-7, D4476, IWR-1-endo (IWR1e), IWP-2 and the like are known Wnt signal transduction pathway inhibiting substances, and commercially available products and the like are available as appropriate. A preferable Wnt signal transduction pathway inhibiting substance is, for example, IWR1e.

The concentration of a Wnt signal transduction pathway inhibiting substance only needs to be a concentration at which differentiation of the cells, that form an aggregate of pluripotent stem cells, into cerebral cells can be induced. For example, in the case of IWR-1-endo, it is added to the medium to a concentration of about 0.1 µM to about 100 µM, preferably about 0.3 µM to about 30 µM, more preferably about 1 µM to about 10 µM, further preferably about 3 µM. When a Wnt signal transduction pathway activating substance other than IWR-1-endo is used, it is desirably used at a concentration conferring a signal transduction pathway inhibitory activity equivalent to that of IWR1e at the above-mentioned concentration.

A TGFβ family signal transduction pathway inhibiting substance and/or a Wnt signal transduction pathway inhibiting substance may be added to the medium simultaneously with the start of the suspension culturing in step (2), or after lapse of a certain time after the start of the suspension culturing in step (2) (e.g., after about 24 hr or later).

In step (3), when a medium change operation is performed, for example, it can be performed by an operation to add a fresh medium without discarding the existing medium (medium addition operation), an operation to discard about a half amount of the existing medium (about 40-80% of the volume of the existing medium) and add about a half amount of a fresh medium (about 40-80% of the volume of the existing medium) (half-medium change operation), and an operation to discard about the whole amount of the existing medium (not less than 90% of the amount of the existing medium) and add about the whole amount of a fresh medium (not less than 90% of the amount of the existing medium) (full-medium change operation) and the like.

When a particular component (e.g., IWR-1-endo) is added at a certain time point, for example, an operation to calculate the final concentration, to discard about a half amount of the existing medium, and to add about a half amount of a fresh medium containing a particular component at a concentration higher than the final concentration (specifically 1.5 times-3.0 times the final concentration, for example, about 2 times the final concentration) (half amount medium change operation, half amount medium change) may be performed.

When the concentration of a particular component contained in the existing medium is to be maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time pointed, for example, the medium change operation may be performed plural times per day, preferably plural times (e.g., 2-3 times) within 1 hr. Also, when the concentration of a component contained in the existing medium is to be decreased by dilution at a certain time point, the cell or aggregate may be transferred to another culture container.

While the tool used for the medium change operation is not particularly limited, for example, pipetter, micropipette, multichannel micropipette, continuous dispenser, and the like can be mentioned. For example, when a 96 well plate is used as a culture container, a multichannel micropipette may be used.

The culture conditions such as culture temperature, $CO_2$ concentration and so on in step (3) can be appropriately determined. The culture temperature is, for example, about 30° C. to about 40° C., preferably about 37° C. The $CO_2$ concentration is, for example, about 1% to about 10%, preferably about 5%.

By such culturing, differentiation of the cells forming the aggregate obtained in step (2) into cerebral neural precursor cells is induced, whereby an aggregate containing the cerebral neural precursor cells can be obtained. The present invention also provides a production method of such aggregate containing cerebral neural precursor cells. That an aggregate comprising cerebral neural precursor cells was obtained can be confirmed by, for example, detecting the presence of a cell expressing FoxG1, Lhx2, PAX6, Emx2 or the like, which is a cerebral neural precursor cell marker, in the aggregate. One embodiment of step (3) is a step comprising culturing the aggregate formed in step (2) in suspension in a serum-free medium or serum-containing medium until a cell expressing FoxG1 gene begins appearing. In one embodiment, the culturing of step (3) is performed until not less than 20% (preferably, not less than 30%, not less than 40%, not less than 50%, not less than 60%) of the cells contained in the aggregate express FoxG1.

In a preferable embodiment in producing cerebral cells and/or a cerebral tissue, in step (1), human pluripotent stem cells (e.g., human iPS cells) are cultured in an adhered state in the absence of feeder cells in a serum-free medium containing a TGFβ signal transduction pathway inhibiting substance (e.g., SB431542) and bFGF; in step (2), the cells obtained in step (1) are cultured in suspension in a serum-free medium; and in step (3), the aggregate obtained in step (2) is cultured in suspension in a serum-free medium containing a Wnt signal transduction pathway inhibiting substance (IWR-1-endo) and a TGFβ signal transduction pathway inhibiting substance (e.g., SB431542).

In addition, in a preferable embodiment in producing cerebral cells and/or a cerebral tissue, in step (1), human pluripotent stem cells (e.g., human iPS cells) are cultured in an adhered state in the absence of feeder cells in a serum-free medium containing a BMP signal transduction pathway inhibiting substance (e.g., LDN193189) and bFGF; in step (2), the cells obtained in step (1) are cultured in suspension in a serum-free medium; and in step (3), the aggregate obtained in step (2) is cultured in suspension in a serum-free medium containing a Wnt signal transduction pathway inhibiting substance (IWR-1-endo) and a TGFβ signal transduction pathway inhibiting substance (e.g., SB431542).

In a preferable embodiment in producing cerebral cells and/or a cerebral tissue, in step (1), human pluripotent stem cells (e.g., human iPS cells) are cultured in an adhered state in the absence of feeder cells in a serum-free medium containing a TGFβ family signal transduction pathway inhibiting substance (e.g., a TGFβ signal transduction pathway inhibiting substance (e.g., SB431542, A-83-01), a Nodal/Activin signal transduction pathway inhibiting substance (e.g., Lefty), a BMP signal transduction pathway inhibiting substance (e.g., LDN193189), or a combination thereof (e.g., SB431542 and LDN193189) etc.);
a Sonic hedgehog signal transduction pathway activating substance (e.g., Shh protein, SAG, PMA); or
a combination of a TGFβ family signal transduction pathway inhibiting substance (e.g., Lefty, SB431542, A-83-01, LDN193189) and a Sonic hedgehog signal transduction pathway activating substance (e.g., Shh protein, SAG, PMA); and bFGF,
in step (2), the cells obtained in step (1) are cultured in suspension in a serum-free medium containing
a TGFβ family signal transduction pathway inhibiting substance (e.g., a TGFβ signal transduction pathway inhibiting substance (e.g., SB431542, A-83-01), a Nodal/Activin signal transduction pathway inhibiting substance (e.g., Lefty), a BMP signal transduction pathway inhibiting substance (e.g., LDN193189), or a combination thereof (e.g., SB431542 and LDN193189) etc.); and a Wnt signal transduction pathway inhibiting substance (IWR-1-endo) to form a cell aggregate, and
in step (3), the aggregate obtained in step (2) is cultured in suspension in a serum-free medium containing
a TGFβ family signal transduction pathway inhibiting substance (e.g., a TGFβ signal transduction pathway inhibiting substance (e.g., SB431542, A-83-01), a Nodal/Activin signal transduction pathway inhibiting substance (e.g., Lefty), a BMP signal transduction pathway inhibiting substance (e.g., LDN193189), or a combination thereof (e.g., SB431542 and LDN193189) etc.); and a Wnt signal transduction pathway inhibiting substance (IWR-1-endo), to give an aggregate containing a cerebral neural precursor cell, a cerebral cell or a cerebral tissue.

The medium of step (2) preferably contains a ROCK inhibiting substance (e.g., Y-27632).

More preferably, in step (2), the cells obtained in step (1) are cultured in suspension in a serum-free medium containing
a TGFβ family signal transduction pathway inhibiting substance (e.g., a TGFβ signal transduction pathway inhibiting substance (e.g., SB431542, A-83-01), a Nodal/Activin signal transduction pathway inhibiting substance (e.g., Lefty);
a Wnt signal transduction pathway inhibiting substance (IWR-1-endo); and
a ROCK inhibiting substance (e.g., Y-27632) to form a cell aggregate, and
in step (3), the aggregate obtained in step (2) is cultured in suspension in a serum-free medium containing
a TGFβ signal transduction pathway inhibiting substance (e.g., SB431542, A-83-01), or a Nodal/Activin signal transduction pathway inhibiting substance (e.g., Lefty); and
a Wnt signal transduction pathway inhibiting substance (IWR-1-endo), to give an aggregate containing a cerebral neural precursor cell, a cerebral cell or a cerebral tissue.

The obtained aggregate containing cerebral neural precursor cells may be used as it is as a reagent for evaluating toxicity or drug efficacy. An aggregate containing cerebral neural precursor cells is subjected to a dispersion treatment (e.g., trypsin/EDTA treatment or papain treatment), and the obtained cells are subjected to selection using FACS or MACS, whereby highly pure cerebral neural precursor cells can also be obtained.

Furthermore, the aggregate containing cerebral neural precursor cells is continuously cultured in a serum-free medium or serum-containing medium to further differentiate the cerebral neural precursor cells or cerebral cells, whereby a cerebral tissue having a layer structure can be produced.

A serum-free medium or serum-containing medium to be used for such medium is not particularly limited as long as it is as mentioned above. For example, a serum-containing medium which is a DMEM-F12 medium supplemented with 10% fetal bovine serum, N2 supplement, and retinoic acid, or a serum-free medium supplemented with an appropriate amount of a commercially available serum alternative such as N2 supplement and the like (e.g., medium such as DMEM-F12 medium supplemented with N2 supplement) and the like can be mentioned.

While the period for the culturing for inducing cerebral tissue from cerebral neural precursor cells varies depending on the intended cerebral layer-specific neuron, it is, for example, about 7 days to about 200 days.

The cerebral tissue is present forming a neuroepithelial structure in the aggregate. After completion of the suspension culturing, the aggregates may be fixed with a fixative such as para-formaldehyde solution and so on, and a frozen section may be prepared, after which formation of a cerebral tissue having a layer structure may be confirmed by immunostaining and the like. Since respective layers of a cerebral tissue are composed of different cerebral neural precursor cells, ventricular zone precursor cells, and cerebral layer structure specific neurons, formation of a layer structure can be confirmed using antibodies against the aforementioned markers expressed in these cells by the immunostaining. In one embodiment, the cerebral tissue is a FoxG1-positive neuroepithelial structure.

The cerebral tissue existing on the surface of the aggregate may be physically cut out from the aggregate by using tweezers and the like. In this case, since a neural tissue other than cerebral tissue may be formed on the surface of each aggregate, a part of the neural tissue cut out from the aggregate may be subjected to confirmation by the below-mentioned immunostaining and the like, whereby the tissue can be confirmed to be a cerebral tissue.

One embodiment of step (3) is a step of culturing the aggregate formed in step (2) in suspension in a serum-free medium or serum-containing medium containing a TGFβ signal transduction pathway inhibiting substance and/or a Wnt signal transduction pathway inhibiting substance at a concentration necessary for differentiation induction into a cerebral cell, until a cell expressing FoxG1 gene begins appearing to give an aggregate comprising cerebral neural precursor cells, and continuously culturing the aggregate containing the cerebral neural precursor cells in suspension in a serum-free medium or serum-containing medium until a cerebral tissue can be formed, whereby obtaining an aggregate comprising a cerebral tissue. In one embodiment, suspension culturing of an aggregate containing cerebral neural precursor cells are performed until not less than 20% (preferably, not less than 30%, not less than 40%, not less than 50%, not less than 60%) of the cells contained in the aggregate expresses FoxG1.

In one embodiment of step (3), the aggregate obtained in step (2), or an aggregate obtained by culturing the aggregate obtained in step (2) in suspension by the above-mentioned method may be subjected to adhesion culturing to form an adhered aggregate. The adhered aggregate is cultured in an adhered state in a serum-free medium or serum-containing medium containing a TGFβ signal transduction pathway inhibiting substance and/or a Wnt signal transduction pathway inhibiting substance at a concentration necessary for differentiation induction into a cerebral cell, until a cell expressing a FoxG1 gene begins appearing to give an aggregate containing cerebral neural precursor cells. The aggregate containing the cerebral neural precursor cells is continuously cultured in suspension in a serum-free medium or serum-containing medium until a cerebral tissue is formed, whereby an aggregate containing a cerebral tissue is obtained. In one embodiment, adhesion culturing of the aggregate containing cerebral neural precursor cells is performed until not less than 10% (preferably, not less than 20%, not less than 30%, not less than 40%, not less than 50%) of the cells express FoxG1.

By the production method 3 of the present invention, a cerebral tissue can be obtained from pluripotent stem cells with high efficiency. Since the retinal tissue obtained by the production method 3 of the present invention contains neurons specific to each of the cerebral layers, it is also possible to obtain cells constituting a cerebral tissue, such as layer structure specific neuron or a precursor cell thereof and the like. Which cell was obtained from the obtained cerebral tissue can be confirmed by a method known per se, for example, expression of a cell marker.

The obtained aggregate containing a cerebral tissue may also be directly used as a reagent for evaluating toxicity or drug efficacy. An aggregate containing a cerebral tissue is subjected to a dispersion treatment (e.g., trypsin/EDTA treatment), and the obtained cells are subjected to selection using FACS or MACS, whereby highly pure cerebral tissue-constituting cell, for example, highly pure cerebral layer structure specific neurons, can also be obtained.

4. Method for Evaluating Toxicity or Efficacy

Since a neural tissue or neural cells (e.g., retinal tissue, retinal progenitor cell, retinal layer-specific neuron, cerebral tissue, cerebral neural precursor cell, cerebral layer-specific neuron) produced by the production method 1, 2 or 3 of the present invention is useful as a material for disease study or drug discovery in a screening for a medicament for treating a disease due to a disorder of a neural tissue or neural cells, or in toxicity evaluation, it can be used as a reagent for evaluating toxicity or efficacy of a test substance. For example, iPS cells are produced from a human patient with a disease due to a disorder of a neural tissue (e.g., retinal tissue, cerebral tissue), particularly a hereditary disease, and using the iPS cells, a neural tissue or neural cells (e.g., retinal tissue, retinal progenitor cell, retinal layer-specific neuron, cerebral tissue, cerebral neural precursor cell, cerebral layer-specific neuron) is produced by the method of the present invention. The neural tissue or neural cells may reproduce the disorder of neural tissue causing the disease of the patient in vitro. Therefore, the present invention provides a method for evaluating toxicity or efficacy of a test substance, which comprises contacting the test substance with a neural tissue or neural cells (e.g., retinal tissue, retinal progenitor cell, retinal layer-specific neuron, cerebral tissue, cerebral neural precursor cell, cerebral layer-specific neuron) produced by the production method 1, 2 or 3 of the present invention, and detecting an influence of the substance on the cells or tissue.

For example, a neural tissue or neural cells (e.g., retinal tissue, retinal progenitor cell, retinal layer-specific neuron, cerebral tissue, cerebral neural precursor cell, cerebral layer-specific neuron) having a particular disorder (e.g., hereditary disorder), which is produced by the production method 1, 2 or 3 of the present invention, are cultured in the presence or absence (negative control) of a test substance. Then, the severity of disorder of the neural tissue or neural cells treated with the test substance is compared with that of the negative control. As a result, a test substance that reduced the severity of the disorder can be selected as a candidate substance for a medicament for treating the disease resulting from the disorder. For example, a test substance that improves the physiological activity (e.g., survival promotion or maturation) of neural cells produced by the production method of the present invention can be searched for as a candidate substance of a pharmaceutical product. Alternatively, according to the production method of the present invention, neural cells are prepared by inducing differentiation of the induced pluripotent stem cells which are prepared from a somatic cell having a gene mutation that causes a particular disorder such as a neurological disease and the like.

A candidate of a test substance effective as a therapeutic drug or prophylactic drug for the disorder can be searched for based on whether the neural cells added with a test substance show the aforementioned disorder, as an index.

For toxicity evaluation, a neural tissue or neural cells (e.g., retinal tissue, retinal progenitor cell, retinal layer-specific neuron, cerebral tissue, cerebral neural precursor cell, cerebral layer-specific neuron) produced by the production method 1, 2 or 3 of the present invention are cultured in the presence or absence (negative control) of a test substance. Then, the severity of toxicity on the neural tissue or neural cells treated with the test substance is compared with that of the negative control. As a result, a test substance that exerted toxicity as compared to the negative control can be judged as a substance having toxicity to the neural tissue or neural cells (e.g., retinal tissue, retinal progenitor cell, retinal layer-specific neuron).

That is, the present invention encompasses a method for evaluating toxicity comprising the following steps:
(step 1) a step of culturing a neural tissue or neural cells produced by the production method 1, 2 or 3 of the present invention under viable culture conditions for a given time in the presence of a test substance, and measuring the severity of cell injury,
(step 2) a step of culturing a neural tissue or neural cells produced by the production method 1, 2 or 3 of the present invention under viable culture conditions for a given time in the absence of test substance or in the presence of a positive control, and measuring the severity of cell injury, (step 3) a step of evaluating the toxicity of the test substance in step 1, based on the difference in the results measured in (step 1) and (step 2).

As used herein, "in the absence of a test substance" encompasses adding only a culture medium or a solvent used to dissolve the test substance instead of adding a test substance. In addition, "positive control" means a known compound having toxicity. Examples of the method for measuring the severity of cell injury include a method for measuring the number of viable cells, for example, a method for measuring intracellular ATP amount, a method for measuring the number of viable cells by cell staining (e.g., nucleus staining) and morphology observation and the like.

In step 3, as a method for evaluating the toxicity of a test substance, the measurement value in step 1 and the measurement value of the negative control in step 2 are compared, and when the severity of cell injury in step 1 is high, the test substance can be judged to have toxicity. In addition, the measurement value in step 1 and the measurement value of the positive control in step 2 are compared, and when the severity of cell injury in step 1 is the same or above, the test substance can be judged to have toxicity.

5. Pharmaceutical Composition

The present invention provides a pharmaceutical composition containing an effective amount of a neural tissue or neural cells (e.g., retinal tissue, retinal progenitor cell, retinal layer-specific neuron, cerebral tissue, cerebral neural precursor cell, cerebral layer-specific neuron) produced by the production method 1, 2 or 3 of the present invention.

The pharmaceutical composition contains an effective amount of a neural tissue or neural cells (e.g., retinal tissue, retinal progenitor cell, retinal layer-specific neuron, cerebral tissue, cerebral neural precursor cell, cerebral layer-specific neuron) produced by the production method 1, 2 or 3 of the present invention, and a pharmaceutically acceptable carrier.

As a pharmaceutically acceptable carrier, a physiological aqueous solvent (saline, buffer, serum-free medium etc.) can be used. Where necessary, in a transplantation therapy, a medicament containing a tissue or cells to be transplanted may contain conventionally used preservative, stabilizer, reducing agent, isotonizing agent and the like.

The pharmaceutical composition of the present invention can be produced as a suspension by suspending neural tissues or neural cells produced by the production method 1, 2 or 3 of the present invention in an appropriate physiological aqueous solvent. Where necessary, the composition may be added with a cryopreservative, cryopreserved, thawed when in use, washed with buffer, and used for a transplantation therapy.

A neural tissue obtained by the production method of the present invention may also be cut in an appropriate size with tweezers and the like to give a sheet preparation.

Cells obtained by the production method of the present invention may also be subjected to adhesion culturing in step (3) for differentiation induction to form a sheet-like cells to give a sheet preparation.

The pharmaceutical composition of the present invention is useful as a medicament for treating a disease due to a disorder of a neural tissue or neural cells (e.g., retinal tissue, retinal progenitor cell, retinal layer-specific neuron, cerebral tissue, cerebral neural precursor cell, cerebral layer-specific neuron).

6. Therapeutic Drug

A neural tissue or neural cells (e.g., retinal tissue, retinal progenitor cell, retinal layer-specific neuron, cerebral tissue, cerebral neural precursor cell, cerebral layer-specific neuron) produced by the production method 1, 2 or 3 of the present invention is useful for a transplantation therapy for a disease due to a disorder of a neural tissue or neural cells. Thus, the present invention provides a medicament for treating a disease due to a disorder of a neural tissue or neural cells, which contains a neural tissue or neural cells (e.g., retinal tissue, retinal progenitor cell, retinal layer-specific neuron, cerebral tissue, cerebral neural precursor cell, cerebral layer-specific neuron) produced by the production method 1, 2 or 3 of the present invention. A neural tissue or neural cells (e.g., retinal tissue, retinal progenitor cell, retinal layer-specific neuron, cerebral tissue, cerebral neural precursor cell, cerebral layer-specific neuron) produced by the production method 1, 2 or 3 of the present invention can be used as a medicament for treating the disease due to a disorder of a neural tissue or neural cells or to complement the corresponding damaged site in a damaged state of a neural tissue. A disease due to a disorder of a neural tissue or neural cells, and a damaged state of a neural tissue can be treated by transplanting a neural tissue or neural cells produced by the production method 1, 2 or 3 of the present invention to a patient with a disease due to a disorder of a neural tissue or neural cells, or a damaged state of a neural tissue, who requires transplantation, to complement the neural cells or disordered neural tissue itself. Examples of the disease due to a disorder of a neural tissue or neural related cells include neurodegenerative diseases (e.g., cerebral ischemic disorder, cerebral infarction, Parkinson's disease, spinal cord injury, cerebrovascular disorders or brain/spinal cord traumatic disorders (e.g., cerebral infarction, head traumatic brain injury (TBI) or spinal cord injury multiple system atrophy), typical neurodegenerative disease (amyotrophic lateral sclerosis (ALS), Parkinson's disease (PD), Parkinson syndrome, dementia of Alzheimer type, progressive supranuclear paralysis (PSP), Huntington's disease, multiple system atrophy (MSA), spinal cord cerebellar degeneration (SCD)), demyelination disease or neuromuscular disease (multiple sclerosis (MS), acute disseminated encephalomyelitis (ADEM), inflammatory pervasive sclerosis (Schilder disease), subacute sclerosing panencephalitis, progressive multifocal leukoencephalopathy, cerebral hypoxia, central pontine myelinolysis, Binswanger disease, Guillain-Barre syndrome, Fisher syndrome, chronic inflammatory demyelinating polyneuropathy, syringomyelia, spinocerebella degeneration, striatonigral denaturation (SND), olivopontocerebellar atrophy (OPCA), Shy-Drager syndrome), ophthalmologic disease (macular degeneration, age-related macular degeneration, retinal pigment denaturation, cataract, glaucoma, cornea disease, retinopathy), refractory epilepsy, progressive supranuclear paralysis, syringomyelia, spinal muscular atrophy (SMA), spinobulbar muscular atrophy (SBMA), primary lateral sclerosis (PLS), progressive supranuclear paralysis (PSP), corticobasal degeneration (CBD), Huntington's disease (HD), choreoacanthocytosis, syringomyelia, Frontotemporal lobar degeneration, Charcot-Marie-Tooth disease, dystonia, Pantothenate kinase-associated neurodegeneration, familial dementia, Parkinson's syndrome, senile dementia, spastic paraplegia, Lewy body dementia and the like. Examples of the disease due to a disorder of a cerebral tissue or cerebral-related cells include neurodegenerative diseases (e.g., cerebral ischemic injury, cerebral infarction, motor neuron disease, ALS, Alzheimer's disease, polyglutamine disease, cotricobasal degeneration). Examples of the disease due to a disorder of a retinal tissue or retinal-related cells include retinal denaturation, pigmentary degeneration of the retina, age-related macular degeneration, organic mercury poisoning, chloroquine retinopathy, glaucoma, diabetic retinopathy, retinopathy of newborn babies, and the like. Examples of a damaged state of a neural tissue include patients after neural tissue isolation, patients after radiation to a tumor in a neural tissue and trauma.

In transplantation therapy, rejection due to the difference in histocompatibility antigens often poses a problem. However, the problem can be solved by using pluripotent stem cells (e.g., induced pluripotent stem cells) established from the somatic cells of the transplantation recipient. That is, in a preferable embodiment, pluripotent stem cells (e.g., induced pluripotent stem cells) established from the somatic cells of the recipient are used as pluripotent stem cells in the method of the present invention, and a neural tissue or neural cells, which is immunologically self for the recipient, are produced and transplanted to the recipient.

In addition, an allogenic neural tissue or neural cell may be produced from a pluripotent stem cell (e.g., induced pluripotent stem cell) established from a somatic cell of others who are immunologically compatible with the recipient (e.g., compatible in HLA type and MHC type), and transplanted to the recipient.

EXAMPLES

The present invention is explained in detail in the following by referring to Examples, which are not to be construed as limitative.

Example 1: Example of Preconditioning of Human iPS Cells Using a TGFβ Family Signal Transduction Pathway Inhibiting Substance in Step 1

Human iPS cells (1231A3 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

As a specific maintenance culture operation, subconfluent human iPS cells (1231A3 strain) were first washed with PBS, and dispersed into single cells by using TrypLE Select (manufactured by Life Technologies). Thereafter, the above human iPS cells dispersed into single cells were seeded in a plastic culture dish coated with Laminin 511-E8, and feeder-free culturing was performed in StemFit medium in the presence of Y27632 (ROCK inhibiting substance, 10 µM). When a 6-well plate (manufactured by Iwaki, for cell culture, culture area 9.4 cm$^2$) was used as the above plastic culture dish, the number of plated cells for the above human iPS cells dispersed into single cells was set to 6×10$^3$. One day after seeding, the medium was changed to StemFit medium free of Y27632. Thereafter, once in 1-2 days, the medium was changed to StemFit medium free of Y27632. Thereafter, 6 days after seeding, the cells were cultured until subconfluent (60% of culture area is covered with cells).

As a specific example of preconditioning in step 1 of the production method of the present invention, the following operation was performed. First, the subconfluent human iPS cells (1231A3 strain) were washed with PBS, and dispersed into single cells by using TrypLE Select (manufactured by Life Technologies). Thereafter, the above human iPS cells dispersed into single cells were seeded in a plastic culture dish (manufactured by Iwaki) coated with Laminin 511-E8, and feeder-free culturing was performed in StemFit medium in the presence of Y27632 (ROCK inhibiting substance, 10 µM). When a 6-well plate (manufactured by Iwaki, culture area 9.4 cm$^2$) was used as the above plastic culture dish, the number of plated cells for the above human iPS cells dispersed into single cells was set to 6×10$^3$. When a 60 mm dish (manufactured by Iwaki, culture area 21 cm$^2$) was used as the above plastic culture dish, the number of plated cells for the above human iPS cells dispersed into single cells was set to 13×10$^3$. One day after seeding, the medium was changed to StemFit medium free of Y27632. Thereafter, once in 1-2 days, the medium was changed to StemFit medium free of Y27632. Thereafter, the cells were cultured until 5 days after seeding, namely, one day before subconfluence (50% of culture area is covered with cells). Even when cultured for 6 days after seeding, similar results are shown. The human iPS cells one day before subconfluence in the above feeder-free culturing were subjected to feeder-free culturing in the presence of SB431542 (TGFβR inhibitor (TGFβRi), 5 µM) (step 1: preconditioning treatment, FIG. 1 "Precondition TGFβRi 24 hr"), or in the absence thereof (step 1: without precondition treatment, FIG. 1 "Control") for 1 day. The bright field observation of cultured cells was performed under an inverted microscope (KEYENCE). As a result, it was found that the morphology of human iPS cell is not largely influenced by a treatment with TGFβR inhibitor (SB431542) during the feeder-free culturing (FIG. 1).

Example 2: Example-2 of Preconditioning of Human iPS Cells Using a TGFβ Family Signal Transduction Pathway Inhibiting Substance or a Shh Activating Substance in Step 1

Figure 2:
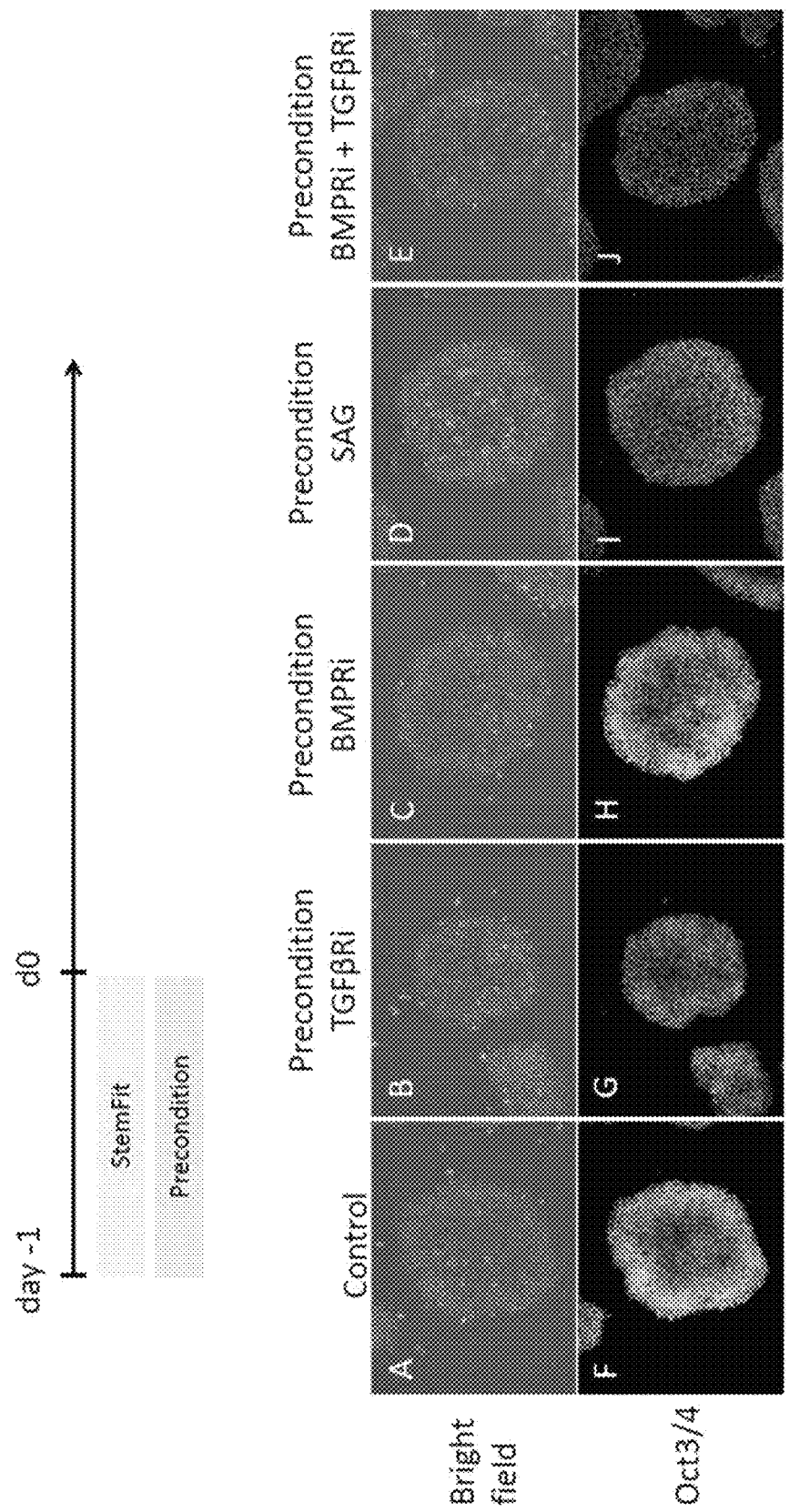
FIG. 2 shows culture conditions of Example 2, bright field images of cells after culture, and immunohistochemical staining images for Oct3/4.

Human iPS cells (1231A3 strain) were subjected to feeder-free culturing according to the method described in Example 1 in StemFit medium until one day before subconfluence. The human iPS cells one day before subconfluence were subjected to feeder-free culturing in the presence of SB431542 (TGFβR inhibitor, 5 µM), LDN193189 (BMPR inhibitor, 100 nM), SAG (Shh activating substance, 300 nM), or TGFβR inhibitor and BMPR inhibitor (SB431542 5 µM, and LDN193189 100 nM) (step 1: preconditioning treatment), or in the absence thereof (step 1: without preconditioning) for 1 day. The obtained cells were each fixed with 4% para-formaldehyde, and immunostaining for Oct3/4, which is one of the pluripotent stem cell markers, was performed and the immunostained cells were subjected to bright field observation and fluorescence image observation under an inverted fluorescence microscope (BIOREVO, KEYENCE). In judgment of whether the above marker is positive in an immunostaining analysis, an intensity value not less than 2 times higher than the background is determined as positive. As a result, it was found that the cells that underwent a preconditioning treatment with any compound are Oct3/4-positive, similar to the cells without preconditioning (FIG. 2). That is, the cells preconditioned under these conditions were found to have maintained pluripotent-like state.

Example 3: Example of Formation of Cell Aggregate from Human iPS Cells by Using TGFβ Family Signal Transduction Pathway Inhibiting Substance in Step 1

Human iPS cells (1231A3 strain) were subjected to feeder-free culturing until one day before subconfluence in StemFit medium according to the method described in Example 1. The human iPS cells one day before subconfluence were subjected to feeder-free culturing in the presence of SB431542 (TGFβR inhibitor, 5 μM) (step 1, precondition: TGFβRi treatment) or in the absence thereof (step 1: without preconditioning) for 1 day.

The above human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.2 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, and 1× Chemically defined lipid concentrate was used. At the time of the start of suspension culturing (day 0 after the start of suspension culturing, start of step 2), Y27632 (final concentration 20 μM) was added to the above serum-free medium. By day 2 after the start of suspension culturing, a cell aggregate was formed under both preconditioning conditions and conditions without preconditioning (step 2 completed, step 3 start). On day 3 after the start of suspension culturing, a serum-free medium (50 μl) free of Y27632 was added.

Figure 3:
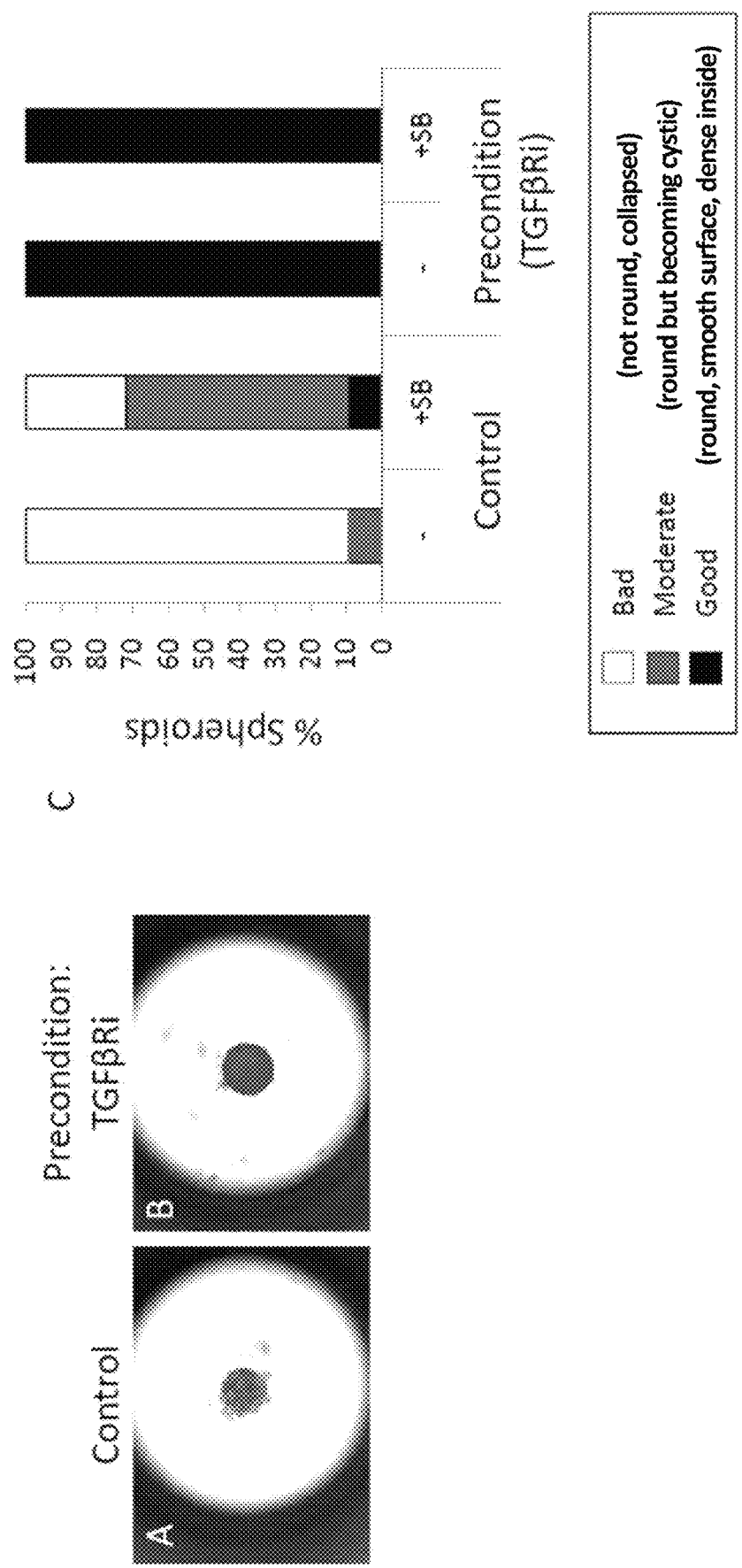
FIG. 3 shows bright field images of aggregates (A and B), and a graph quantifying the level of the morphology of aggregates (C).

The thus-prepared cells on day 6 after the start of suspension culturing were subjected to bright field observation under an inverted microscope (KEYENCE) (FIG. 3). As a result, it was found that a cell aggregate of the cells that underwent a preconditioning treatment in the presence of a TGFβR inhibitor (SB431542) (FIG. 3B) had a better shape than the aggregate of the cells that did not undergo a preconditioning treatment (FIG. 3A).

Furthermore, bright field observation of the form of the cell aggregate on day 6 after the start of suspension culturing was performed under an inverted microscope, and the form was categorized into good form (FIG. 3C black bar, spherical, smooth surface and dense inside), medium form (FIG. 3 gray bar, spherical, forming cyst), and bad form (FIG. 3C white bar, not spherical, collapsed) and quantified. As a result, it was found that, under conditions without preconditioning, about 90% of cell aggregates had a bad form, about 10% of cell aggregates had a medium form, and 0% of cell aggregates had a good form (FIG. 3C "Control", first bar graph from the left). In contrast, it was found that, under conditions with preconditioning treatment, about 0% of cell aggregate had a bad form, about 0% of cell aggregates had a medium form, and about 100% of cell aggregates had a good form (FIG. 3C "precondition (TGFβRi)", third bar graph from the left). That is, it was found that preconditioning treatment with a TGFβR inhibitor (SB431542, 5 μM) in step 1 results in a good form of the cell aggregate in steps 2 and 3.

Example 4: Example of Formation of Cell Aggregate from Human iPS Cells by Using TGFβ Family Signal Transduction Pathway Inhibiting Substance in Step 1 or Step 2

Human iPS cells (1231A3 strain) were subjected to feeder-free culturing until one day before subconfluence in StemFit medium according to the method described in Example 1. The human iPS cells one day before subconfluence were subjected to feeder-free culturing in the presence of SB431542 (TGFβR inhibitor, 5 μM) (step 1, precondition: TGFβRi treatment) or in the absence thereof (step 1: without precondition) for 1 day.

The above human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.2 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culturing (day 0 after the start of suspension culturing, start of step 2), Y27632 (final concentration 20 μM) and TGFβR inhibitor (SB431542, 5 μM) were added to the above serum-free medium. By day 2 after the start of suspension culturing, a cell aggregate was formed under both preconditioning conditions and conditions without preconditioning (step 2 completed, step 3 start). On day 3 after the start of suspension culturing, a serum-free medium (50 μl) free of Y27632 and supplemented with a TGFβR inhibitor (SB431542, 5 μM) was added.

The form of the thus-prepared cell aggregates on day 6 after the start of suspension culturing was observed according to the method described in Example 3. As a result, under conditions without a preconditioning treatment in step 1 and supplemented with a TGFβR inhibitor (SB431542) in step 2, it was found that about 30% of cell aggregates had a bad form, about 60% of cell aggregates had a medium form, and about 10% of cell aggregates had a good form (FIG. 3C, 'Control+SB', second bar graph from the left). In contrast, it was found that, under conditions with a preconditioning treatment in step 1 and addition of a TGFβR inhibitor (SB431542) in step 2, about 0% of cell aggregates had a bad form, about 0% of cell aggregates had a medium form, and about 100% of cell aggregates had a good form (FIG. 3C, 'Precondition (TGFβRi)+SB', fourth bar graph from the left). That is, it was found that a preconditioning treatment with a TGFβW inhibitor (SB431542, 5 μM) in step 1 even under conditions with the addition of a TGFβR inhibitor (SB431542) in step 2 and step 3 results in a good form of the cell aggregate as compared to the absence of a preconditioning treatment in step 1.

Furthermore, a comparison of Example 3 and Example 4 reveals that conditions with a preconditioning treatment with a TGFβR inhibitor (SB431542) in step 1, and without addition of a TGFβR inhibitor (SB431542) in step 2 and step 3 (FIG. 3C "precondition (TGFβRi)", the third bar graph from the left), produce higher proportion of the cell aggregates with good shape than the conditions without a preconditioning treatment in step 1, and with addition of TGFβR inhibitor (SB431542) in step 2 and step 3 (FIG. 3C "Control+SB", the second bar graph from the left). That is, it was found that the preferable timing of addition of a TGFβR inhibitor (SB431542) is in step 1 (preconditioning).

Example 5: Example of Formation of Cell Aggregate from Human iPS Cells by Using TGFβ Family Signal Transduction Pathway Inhibiting Substance in Step 1

Human iPS cells (1231A3 strain) were subjected to feeder-free culturing until one day before subconfluence in StemFit medium according to the method described in Example 1. The human iPS cells on one day before subconfluence were subjected to feeder-free culturing in the presence of SB431542 (TGFβR inhibitor, 5 μM) or LDN193189 (BMPR inhibitor, 100 nM) (step 1: preconditioning treatment) or in the absence thereof (step 1: without preconditioning) for 1 day.

The above human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.2 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol and 1× Chemically defined lipid concentrate was used. At the time of the start of suspension culturing (day 0 after the start of suspension culturing, start of step 2), Y27632 (final concentration 20 μM) was added to the above serum-free medium. By day 2 after the start of suspension culturing, a cell aggregate was formed under both preconditioning conditions and conditions without preconditioning (step 2 completed, step 3 start). On day 3 after the start of suspension culturing, a serum-free medium (50 μl) free of Y27632 was added. On day 6 or later after the start of suspension culturing, 50-70% volume of the medium was changed with the above serum-free medium free of Y27632 once per 2-4 days.

The thus-prepared cell aggregates on day 9 after the start of suspension culturing were subjected to bright field observation under an inverted microscope (KEYENCE) (FIG. 4). As a result, it was found that, similar to Example 3, the cells that underwent a preconditioning treatment in the presence of a TGFβR inhibitor (SB431542) in step 1 showed a good shape of cell aggregate in step 3 (FIG. 4B), as compared to the untreated group (FIG. 4A). Furthermore, it was found that even the cells that underwent a preconditioning treatment in the presence of a BMPR inhibitor (SB431542) in step 1 showed a good shape of cell aggregate in step 3 (FIG. 4C), as compared to the untreated group (FIG. 4A). That is, it was found that use of any of TGFβR inhibitor (SB431542) and BMPR inhibitor (LDN193189), which are TGFβ family signal transduction pathway inhibiting substances, for a preconditioning treatment (step 1) provides an effect of achieving a good shape of a cell aggregate.

Example 6: Example of Formation of Neural Tissue from Human iPS Cells with Preconditioned by Using TGFβ Family Signal Transduction Pathway Inhibiting Substance in Step 1

Human iPS cells (1231A3 strain) were subjected to feeder-free culturing until one day before subconfluence in StemFit medium according to the method described in Example 1. The human iPS cells on one day before subconfluence were subjected to feeder-free culturing in the presence of LDN193189 (BMPR inhibitor, 100 nM) (step 1: preconditioning) or in the absence thereof (step 1: without preconditioning) for 1 day.

The above human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.2 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culturing (day 0 after the start of suspension culturing, start of step 2), Y27632 (final concentration 20 μM) was added to the above serum-free medium. By day 2 after the start of suspension culturing, cell aggregates were formed under both conditions with preconditioning and conditions without preconditioning (step 2 completed, step 3 start). On day 3 after the start of suspension culturing, a serum-free medium (50 μl) free of Y27632 was added. On day 6 or later after the start of suspension culturing, a half amount of the medium was changed to the above serum-free medium free of Y27632 once per 2-4 days. In the half-medium change operation, a half volume, namely 75 μl, of the medium in the culture vessel was discarded, the above fresh serum-free medium (75 μl) was added to make the total medium amount 150 μl.

Thus-prepared cells on day 23 after the start of suspension culturing were subjected to the bright field observation suspension culturing under an inverted microscope (KEYENCE) (FIG. 5A, B). As a result, it was found that, under conditions without a preconditioning treatment in step 1, the cell aggregate collapsed and a neural tissue was not formed at all in step 3 (FIG. 5A). On the other hand, it was found that the cells that underwent a preconditioning treatment in the presence of a BMPR inhibitor (LDN193189) in step 1 formed cell aggregates with good shape in step 3, and a neural tissue having a neuroepithelial structure was formed (FIG. 5B). Furthermore, the cells on day 23 after the start of suspension culturing was subjected to the bright field observation under an inverted microscope (KEYENCE), and "collapsed cell aggregate in which a neural tissue is not more than 3% (cell aggregate with a bad form)", "maintained cell aggregate in which a neural tissue is not more than 10% (cell aggregate with a medium level form)" and "maintained cell aggregate in which a neural tissue is not less than 10% (cell aggregate containing a neural tissue)" were each quantified. As a result, it was found that, under the conditions without preconditioning in step 1, about 100% was cell aggregate with a bad form, about 0% was cell aggregate with a medium level form, and about 0% was cell aggregate containing a neural tissue. In contrast, it was found that, under the conditions with preconditioning in step 1, about 0% was cell aggregate with a bad form, about 0% was cell aggregate with a medium level form, and about 100% was cell aggregate containing a neural tissue.

Furthermore, cell aggregates on day 23 after the start of suspension culturing, which were produced from the above iPS cells that underwent a preconditioning treatment as a starting material (conditions of FIG. 5B) were fixed with 4% para-formaldehyde to prepare frozen sections. These frozen sections were immunostained for Nestin (anti-Nestin antibody, Millipore K.K., mouse), which is one of the neural tissue markers (neural precursor cells), TuJ1 (anti-βIII-tubulin antibody, Promega K.K., mouse), which is one of the neural tissue markers (neuron), or PSA-NCAM (anti-PSA-NCAM antibody, Millipore K.K., mouse IgM), which is one of the neural tissue markers. These immunostained sections were observed under an inverted fluorescence microscope. As a result, it was found that, in the cell aggregates prepared under conditions with preconditioning with a BMPR inhibitor (LDN193189), the proportion of Nestin-positive cells in the total cells was about 20%, the proportion of TuJ1-positive cells in the total cells was about 70%, and the proportion of PSA-NCAM-positive cells in the total cells was about 70% (FIG. 5C-E). Furthermore, it could be confirmed from the analysis of serial sections, that the regions that could be determined to be neural tissue by morphology observation in the bright field under an inverted microscope were Nestin-positive, TuJ1-positive, and PSA-NCAM-positive (FIG. 5C-E). From the results, it was found that a neural tissue can be produced efficiently in step 3 by using human iPS cells subjected to feeder-free culturing as a starting material and preconditioning with a TGFβ family signal transduction pathway inhibiting substance in step 1.

Example 7: Example of Formation of Retinal Tissue from Human iPS Cells, Including Preconditioning Using TGFβ Family Signal Transduction Pathway Inhibiting Substance in Step 1 and Using BMP Signal Transduction Pathway Activating Substance as Differentiation-Inducing Factor in Step 3

Human iPS cells (1231A3 strain) were subjected to feeder-free culturing until one day before subconfluence in StemFit medium according to the method described in Example 1. The human iPS cells one day before subconfluence were subjected to feeder-free culturing in the presence of LDN193189 (BMPR inhibitor, 100 nM) (step 1: preconditioning) for 1 day.

The above human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.2 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culturing (day 0 after the start of suspension culturing, start of step 2), Y27632 (final concentration 20 µM) was added to the above serum-free medium. By day 2 after the start of suspension culturing, a cell aggregate was formed under conditions with preconditioning (step 2 completed, step 3 start). On day 3 after the start of suspension culturing, a serum-free medium (50 µl) free of Y27632 was added.

Figure 6:
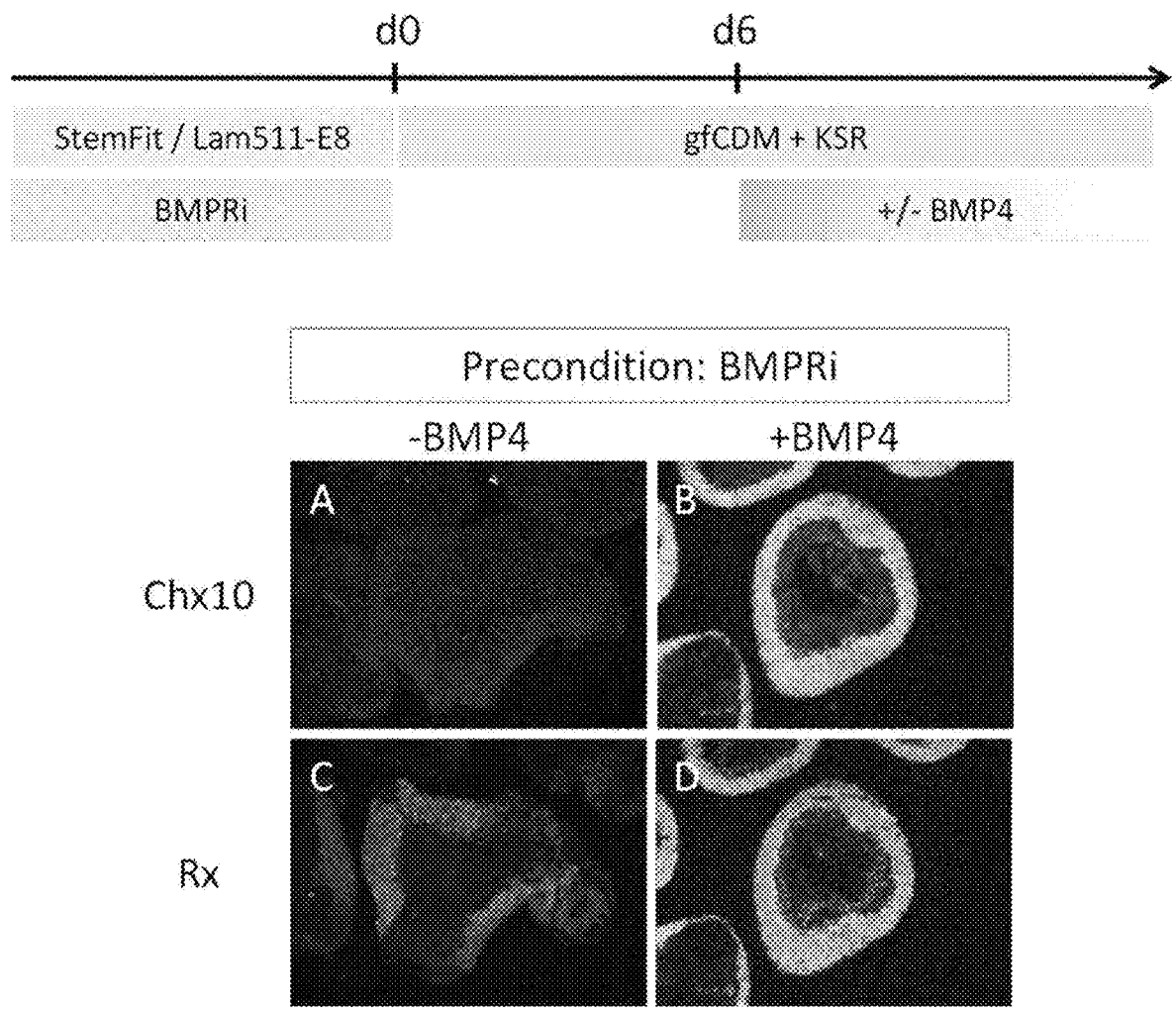
FIG. 6 shows culture conditions of Example 7, and immunohistochemical staining images (A-D) of aggregates for retinal tissue markers (Chx10, Rx).

Here, as step 3, culturing was performed under the following condition 1 and condition 2: Under condition 1(+BMP), on day 6 after the start of suspension culturing, the medium was changed to a medium free of Y27632 and containing human recombinant BMP4 (manufactured by R&D) such that the final concentration of exogenous human recombinant BMP4 was 1.5 nM (55 ng/ml) (FIG. 6B, D). Under condition 2(−BMP), on day 6 after the start of suspension culturing, a half amount of the medium was changed to a medium free of Y27632 and free of a BMP signal transduction pathway activating substance, without adding exogenous human recombinant BMP4 (FIG. 6A, C).

On day 6 or later from the start of suspension culturing, a half amount of the medium was changed to the above serum-free medium free of Y27632 and human recombinant BMP4 once per 2-4 days. On day 23 after the start of suspension culturing, the morphology was observed by inverted microscope. As a result, it was found that the cell aggregates were maintained and neural tissues were formed in this Example using preconditioned iPS cells as a starting material.

The thus-prepared cell aggregates on day 23 after the start of suspension culturing, which were produced from the above iPS cells that underwent a preconditioning treatment in step 1 as a starting material were fixed with 4% paraformaldehyde to prepare frozen sections. These frozen sections were immunostained for Chx10 (anti-Chx10 antibody, Exalpha, sheep), which is one of the retinal tissue markers, or Rx (anti-Rx antibody, Takara, guinea pig), which is one of the retinal tissue markers. These immunostained sections were observed under an inverted fluorescence microscope. As a result, it was found that, in the cell aggregates prepared under conditions with preconditioning with a BMPR inhibitor (LDN193189) in step 1 and without addition of BMP4 in step 3, the proportion of Rx-positive cells in the total cells was less than 10% (Rx-strong positive (corresponding to retina) was less than 3%, Rx-weak positive (corresponding to neural tissue other than retina) was less than 7%), and the proportion of Chx10-positive cells was also less than 3% (FIG. 6A, C). On the other hand, it was found that, in the cell aggregates prepared under conditions with preconditioning with a BMPR inhibitor (LDN193189) in step 1 and addition of BMP4 in step 3, the proportion of Rx-positive cells in the total cells was about 60%, and the proportion of Chx10-positive cells in the total cells was also about 60% (FIG. 6B,D). Furthermore, from the analysis of serial sections, it was suggested that, in a neural tissue having a high (about 95%) proportion of Chx10-positive cells, Rx is also strongly positive (FIG. 6B,D). From the results, it was found that a neural tissue is formed under the conditions involving preconditioning in step 1, and further that a retinal tissue can be efficiently produced from feeder-free-cultured human iPS cells (hereinafter sometimes to be referred to as feeder-free human iPS cells), by the addition of a BMP signal transduction pathway activating substance into the suspension culturing in step 3 as a differentiation-inducing factor during suspension culturing.

Example 8: Example of Formation of Neural Tissue from Feeder-Free Human iPS Cells, Using TGFβ Family Signal Transduction Pathway Inhibiting Substance or Shh Signal Transduction Pathway Activating Substance in Step 1, and Shh Signal Transduction Pathway Activating Substance in Step 2

Human iPS cells (1231A3 strain) were subjected to feeder-free culturing until one day before subconfluence in StemFit medium according to the method described in Example 1. The human iPS cells one day before subconfluence were subjected to feeder-free culturing in the presence of SB431542 (TGFβR inhibitor, 5 µM), LDN193189 (BMPR inhibitor, 100 nM) or SAG (Shh signal transduction pathway activating substance, 300 nM), or in the absence thereof (step 1: without preconditioning) for 1 day.

The above human iPS cells were treated with the cell dispersion solution by using TrypLE Select (Life Technologies), further dispersed into single cells by pipetting operation, and the above human iPS cells dispersed into single cells were suspended in 100 µl of a serum-free medium at $1.2 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used.

At the time of the start of suspension culturing (day 0 after the start of suspension culturing, start of step 2), the cells were cultured under the following condition 1 and condition 2. In condition 1(+SAG), Y27632 (final concentration 20 μM) and SAG (Shh signal transduction pathway activating substance, 300 nM) were added to the above serum-free medium at the time of the start of suspension culturing (FIG. 7B-D, F-H, '+SAG'). In condition 2 (−SAG), Y27632 (final concentration 20 μM) was added and SAG was not added to the above serum-free medium at the time of the start of suspension culturing (FIG. 7A, E, '−'). By day 2 after the start of suspension culturing, cell aggregates were formed under both conditions (step 2 completed, step 3 start). On day 3 after the start of suspension culturing, a serum-free medium (50 μl) free of Y27632 and SAG was added.

On day 6 after the start of suspension culturing, the medium was changed with a medium free of Y27632 and SAG and containing or not containing human recombinant BMP4 (manufactured by R&D) to give a medium containing an exogenous human recombinant BMP4 at a final concentration of 1.5 nM (FIG. 7E-H), or a medium free of a BMP signal transduction pathway activating substance (FIG. 7A-D). On day 6 or later from the start of suspension culturing, a half amount of the medium was changed to the above serum-free medium free of Y27632, SAG and human recombinant BMP4 once per 2-4 days.

Figure 7:
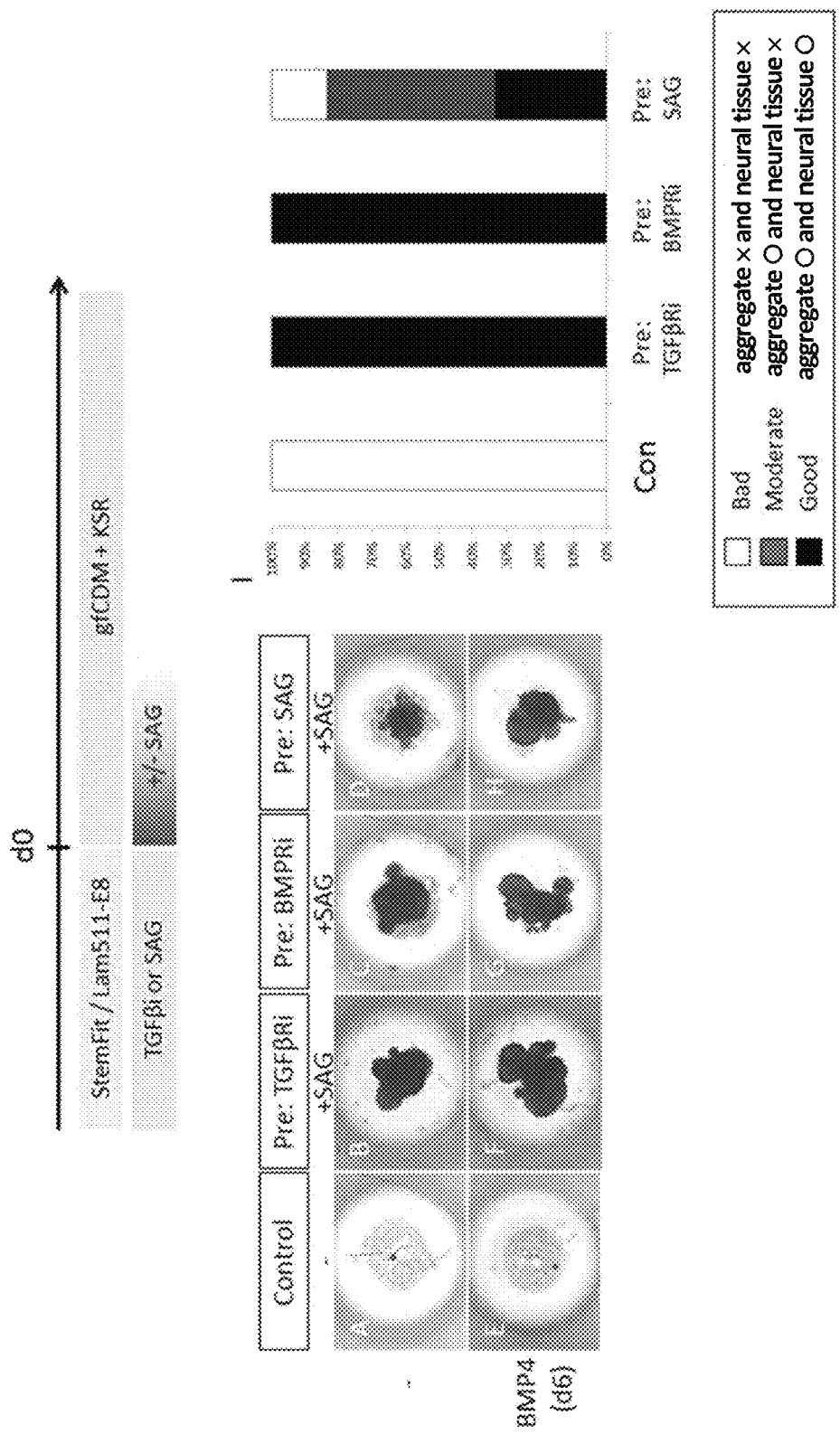
FIG. 7 shows culture conditions of Example 8, bright field images of aggregates after culture (A-H), and a graph quantifying the level of the morphology of aggregates (I).
Figure 8:
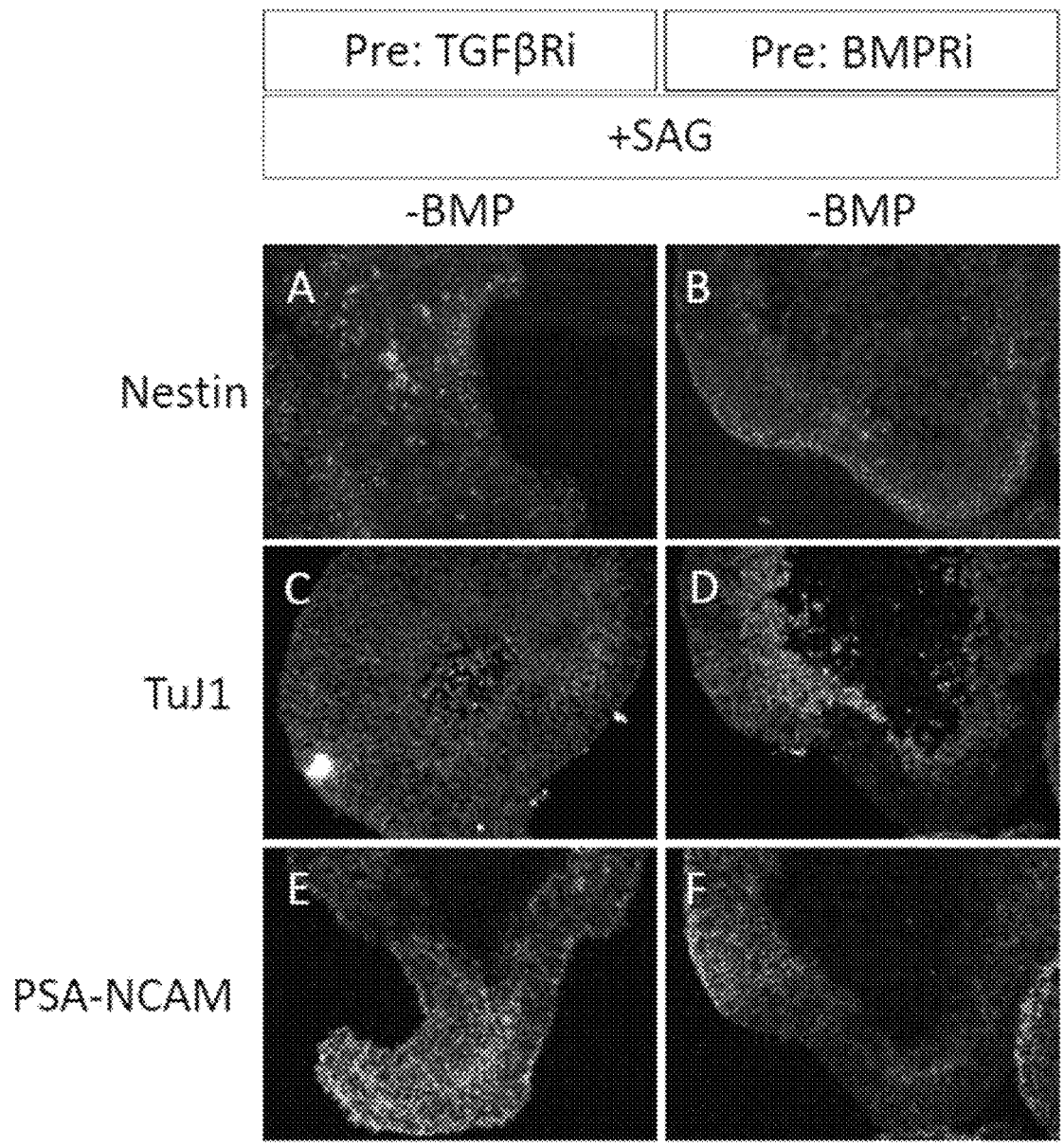
FIG. 8 shows immunohistochemical staining images of aggregates for neural tissue markers (Nestin, TuJ1, PSA-NCAM).

The thus-prepared cells were subjected to bright field observation on day 23 after the start of suspension culturing under an inverted microscope (KEYENCE) (FIG. 7). Furthermore, the form of the cell aggregate was quantified according to the method described in Example 6 on day 23 after the start of suspension culturing (FIG. 7I). As a result, it was found that, under conditions without preconditioning in step 1 and without addition of SAG in step 2, the cell aggregates are collapsed, and a neural tissue is not formed (FIG. 7A,E). On the other hand, it was found that, under conditions involving preconditioning with TGFβR inhibitor (SB431542), BMPR inhibitor (LDN193189), or Shh signal transduction pathway activating substance in step 1, and addition of a Shh signal transduction pathway activating substance in step 2, the cell aggregates are formed, and a neural tissue can be formed efficiently (FIG. 7B-D, F-I).

Furthermore, the above cell aggregates on day 23 after the start of suspension culturing, which were produced from the above iPS cells that underwent a preconditioning treatment with TGFβR inhibitor (SB431542) or BMPR inhibitor (LDN193189) as a starting material were fixed with 4% para-formaldehyde to prepare frozen sections. These frozen sections were immunostained for Nestin (anti-Nestin antibody, Nihon Millipore K.K., mouse), which is one of the neural tissue markers (neural precursor cells), TuJ1 (anti-βIII-tubulin antibody, Promega KK, mouse), which is one of the neural tissue markers (neurons), or PSA-NCAM (anti-PSA-NCAM antibody, Millipore K.K., mouse IgM), which is one of the neural tissue markers. These immunostained sections were observed under an inverted fluorescence microscope. As a result, it was found that, in the cell aggregates prepared under conditions with preconditioning with a TGFβR inhibitor (SB431542) or BMPR inhibitor (LDN193189), the proportion of Nestin-positive cells in the total cells was about 20%, the proportion of TuJ1-positive cells in the total cells was about 70%, and the proportion of PSA-NCAM-positive cells was about 70% (FIG. 8A-F). Furthermore, it could be confirmed from the analysis of serial sections, that the regions that could be identified to be neural tissue by morphology observation in the bright field images were Nestin-positive, TuJ1-positive, and PSA-NCAM-positive (FIG. 8A-F).

From these results, it was found that a neural tissue can be produced efficiently from feeder-free human iPS cells under conditions involving preconditioning with a TGFβ family signal transduction pathway inhibiting substance or a Shh signal transduction pathway activating substance in step 1, and further involving addition of a Shh signal transduction pathway activating substance in step 2, even when a BMP signal transduction pathway activating substance is added or not added in step 3.

Figure 9:
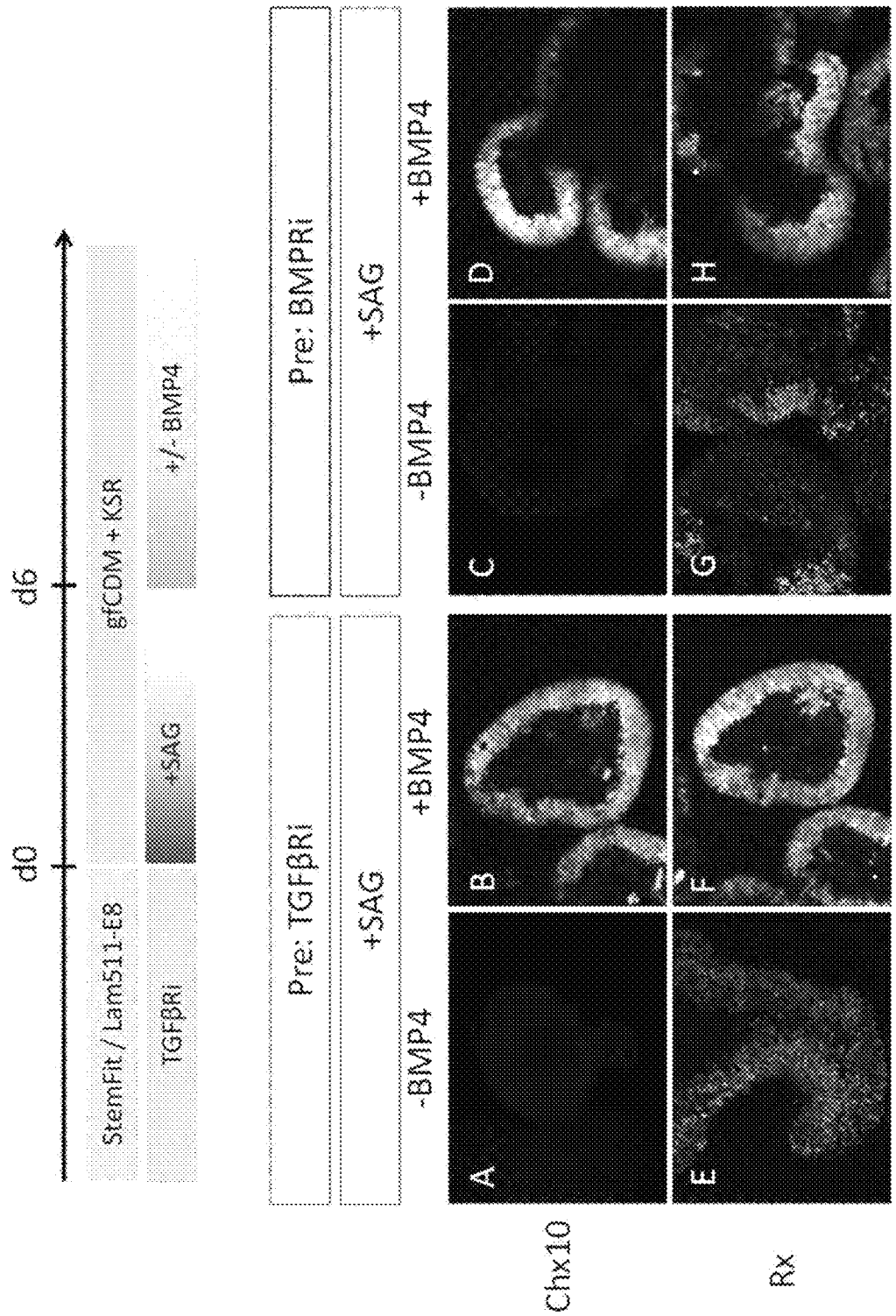
FIG. 9 shows culture conditions of Example 9, and immunohistochemical staining images of aggregates for retinal tissue markers (Chx10, Rx) (A-H).

Example 9: Example of Formation of Retinal Tissue from Feeder-Free Human iPS Cells Using TGFβ Family Signal Transduction Pathway Inhibiting Substance in Step 1, Shh Signal Transduction Pathway Activating Substance in Step 2, and BMP Signal Transduction Pathway Activating Substance in Step 3 as Differentiation-Inducing Factor Cell aggregate were prepared according to the method described in Example 8 under conditions in which human iPS cells using StemFit medium as a feeder-free medium were used as a starting material, TGFβR inhibiting substance (SB431542) or BMPR inhibiting substance (LDN193189) was used in step 1, Shh signal transduction pathway activating substance was used in step 2, and BMP signal transduction pathway activating substance was added or not added in step 3. Neural tissues were formed in all the aggregates formed under all these conditions on day 23 after the start of suspension culturing. The above cell aggregates were fixed with 4% para-formaldehyde to prepare frozen sections. These frozen sections were immunostained for Chx10 (anti-Chx10 antibody, Exalpha, sheep), which is one of the retinal tissue markers, or Rx (anti-Rx antibody, Takara, guinea pig), which is one of the retinal tissue markers. These immunostained sections were observed under an fluorescence microscope. As a result, it was found that, in the cell aggregates produced under conditions involving preconditioning with a TGFβR inhibitor (SB431542) or BMPR inhibitor (LDN193189) in step 1, addition of a Shh signal transduction pathway activating substance in step 2, and without addition of BMP4 in step 3, the proportion of Rx-positive cells in the total cells was less than 10% (Rx-strong positive (corresponding to retina) was less than 3%, Rx-weak positive (corresponding to neural tissue other than retina) was less than 7%), and the proportion of Chx10-positive cell was also less than 3% (FIG. 9A, C, E, G). On the other hand, it was found that, in the cell aggregates produced under conditions involving preconditioning with a TGFβR inhibitor (SB431542) in step 1, addition of a Shh signal transduction pathway activating substance in step 2, and addition of BMP4 in step 3, the proportion of Rx-positive cells in the total cells was 80% or more, and the proportion of Chx10-positive cells in the total cells was also 70% or more (FIG. 9B, F). Also, it was found that, in the cell aggregates produced under conditions involving preconditioning with a BMPR inhibitor (LDN193189) in step 1, addition of a Shh signal transduction pathway activating substance in step 2, and addition of BMP4 in step 3, the proportion of Rx-positive cells in the total cells was 50% or more, the proportion of Chx10-positive cells in the total cells was also 40% or more (FIG. 9D, H). Furthermore, it was found from the analysis of serial sections that, in a neural tissue having a high (not less than 95%) proportion of Chx10-positive cells, Rx is also strongly positive (FIG. 9B, D, F, H).

From these results, it was found that retinal tissue can be produced efficiently from feeder-free human iPS cells by preconditioning with a TGFβ family signal transduction pathway inhibiting substance in step 1, adding a Shh signal transduction pathway activating substance in step 2, and adding a BMP signal transduction pathway activating substance as a differentiation-inducting substance into suspension culturing in step 3.

Example 10: Example of Formation of Cell Aggregate Using Human iPS Cells in Essential 8 Medium as Feeder-Free Medium as Starting Material, and TGFβ Family Signal Transduction Pathway Inhibiting Substance in Step 1

Human iPS cell (1231A3 strain, obtained from Kyoto University) was subjected to feeder-free culturing according to the method described in "Scientific Reports, 4, 3594 (2014)". As a feeder-free medium, Essential 8 medium (manufactured by Life technologies, Nature Methods, 8, 424-429 (2011)) was used, and as a feeder-free scaffold, Laminin 511-E8 (manufactured by Nippi, Inc.) was used.

As a specific maintenance culture operation, subconfluent (about 60% of culture area is covered with cells) human iPS cells (1231A3 strain) were first washed with PBS, and dispersed into single cells by using TrypLE Select (manufactured by Life Technologies). Thereafter, the above human iPS cells dispersed into single cells were seeded in a plastic culture dish (manufactured by Iwaki) coated with Laminin 511-E8, and feeder-free culturing was performed in Essential 8 medium in the presence of Y27632 (10 μM, ROCK inhibiting substance). When a 6-well plate (manufactured by Iwaki, culture area 9.4 cm$^2$) was used as the above plastic culture dish, the number of plated cells for the above human iPS cells dispersed into single cells was set to 6×10$^3$. One day after seeding, the medium was changed to Essential 8 medium free of Y27632. Thereafter, the cells were cultured until 6 days after seeding, namely, subconfluence (60% of culture area is covered with cells).

As a preconditioning operation, subconfluent human iPS cells (1231A3 strain) were first washed with PBS, and dispersed into single cells by using TrypLE Select (manufactured by Life Technologies). Thereafter, the above human iPS cells dispersed into single cells were seeded in a plastic culture dish (manufactured by Iwaki) coated with Laminin 511-E8, and feeder-free culturing was performed in Essential 8 medium in the presence of Y27632 (10 μM, ROCK pathway inhibiting substance). When a 6-well plate (manufactured by Iwaki, for cell culture, culture area 9.4 cm$^2$) was used as the above plastic culture dish, the number of plated cells for the above human iPS cells dispersed into single cells was set to 6×10$^3$. One day after seeding, the medium was changed to Essential 8 medium free of Y27632. Thereafter, the cells were cultured until 5 days after seeding, namely, one day before subconfluence (50% of culture area is covered with cells). The above feeder-free cultured human iPS cells one day before subconfluence were subjected to feeder-free culturing in the presence of SB431542 (TGFβR inhibitor, 5 μM), LDN193189 (BMPR inhibitor, 100 nM), or TGFβR and BMPR dual inhibitions (5 μM SB431542, and 100 nM LDN193189) (step 1: preconditioning), or in the absence thereof (step 1: without preconditioning, control) for 1 day. The bright field observation of the cultured cells was performed under an inverted microscope (KEYENCE). As a result, it was found that the morphology of human iPS cell is not largely influenced by a treatment with TGFβ family signal transduction pathway inhibitor during the feeder-free culturing.

The above human iPS cells were treated with the cell dispersion solution by using TrypLE Select (Life Technologies), further dispersed into single cells by pipetting operation, and the above human iPS cells dispersed into single cells were suspended in 100 μl of a serum-free medium at 1.2×10$^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used.

At the time of the start of suspension culturing (day 0 after the start of suspension culturing, start of step 2), the cells were cultured under the following 2 conditions including condition 1 and condition 2. In condition 1(+SAG), Y27632 (final concentration 20 μM) and SAG (Shh signal transduction pathway activating substance, 300 nM) were added to the above serum-free medium at the time of the start of suspension culturing (FIG. 10C, F, H, J, L, N "+SAG"). In condition 2 (−SAG), Y27632 (final concentration 20 μM) was added and SAG was not added to the above serum-free medium at the time of the start of suspension culturing (FIG. 10A, B, D, E, G, I, K, M "−"). By day 2 after the start of suspension culturing, cell aggregates were formed under both conditions (step 2 completed, step 3 start). On day 3 after the start of suspension culturing, a serum-free medium (50 μl) free of Y27632 and SAG was added.

On day 6 after the start of suspension culturing, the medium was changed with a medium free of Y27632 and SAG and containing or not containing human recombinant BMP4 (manufactured by R&D) such that a medium contained an exogenous human recombinant BMP4 at a final concentration of 1.5 nM (FIG. 10D-F), or a medium did not contain a BMP signal transduction pathway activating substance (FIG. 10K-N). On day 6 or later from the start of suspension culturing, a half amount of the medium was changed to the above serum-free medium free of Y27632, SAG and human recombinant BMP4 once per 2-4 days.

Figure 10:
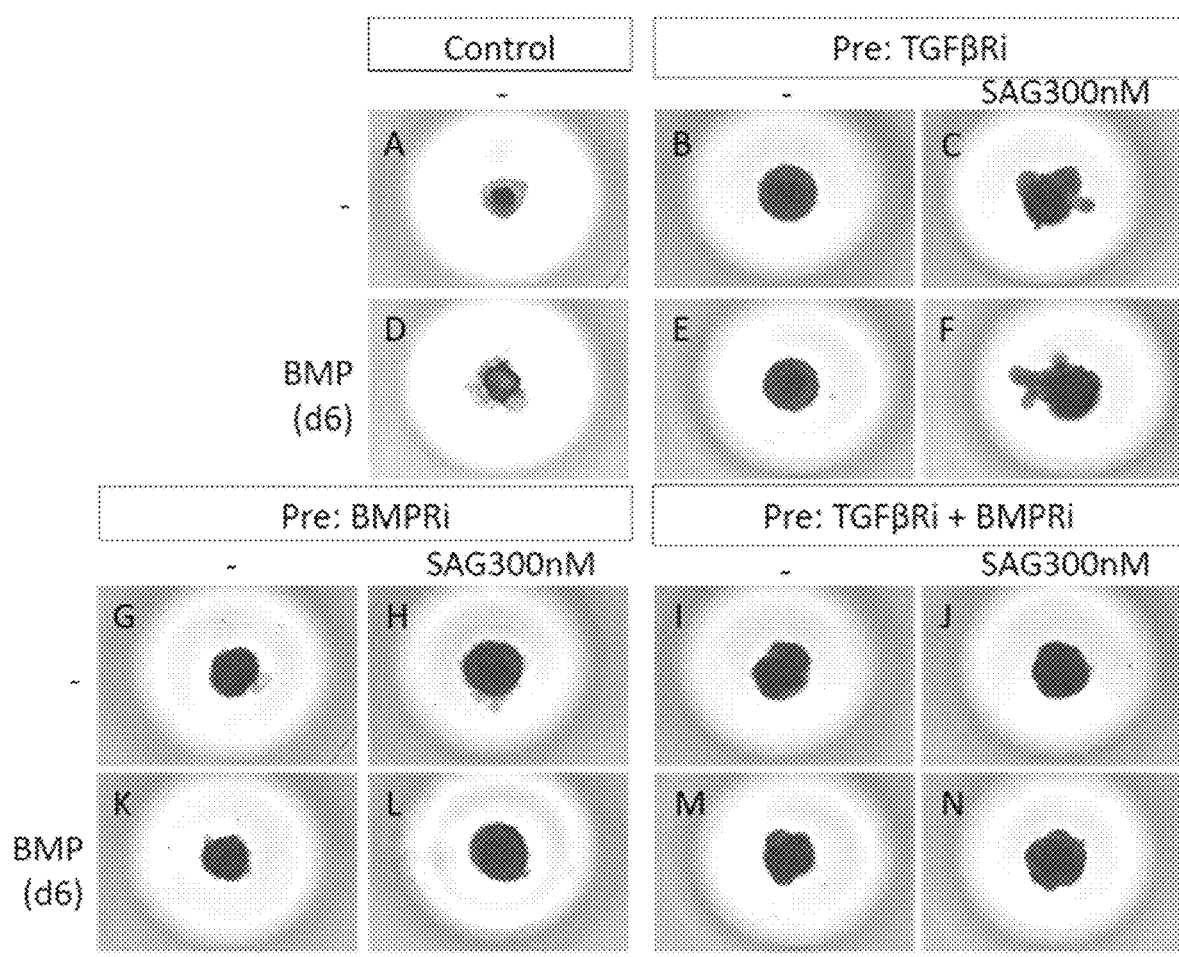
FIG. 10 shows bright field images of aggregates formed under various conditions.

The thus-prepared cells were subjected to bright field observation on day 7 after the start of suspension culturing under an inverted microscope (KEYENCE) (FIG. 10). As a result, it was found that, under conditions without preconditioning in step 1 and without addition of SAG in step 2, the cell aggregates were collapsed, and a neural tissue was not formed (FIG. 10A). It was found that cell aggregates can be formed under the conditions with preconditioning in step 1, even when a Shh signal transduction pathway activating substance was not added in step 2 or a Shh signal transduction pathway activating substance was added in step 2 (FIG. 10). That is, it was found that the form of the cell aggregate formed from human iPS cells becomes good by a preconditioning treatment using a TGFβ family signal transduction pathway inhibiting substance in step 1, even when Essential 8 medium is used as a feeder-free medium.

Example 11: Example of Formation of Neural Tissue Using Human iPS Cells in Essential 8 Medium as Feeder-Free Medium as Starting Material, TGFβ Family Signal Transduction Pathway Inhibiting Substance in Step 1 and Shh Signal Transduction Pathway Activating Substance Step 2

Figure 11:
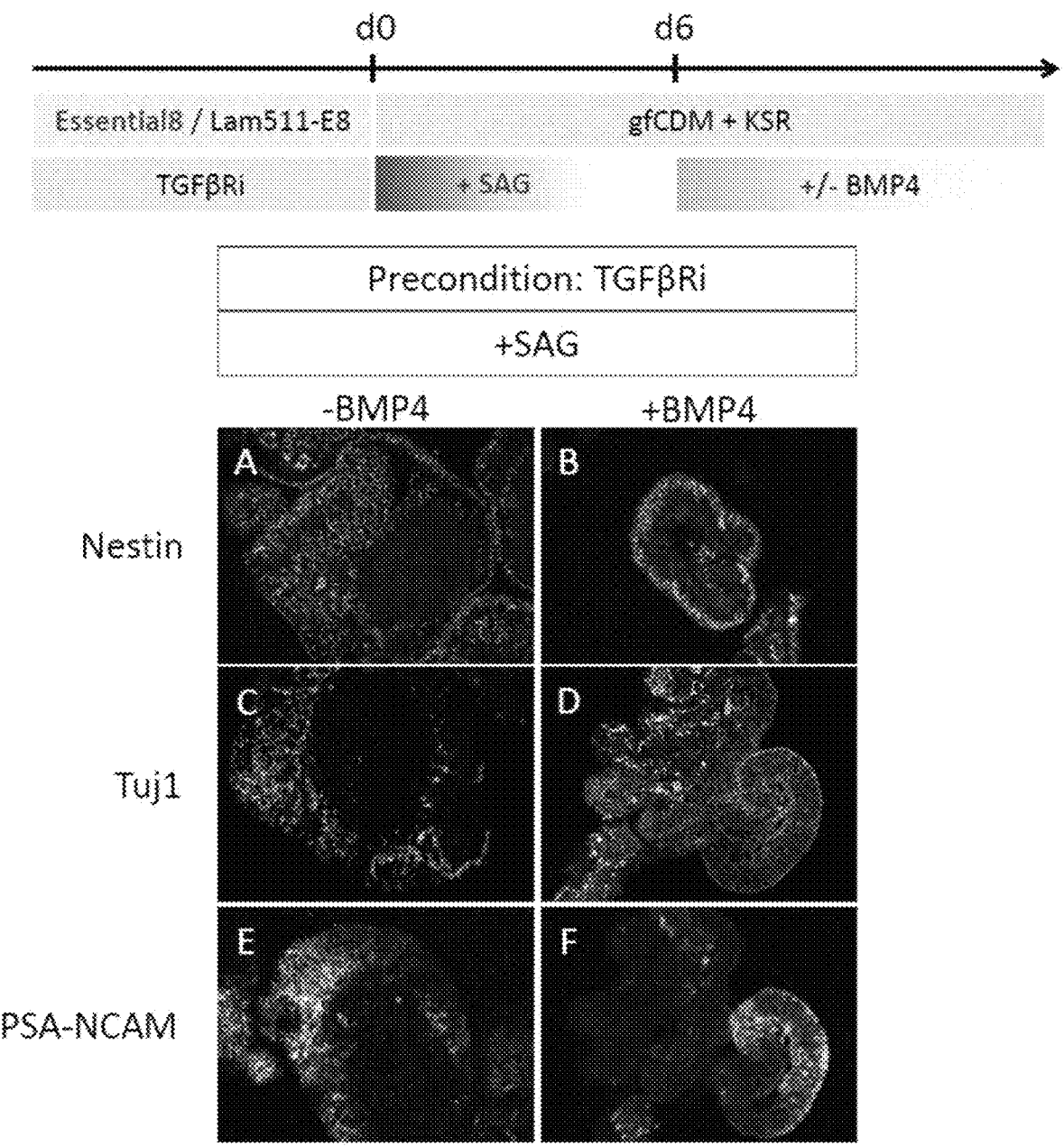
FIG. 11 shows culture conditions of Example 11, and immunohistochemical staining images of aggregates for neural tissue markers (Nestin, TuJ1, PSA-NCAM) (A-F).

Cell aggregates were prepared according to the method described in Example 10 by using, as a starting material, human iPS cells using Essential 8 medium as a feeder-free culturing, TGFβR inhibiting substance (SB431542) in step 1, and a Shh signal transduction pathway activating substance in step 2. The cell aggregates on day 18 after the start of suspension culturing were fixed with 4% para-formaldehyde to prepare frozen section. These frozen sections were immunostained for Nestin (anti-Nestin antibody, Nihon Millipore K.K., mouse), which is one of the neural tissue markers (neural precursor cells), TuJ1 (anti-βIII-tubulin antibody, Promega KK, mouse), which is one of the neural tissue markers (neurons), or PSA-NCAM (anti-PSA-NCAM antibody, Millipore K.K., mouse IgM), which is one of the neural tissue markers, and observed under an fluorescence microscope. As a result, it was found that, in the above cell aggregates, the proportion of Nestin-positive cells in the total cells was about 30%, the proportion of TuJ1-positive cells in the total cells was about 70%, and the proportion of PSA-NCAM-positive cells was about 70% (FIG. 11). Furthermore, it could be confirmed from the analysis of serial sections, that the regions that could be identified to be neural tissue by morphology observation in the bright field images were Nestin-positive, TuJ1-positive, and PSA-NCAM-positive (FIG. 11). That is, it was found that a neural tissue can be formed efficiently in the cell aggregate produced under the conditions involving preconditioning with a TGFβR inhibiting substance in step 1 and addition of SAG in step 2.

Example 12: Example of Formation of Retinal Tissue Using Human iPS Cells in Essential 8 Medium as Feeder-Free Culturing as Starting Material, TGFβ Family Signal Transduction Pathway Inhibiting Substance in Step 1, Shh Signal Transduction Pathway Activating Substance Step 2 and BMP Signal Transduction Pathway Activating Substance in Step 3

Figure 12:
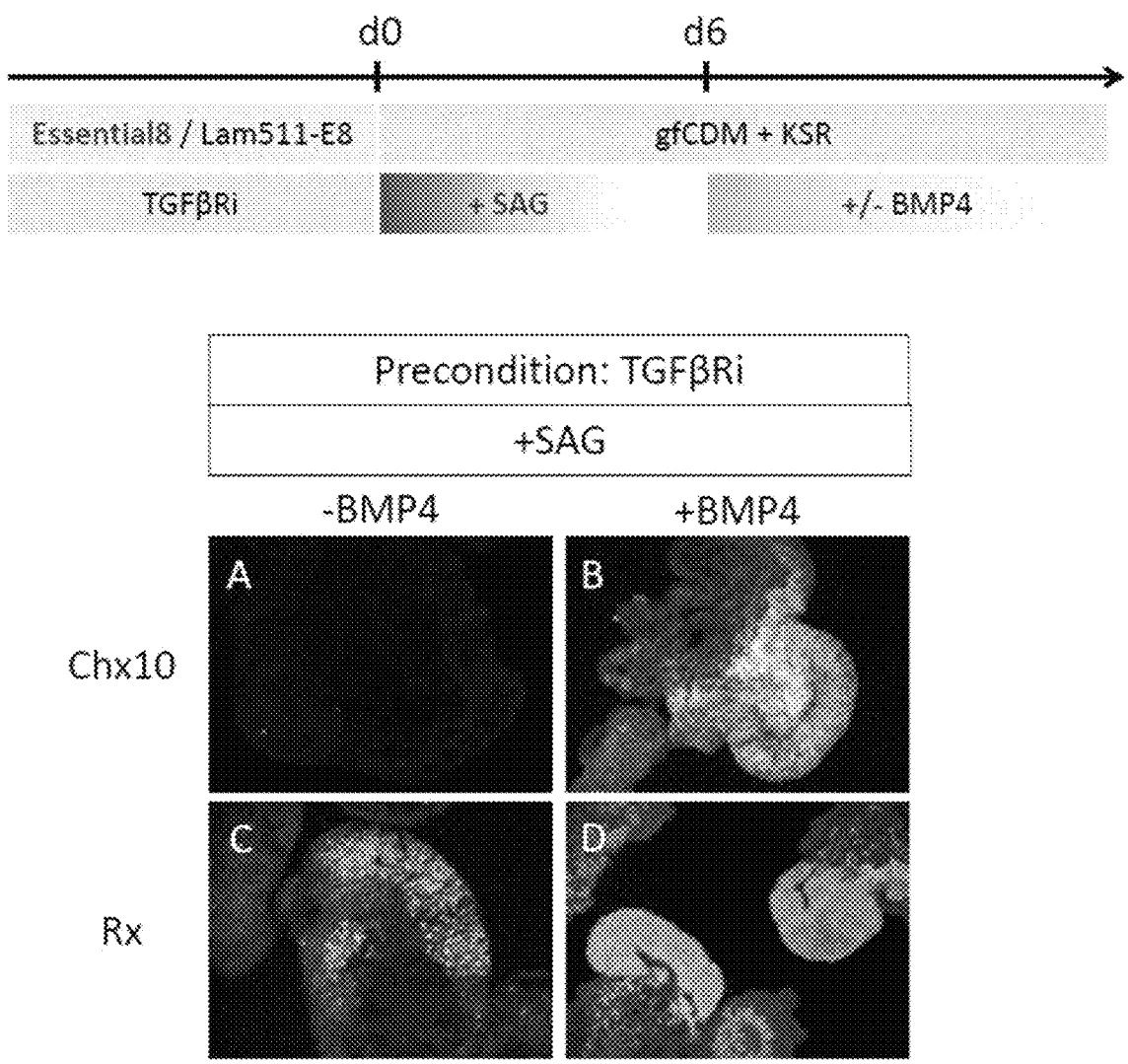
FIG. 12 shows culture conditions of Example 12, and immunohistochemical staining images of aggregates for retinal tissue markers (Chx10, Rx) (A-D).

Cell aggregates were prepared according to the method described in Example 10 by using, as a starting material, human iPS cells using Essential 8 medium as a feeder-free culturing, under conditions that TGFβR inhibiting substance (SB431542) are used in step 1, a Shh signal transduction pathway activating substance are used in step 2, and a BMP signal transduction pathway activating substance are added or are not added in step 3. The cell aggregates on day 18 after the start of suspension culturing were each fixed with 4% para-formaldehyde to prepare frozen section. These frozen sections were immunostained for Chx10 (anti-Chx10 antibody, Exalpha, sheep), which is one of the retinal tissue markers, or Rx (anti-Rx antibody, Takara, guinea pig), which is one of the retinal tissue markers, and observed under a fluorescence microscope. As a result, it was found that, in the cell aggregates prepared under conditions of preconditioning with a TGFβR inhibitor (SB431542) in step 1, addition of a Shh signal transduction pathway activating substance in step 2, and no addition of BMP4 in step 3, the proportion of Rx-positive cells in the total cells was less than 10% (Rx-strong positive (corresponding to retina) was less than 3%, Rx-weak positive (corresponding to neural tissue other than retina) was less than 7%), and the proportion of Chx10-positive cells was also less than 3% (FIG. 12). On the other hand, it was found that, in the cell aggregates produced under conditions of preconditioning with a TGFβR inhibitor (SB431542) in step 1, addition of a Shh signal transduction pathway activating substance in step 2, and addition of BMP4 in step 3, the proportion of Rx-strong positive cells in the total cells was about 30% or more, and the proportion of Chx10-positive cells in the total cells was also about 20% or more (FIG. 12). Furthermore, it was found from the analysis of serial sections that, in a neural tissue having a high (not less than 95%) proportion of Chx10-positive cells, Rx is also strongly positive. From the results, it was found that a retinal tissue can be produced under the conditions using, as a starting material, human iPS cells feeder-free cultured using Essential 8 medium, TGFβR inhibiting substance in step 1, a Shh signal transduction pathway activating substance in step 2, and a BMP signal transduction pathway activating substance in step 3.

Example 13: Example of Formation of Retinal Tissue Using Human iPS Cells in StemFit as Feeder-Free Medium as Starting Material, TGFβ Signal Transduction Pathway Inhibiting Substance and Shh Signal Transduction Pathway Activating Substance in Step 1, and BMP Signal Transduction Pathway Activating Substance in Step 3

Human iPS cells (1231A3 strain) were subjected to feeder-free culturing according to the method described in Example 1 in StemFit medium until one day before subconfluence. The human iPS cells one day before subconfluence were subjected to feeder-free culturing in the presence of SB431542 (TGFβR inhibitor, 5 μM) and SAG (Shh signal transduction pathway activating substance, 300 nM) for one day (step 1, preconditioning: TGFβRi+SAG treatment).

The above human iPS cells were treated with the cell dispersion solution by using TrypLE Select (Life Technologies), further dispersed into single cells by pipetting operation, and the above human iPS cells dispersed into single cells were suspended in 100 μl of a serum-free medium at $1.2 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium therefor, a serum-free medium which is a 1:1 mixture of F-12 medium and IMDM medium supplemented with 10% KSR and 450 μM 1-monothioglycerol, 1× Chemically defined lipid concentrate was used. At the time of the start of suspension culturing (day 0 after the start of suspension culturing, start of step 2), Y27632 (final concentration 20 μM) and SAG (Shh signal transduction pathway activating substance, 300 nM) were added to the above serum-free medium. In one day up to day 2 after the start of suspension culturing, cell aggregates were formed (step 2 completed, step 3 start), after which culturing under the following conditions 1-3 was performed in step 3.

Condition 1: On day 3 after the start of suspension culturing, a serum-free medium (50 μl) free of Y27632, SAG and BMP signal transduction pathway activating substance was added. On day 6 or later from the start of suspension culturing, a half amount of medium was changed, once every 3 days, with the above serum-free medium free of Y27632, SAG and BMP signal transduction pathway activating substance (a half volume, namely 75 μl, of the medium was discarded, and 75 µl of the above serum-free medium free of Y27632, SAG and BMP activating substance was added).

Condition 2: On day 3 from the start of suspension culturing, a serum-free medium free of Y27632 and SAG and containing human recombinant BMP4 at a final concentration of 1.5 nM was added. On day 6 or later from the start of suspension culturing, a half amount of the medium was changed, once every 3 days, with the above serum-free medium free of Y27632, SAG and BMP activating substance (a half volume, namely 75 µl, of the medium was discarded, and 75 µl of the above serum-free medium free of Y27632, SAG and BMP activating substance was added).

Condition 3: On day 3 from the start of suspension culturing, a serum-free medium free of Y27632, SAG and BMP signal transduction pathway activating substance was added (50 µl). On day 6 after the start of suspension culturing, a serum-free medium free of Y27632 and SAG and containing human recombinant BMP4 at a final concentration of 1.5 nM was added. On day 6 or later from the start of suspension culturing, a half amount of the medium was changed with the above serum-free medium free of Y27632, SAG and BMP activating substance (a half volume, namely 75 µl, of the medium was discarded, and 75 µl of the above serum-free medium free of Y27632, SAG and BMP activating substance was added).

Figure 13:
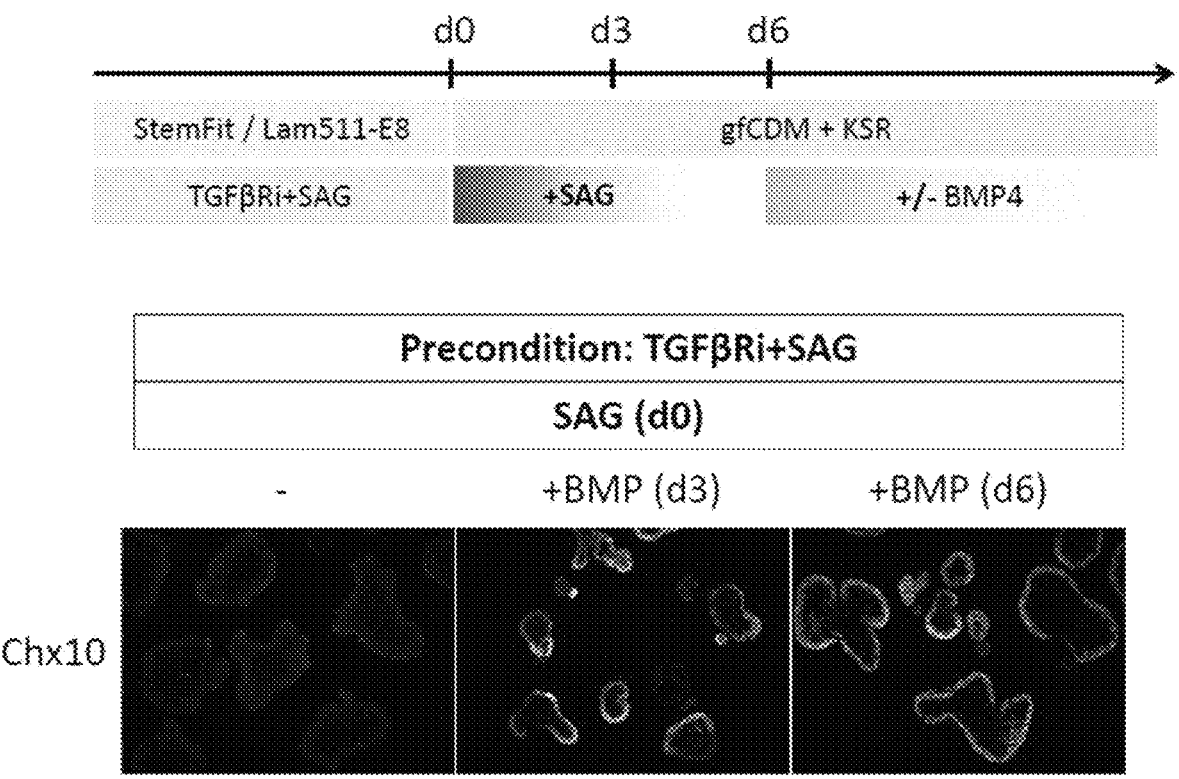
FIG. 13 shows culture conditions of Example 13, and immunohistochemical staining images of aggregates relating to Chx10 (A-D).

When cultured under the above-mentioned conditions 1-3, a cell aggregate was formed on day 26 after the start of suspension culturing under every condition, and a neural tissue was formed. The above cell aggregates on day 26 after the start of suspension culturing were each fixed with 4% para-formaldehyde to prepare frozen sections. These frozen sections were immunostained for Chx10 (anti-Chx10 antibody, Exalpha, sheep), which is one of the retinal tissue markers. As a result, it was found that, in the cell aggregate of condition 1, the proportion of Chx10-positive cells in the total cells is less than 3% (FIG. 13, left). On the other hand, in the cell aggregates of condition 2 and condition 3, the proportion of Chx10-positive cells in the total cells is not less than 60% (FIG. 13, middle, right). From the results, it was found that a retinal tissue can be produced under the conditions using a TGFβR inhibiting substance (SB431542) and a Shh signal transduction pathway activating substance in step 1, a Shh signal transduction pathway activating substance in step 2, and a BMP signal transduction pathway activating substance in step 3.

Example 14: Consideration of Plated Cell Number in Step 2 (Human iPS Cells in StemFit as Feeder-Free Medium was Used as Starting Material, TGFβ Signal Transduction Pathway Inhibiting Substance and Shh Signal Transduction Pathway Activating Substance were Used in Step 1)

Human iPS cells (1231A3 strain) were subjected to feeder-free culturing according to the method described in Example 1 in StemFit medium until one day before subconfluence. The human iPS cells one day before subconfluence were subjected to feeder-free culturing in the presence of SB431542 (TGFβR inhibitor, 5 µM) and SAG (Shh signal transduction pathway activating substance, 300 nM) for one day (step 1, preconditioning: TGFβRi+SAG treatment).

The above human iPS cells were treated with the cell dispersion solution by using TrypLE Select (Life Technologies), further dispersed into single cells by pipetting operation, and the above human IFS cells dispersed into single cells were suspended in 100 µl of a serum-free medium at the following 4 conditions, i.e., $0.4 \times 10^4$, $0.8 \times 10^4$, $1.2 \times 10^4$, or $1.6 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culturing (day 0 after the start of suspension culturing, start of step 2), Y27632 (final concentration 20 µM) and SAG (Shh signal transduction pathway activating substance, 300 nM) were added to the above serum-free medium. In one day up to day 2 after the start of suspension culturing, cell aggregates were formed (step 2 completed, step 3 start). Thereafter, in step 3, on day 3 after the start of suspension culturing, a serum-free medium free of Y27632 and SAG and containing human recombinant BMP4 at a final concentration of 1.5 nM was added. On day 6 or later from the start of suspension culturing, a half amount of the medium was changed, once every 2-4 days, with the above serum-free medium free of Y27632, SAG and BMP activating substance.

Figure 14:
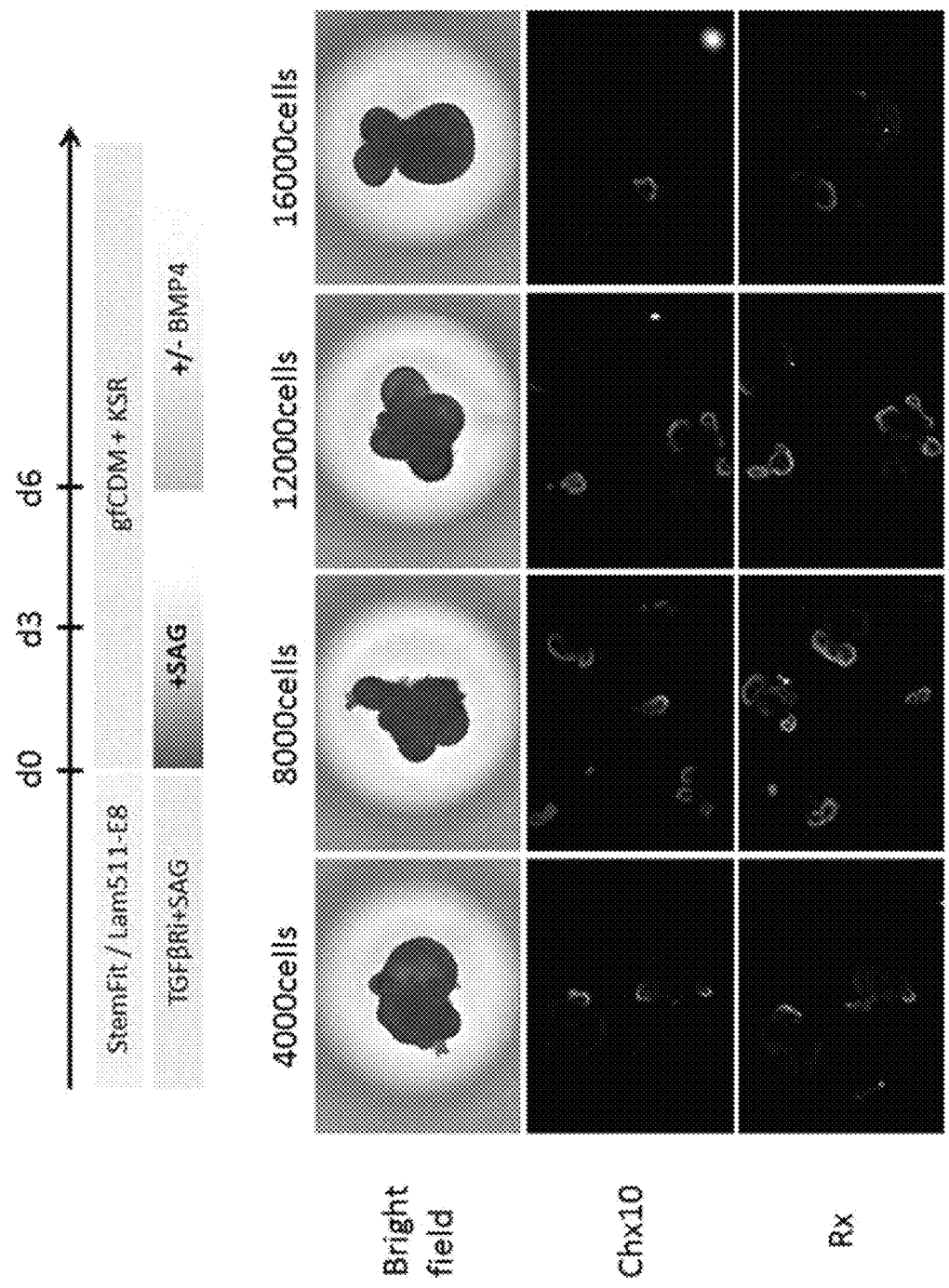
FIG. 14 shows culture conditions of Example 14, bright field images of aggregates, and immunohistochemical staining images of aggregates for retinal tissue markers (Chx10, Rx).

A Cell aggregate was formed on day 18 after the start of suspension culturing under every conditions, and a neural tissue was formed (FIG. 14, upper panel). The above cell aggregates on day 18 after the start of suspension culturing were each fixed with 4% para-formaldehyde to prepare frozen section. These frozen sections were immunostained for Chx10 (anti-Chx10 antibody, Exalpha, sheep), which is one of the retinal tissue markers, or Rx (anti-Rx antibody, Takara, guinea pig), which is one of the retinal tissue markers, and observed under a fluorescence microscope. As a result, it was found that, in any plated cell number ($0.4 \times 10^4$, $0.8 \times 10^4$, $1.2 \times 10^4$, or $1.6 \times 10^4$ cells), the proportion of Chx10-positive cells in the total cells is not less than 20% (FIG. 14, middle, right). Particularly, the conditions with plated cell number of $0.8 \times 10^4$ or $1.2 \times 10^4$ cells showed a particularly high proportion of Chx10-positive cells. The results of the proportion of Rx-positive cells were the same as those of Chx10. From the results, it was found that a retinal tissue can be produced under the plated cell number conditions of $0.4 \times 10^4$-$1.6 \times 10^4$ cells in step 2.

Example 15: Example of Formation of Neural Tissue from Feeder-Free Human iPS Cells by Using a TGFβ Family Signal Transduction Pathway Inhibiting Substance, Lefty, in Step 1, a Shh Signal Transduction Pathway Activating Substance, SAG, in Step 2

Human iPS cells (1231A3 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

Human iPS cells (1231A3 strain) were subjected to feeder-free culturing according to the method described in Example 1 in StemFit medium until one day before subconfluence. Thereafter, the cells were subjected to feeder-free culturing under the following 3 conditions for one day.

Condition 1: human recombinant Lefty-A (Nodal/Activin signal transduction pathway inhibiting substance, manufactured by R&D, Lefty-A C-terminus, 20 µg/ml)

Condition 2: human recombinant Lefty-A (Nodal/Activin signal transduction pathway inhibiting substance, manufactured by R&D Lefty-A C-terminus, 20 μg/ml) and SAG (Shh signal transduction pathway activating substance, 300 nM)

Condition 3: Free of exogenous TGFβ family signal transduction pathway inhibiting substance and Shh signal transduction pathway activating substance (without preconditioning)

The thus-prepared human iPS cells under the above conditions 1-3 were treated with the cell dispersion solution by using TrypLE Select (manufactured by Life Technologies), further dispersed into single cells by pipetting operation, and the above human iPS cells dispersed into single cells were suspended in 100 μl of a serum-free medium at $1.2 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used.

At the time of the start of suspension culturing (day 0 after the start of suspension culturing, start of step 2), the cells were cultured under the following 2 conditions including condition 1 and condition 2. As condition 1(+SAG), at the time of the start of suspension culturing, Y27632 (final concentration 20 μM) and SAG (Shh signal transduction pathway activating substance, 300 nM) were added to the above serum-free medium. As condition 2(−SAG), at the time of the start of suspension culturing, Y27632 (final concentration 20 μM) was added to the above serum-free medium and SAG was not added. By day 2 after the start of suspension culturing, cell aggregates were formed (step 2 completed, step 3 start) under both conditions. On day 3 after the start of suspension culturing, a medium (50 μl) free of Y27632, SAG and containing human recombinant BMP4 (manufactured by R&D) was added such that the final concentration of exogenous human recombinant BMP4 was 1.5 nM (55 ng/ml). On day 6 after the start of suspension culturing, a half amount of the medium was changed with a serum-free medium free of Y27632, SAG and human recombinant BMP4. Thereafter, a half amount of the medium was changed, once every 2-4 days, with the above serum-free medium free of Y27632, SAG, and human recombinant BMP4.

Figure 15:
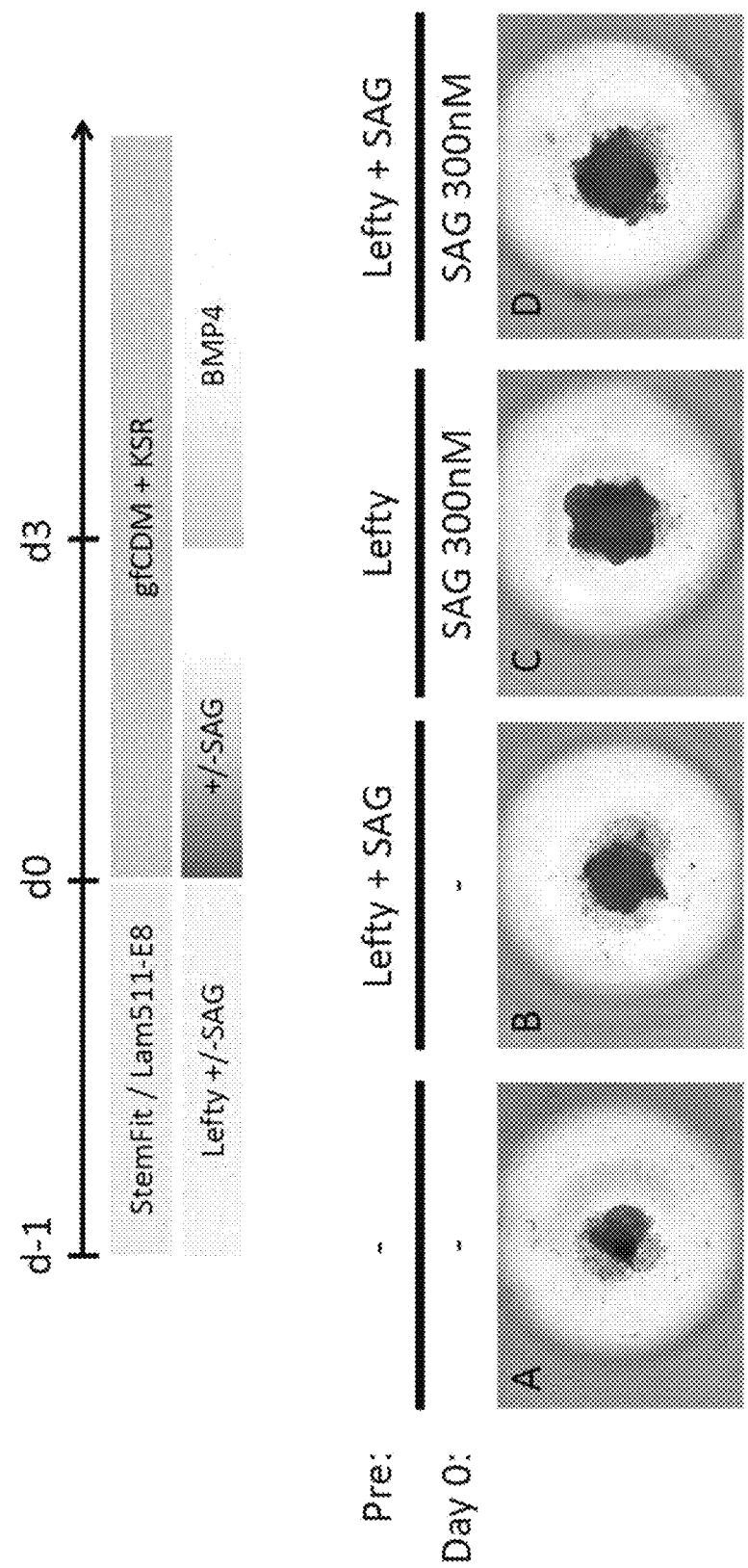
FIG. 15 shows culture conditions of Example 15, and bright field images of cells after culture (A-D).

The thus-prepared cells were subjected to bright field observation on day 18 after the start of suspension culturing under an inverted microscope (KEYENCE) (FIG. 15). As a result, it was found that, under conditions without preconditioning in step 1 and without addition of SAG in step 2, the cell aggregates were collapsed, and a neural tissue was not formed (FIG. 15, A). On the other hand, it was found that, under conditions involving preconditioning with a Nodal/Activin signal transduction pathway inhibiting substance, or a Nodal/Activin signal transduction pathway inhibiting substance and a Shh signal transduction pathway activating substance in step 1, and addition of or without addition of a Shh signal transduction pathway activating substance in step 2, the cell aggregate was formed, and a neural tissue could be formed efficiently (FIG. 15, B, C, D).

From these results, it was found that a high quality aggregate is formed from feeder-free human iPS cells and the production efficiency of neuroepithelium is improved even under conditions involving preconditioning with a Nodal/Activin signal transduction pathway inhibiting substance, Lefty, as a TGFβ family signal transduction pathway inhibiting substance.

Example 16: Example of Formation of Neural Tissue and Retinal Tissue from Feeder-Free Human iPS Cells by Using a TGFβ Family Signal Transduction Pathway Inhibiting Substance, A83-01, in Step 1, and a Shh Signal Transduction Pathway Activating Substance, SAG, in Step 2

Human iPS cells (1231A3 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

Human iPS cells at one day before subconfluence, which were prepared according to the method described in Example 15 were subjected to feeder-free culturing in the presence of A83-01 (manufactured by Wako, TGFβR inhibitor, 0.5 μM) (preconditioning treatment) or in the absence thereof (step 1: without preconditioning) for one day.

The above human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used.

At the time of the start of suspension culturing (day 0 after the start of suspension culturing, start of step 2), the cells were cultured under the following 2 conditions including condition 1 and condition 2. As condition 1(+SAG), at the time of the start of suspension culturing, Y27632 (final concentration 20 μM) and SAG (Shh signal transduction pathway activating substance, final concentration 30 nM) were added to the above serum-free medium. As condition 2(−SAG), at the time of the start of suspension culturing, Y27632 (final concentration 20 μM) was added to the above serum-free medium and SAG was not added. By day 2 after the start of suspension culturing, cell aggregates were formed under both conditions (step 2 completed, step 3 start). On day 3 after the start of suspension culturing, a medium (50 μl) free of Y27632 and SAG and containing human recombinant BMP4 (manufactured by R&D) was added such that the final concentration of exogenous human recombinant BMP4 was 1.5 nM (55 ng/ml). On day 6 from the start of suspension culturing, a half amount of the medium was changed to a serum-free medium free of Y27632, SAG and human recombinant BMP4. Thereafter, a half amount of the medium was changed, once every 2-4 days, with the above serum-free medium free of Y27632, SAG, and human recombinant BMP4.

Figure 16:
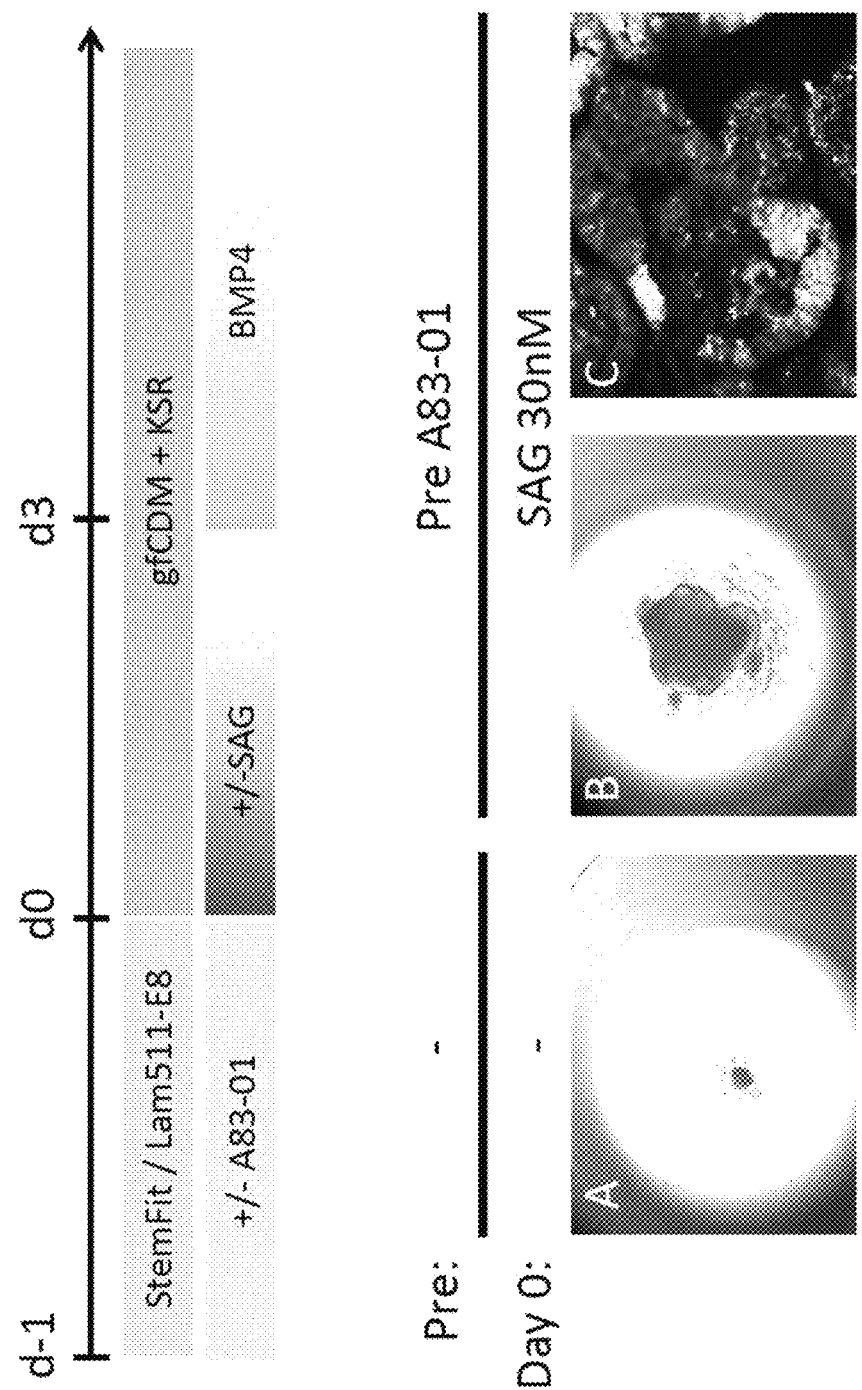
FIG. 16 shows culture conditions of Example 16, bright field images of cells after culture (A,B), and immunohistochemical staining image of aggregate for Chx10 (C).

The thus-prepared cells were subjected to bright field observation on day 20 after the start of suspension culturing under an inverted microscope (KEYENCE) (FIG. 16, A-B). As a result, it was found that, under conditions without preconditioning in step 1 and without addition of SAG in step 2, the cell aggregates were collapsed, and a neural tissue was not formed (FIG. 16, A). On the other hand, it was found that a cell aggregate was formed and a neural tissue can be formed efficiently under conditions involving preconditioning with A83-01 in step 1 and addition of SAG in step 2(FIG. 16, B).

Cell aggregates on day 20 after the start of suspension culturing were fixed with 4% para-formaldehyde to prepare frozen sections. These frozen sections were immunostained for Chx10 (anti-Chx10 antibody, Exalpha, sheep), which is one of the retinal tissue markers, and observed under a fluorescence microscope. As a result, it was found that the proportion of Chx10-positive cells in the total cells was about 20% when step 1 involves preconditioning with A83-01 and step 2 involves addition of SAG (FIG. 16, C).

From these results, it was found that a retinal tissue can be produced under the conditions involving preconditioning with TGFβR inhibitor, A83-01, as a TGFβ family signal transduction pathway inhibiting substance in step 1, and addition of a Shh signal transduction pathway activating substance in step 2.

Example 17: Example of Formation of Neural Tissue from Feeder-Free Human iPS Cells by Using TGFβ Family Signal Transduction Pathway Inhibiting Substance, A83-01 or Combination of TGFβ Family Signal Transduction Pathway Inhibiting Substance (A83-01) and Shh Signal Transduction Pathway Activating Substance (SAG, Puimorphamine, or Human Recombinant Shh) in Step 1, and Shh Signal Transduction Pathway Activating Substance in Step 2

Human iPS cells (1231A3 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

Human iPS cells at one day before subconfluence, which were prepared according to the method described in Example 15, were subjected to feeder-free culturing under the following 6 conditions for one day.

Condition 1: A83-01 (manufactured by Wako, TGFβR inhibitor, 0.5 μM)

Condition 2: A83-01 (manufactured by Wako, TGFβR inhibitor, 0.5 μM) and SAG (manufactured by Enzo, Shh signal transduction pathway activating substance, 300 nM)

Condition 3: A83-01 (manufactured by Wako, TGFβR inhibitor, 0.5 TIM) and Purmorphamine (manufactured by Wako, Shh signal transduction pathway activating substance, 0.2 μM)

Condition 4: A83-01 (manufactured by Wako, TGFβR inhibitor, 0.5 μM) and human recombinant Shh (manufactured by R&D, Shh signal transduction pathway activating substance, 50 ng/ml)

Condition 5: A83-01 (manufactured by Wako, TGFβR inhibitor 0.5 μM) and human recombinant Shh (manufactured by R&D, Shh signal transduction pathway activating substance, 300 ng/ml)

Condition 6: Free of exogenous TGFβ family signal transduction pathway inhibiting substance and Shh signal transduction pathway activating substance (without preconditioning)

The above human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used.

At the time of the start of suspension culturing (day 0 after the start of suspension culturing, start of step 2), the cells were cultured under the following two conditions including condition (A) and condition (B). As condition (A)(+SAG), at the time of the start of suspension culturing, Y27632 (final concentration 20 μM) and SAG (Shh signal transduction pathway activating substance, 30 nM) were added to the above serum-free medium. As condition (B)(−SAG), at the time of the start of suspension culturing, Y27632 (final concentration 20 μM) was added to the above serum-free medium and SAG was not added.

By day 2 after the start of suspension culturing, cell aggregates were formed under both conditions (step 2 completed, step 3 start). On day 3 after the start of suspension culturing, a medium (50 μl) free of Y27632, SAG, Purmorphamine and human recombinant Shh, and containing human recombinant BMP4 (manufactured by R&D) was added such that the final concentration of exogenous human recombinant BMP4 was 1.5 nM (55 ng/ml). On day 6 from the start of suspension culturing, a half amount of the medium was changed to a serum-free medium free of Y27632, SAG, Purmorphamine, human recombinant Shh, and human recombinant BMP4. Thereafter, a half amount of the medium was changed, once every 2-4 days, to the above serum-free medium free of Y27632, SAG, Purmorphamine, human recombinant Shh, and human recombinant BMP4.

Figure 17:
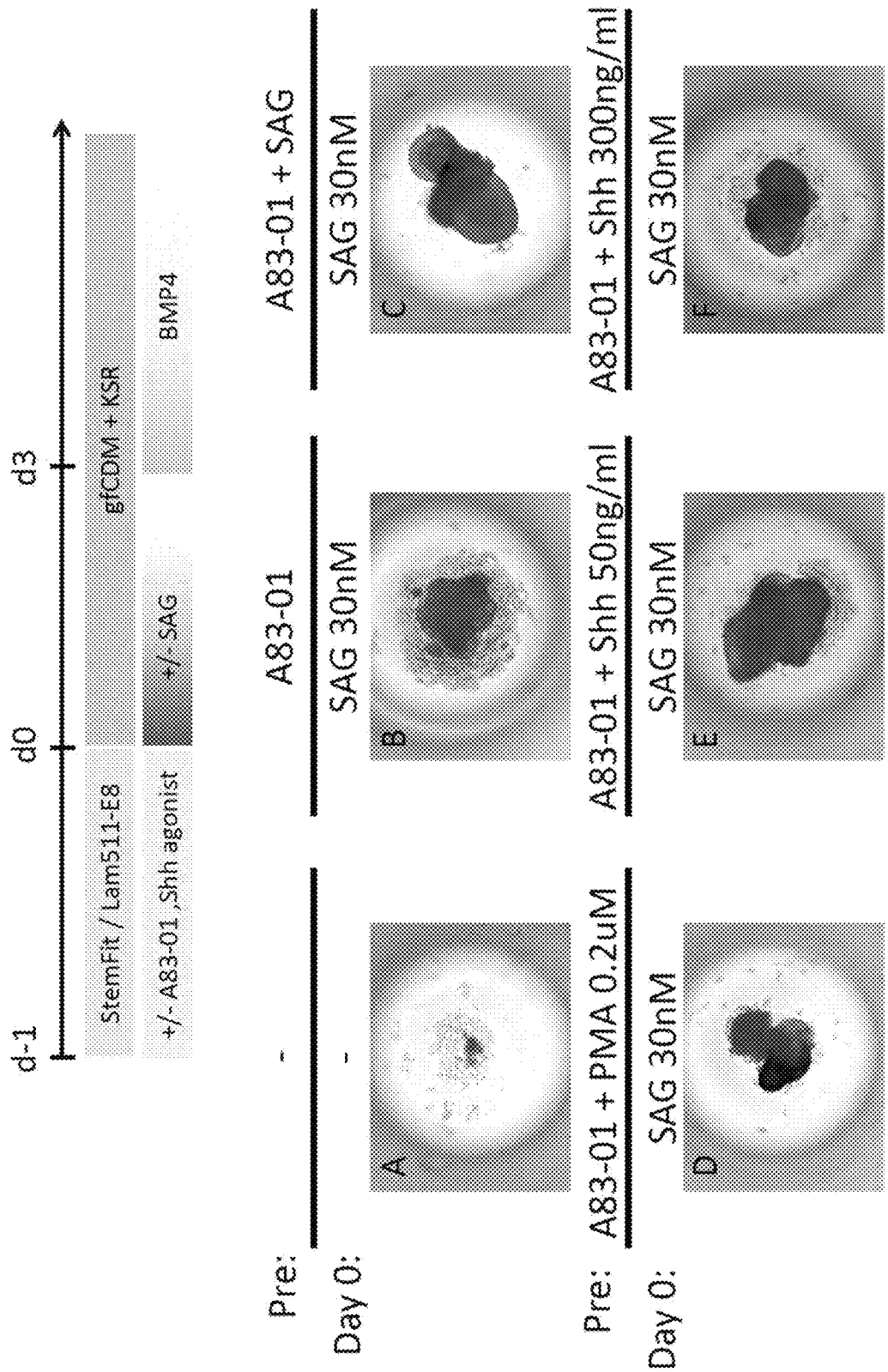
FIG. 17 shows culture conditions of Example 17, and bright field images of cells after culture (A-F).

The thus-prepared cells were subjected to bright field observation on day 20 after the start of suspension culturing under an inverted microscope (KEYENCE) (FIG. 17). As a result, it was found that, under the above condition 6, the condition without preconditioning in step 1 and without addition of SAG in step 2, the cell aggregate was collapsed, and a neural tissue is not formed (FIG. 17, A). On the other hand, it was found that, under the above conditions 1-5, conditions involving adding A83-01 and Shh signal transduction pathway activating substance (SAG, PMA, human recombinant Shh 50 ng/ml, human recombinant Shh 300 ng/ml) in step 1, and adding SAG in step 2 (conditions (A)(+SAG)), cell aggregate was formed and a neural tissue could be formed efficiently (FIG. 17, B-F).

From these results, it was found that a neural tissue can be produced efficiently from feeder-free-cultured human iPS cells under conditions involving preconditioning with a TGFβ family signal transduction pathway inhibiting substance (A83-01), or a TGFβ family signal transduction pathway inhibiting substance (A83-01) and a Shh signal transduction pathway activating substance (any of SAG, PMA, human recombinant Shh) in step 1.

Example 18: Example of Formation of Retinal Tissue from Feeder-Free Human iPS Cells by Using TGFβ Family Signal Transduction Pathway Inhibiting Substance and Shh Signal Transduction Pathway Activating Substance in Step 1, and Shh Signal Transduction Pathway Activating Substance (any of SAG, Purmorphamine, or Human Recombinant Shh) in Step 2

Human iPS cells (1231A3 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

Human iPS cells at one day before subconfluence, which were prepared according to the method described in Example 15, were subjected to feeder-free culturing in the presence of A83-01 (manufactured by Wako, TGFβR inhibitor 0.5 μM) and SAG (Shh signal transduction pathway activating substance, 300 nM) (preconditioning treatment) or in the absence thereof (step 1: without preconditioning) for one day.

The above human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used.

Using the cells obtained in step 1, suspension culturing was started as step 2 under the following conditions. In any conditions, the above serum-free medium supplemented with Y27632 (final concentration 20 μM) was used.

Condition 1: SAG (manufactured by Enzo, Shh signal transduction pathway activating substance, 30 nM) was added.

Condition 2: Purmorphamine (manufactured by Wako, Shh signal transduction pathway activating substance, 0.2 μM) was added.

Condition 3: Human recombinant Shh (manufactured by R&D, Shh signal transduction pathway activating substance, 300 ng/ml) was added.

Condition 4: Exogenous Shh signal transduction pathway activating substance was not added at the time of the start of suspension culturing.

By day 2 after the start of suspension culturing, cell aggregates were formed (step 2 completed, step 3 start) under any conditions. On day 3 after the start of suspension culturing, a medium (50 μl) free of Y27632, SAG, Purmorphamine and human recombinant Shh, and containing human recombinant BMP4 (manufactured by R&D) was added such that the final concentration of exogenous human recombinant BMP4 was 1.5 nM (55 ng/ml). On day 6 from the start of suspension culturing, a half amount of the medium was changed to a serum-free medium free of Y27632, SAG, Purmorphamine, human recombinant Shh, and human recombinant BMP4. Thereafter, a half amount of the medium was changed, once every 2-4 days, to the above serum-free medium free of Y27632, SAG, and human recombinant BMP4.

Figure 18:
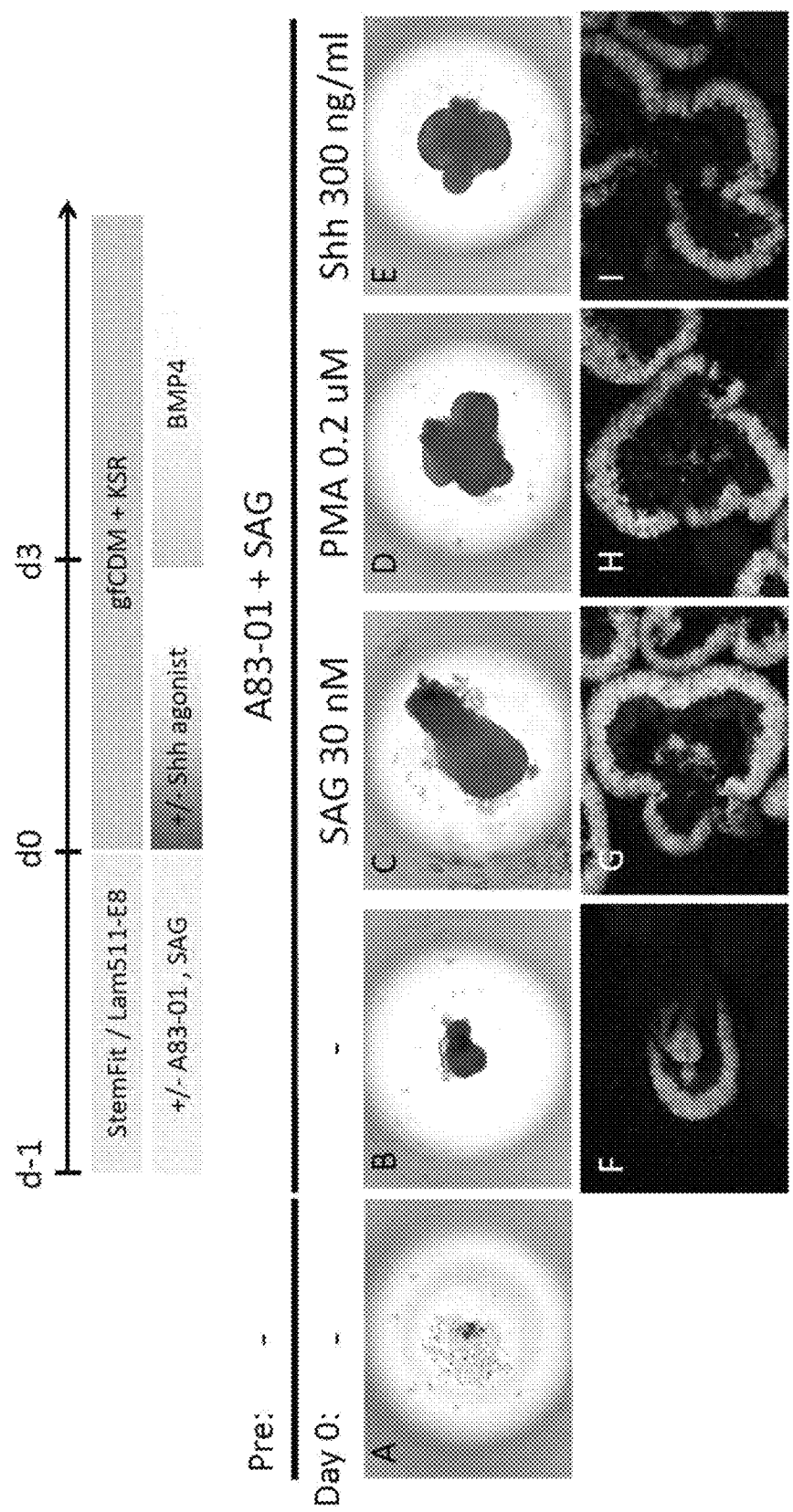
FIG. 18 shows culture conditions of Example 18, bright field images of cells after culture (A-E), and immunohistochemical staining images of aggregates for Chx10 (F-I).

The thus-prepared cells were subjected to bright field observation on day 20 after the start of suspension culturing under an inverted microscope (KEYENCE) (FIG. 18, A-E). As a result, it was found that under conditions without preconditioning in step 1 and without addition of Shh signal transduction pathway activating substance in step 2 (the above condition 4), the cell aggregate was collapsed, and a neural tissue was not formed (FIG. 18, A). On the other hand, it was found that cell aggregate was formed and a neural tissue was formed efficiently under the conditions involving preconditioning with A83-01 and SAG in step 1, and no addition of an exogenous Shh signal transduction pathway activating substance or addition of any of SAG, Purmorphamine (PMA), or human recombinant Shh as a Shh signal transduction pathway activating substance in step 2 (FIG. 18, B-E).

From these results, it was found that a neural tissue can be produced efficiently from feeder-free human iPS cells under conditions involving preconditioning with a TGFβ family signal transduction pathway inhibiting substance and a Shh signal transduction pathway activating substance in step 1 and adding any of SAG, Purmorphamine, or human recombinant Shh, as a Shh signal transduction pathway activating substance, at the time of the start of suspension culturing.

Cell aggregates on day 20 after the start of suspension culturing were fixed with 4% para-formaldehyde to prepare frozen sections. These frozen sections were immunostained for Chx10 (anti-Chx10 antibody, Exalpha, sheep), which is one of the retinal tissue markers, and observed under a fluorescence microscope. As a result, it was found that the proportion of Chx10-positive cells in the total cells was about 40% when step 1 involves preconditioning with A83-01 and SAG, and step 2 involves no addition of an exogenous Shh signal transduction pathway activating substance (FIG. 18, F). On the other hand, it was found that the proportion of Chx10-positive cells in the total cells was about 90% under conditions involving preconditioning with A83-01 and SAG in step 1, and addition of any of SAG, Purmorphamine, or human recombinant Shh as a Shh signal transduction pathway activating substance at the time of the start of suspension culturing (FIG. 18, G-I).

From these results, it was found that a retinal tissue can be produced efficiently from feeder-free human iPS cells under the conditions involving preconditioning with a TGFβ family signal transduction pathway inhibiting substance and a Shh signal transduction pathway activating substance in step 1, and addition of any of SAG, Purmorphamine, or human recombinant Shh as a Shh signal transduction pathway activating substance in step 2.

Example 19: Example of Formation of Retinal Tissue from Feeder-Free Human iPS Cells by Using a TGFβ Family Signal Transduction Pathway Inhibiting Substance, SB431542, and a Shh Signal Transduction Pathway Activating Substance, Purmorphamine, in Step 1, and a Shh Signal Transduction Pathway Activating Substance, Purmorphamine, in Step 2

Human iPS cells (1231A3 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

Human iPS cells at one day before subconfluence, which were prepared according to the method described in Example 15, were subjected to feeder-free culturing in the presence of SB431542 (TGFβR inhibitor, 5 μM) and Purmorphamine (PMA; Shh signal transduction pathway activating substance, 0.02 μM or 0.2 μM) for one day.

The above human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at 1.0×10⁴ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used.

Figure 19:
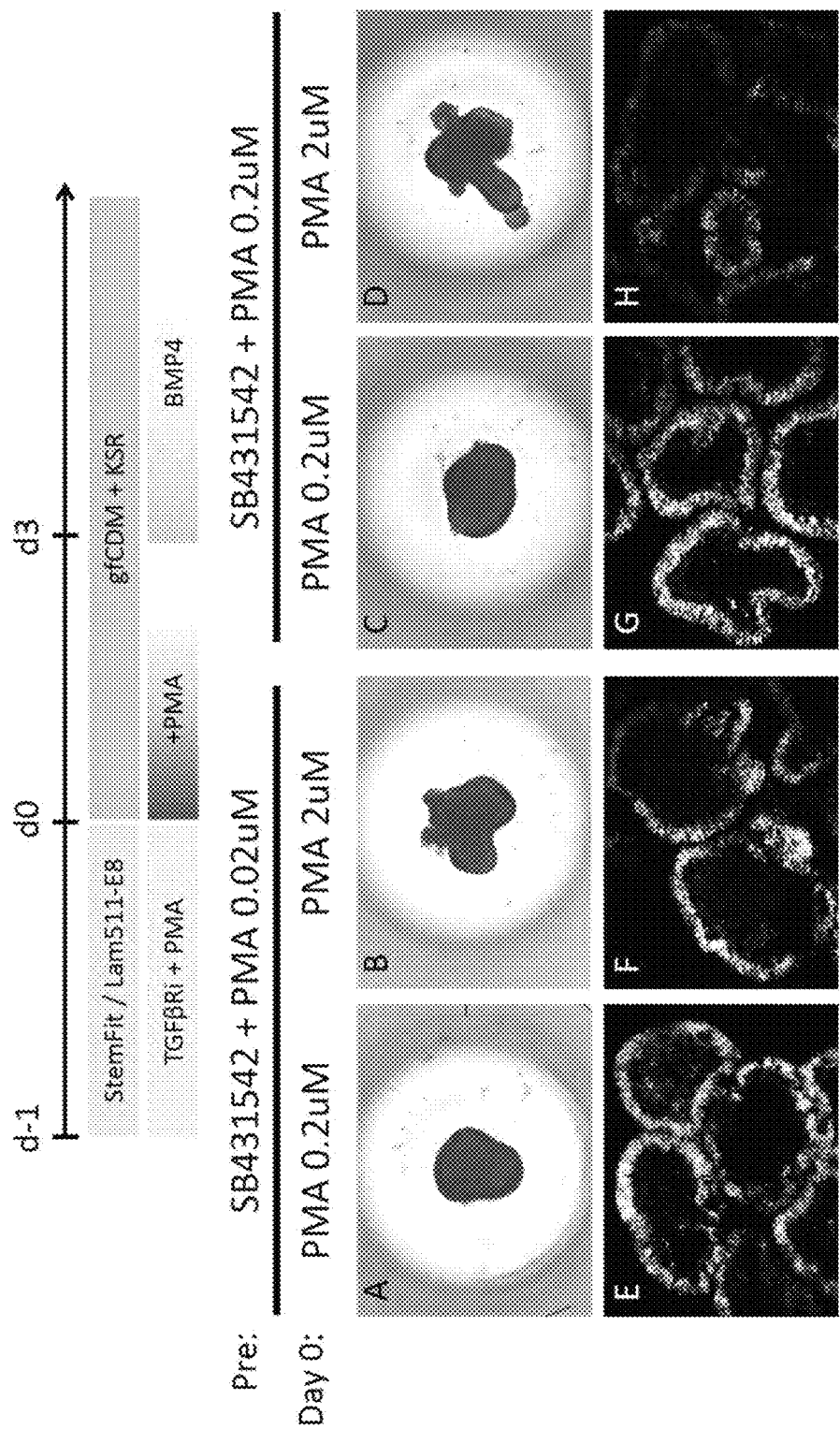
FIG. 19 shows culture conditions of Example 19, bright field images of cells after culture (A-D), and immunohistochemical staining images of aggregates for Chx10 (E-H).

At the time of the start of suspension culturing (day 0 after the start of suspension culturing, start of step 2), Y27632 (20 µM) and Purmorphamine (manufactured by Wako, Shh signal transduction pathway activating substance, 0.2 µM or 2 µM) were added to the above serum-free medium (FIG. 19). By day 2 after the start of suspension culturing, cell aggregates were formed (step 2 completed, step 3 start). On day 3 after the start of suspension culturing, a medium (50 µl) free of Y27632 and Purmorphamine, and containing human recombinant BMP4 (manufactured by R&D) was added such that the final concentration of exogenous human recombinant BMP4 was 1.5 nM (55 ng/ml). On day 6 from the start of suspension culturing, a half amount of the medium was changed to a serum-free medium free of Y27632, Purmorphamine, and human recombinant BMP4. Thereafter, a half amount of the medium was changed, once every 2-4 days, to the above serum-free medium free of Y27632, Purmorphamine, and human recombinant BMP4.

The thus-prepared cells were subjected to bright field observation on day 17 after the start of suspension culturing under an inverted microscope (KEYENCE) (FIG. 19, A-D). As a result, it was found that a cell aggregate was formed, and a neural tissue could be formed efficiently at any Purmorphamine concentration under conditions involving preconditioning with SB431542 and Purmorphamine (0.02 µM or 0.2 µM) in step 1, and addition of Purmorphamine (0.2 µM or 2 µM) in step 2 (FIG. 19, A-D).

Cell aggregates on day 17 after the start of suspension culturing were fixed with 4% para-formaldehyde to prepare frozen sections. These frozen sections were immunostained for Chx10 (anti-Chx10 antibody, Exalpha, sheep), which is one of the retinal tissue markers. These frozen sections were observed under an inverted fluorescence microscope. As a result, it was found that the proportion of Chx10-positive cells in the total cells was about 60% at any Purmorphamine concentration under conditions involving preconditioning with SB431542 and Purmorphamine (0.02 µM or 0.2 µM) in step 1, and addition of Purmorphamine (0.2 µM or 2 µM) in step 2 (FIG. 19, E-H).

From these results, it was found that a retinal tissue can be produced efficiently from feeder-free human iPS cells under the conditions involving preconditioning with a TGFβ family signal transduction pathway inhibiting substance, SB431542, and a Shh signal transduction pathway activating substance, Purmorphamine, in step 1, and addition of a Shh signal transduction pathway activating substance (Purmorphamine) at the time of the start of suspension culturing.

Example 20: Example of Formation of Neural Tissue from Feeder-Free Human iPS Cells by Preconditioning with Shh Signal Transduction Pathway Activating Substance, or a Combination of TGFβ Family Signal Transduction Pathway Inhibiting Substance and Shh Signal Transduction Pathway Activating Substance for 1, 2, or 3 Days in Step 1

Human iPS cell (1231A3 strain, obtained from Kyoto University) was subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

The above human iPS cells were subjected to feeder-free culturing under the following 6 conditions.

Condition 1: SAG (manufactured by Enzo, Shh signal transduction pathway activating substance, 300 nM) for 48 hr Condition 2: SAG (manufactured by Enzo, Shh signal transduction pathway activating substance, 300 nM) for 72 hr Condition 3: A83-01 (manufactured by Wako, TGFβR inhibitor, 0.5 µM) and SAG (manufactured by Enzo, Shh signal transduction pathway activating substance, 300 nM) for 24 hr Condition 4: A83-01 (manufactured by Wako, TGFβR inhibitor, 0.5 µM) and SAG (manufactured by Enzo, Shh signal transduction pathway activating substance, 300 nM) for 48 hr Condition 5: A83-01 (manufactured by Wako, TGFβR inhibitor, 0.5 µM) and SAG (manufactured by Enzo, Shh signal transduction pathway activating substance, 300 nM) for 72 hr Condition 6: Free of exogenous TGFβ family signal transduction pathway inhibiting substance and Shh signal transduction pathway activating substance (without preconditioning)

The above human iPS cells were treated with the cell dispersion solution by using TrypLE Select (manufactured by Life Technologies), further dispersed into single cells by pipetting operation, and the above human iPS cells dispersed into single cells were suspended in 100 µl of a serum-free medium at 1.0×10⁴ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used.

At the time of the start of suspension culturing (day 0 after the start of suspension culturing, start of step 2), the cells were cultured under the following two conditions including condition (A) and condition (B). As condition (A), at the time of the start of suspension culturing, Y27632 (final concentration 20 µM) and SAG (Shh signal transduction pathway activating substance, 30 nM) were added to the above serum-free medium. As condition (B), at the time of the start of suspension culturing, Y27632 (final concentration 20 µM) was added to the above serum-free medium and SAG was not added. By day 2 after the start of suspension culturing, cell aggregates were formed (step 2 completed, step 3 start) under both conditions. On day 3 after the start of suspension culturing, a medium (50 µl) free of Y27632 and SAG, and containing human recombinant BMP4 (manufactured by R&D) was added such that the final concentration of exogenous human recombinant BMP4 was 1.5 nM (55 ng/ml). On day 6 from the start of suspension culturing, a half amount of the medium was changed to a serum-free medium free of Y27632, SAG, and human recombinant BMP4. Thereafter, a half amount of the medium was changed, once every 2-4 days, to the above serum-free medium free of Y27632, SAG, and human recombinant BMP4.

Figure 20:
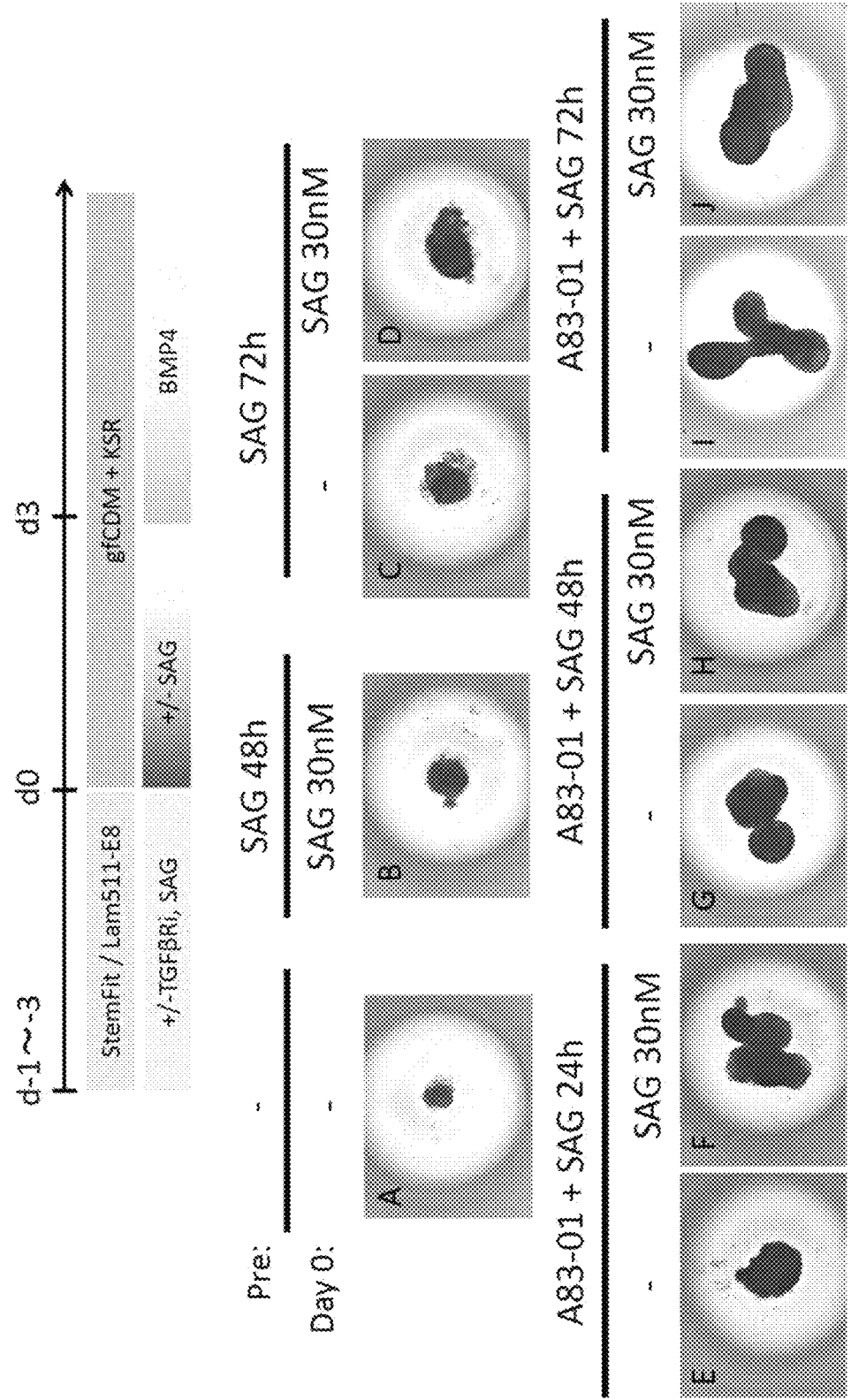
FIG. 20 shows culture conditions of Example 20, and bright field images of cells after culture (A-J).

The thus-prepared cells were subjected to bright field observation under an inverted microscope (KEYENCE) on day 17 after the start of suspension culturing (FIG. 20, A-J). As a result, it was found that a cell aggregate was collapsed, and a neural tissue was not formed under conditions without preconditioning in step 1, and without addition of SAG in step 2 (FIG. 20, A). On the other hand, it was found that a cell aggregate was formed, and a neural tissue can be formed efficiently when preconditioning was performed with SAG for 48 or 72 hr in step 1, and SAG was added (condition (A)) or not added (condition (B)) in step 2(FIG. 20, B-D). In addition, it was found that a cell aggregate was formed, and a neural tissue can be formed efficiently when preconditioning was performed with A83-01 and SAG for 24, 48 or 72 hr in step 1, and SAG was added (condition (A)) or not added (condition (B)) in step 2 (FIG. 20, E-J).

From these results, it was found that a neural tissue can be produced efficiently from feeder-free human iPS cells under the conditions involving preconditioning with a Shh signal transduction pathway activating substance for 48 or 72 hr in step 1, and conditions involving preconditioning with a TGFβ family signal transduction pathway inhibiting substance and a Shh signal transduction pathway activating substance for 24, 48 or 72 hr in step 1.

Example 21: Example of Formation of Neural Tissue from Feeder-Free Human iPS Cells by Preconditioning with Shh Signal Transduction Pathway Activating Substance for 24, 48, 72, 96, 120 or 144 hr in Step 1, and in the Co-Presence of TGFβ Family Signal Transduction Pathway Inhibiting Substance and Shh Signal Transduction Pathway Activating Substance for the Last 24 hr Human iPS cells (1231A3 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

Feeder-free culturing of the human iPS cells was started in the presence of SAG (Shh signal transduction pathway activating substance, 300 nM) (preconditioning treatment). The culture in the presence of SAG was continued for 24, 48, 72, 96, 120 or 144 hr, and for the last 24 hr, the culturing was performed in the co-presence of A83-01 (manufactured by Wako, TGFβ inhibitor, 0.5 μM) and SAG.

The above human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used.

At the time of the start of suspension culturing (day 0 after the start of suspension culturing, start of step 2), the cells were cultured under the following two conditions including condition (A) and condition (B). As condition (A), at the time of the start of suspension culturing, Y27632 (final concentration 20 μM) and SAG (Shh signal transduction pathway activating substance, 30 nM) were added to the above serum-free medium. As condition (B), at the time of the start of suspension culturing, Y27632 (final concentration 20 μM) was added to the above serum-free medium and SAG was not added. By day 2 after the start of suspension culturing, a cell aggregate was formed (step 2 completed, step 3 start) under both conditions. On day 3 after the start of suspension culturing, a serum-free medium (50 μl) free of Y27632 and SAG was added.

On day 6 or later from the start of suspension culturing, a half amount of the medium was changed, once every 2-4 days, to the above serum-free medium free of Y27632, SAG, and human recombinant BMP4.

Figure 21:
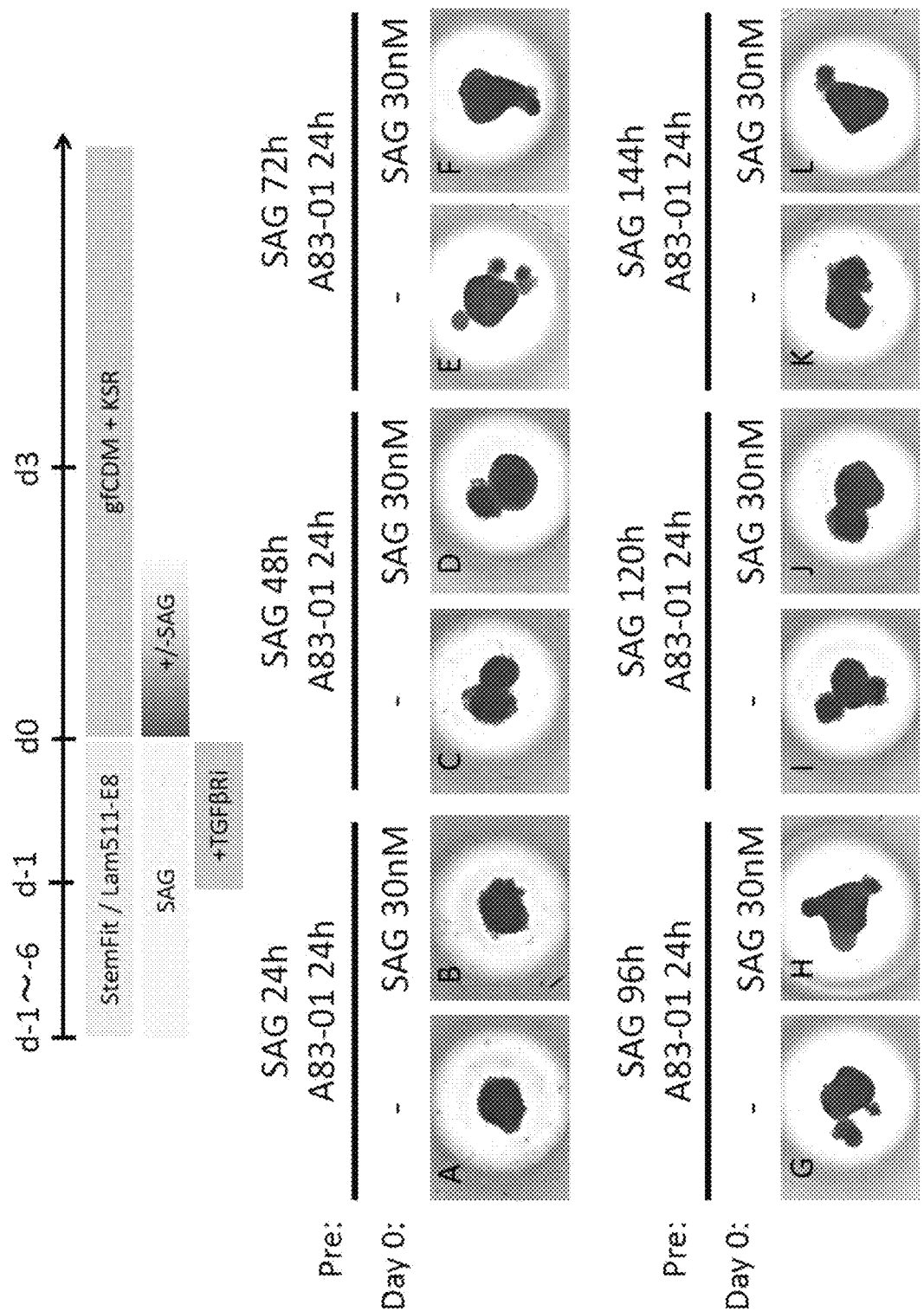
FIG. 21 shows culture conditions of Example 21, and bright field images of cells after culture (A-L).

The thus-prepared cells were subjected to bright field observation on day 16 after the start of suspension culturing under an inverted microscope (KEYENCE). As a result, it was found that a cell aggregate grew, and a neural tissue could be formed efficiently under any conditions involving preconditioning with SAG for 24-144 hr, and in the co-presence of A83-01 and SAG for the last 24 hr in step 1 (FIG. 21, A-L).

From these results, it was found that a neural tissue can be produced efficiently from feeder-free human iPS cells under any conditions involving preconditioning with a Shh signal transduction pathway activating substance for the period of 24-144 hr in step 1.

Example 22: Example of Formation of Retinal Tissue from Feeder-Free Human iPS Cells by Preconditioning with Shh Signal Transduction Pathway Activating Substance for 2 Days in Step 1, Using Shh Signal Transduction Pathway Activating Substance in Step 2, and Adding BMP Activating Substance Once or Plural Times in Step 3

Human iPS cells (Ff-I01 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

The human iPS cells 2 days before subconfluence were subjected to feeder-free culturing in the presence of SAG (Shh signal transduction pathway activating substance, 300 nM) for 2 days (preconditioning treatment).

The above human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used.

Figure 22:
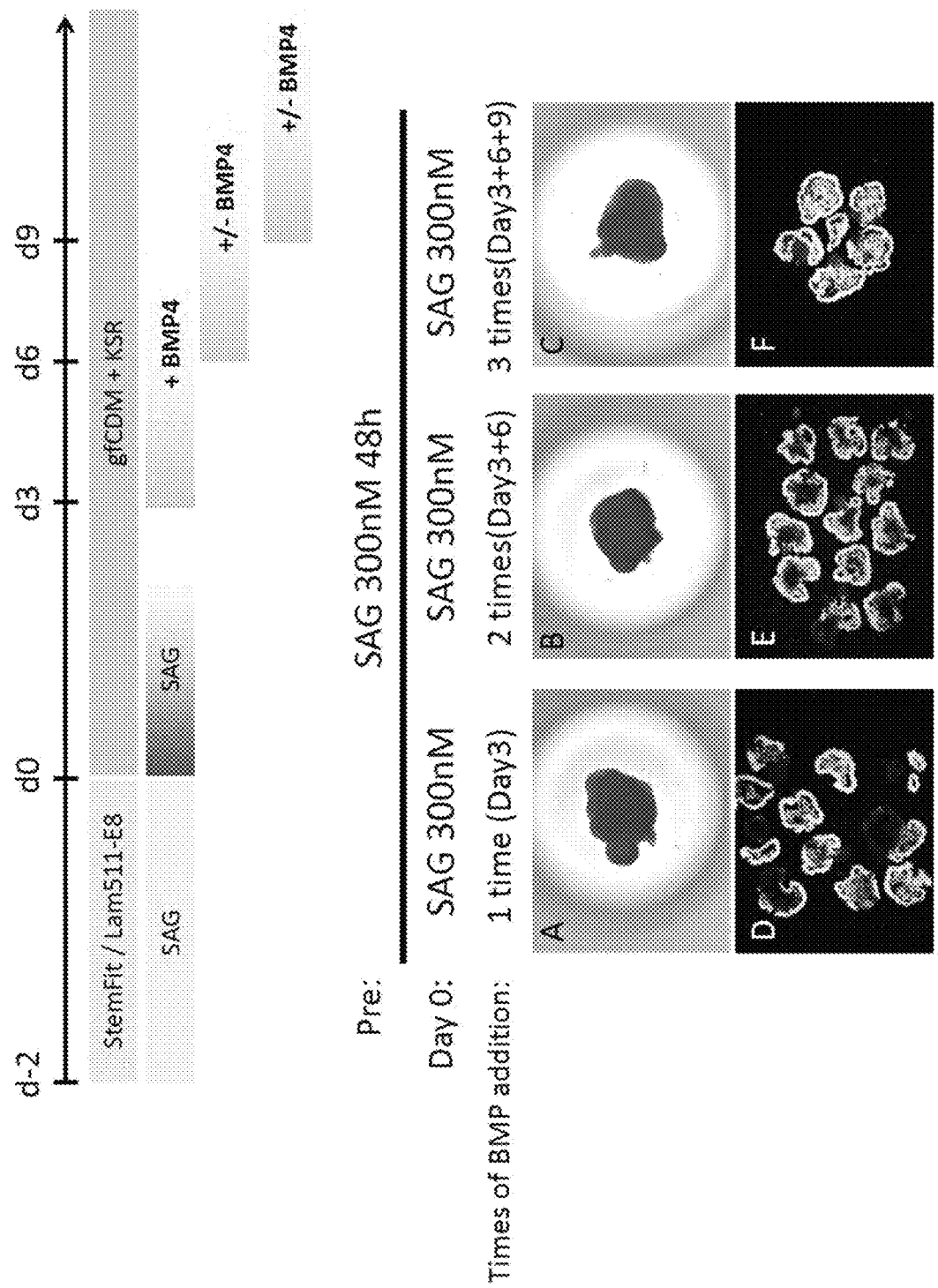
FIG. 22 shows culture conditions of Example 22, bright field images of cells after culture (A-C), and immunohistochemical staining images of aggregates for Chx10 (D-F).

At the time of the start of suspension culturing (day 0 after the start of suspension culturing, start of step 2), Y27632 (final concentration 20 μM) and SAG (Shh signal transduction pathway activating substance, 300 nM) were added to the above serum-free medium (FIG. 22). By day 2 after the start of suspension culturing, a cell aggregate was formed (step 2 completed, step 3 start) under any conditions. On day 3 or later from the start of suspension culturing, BMP4 was added under 3 conditions including the following conditions 1-3.

Condition 1: (+BMP4 addition once) On day 3 of suspension culturing, a medium (50 µl) free of Y27632 and SAG, and containing human recombinant BMP4 (manufactured by R&D) was added such that the final concentration of exogenous human recombinant BMP4 was 1.5 nM (55 ng/ml). On day 6 or later from the start of suspension culturing, a half amount of the medium was changed to a serum-free medium free of Y27632, SAG and human recombinant BMP4.

Condition 2: (+BMP4 addition twice) On day 3 of suspension culturing, a medium (50 µl) free of Y27632, SAG and containing human recombinant BMP4 (manufactured by R&D) was added such that the final concentration of exogenous human recombinant BMP4 was 1.5 nM (55 ng/ml). On day 6 from the start of suspension culturing, 50 µl of the medium was discarded, and 50 µl of a medium free of Y27632 and SAG and containing human recombinant BMP4 (manufactured by R&D) was added to maintain the final concentration of exogenous human recombinant BMP4 at 1.5 nM (55 ng/ml). On day 9 or later from the start of suspension culturing, a half amount of the medium was changed with a serum-free medium free of Y27632, SAG, and human recombinant BMP4.

Condition 3: (+BMP4 addition three times) On day 3 of suspension culturing, a medium (50 µl) free of Y27632, SAG and containing human recombinant BMP4 (manufactured by R&D) was added such that the final concentration of exogenous human recombinant BMP4 was 1.5 nM (55 ng/ml). On days 6 and 9 from the start of suspension culturing, 50 µl of the medium was discarded, and 50 µl of a medium free of Y27632 and SAG and containing human recombinant BMP4 (manufactured by R&D) was added to maintain the final concentration of exogenous human recombinant BMP4 at 1.5 nM (55 ng/ml). On day 12 or later from the start of suspension culturing, a half amount of the medium was changed with a serum-free medium free of Y27632, SAG and human recombinant BMP4.

Thereafter, a half amount of the medium was changed, once every 2-4 days, with the above serum-free medium free of Y27632, SAG, and human recombinant BMP4.

The thus-prepared cells were subjected to bright field observation under an inverted microscope (KEYENCE) on day 16 after the start of suspension culturing (FIG. 22, A-C). As a result, it was found that a cell aggregate grew and a neural tissue could be formed efficiently under respective conditions involving addition of BMP4 1, 2 or 3 times (FIG. 22, A-C).

From these results, it was found that a neural tissue can be produced efficiently from feeder-free human iPS cells under conditions involving preconditioning with a Shh signal transduction pathway activating substance (SAG) for 2 days in step 1, and addition of a BMP signal transduction pathway activating substance 1, 2 or 3 times in step 3.

Cell aggregates on day 16 after the start of suspension culturing were fixed with 4% para-formaldehyde to prepare frozen sections. These frozen sections were immunostained for Chx10 (anti-Chx10 antibody, Exalpha, sheep), which is one of the retinal tissue markers. These immunostained sections were observed under a fluorescence microscope. As a result, it was found that the proportion of Chx10-positive cells in the total cells was about 60% under conditions with the addition of BMP4 once, and about 80% under conditions with the addition thereof 2 or 3 times (FIG. 22, D-F).

From these results, it was found that a retinal tissue can be produced efficiently from feeder-free human iPS cells under conditions involving preconditioning with a Shh signal transduction pathway activating substance (SAG) for 2 days in step 1, and addition of a BMP signal transduction pathway activating substance 1, 2 or 3 times in step 3 (i.e., conditions to maintain BMP signal transduction pathway activating substance concentration (1.5 nM) for 3, 6, 9 days).

Example 23: Example of Formation of Retinal Tissue from Feeder-Free Human iPS Cells by Preconditioning with Shh Signal Transduction Pathway Activating Substance for 2 Days in Step 1, Using Shh Signal Transduction Pathway Activating Substance in Step 2, and Adding BMP4 (1.5 nM or 5 nM) in Step 3

Human iPS cells (Ff-I01 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

The human iPS cells 2 days before subconfluence were subjected to feeder-free culturing in the presence of SAG (Shh signal transduction pathway activating substance, 300 nM) for 2 days (preconditioning treatment).

The above human iPS cells were treated with the cell dispersion solution by using TrypLE Select (manufactured by Life Technologies), further dispersed into single cells by pipetting operation, and the above human iPS cells dispersed into single cells were suspended in 100 µl of a serum-free medium at $1.0 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used.

At the time of the start of suspension culturing (day 0 after the start of suspension culturing, start of step 2), Y27632 (final concentration 20 µM) and SAG (Shh signal transduction pathway activating substance, 1000 nM) were added to the above serum-free medium. By day 2 after the start of suspension culturing, cell aggregates were formed under any conditions (step 2 completed, step 3 start).

On day 3 after the start of suspension culturing, a medium (50 µl) free of Y27632 and SAG, and containing human recombinant BMP4 (manufactured by R&D) was added such that the final concentration of exogenous human recombinant BMP4 was 1.5 nM (55 ng/ml) or 5 nM (183 ng/ml). On day 6 after the start of suspension culturing, 50 µl of the medium was discarded, and 50 µl of a medium free of Y27632 and SAG and containing human recombinant BMP4 (manufactured by R&D) was added to maintain the final concentration of exogenous human recombinant BMP4 at 1.5 nM (55 ng/ml) or 5 nM (183 ng/ml). Thereafter, a half amount of the medium was changed, once every 2-4 days, with the above serum-free medium free of Y27632, SAG, and human recombinant BMP4.

Figure 23:
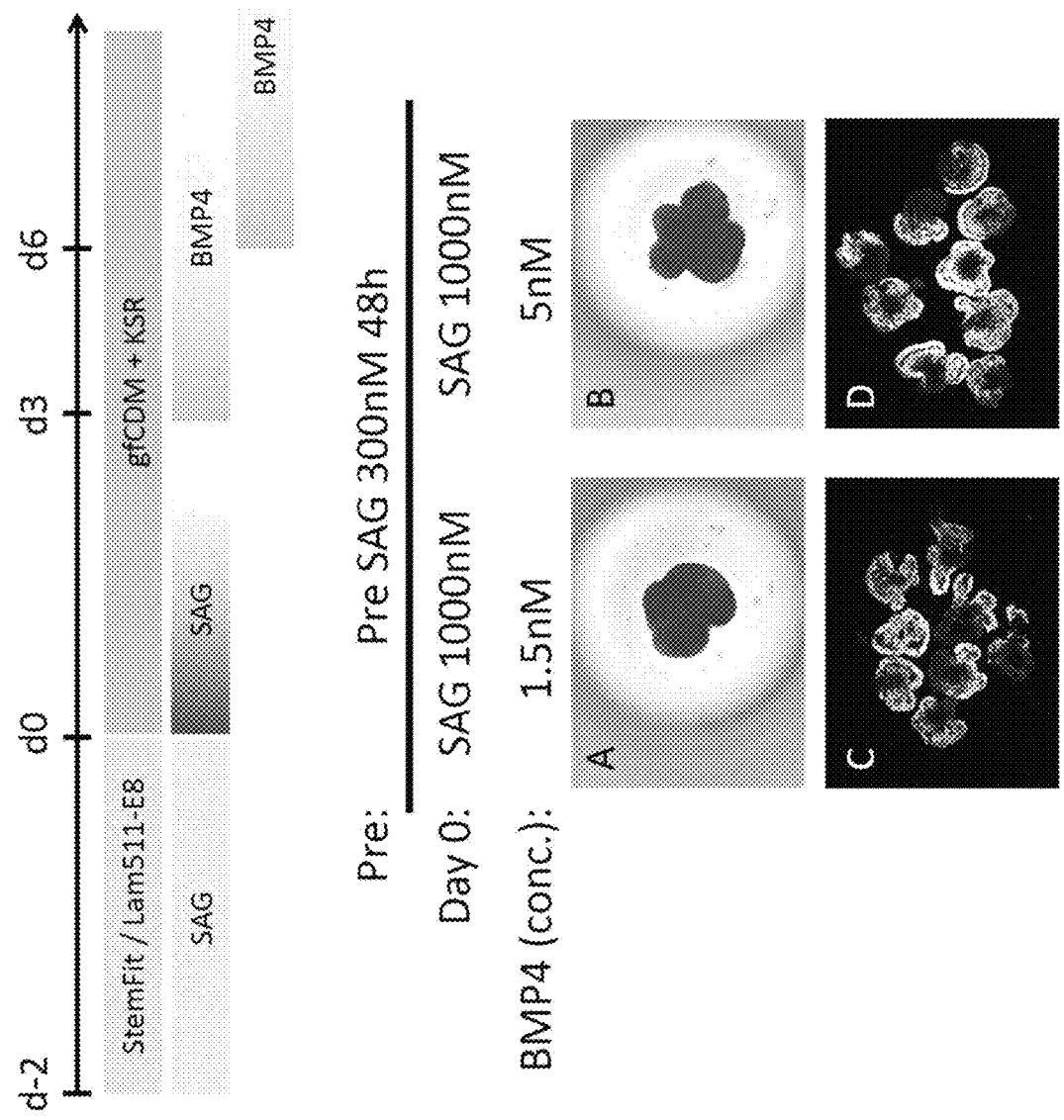
FIG. 23 shows culture conditions of Example 23, bright field images of cells after culture (A,B), and immunohistochemical staining images of aggregates for Chx10 (C,D).

The thus-prepared cells were subjected to bright field observation under an inverted microscope (KEYENCE) on day 16 after the start of suspension culturing. As a result, it was found that a cell aggregate was formed and a neural tissue could be formed efficiently under respective conditions involving addition of BMP4 at 1.5 nM and 5 nM (FIG. 23, A, B).

Cell aggregates on day 16 after the start of suspension culturing were fixed with 4% para-formaldehyde to prepare frozen sections. These frozen sections were immunostained for Chx10 (anti-Chx10 antibody, Exalpha, sheep), which is one of the retinal tissue markers, and observed under a fluorescence microscope. As a result, it was found that the proportion of Chx10-positive cells in the total cells is about 70% under conditions with the addition of BMP4 twice to maintain the final concentration of 1.5 nM (FIG. 23, C). In addition, the proportion of Chx10-positive cells in the total cells is about 80% under conditions with the addition of BMP4 twice to maintain the final concentration of 5 nM (FIG. 23, D)

From these results, it was found that a retinal tissue can be produced efficiently under conditions involving preconditioning with a Shh signal transduction pathway activating substance for 2 days in step 1, addition of a Shh signal transduction pathway activating substance in step 2, and addition of BMP4 twice at 1.5 nM or 5 nM in step 3 (i.e., conditions to maintain BMP signal transduction pathway activating substance concentration (1.5 nM or 5 nM) for 6 days).

Example 24: Example of Formation of Neural Tissue from Feeder-Free Human iPS Cells by Preconditioning with TGFβ Family Signal Transduction Pathway Inhibiting Substance (A83-01) and Shh Signal Transduction Pathway Activating Substance (SAG, 30 nM, 300 nM, 500 nM, or 1000 nM) for One Day in Step 1, and Using Shh Signal Transduction Pathway Activating Substance (SAG) in Step 2

Human iPS cells (Ff-I01 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

Human iPS cells one day before subconfluence were subjected to feeder-free culturing in the presence of A83-01 (manufactured by Wako, TGFβR inhibitor 0.5 μM) and SAG (Shh signal transduction pathway activating substance, 30 nM, 300 nM, 500 nM, or 1000 nM) for one day (preconditioning treatment).

The above human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used.

At the time of the start of suspension culturing (day 0 after the start of suspension culturing, start of step 2), Y27632 (final concentration 20 μM) and SAG (Shh signal transduction pathway activating substance, 300 nM) were added to the above serum-free medium. By day 2 after the start of suspension culturing, a cell aggregate was formed under any conditions (step 2 completed, step 3 start). On day 3 after the start of suspension culturing, a medium (50 μl) free of Y27632 and SAG, and containing human recombinant BMP4 (manufactured by R&D) was added such that the final concentration of exogenous human recombinant BMP4 was 1.5 nM (55 ng/ml). On day 6 after the start of suspension culturing, 50 μl of the medium was discarded, and 50 μl of a medium free of Y27632 and SAG and containing human recombinant BMP4 (manufactured by R&D) was added to maintain the final concentration of exogenous human recombinant BMP4 at 1.5 nM (55 ng/ml). Thereafter, a half amount of the medium was changed, once every 2-4 days, with the above serum-free medium free of Y27632, SAG, and human recombinant BMP4.

Figure 24:
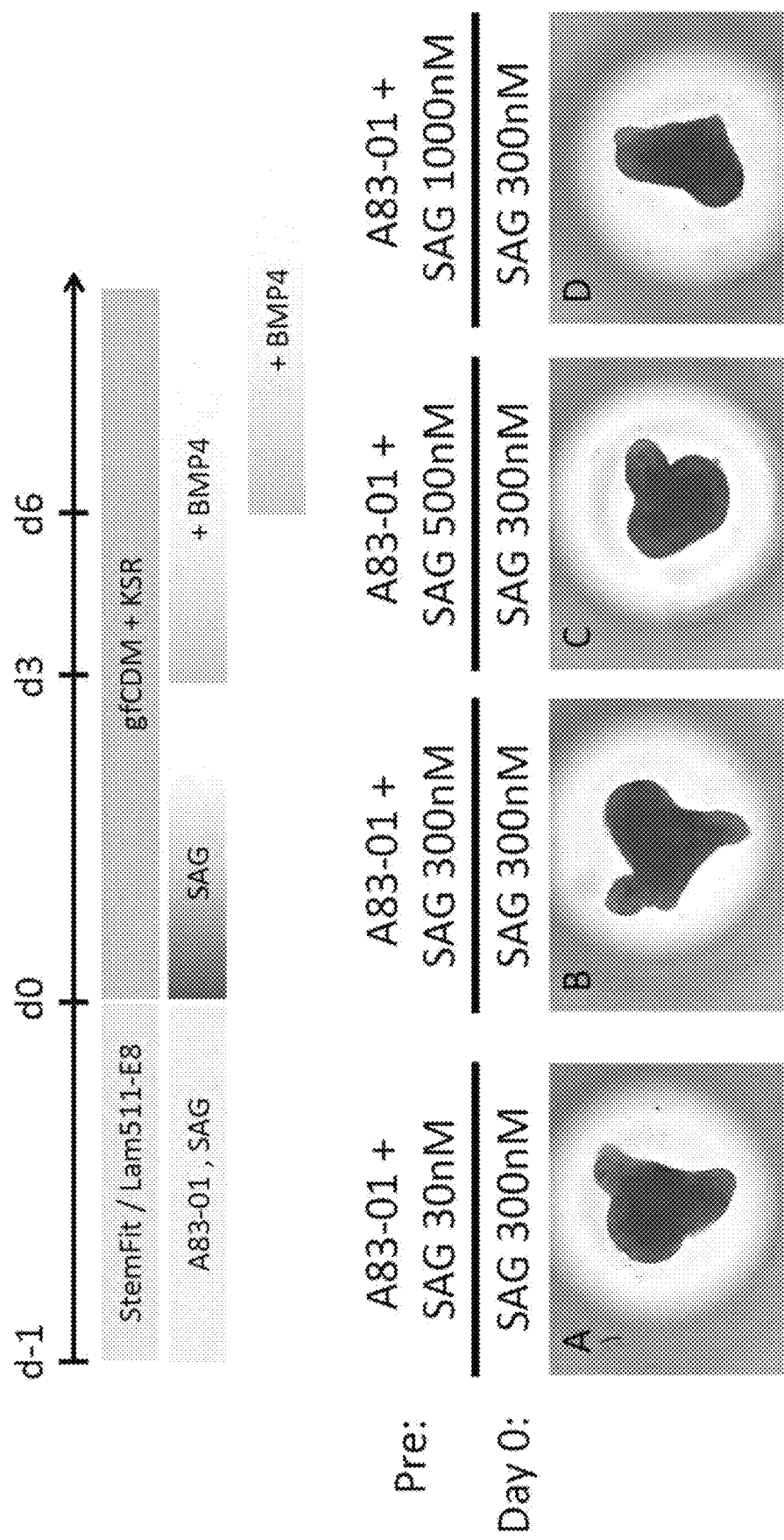
FIG. 24 shows culture conditions of Example 24, and bright field images of cells after culture (A-D).

The thus-prepared cells were subjected to bright field observation under an inverted microscope (KEYENCE) on day 17 after the start of suspension culturing (FIG. 24). As a result, it was found that a cell aggregate was formed and a neural tissue could be formed efficiently under the conditions involving preconditioning with A83-01 and SAG (concentration range of 30-1000 nM) in step 1 and addition of SAG in step 2 (FIG. 24, A-D).

From these results, it was found that a neural tissue can be produced efficiently from feeder-free human iPS cells under conditions involving preconditioning with TGFβ family signal transduction pathway inhibiting substance (A83-01) and Shh signal transduction pathway activating substance (SAG, concentration range of 30 nM-1000 nM) in step 1.

Example 25: Example of Formation of Neural Tissue from Feeder-Free Human iPS Cells by Preconditioning with TGFβ Family Signal Transduction Pathway Inhibiting Substance (A83-01) and Shh Signal Transduction Pathway Activating Substance (SAG) for One Day in Step 1, and Using Shh Signal Transduction Pathway Activating Substance (SAG) at Concentration of 30 nM, 300 nM, 500 nM, or 1000 nM in Step 2

Human iPS cells (Ff-I01 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

Human iPS cells one day before subconfluence were subjected to feeder-free culturing in the presence of A83-01 (manufactured by Wako, TGFβR inhibitor 0.5 μM) and SAG (Shh signal transduction pathway activating substance, 1000 nM) (preconditioning treatment) for one day.

The above human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at $1.0 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used.

At the time of the start of suspension culturing (day 0 after the start of suspension culturing, start of step 2), Y27632

Figure 25:
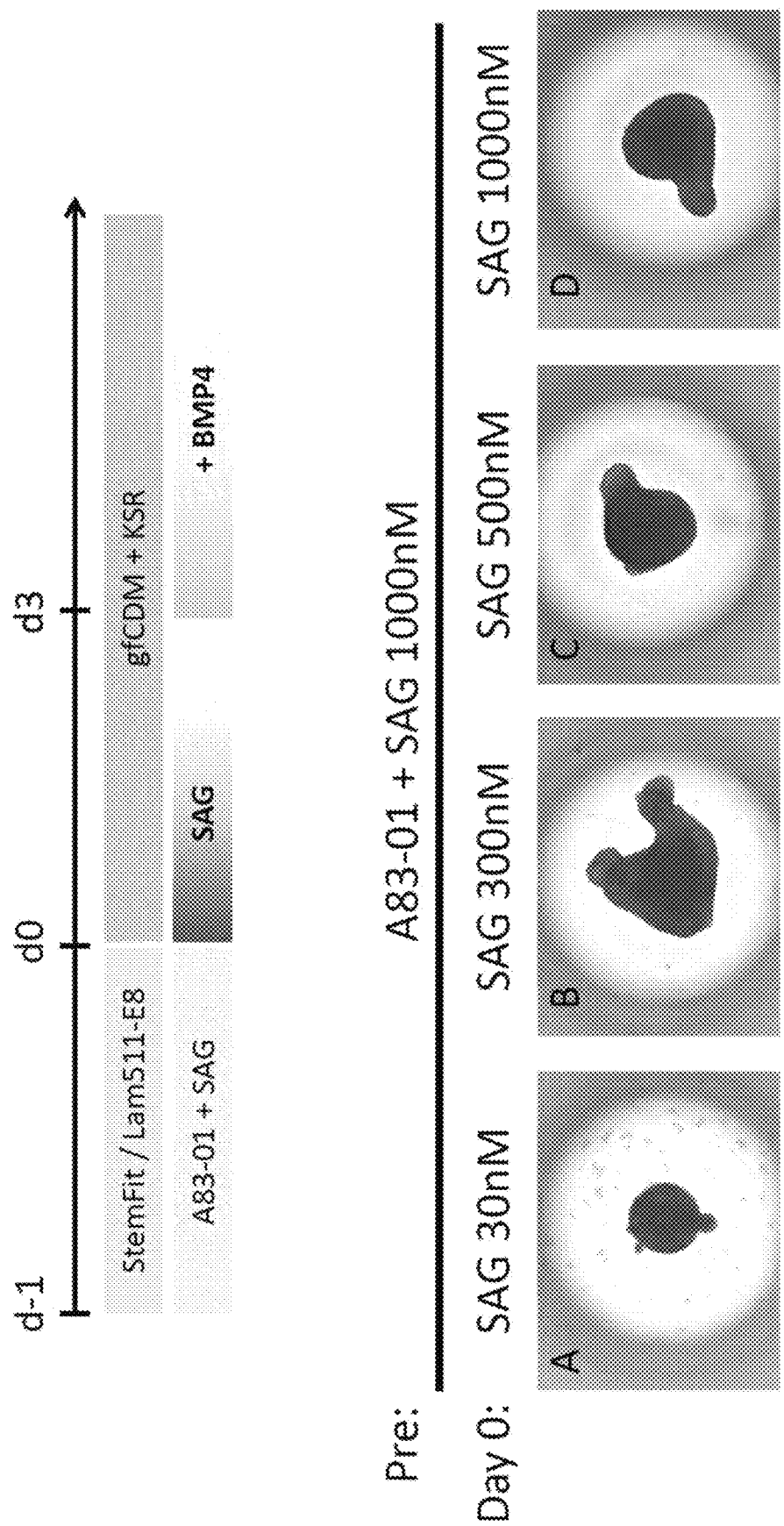
FIG. 25 shows culture conditions of Example 25, bright field images of cells after culture (A-D).

(final concentration 20 µM) and SAG (Shh signal transduction pathway activating substance, 30 nM, 300 nM, 500 nM, 1000 nM) were added to the above serum-free medium (FIG. 25). By day 2 after the start of suspension culturing, cell aggregates were formed (step 2 completed, step 3 start) under any conditions.

On day 3 after the start of suspension culturing, a medium (50 µl) free of Y27632 and SAG, and containing human recombinant BMP4 (manufactured by R&D) was added such that the final concentration of exogenous human recombinant BMP4 (manufactured by R&D) was 1.5 nM (55 ng/ml).

On day 6 after the start of suspension culturing, a half amount of the medium was changed with a serum-free medium free of Y27632, SAG and human recombinant BMP4. Thereafter, once every 2-4 days, a half amount of the medium was changed with the above serum-free medium free of Y27632, SAG and human recombinant BMP4.

The thus-prepared cells were subjected to bright field observation under an inverted microscope (KEYENCE) on day 17 after the start of suspension culturing. As a result, it was found that a cell aggregate was formed and a neural tissue could be formed efficiently under the conditions involving preconditioning with A83-01 and SAG in step 1 and addition of SAG at concentration 30 nM, 300 nM, 500 nM, or 1000 nM in step 2 (FIG. 25, A-D).

From these results, it was found that a neural tissue can be produced efficiently from feeder-free human iPS cells under conditions involving preconditioning with TGFβ family signal transduction pathway inhibiting substance (A83-01) and Shh signal transduction pathway activating substance (SAG) in step 1 and addition of SAG at a concentration range of 30 to 1000 nM, at the time of the start of differentiation induction.

Example 26: Production Example of Retinal Tissue from Human iPS Cells by Using Human iPS Cell Established Using Sendaivirus and Subjected to Feeder-Free Culturing as a Starting Material, TGFβ Family Signal Transduction Pathway Inhibiting Substance in Step 1, and BMP Signal Transduction Pathway Activating Substance in Step 3

Human iPS cells (DSPC-3 strain, established by Sumitomo Dainippon Pharma Co., Ltd.) were established using commercially available Sendaivirus vectors (4 factors including Oct3/4, Sox2, KLF4, and c-Myc, CytoTune kit manufactured by DNAVEC (now ID Pharma)) and StemFit medium (AK03; manufactured by Ajinomoto Co., Inc.), Laminin 511-E8 (manufactured by Nippi, Inc.), and according to the methods described in published protocol of Life Technologies (iPS 2.0 Sendai Reprogramming Kit, Publication Number MAN0009378, Revision 1.0), and published protocol of Kyoto University (establishment • maintenance culture of human iPS cells, CiRA_Ff-iPSC_protocol_JP_v140310, http://www.cira.kyoto-u.ac.jp/j/research/protocol.html).

The human iPS cells (DSPC-3 strain) were subjected to feeder-free culturing according to the method described in Scientific Reports, 4, 3594 (2014). As a feeder-free medium, StemFit medium (AK03, manufactured by Ajinomoto Co., Inc.) was is used, and as a feeder-free scaffold, Laminin 511-E8 (manufactured by Nippi, Inc.) was used.

Human iPS cells (DSPC-3 strain) were subjected to feeder-free culturing until one day before subconfluence by using StemFit medium according to the method described in Example 1. The human iPS cells one day before subconfluence were subjected to feeder-free culturing for one day under the following 3 conditions.

Figure 26:
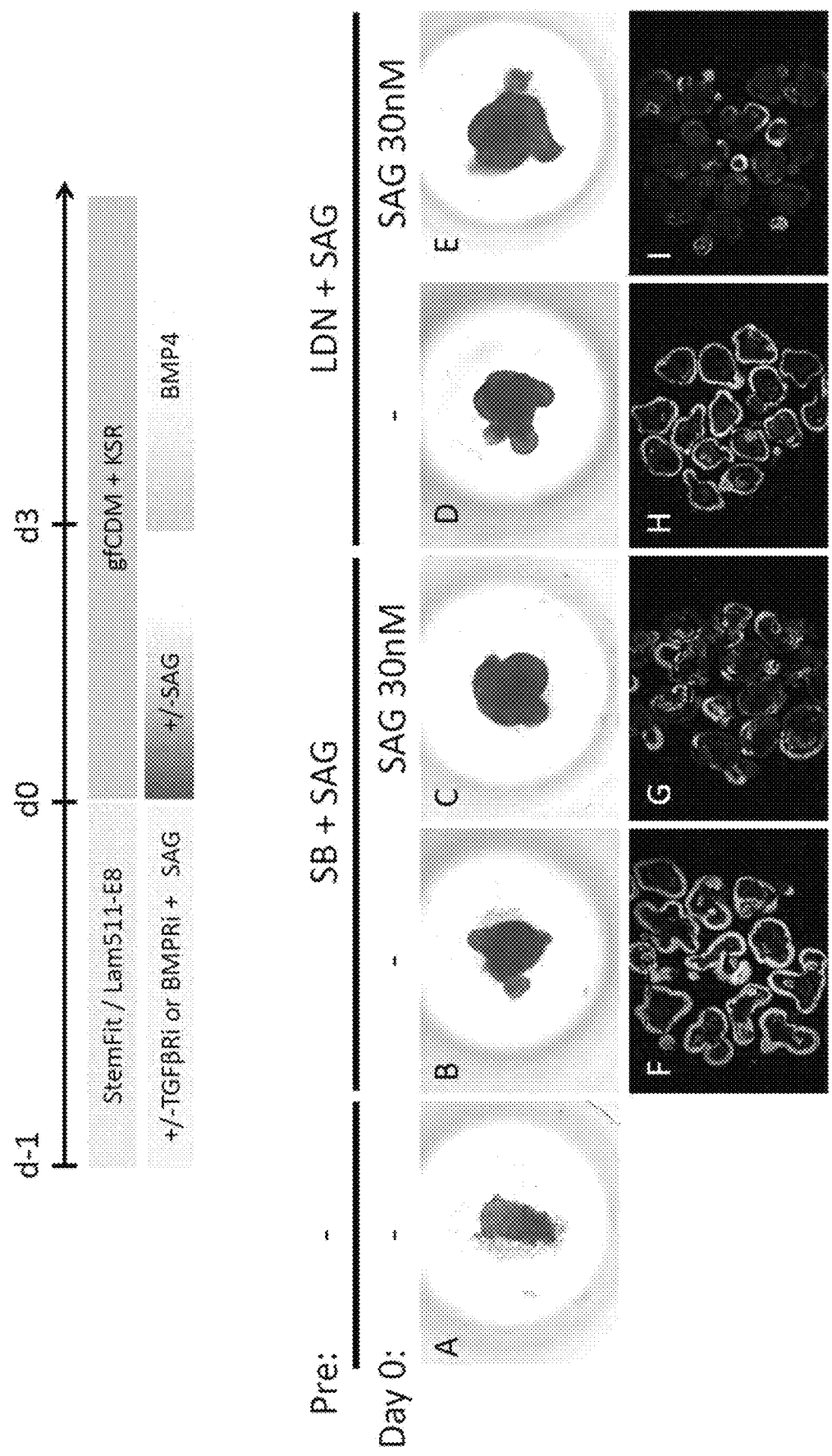
FIG. 26 shows culture conditions of Example 26, bright field images of cells after culture (A-E), and immunohistochemical staining images of aggregates for Chx10 (F-I).

Condition 1: SB431542 (TGFβR inhibitor, 5 µM) and SAG (Shh signal transduction pathway activating substance, 300 nM) (FIG. 26, B, C, F, G)

Condition 2: LDN193189 (BMP signal transduction pathway inhibiting substance, 100 nM) and SAG (Shh signal transduction pathway activating substance, 300 nM) (FIG. 26, D, E, H, I)

Condition 3: Free of exogenous TGFβ family signal transduction pathway inhibiting substance and Shh signal transduction pathway activating substance (FIG. 26, A)

The thus-prepared human iPS cells of conditions 1-3 were treated with a cell dispersion solution using TrypLE Select (manufactured by Life Technologies), and further dispersed into single cells by pipetting operation. Thereafter, the above human iPS cells dispersed into single cells were suspended in 100 µl of a serum-free medium at $1.2 \times 10^4$ cells per well of a non-cell-adhesive 96-well culture plate (SUMILON Spheroid V-bottom plate PrimeSurface 96V-bottom plate, SUMITOMO BAKELITE), and subjected to suspension culturing at 37° C., 5% $CO_2$. As the serum-free medium therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culturing (day 0 after the start of suspension culturing, start of step 2), Y27632 (20 µM) was added to the above serum-free medium, and the medium was used under conditions with further is addition of a SAG exogenous Shh signal transduction pathway activating substance (final concentration 30 nM), or under conditions without further addition of SAG. On day 2 after the start of suspension culturing, a cell aggregate was formed. On day 3 after the start of suspension culturing, a medium (50 µl) free of Y27632 and SAG and containing human recombinant BMP4 (manufactured by R&D) was added such that the final concentration of the exogenous human recombinant BMP4 was 1.5 nM (55 ng/ml). On day 6 after the start of suspension culturing, a half amount of the medium was changed to a serum-free medium free of Y27632, SAG and human recombinant BMP4. Thereafter, once every 2-4 days, a half amount of the medium was changed with the above serum-free medium free of Y27632, SAG, and human recombinant BMP4.

The thus-prepared cell aggregates were subjected to bright field observation under an inverted microscope (BIOREVO manufactured by KEYENCE) on day 22 after the start of suspension culturing (FIG. 26, A-E). As a result, it was found that, without preconditioning (condition 3), a cell aggregate did not grow, and a neuroepithelium was not formed (FIG. 26, A). On the other hand, it was found that a cell aggregate grew and a neuroepithelium was formed under conditions involving preconditioning with SB431542 and SAG, or LDN193189 and SAG (condition 1, 2) in step 1 (FIG. 26, B-E).

The thus-prepared cell aggregates were fixed with 4% para-formaldehyde on day 22 after the start of suspension culturing to prepare frozen sections. These frozen sections were immunostained for Chx10 (anti-Chx10 antibody, Exalpha, sheep), which is one of the retinal tissue markers, and observed under a fluorescence microscope (BIOREVO manufactured by KEYENCE).

As a result, it was found that, in a cell aggregate produced under the conditions involving preconditioning with SB431542 and SAG in step 1, no addition of SAG in step 2, and addition of BMP4 in step 3, the proportion of Chx10- positive cells in the total cells is about 90% (FIG. 26, F). In addition, in a cell aggregate produced under conditions involving preconditioning with SB431542 and SAG in step 1, addition of SAG in step 2, and addition of BMP4 in step 3, the proportion of Chx10-positive cells in the total cells is about 70% (FIG. 26, G). That is, it was found that a retinal tissue can be produced under conditions involving preconditioning with TGFβR inhibitor (5B431542) and Shh signal transduction pathway activating substance in step 1, and addition of BMP signal transduction pathway activating substance in step 3, even when Shh signal transduction pathway activating substance is added or not added in step 2.

Furthermore, it was found that, in a cell aggregate produced under the conditions involving preconditioning with LDN193189 and SAG in step 1, no addition of SAG in step 2, and addition of BMP4 in step 3, the proportion of Chx10-positive cells in the total cells is about 90% (FIG. 26, I). In addition, in a cell aggregate produced under conditions involving preconditioning with LDN193189 and SAG in step 1, addition of SAG in step 2, and addition of BMP4 in step 3, the proportion of Chx10-positive cells in the total cells is about 60% (FIG. 26, H). That is, it was found that a retinal tissue can be produced under conditions involving preconditioning with BMPR inhibitor (LDN193189) and Shh signal transduction pathway activating substance in step 1, and addition of BMP signal transduction pathway activating substance in step 3, even when Shh signal transduction pathway activating substance is added or not added in step 2.

From these results, it was found that a retinal tissue can be produced from human iPS cells produced by Sendaivirus and subjected to feeder-free culturing as a starting material, by adding TGFβ family signal transduction pathway inhibiting substance and Shh signal transduction pathway activating substance in step 1, and adding BMP signal transduction pathway activating substance in step 3.

Example 27: Production Example of Retinal Tissue from Human iPS Cells by Using Human ES Cell Subjected to Feeder-Free Culturing as a Starting Material, TGFβ Family Signal Transduction Pathway Inhibiting Substance in Step 1, Shh Signal Transduction Pathway Activating Substance in Step 2, and BMP Signal Transduction Pathway Activating Substance in Step 3

Figure 27:
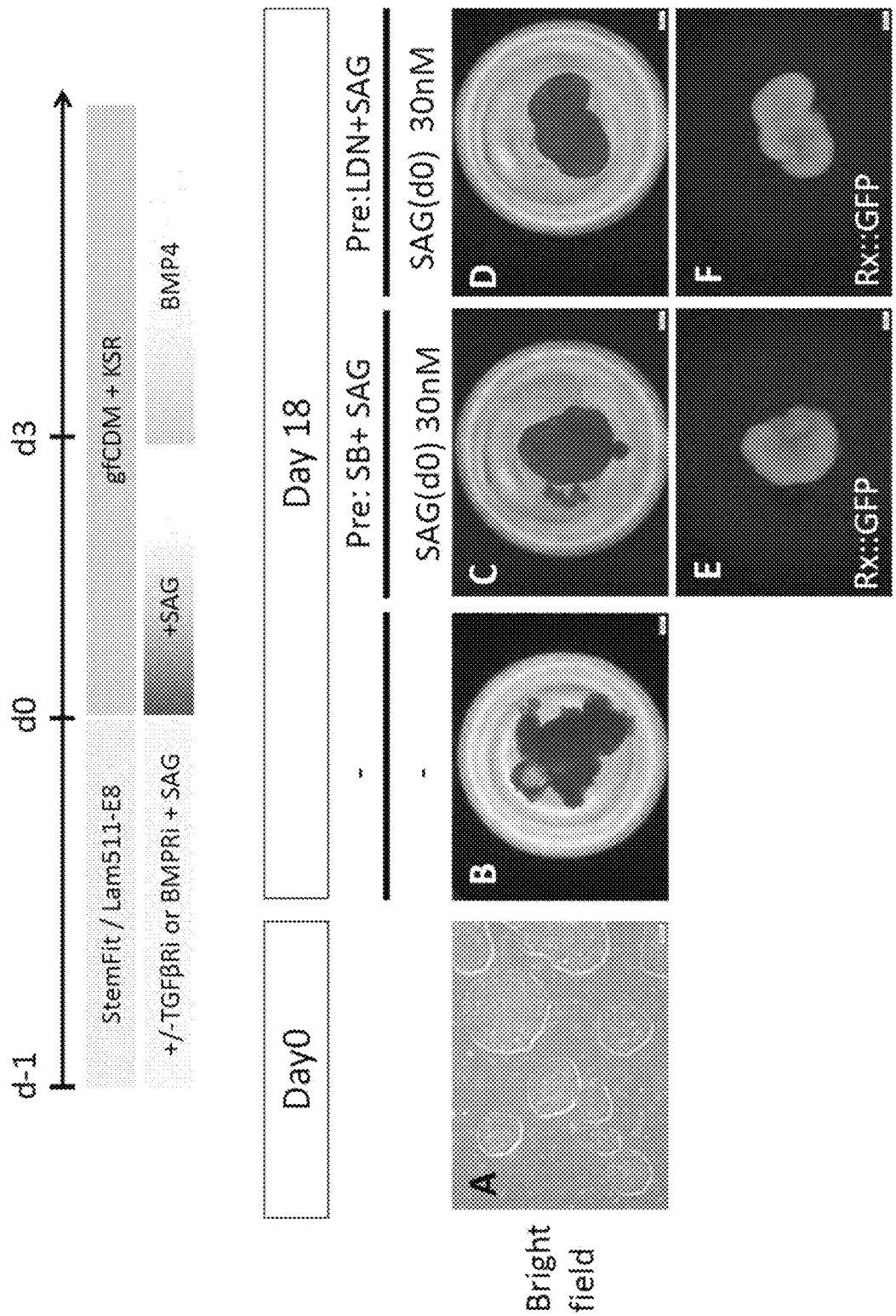
FIG. 27 shows culture conditions of Example 27, culture image of human ES cells (A), bright field images of cells after culture (B-D), and fluorescence images for Rx::GFP (E,F).

Rx::GFP knock-in human ES cells (derived from KhES-1 strain; Cell Stem Cell, 2012, 10(6) 771-785) were subjected to feeder-free culturing according to the method described in Scientific Reports, 4, 3594 (2014) (FIG. 27, A). As a feeder-free medium, StemFit medium (AK03, manufactured by Ajinomoto Co., Inc.) was used, and as a feeder-free scaffold, Laminin 511-E8 (manufactured by Nippi, Inc.) was used.

Human ES cells (Rx::GFP strain) were subjected to feeder-free culturing until one day before subconfluence by using StemFit medium and according to the method described in Example 1. The human iPS cells one day before subconfluence were subjected to feeder-free culturing for one day under the following 3 conditions.

Condition 1: SB431542 (TGFβR inhibitor, 5 µM) and SAG (Shh signal transduction pathway activating substance, 30 nM) (FIG. 27, C, E)

Condition 2: LDN193189 (BMPR inhibitor, 100 nM) and SAG (Shh signal transduction pathway activating substance, 30 nM) (FIG. 27, D, F)

Condition 3: Free of exogenous TGFβ family signal transduction pathway inhibiting substance and Shh signal transduction pathway activating substance (FIG. 27, B)

The thus-prepared human ES cells of conditions 1-3 were treated with a cell dispersion solution using TrypLE Select (manufactured by Life Technologies), and further dispersed into single cells by pipetting operation. Thereafter, the above human ES cells dispersed into single cells were suspended in 100 µl of a serum-free medium at $1.2 \times 10^4$ cells per well of a non-cell-adhesive 96-well culture plate (SUMILON Spheroid V-bottom plate PrimeSurface 96V-bottom plate, SUMITOMO BAKELITE), and subjected to suspension culturing at 37° C., 5% $CO_2$. As the serum-free medium therefor, a serum-free medium which is a 1:1 mixture of F-12 medium and IMDM medium supplemented with 10% KSR, 450 µM 1-monothioglycerol, 1× Chemically defined lipid concentrate was used.

Under condition 3 without preconditioning, at the time of the start of suspension culturing (day 0 after the start of suspension culturing, step 2 start), Y27632 (20 µM) was added to the above serum-free medium, and a serum-free medium under conditions without further addition of exogenous Shh signal transduction pathway activating substance was used.

Under conditions 1 and 2, at the time of the start of suspension culturing (day 0 after the start of suspension culturing, start of step 2), Y27632 (20 µM) was added to the above serum-free medium, and the medium was used under conditions with further addition of a SAG, an exogenous Shh signal transduction pathway activating substance (final concentration 30 nM) (FIG. 27). Under any of conditions 1-3, a cell aggregate was formed on day 2 after the start of suspension culturing. On day 3 after the start of suspension culturing, a medium (50 µl) free of Y27632 and SAG and containing human recombinant BMP4 (manufactured by R&D) was added such that the final concentration of the exogenous human recombinant BMP4 was 1.5 nM (55 ng/ml). On day 6 after the start of suspension culturing, a half amount of the medium was changed to a serum-free medium free of Y27632, SAG and human recombinant BMP4. Thereafter, once every 3 days, a half amount of the medium was changed to the above serum-free medium free of Y27632, SAG, and human recombinant BMP4.

The thus-prepared cell aggregate was subjected to bright field observation under an inverted microscope (BIOREVO manufactured by KEYENCE) on day 18 after the start of suspension culturing. As a result, it was found that, without preconditioning (condition 3), the efficiency of neuroepithelial formation in cell aggregate was poor (FIG. 27, B). On the other hand, it was found that a cell aggregate grew and a neuroepithelium was formed under conditions involving preconditioning with SB431542 and SAG, or LDN193189 and SAG in step 1 (condition 1, 2) (FIG. 27, C,D). That is, it was found that the precondition operation in step 1 improves efficiency of neuroepithelial production.

The expression of GFP under the regulation of Rx gene promoter in the thus-prepared cell aggregate (human ES cell Rx::GFP-derived strain) was observed under a fluorescence microscope (BIOREVO manufactured by KEYENCE). As a result, it was found that, under conditions involving preconditioning with a combination of SB431542 and SAG, or a combination of LDN193189 and SAG in step 1, addition of SAG in step 2, and addition of BMP4 in step 3, about 90% of the total cells are GFP-strong positive (FIG. 27, E, F).

From these results, it was found that a retinal tissue can be produced from human ES cells subjected to feeder-free culturing as a starting material, by adding TGFβ family signal transduction pathway inhibiting substance and Shh signal transduction pathway activating substance in step 1, and adding BMP signal transduction pathway activating substance in step 3.

Example 28: Production Example of Retinal Tissue from Human iPS Cells by Using Human iPS Cell Subjected to Feeder-Free Culturing as a Starting Material, TGFβ Family Signal Transduction Pathway Inhibiting Substance in Step 1, Shh Signal Transduction Pathway Activating Substance in Step 2, and BMP Signal Transduction Pathway Activating Substance in Step 3

Human iPS cell (1231A3 strain) were subjected to feeder-free culturing until one day before subconfluence by using StemFit medium according to the method described in Example 1. The human iPS cells one day before subconfluence were subjected to feeder-free culturing with TGFβR inhibitor (SB431542, 5 µM) and Shh signal transduction pathway activating substance (SAG, 300 nM) for one day (Precondition).

The above human iPS cells were treated with a cell dispersion solution using TrypLE Select (manufactured by Life Technologies), and further dispersed into single cells by pipetting operation. Thereafter, the above human iPS cells dispersed into single cells were suspended in 100 µl of a serum-free medium at $1.2 \times 10^4$ cells per well of a non-cell-adhesive 96-well culture plate, and subjected to suspension culturing at 37° C., 5% $CO_2$. As the serum-free medium therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culturing (day 0 after the start of suspension culturing, step 2 start), at the time of the start of suspension culturing, Y27632 (final concentration 20 µM) and Shh signal action substance (SAG, 30 nM) was added to the above serum-free medium. By day 2 after the start of suspension culturing, a cell aggregate was formed (step 2 completed, step 3 start).

On day 3 after the start of suspension culturing, the medium was changed to the above serum-free medium free of Y27632 and SAG and containing human recombinant BMP4 (manufactured by R&D) to set the final concentration of the exogenous human recombinant BMP4 to 1.5 nM. On day 3 or later from the start of suspension culturing, a half amount of the medium was changed with the above serum-free medium free of Y27632, SAG, and human recombinant BMP4, once every 2-4 days. On day 17 after the start of suspension culturing, a cell aggregate grew, and neuroepithelium was formed.

The cell aggregate on day 17 after the start of suspension culturing was transferred to a 90 mm low-adhesion culture dish (manufactured by SUMITOMO BAKELITE), and cultured in a serum-free medium (DMEM/F12 medium supplemented with 1% N2 supplement) containing Wnt signal transduction pathway activating substance (CHIR99021, 3 µM) and FGF signal transduction pathway inhibiting substance (SU5402, 5 µM) at 37° C., 5% $CO_2$ for 3 days, that is, until day 20 after the start of suspension culturing. During this period, about 50 aggregates were subjected to suspension culturing in 10 ml of the above serum-free medium containing CHIR99021 and SU5402, per one 90 mm low-adhesion culture dish. On day 20 after the start of suspension culturing, thin neuroepithelium was formed, and a retinal pigment epithelium (RPE)-like tissue was formed.

Furthermore, the cell aggregates on day 20 after the start of suspension culturing were subjected to suspension culturing in a 90 mm low-adhesion culture dish (manufactured by SUMITOMO BAKELITE) in a serum-containing medium (DMEM/F12 medium supplemented with 10% fetal calf serum, 1% N2 supplement, 0.5 µM retinoic acid, and 100 µM taurine) free of Wnt signal transduction pathway activating substance and FGF signal transduction pathway inhibiting substance at 37° C., 5% $CO_2$, atmospheric oxygen concentration (about 20%) for 81 days, i.e., until day 101 after the start of suspension culturing. From day 20 to day 101 after the start of suspension culturing, a half amount of the medium was changed to the above serum-containing medium once every 2-4 days. During this period, about 30 aggregates were subjected to suspension culturing in 15 ml of the above serum-free medium, per one 90 mm low-adhesion culture dish. On day 30 or later from the start of suspension culturing, a neural retina-like tissue was present.

The thus-prepared cell aggregates on day 101 after the start of suspension culturing were each fixed with 4% para-formaldehyde to give frozen sections. These frozen sections were immunostained for Rx (anti-Rax/Rx antibody, manufactured by Takara, guinea pig), which is one of the retinal tissue markers, Ki67 (anti-Ki67 antibody, manufactured by Leica, rabbit), which is one of the proliferating cell markers, Chx10 (anti-Chx10 antibody, Exalpha, sheep), which is one of the neural retinal progenitor cell markers, Crx (anti-Crx antibody, manufactured by Takara, rabbit), which is one of the photoreceptor precursor cell markers, Blimp1 (anti-Blimp1 antibody, manufactured by Santa Cruz, rat), which is one of the photoreceptor precursor cell markers, and Brn3b (anti-Brn3b antibody, manufactured by Santa Cruz, goat), which is one of the ganglion cell markers, and observed under a fluorescence microscope (BIOREVO manufactured by KEYENCE).

Figure 28:
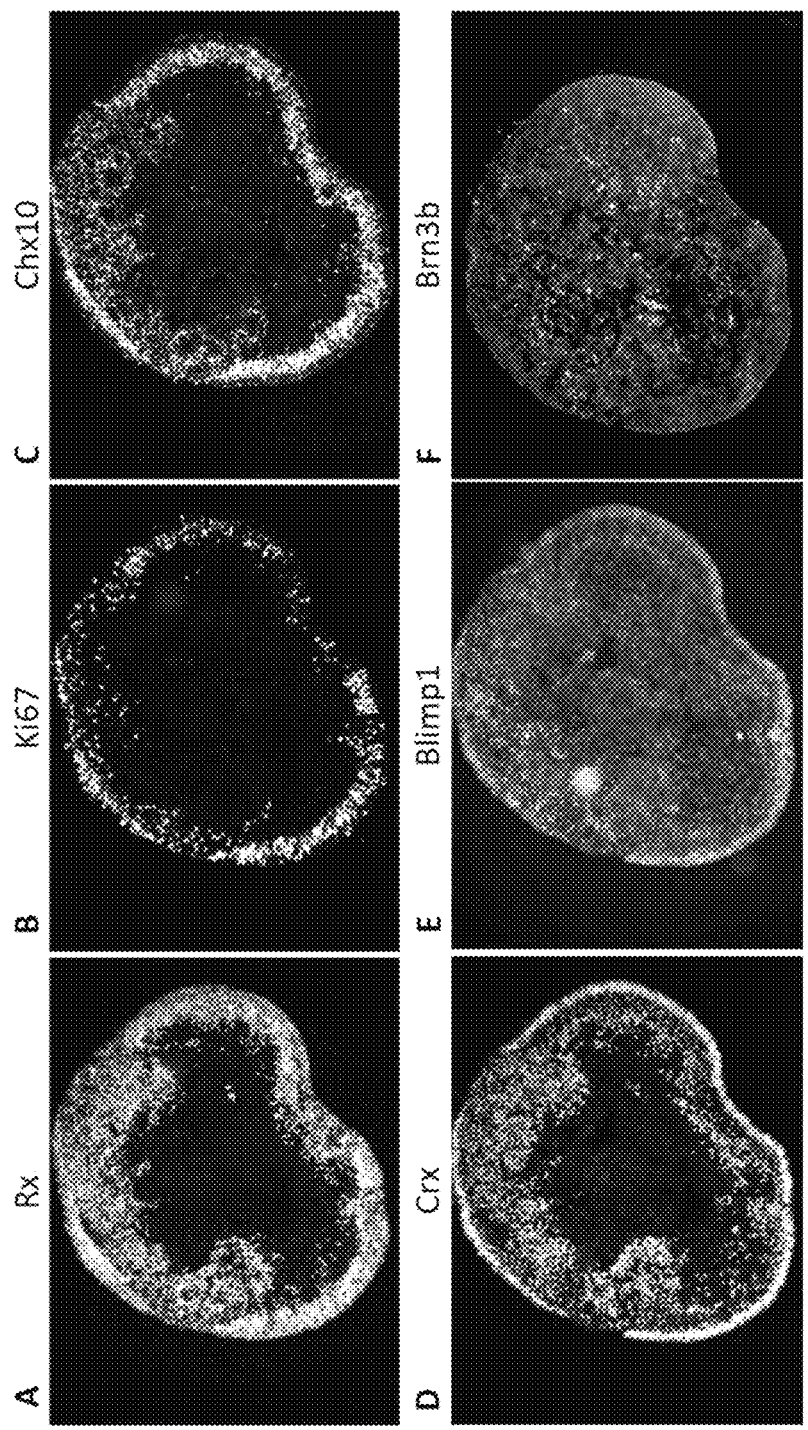
FIG. 28 shows immunohistochemical staining images of aggregates for retinal tissue markers (Rx, Chx10, Crx, Blimp1, Brn3b) and Ki67 (A-F).

As a result, it was found that, in the thus-prepared cell aggregate, the proportion of Rx-positive cells in the total cells is about 90% (FIG. 28, A). From the analysis of the serial sections, it was found that Ki67-positive and Chx10-positive neural retinal progenitor cells are contained in Rx-strong positive cells (FIG. 28, B, C). Also, it was found that the cell aggregate contains Crx-strong positive photoreceptor precursor cells (FIG. 28, D). From the analysis of the serial sections, it was found that a part of the Crx-strong positive cells are Blimp1-positive photoreceptor precursor cells (FIG. 28, E). Also, it was found that the cell aggregate contains Brn3b-positive ganglion cells (FIG. 28, F).

From these results, it was found that a retinal tissue produced by the production method of the present invention differentiates and matures into a retinal tissue containing neural retinal progenitor cells, photoreceptor precursor cells, and ganglion cells, by continuing the culturing.

Example 29: Production Example of Retinal Tissue from Human iPS Cells by Using Human iPS Cell Subjected to Feeder-Free Culturing as a Starting Material, TGFβ Family Signal Transduction Pathway Inhibiting Substance in Step 1, Shh Signal Transduction Pathway Activating Substance in Step 2, and BMP Signal Transduction Pathway Activating Substance in Step 3

According to the method described in Example 28, cell aggregates were prepared from human iPS cells (1231A3 strain) in StemFit medium as a feeder-free medium, as a starting material, under the conditions involving preconditioning with TGFβR inhibitor (SB431542, 5 µM) and Shh signal transduction pathway activating substance (SAG, 300 nM) for one day in step 1, using Shh signal transduction pathway activating substance (SAG, 30 nM) in step 2, and adding BMP signal transduction pathway activating substance (BMP4, final concentration 1.5 nM) in step 3. On day 18 after the start of suspension culturing, a neuroepithelium was formed.

The cell aggregates on day 18 after the start of suspension culturing were transferred to a 90 mm low-adhesion culture dish (manufactured by SUMITOMO BAKELITE), and cultured in a serum-free medium (DMEM/F12 medium supplemented with 1% N2 supplement) containing Wnt signal transduction pathway activating substance (CHIR99021, 3 µM) and FGF signal transduction pathway inhibiting substance (SU5402, 5 µM) at 37° C., 5% $CO_2$ for 5 days, that is, until day 23 after the start of suspension culturing. During this period, about 50 aggregates were subjected to suspension culturing in 10 ml of the above serum-free medium containing CHIR99021 and SU5402, per one 90 mm low-adhesion culture dish. On day 23 after the start of suspension culturing, thin neuroepithelium was formed, and a retinal pigment epithelium (RPE)-like tissue was formed.

Furthermore, the cell aggregates on day 23 after the start of suspension culturing were subjected to suspension culturing in a 90 mm low adhesion culture dish (manufactured by SUMITOMO BAKELITE) in a serum-containing medium (DMEM/F12 medium supplemented with 10% fetal calf serum, 1% N2 supplement, 0.5 µM retinoic acid, and 100 µM taurine) free of Wnt signal transduction pathway activating substance and FGF signal transduction pathway inhibiting substance at 37° C., 5% $CO_2$, atmospheric oxygen concentration (about 20%) until day 130 (for 107 days), until day 137 (for 114 days), or until day 178 (for 155 days), after the start of suspension culturing. During day 23 after the start of suspension culturing to completion of suspension culturing, a half amount of the medium was changed to the above serum-containing medium once every 2-4 days. During this period, about 30 aggregates were subjected to suspension culturing in 15 ml of the above serum-containing medium, per one 90 mm low adhesion culture dish. On day 35 or later from the start of suspension culturing, a neural retina-like tissue was present.

The thus-prepared cell aggregates on day 130, day 137 and day 178 after the start of suspension culturing were each fixed with 4% para-formaldehyde to give frozen sections. These frozen sections were immunostained for Calretinin (anti-Calretinin antibody, manufactured by Millipore, rabbit) which is one of the interneuron markers (ganglion cell and amacrine cell), S-opsin (anti-S-opsin antibody, manufactured by Millipore, rabbit) which is one of the cone photoreceptor cell markers, Rx (anti-Rax/Rx antibody, manufactured by Takara, guinea pig) which is one of the retinal tissue markers, Pax6 (anti-Pax6 antibody, manufactured by BD, mouse) which is one of the interneuron markers (ganglion cell and amacrine cell), Recoverin (anti-Recoverin antibody, manufactured by Millipore, rabbit) which is one of the photoreceptor cell markers, Rhodopsin (anti-Rhodopsin antibodyRet-P1, manufactured by Sigma, mouse) which is one of the rod photoreceptor cell markers, NRL (anti-NRL antibody, manufactured by R and D, goat) which is one of the rod photoreceptor precursor cell markers, and Calbindin (anti-Calbindin antibody, manufactured by Millipore, rabbit) which is one of the interneuron markers (horizontal cell), and observed under a confocal laser microscope (LSM780 manufactured by Zeiss).

From the analysis of the cell aggregate on day 130 after the start of suspension culturing, it was found that the proportion of Rx-positive cells in the total cells is about 90%. In addition, the Rx-strong positive retinal tissue was found to contain Calretinin-positive interneuron in the inside (FIG. 29, A).

From the analysis of the cell aggregate on day 137 after the start of suspension culturing, it was found that the proportion of Rx-positive cells in the total cells is about 90%. In addition, it was found that Rx-strong positive retinal tissue contains Crx-positive photoreceptor precursor cells and Recoverin-positive photoreceptor cells. Furthermore, it was found that the Rx-strong positive retinal tissue contains S-opsin-positive cone photoreceptor cells (FIG. 29, B).

Figure 29:
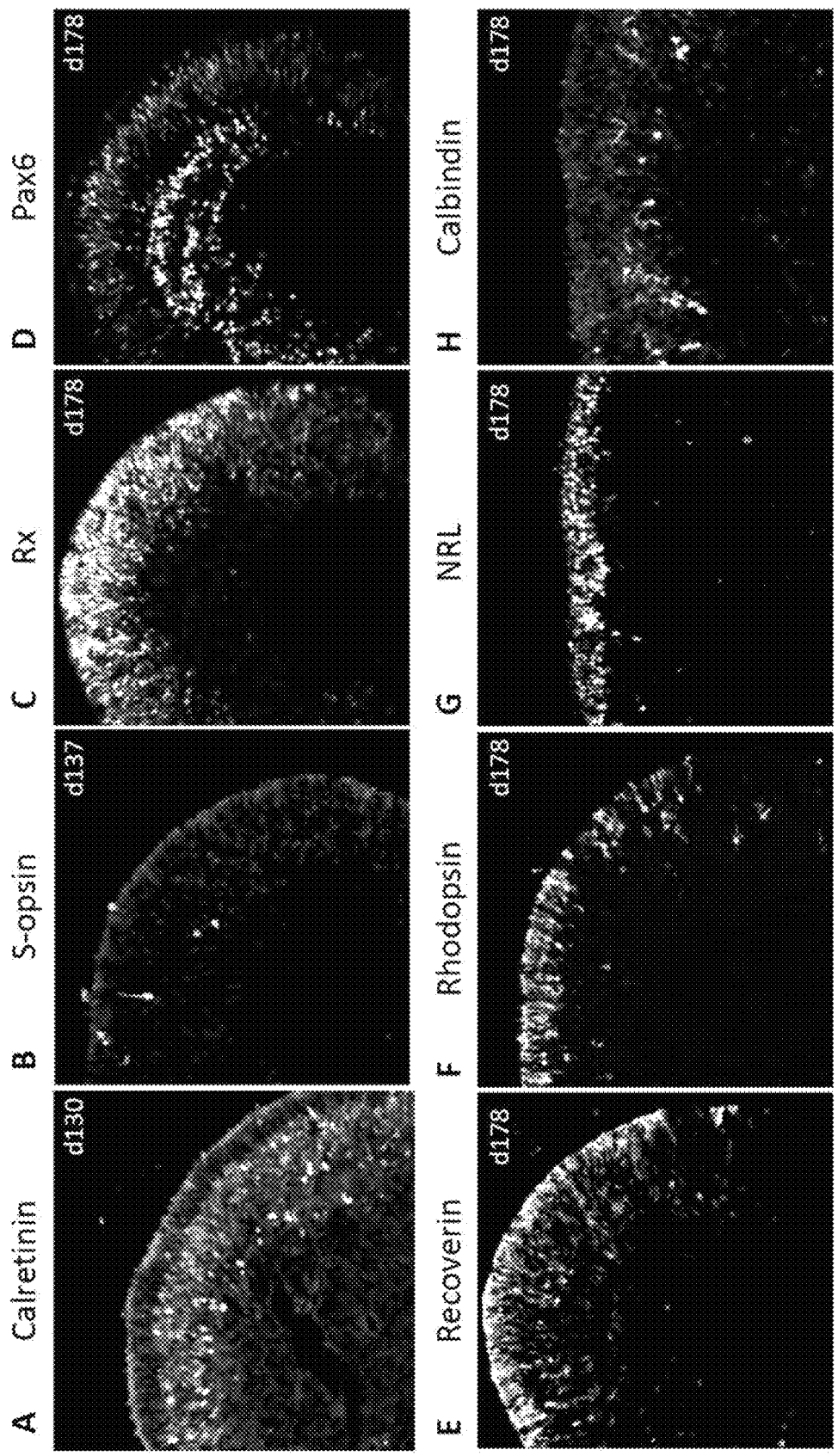
FIG. 29 shows immunohistochemical staining images of aggregates for retinal tissue markers (Calretinin, S-opsin, Rx, Pax6, Recoverin, Rhodopsin, NRL, Calbindin) (A-H).

From the analysis of the cell aggregate on day 178 after the start of suspension culturing, it was found that the proportion of Rx-positive cells in the total cells was about 90% (FIG. 29, C). From the analysis of the serial sections, it was found that the Rx-strong positive retinal tissue contains Pax6-positive interneurons (amacrine cells and ganglion cells) in the inside (FIG. 29, D). The Rx-strong positive retinal tissue was found to contain Recoverin-positive photoreceptor cells, Rhodopsin-positive rod photoreceptor cells, NRL-positive rod photoreceptor precursor cells, and Calbindin-positive horizontal cells on the outside (FIG. 29, E-H).

From these results, it was found that a retinal tissue produced by the production method of the present invention differentiates and matures into a retinal tissue containing photoreceptor precursor cell, photoreceptor cell, cone photoreceptor cell, rod photoreceptor cell, horizontal cell, and other interneuron, by continuing the culturing.

Example 30: Production Example of Retinal Tissue from Human iPS Cells by Using Human iPS Cell Subjected to Feeder-Free Culturing as a Starting Material, TGFβ Family Signal Transduction Pathway Inhibiting Substance in Step 1, Shh Signal Transduction Pathway Activating Substance in Step 2, and BMP Signal Transduction Pathway Activating Substance in Step 3

According to the method described in Example 29, cell aggregates were prepared from human iPS cells (1231A3 strain) in StemFit medium as a feeder-free medium, as a starting material, under the conditions involving preconditioning with TGFβR inhibitor (SB431542, 5 µM) and Shh signal transduction pathway activating substance (SAG, 300 nM) for one day in step 1, using Shh signal transduction pathway activating substance (SAG, 30 nM) in step 2, and adding BMP signal transduction pathway activating substance (BMP4, final concentration 1.5 nM) in step 3. On day 18 after the start of suspension culturing, a neuroepithelium was formed.

The cell aggregates on day 18 after the start of suspension culturing were transferred to a 90 mm low adhesion culture dish (manufactured by SUMITOMO BAKELITE), and cultured in a serum-free medium (DMEM/F12 medium supplemented with 1% N2 supplement) containing Wnt signal transduction pathway activating substance (CHIR99021, 3 µM) and FGF signal transduction pathway inhibiting substance (SU5402, 5 µM) at 37° C., 5% $CO_2$ for 5 days, that is, until day 23 after the start of suspension culturing. During this period, about 50 aggregates were subjected to suspension culturing in 10 ml of the above serum-free medium containing CHIR99021 and SU5402, per one 90 mm low-adhesion culture dish. On day 23 after the start of suspension culturing, thin neuroepithelium was formed, and a retinal pigment epithelium (RPE)-like tissue was formed.

Furthermore, the cell aggregates on day 23 after the start of suspension culturing were subjected to suspension culturing in a 90 mm low-adhesion culture dish (manufactured by SUMITOMO BAKELITE) in a serum-containing medium (DMEM/F12 medium supplemented with 10% fetal calf serum, 1% N2 supplement, 0.5 µM retinoic acid, and 100 µM taurine) free of Wnt signal transduction pathway activating substance and FGF signal transduction pathway inhibiting substance at 37° C., 5% $CO_2$, atmospheric oxygen concentration (about 20%) until day 63 (for 41 days) after the start of suspension culturing. From day 23 after the start of suspension culturing to completion of suspension culturing, a half amount of the medium was changed to the above serum-containing medium once every 2-4 days. During this period, about 30 aggregates were subjected to suspension culturing in 15 ml of the above serum-containing medium, per one 90 mm low-adhesion culture dish. On day 35 or later from the start of suspension culturing, a neural retina-like tissue was present.

Figure 30:
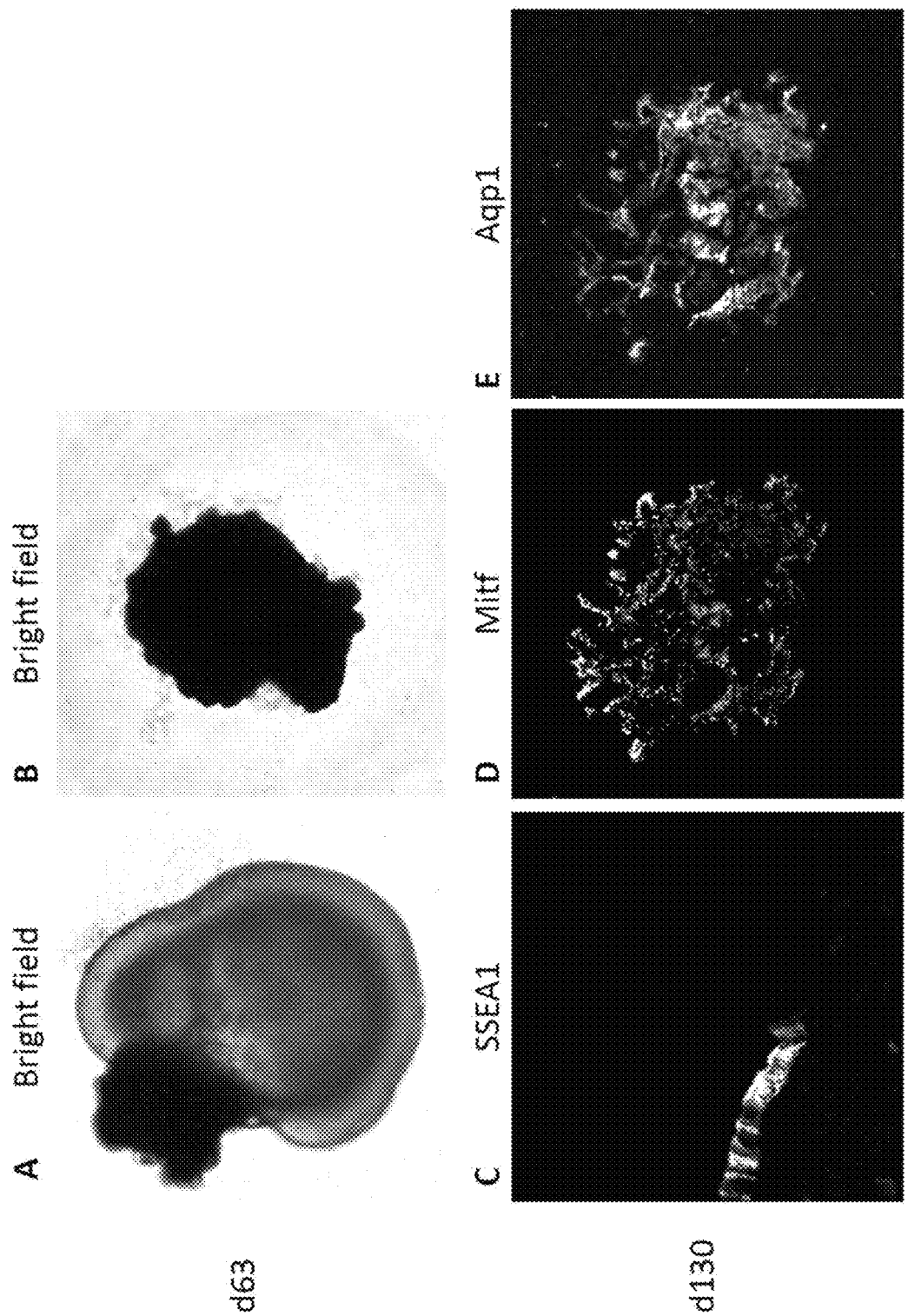
FIG. 30 shows bright field images of cells after culture (A, B), and immunohistochemical staining images of aggregates for retinal tissue markers (SSEA1, Mitf, Aqp1) (C-E).

Bright field observation of the thus-prepared cell aggregate on day 63 after the start of suspension culturing under an inverted microscope (manufactured by Nicon) revealed the presence of neural retinal tissue and pigmentated RPE-like tissue. When the obtained 100 cell aggregates were analyzed in detail, not less than 90% of the total cells were constituted of neural retina in 40 cell aggregates, composite retinal tissue concurrently containing neural retina and retinal pigment epithelium (RPE, distinguishable by pigmentation) was found in 40 cell aggregates (FIG. 30, A), and not less than 90% of the total cells were constituted of retinal pigment epithelium (RPE, distinguishable by pigmentation) in 20 cell aggregates (FIG. 30, B).

Furthermore, the above cell aggregates on day 63 after the start of suspension culturing were subjected to suspension culturing in a serum-containing medium (DMEM/F12 medium supplemented with 10% fetal calf serum, 1% N2 supplement, 0.5 µM retinoic acid, and 100 µM taurine) free of Wnt signal transduction pathway activating substance and FGF signal transduction pathway inhibiting substance until day 130 (for 107 days) after the start of suspension culturing. These cell aggregates were fixed with 4% para-formaldehyde to give frozen sections. These frozen sections were immunostained for SSEA1 (anti-SSEA1 antibody, manufactured by Millipore, mouse) which is one of the ciliary marginal zone (CMZ) markers, Mitf (anti-Mitf antibody, Exalpha, mouse) which is one of the RPE markers, and Aqp1 (anti-Aqp1 antibody, manufactured by Millipore, rabbit) which is one of the RPE and ciliary body markers, and observed under a confocal laser microscope (LSM780 manufactured by Zeiss).

Analysis of RPE-like tissue in which the whole aggregates suspension culturing showed pigmentation on day 130 after the start of suspension culturing revealed that about 80% of the total cells were Rx-weak positive. In addition, the analysis of serial sections revealed that Rx-weak positive cells were Mitf-positive RPE (FIG. 30, D). Furthermore, the above RPE-like tissue was found to be Aqp1-positive (FIG. 30, E). From these results, it was found that a retinal tissue produced by the production method of the present invention can differentiate and mature into RPE.

By the analysis of the composite retinal tissue containing both neural retina and RPE-like tissue on day 130 after the start of suspension culturing, it was found that the proportion of Rx-positive cells in the total cells was about 90%, and Rx-strong positive neural retina and Rx-weak positive RPE-like tissue were contained. In addition, it was found that SSEA1-positive ciliary marginal zone is formed in the boundary between neural retina (FIG. 30, C, right) and RPE (FIG. 30, C). From the results, it was found that a retinal tissue produced by the production method of the present invention can differentiate and mature into ciliary marginal zone.

Example 31: Production Example of Cerebral Tissue from Human iPS Cells by Using Human iPS Cells Subjected to Feeder-Free Culturing as a Starting Material, TGFβ Family Signal Transduction Pathway Inhibiting Substance in Step 1

Human iPS cells (1231A3 strain) were subjected to feeder-free culturing according to the method described in Example 1 according to the method described in Scientific Reports, 4, 3594 (2014). As a feeder-free medium, StemFit medium (AK03, manufactured by Ajinomoto Co., Inc.) was used, and as a feeder-free scaffold, Laminin 511-E8 (manufactured by Nippi, Inc.) was used.

Human iPS cells (1231A3 strain) were subjected to feeder-free culturing until one day before subconfluence by using StemFit medium according to the method described in Example 1. The human iPS cells one day before subconfluence were subjected to feeder-free culturing for one day under the following 3 conditions.

Condition 1: SB431542 (TGFβR inhibitor, 5 µM) and SAG (Shh is signal transduction pathway activating substance, 300 nM)

Condition 2: LDN193189 (BMPR inhibitor, 100 nM) and SAG (Shh signal transduction pathway activating substance, 300 nM)

Condition 3: Free of exogenous TGFβ family signal transduction pathway inhibiting substance and Shh signal transduction pathway activating substance (without preconditioning)

The thus-prepared human iPS cells of the above conditions 1-3 were treated with a cell dispersion solution using TrypLE Select (manufactured by Life Technologies), and further dispersed into single cells by pipetting operation. Thereafter, the above human iPS cells dispersed into single cells were suspended in 100 µl of a serum-free medium at $0.9 \times 10^4$ cells per well of a non-cell-adhesive 96-well culture plate (SUMILON Spheroid V-bottom plate PrimeSurface 96V-bottom plate, SUMITOMO BAKELITE), and subjected to suspension culturing at 37° C., 5% $CO_2$. As the serum-free medium (GMEM+KSR) therefor, a serum-free medium which is GMEM medium (manufactured by Life Technologies) supplemented with 20% KSR (manufactured by Life Technologies), 0.1 mM 2-mercaptoethanol, 1× non-essential amino acid (manufactured by Life Technologies), and 1 mM pyruvic acid (manufactured by Life Technologies) was used.

At the time of the start of suspension culturing (day 0 after the start of suspension culturing, start of step 2), Wnt signal transduction pathway inhibiting substance (IWR-1-endo, 3 µM), TGFβR inhibitor (SB431542, 5 µM), and Y27632 (20 µM) were added to the above serum-free medium, and the cells were cultured under conditions (A) containing SAG (Shh signal action substance, 100 nM) or conditions (B) without containing SAG. On day 2 after the start of suspension culturing, a cell aggregate was formed under any conditions.

On day 3 after the start of suspension culturing, a half amount of the medium was changed to a serum-free medium free of Y27632 and SAG and containing Wnt signal transduction pathway inhibiting substance (IWR-1-endo, 3 µM)

and TGFβR inhibitor (SB431542, 5 μM). Thereafter, until day 25 or day 27 after the start of suspension culturing, a half amount of the medium was changed to the above serum-free medium free of Y27632 and SAG and containing Wnt signal transduction pathway inhibiting substance (IWR-1-endo, 3 μM) and TGFβR inhibitor (SB431542, 5 μM), once per 2-4 days.

Figure 31:
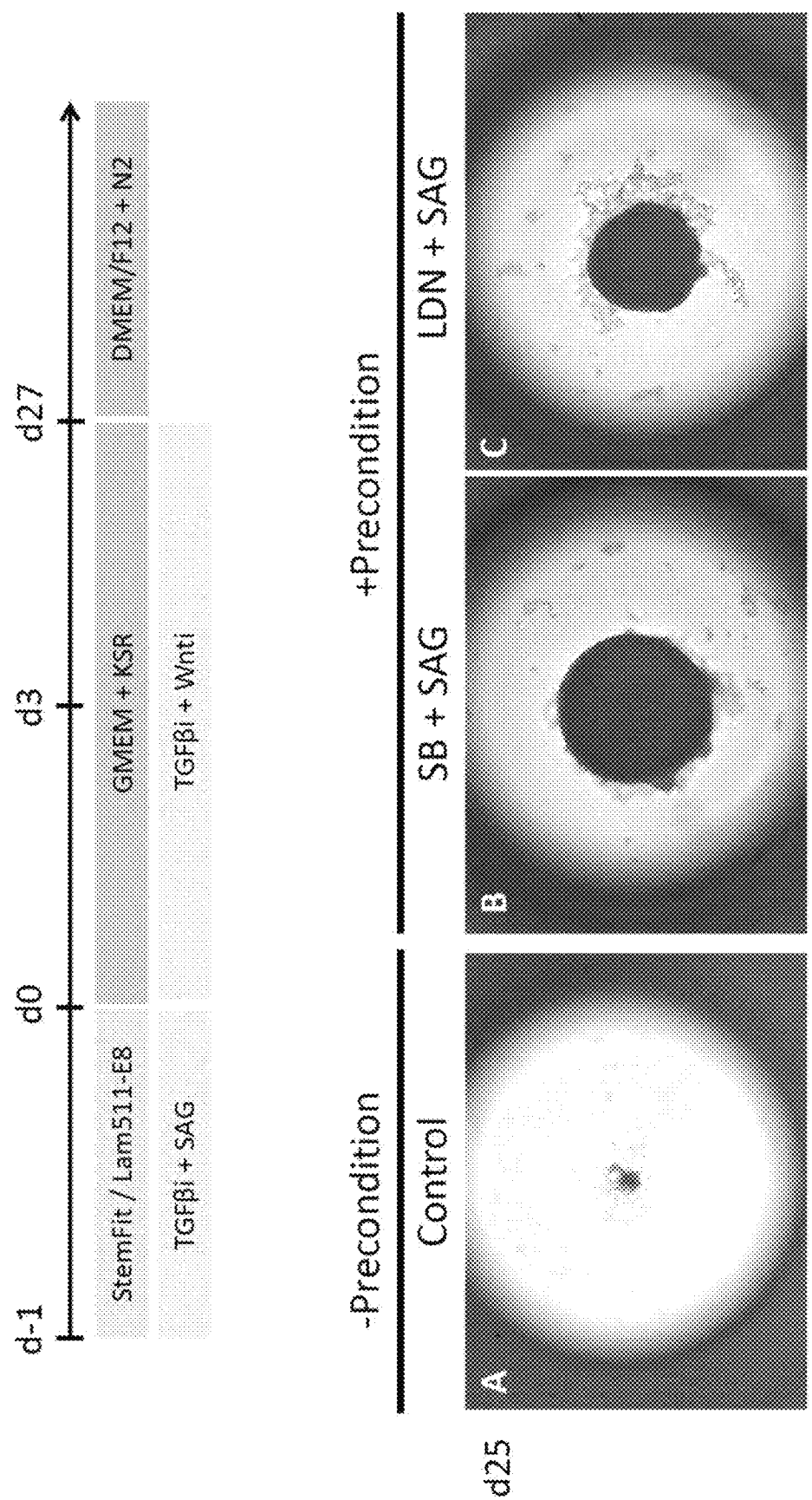
FIG. 31 shows culture conditions of Example 31, and bright field images of cells after culture (A-C).

The cell aggregates on day 25 after the start of suspension culturing were subjected to bright field observation under an inverted microscope (BIOREVO manufactured by KEYENCE). As a result, without preconditioning (condition 3), a cell aggregate did not grow, and a neuroepithelium was hardly formed (FIG. 31, A). On the other hand, under conditions with preconditioning with SB431542 and SAG, or LDN193189 and SAG in step 1 (condition 1, 2), a cell aggregate grew and a neuroepithelium was formed even under conditions (B) without addition of SAG in step 2 (FIG. 31, B,C). Similarly, under conditions with preconditioning with SB431542 and SAG, or LDN193189 and SAG in step 1 (conditions 1 and 2) and conditions (A) with addition of SAG in step 2, cell aggregates grew and a neuroepithelium was formed. That is, it was found that the production efficiency of neuroepithelium is improved as long as TGFβ family signal transduction pathway inhibiting substance and/or Shh signal action substance are/is added in step 1, irrespective of whether Shh signal action substance is added or not added in step 2.

The thus-prepared cell aggregates on day 27 after the start of suspension culturing were each fixed with 4% paraformaldehyde to give frozen sections. These frozen sections were immunostained for Sox2 (anti-Sox2 antibody, manufactured by Santa Cruz, goat) which is one of the neural precursor cell markers, and FoxG1 (anti-FoxG1 antibody, produced by RIKEN, As3514, rabbit) which is one of the cerebrum markers, and observed under a confocal laser microscope (manufactured by Olympus).

Figure 32:
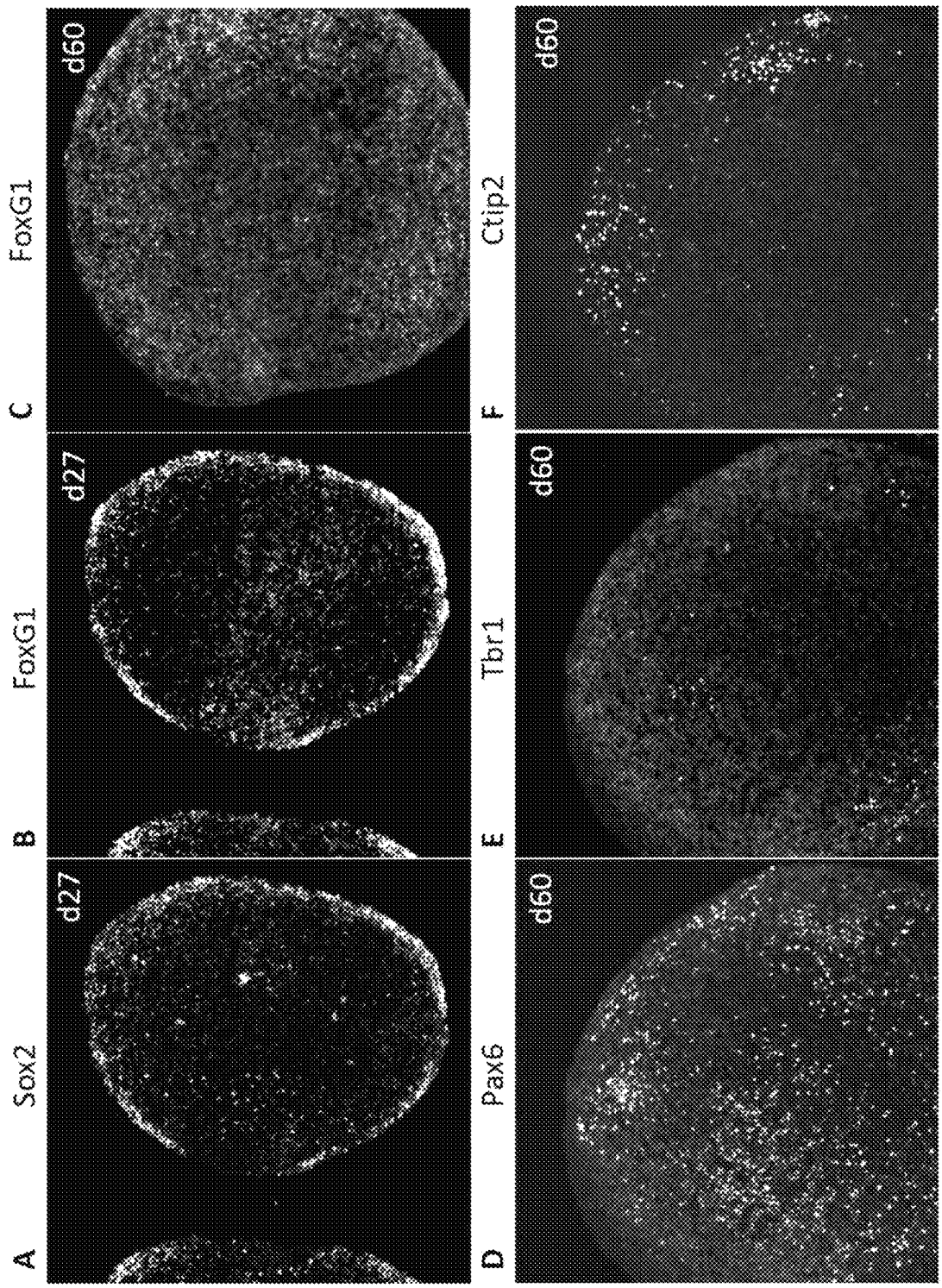
FIG. 32 shows immunohistochemical staining images of aggregates for cerebral tissue markers (Sox2, FoxG1, Pax6, Tbr1, Ctip2) (A-F).

As a result, it was found that in the cell aggregate on day 27 after the start of suspension culturing, which were cultured under condition 1 in step 1, Sox2-positive neural precursor cells were present on the surface of the cell aggregates (FIG. 32, A). Furthermore, costaining analysis revealed that about 98% of the Sox2-positive neural precursor cells were Sox2-positive and FoxG1-positive cerebral neural precursor cells (FIG. 32, B). In addition, it was found that the cell aggregate on day 27 after the start of suspension culturing, which were cultured under condition 2 in step 1, also have Sox2-positive neural precursor cells on the surface of the cell aggregates, like condition 1, and about 98% of the Sox2-positive neural precursor cells are Sox2-positive and FoxG1-positive cerebral neural precursor cells.

From these results, it was found that a cerebral tissue can be produced from human iPS cells subjected to feeder-free culturing as a starting material by adding TGFβ family signal transduction pathway inhibiting substance and/or Shh signal transduction pathway activating substance in step 1, and TGFβ family signal transduction pathway inhibiting substance and Wnt signal transduction pathway inhibiting substance in step 3.

Example 32: Production Example of Cerebral Tissue from Human iPS Cells by Using Human iPS Cell Subjected to Feeder-Free Culturing as a Starting Material, and TGFβ Family Signal Transduction Pathway Inhibiting Substance in Step 1

The cell aggregates on day 27 after the start of suspension culturing, which were prepared according to the method described in Example 31, were transferred to a 90 mm low-adhesion culture dish (manufactured by SUMITOMO BAKELITE), and subjected to suspension culturing in a serum-free medium (DMEM/F12 medium (manufactured by Life Technologies) supplemented with 1% N2 supplement (manufactured by Life Technologies)), at 37° C., 5% $CO_2$. During this period, about 30 aggregates were subjected to suspension culturing in 10 ml of a serum-free medium, per one 90 mm low-adhesion culture dish. Thereafter, until day 40 after the start of suspension culturing, a half amount of the medium was changed, once every 2-4 days, with a serum-free medium (DMEM/F12 medium (manufactured by Life Technologies) supplemented with 1% N2 supplement (manufactured by Life Technologies)).

The obtained cell aggregates on day 40 after the start of suspension culturing were subjected to suspension culturing in a serum-containing medium which was DMEM/F12 medium (manufactured by Life Technologies) supplemented with 10% fetal calf serum, 1% N2 supplement, and 0.5 μM retinoic acid, in a 90 mm low-adhesion culture dish (manufactured by SUMITOMO BAKELITE) at 37° C., 5% $CO_2$. During this period, about 30 aggregates were subjected to suspension culturing in 10 ml of a serum-free medium, per one 90 mm low-adhesion culture dish. Thereafter, until day 60 after the start of suspension culturing, a half amount of the medium was changed, once every 2-4 days, to the above serum-containing medium.

The thus-prepared cell aggregates on day 60 after the start of suspension culturing were each fixed with 4% paraformaldehyde to give frozen sections. These frozen sections were immunostained for FoxG1 (anti-FoxG1 antibody, produced by RIKEN, As3514, rabbit) which is one of the cerebrum markers, Pax6 (anti-Pax6 antibody, manufactured by BD, mouse) which is one of the dorsal cerebral neural precursor cell markers, Tbr1 (anti-Tbr1 antibody, manufactured by Abcam, rabbit) which is one of the cerebrum layer 6 neuron markers, and Ctip2 (anti-Ctip2 antibody, manufactured by Abcam, rat) which is one of the cerebrum layer 5 neuron markers, and observed under a confocal laser microscope (manufactured by Olympus).

As a result, in the cell aggregates on day 60 after the start of suspension culturing, which were cultured under conditions with preconditioning with SB431542 and SAG in step 1 (condition 1), about 40% of the total cells in the cell aggregates were FoxG1-positive cerebral cells (FIG. 32, C). The analysis of serial sections revealed that cell aggregates containing FoxG1-positive cells contain Pax6-positive dorsal cerebral neural precursor cells at about 30% in the total cells (FIG. 32, D), Tbr1-positive layer 6 neurons at about 5% in the total cells, and Ctip2-positive layer 5 neurons at about 15%.

In addition, it was found that the cell aggregates on day 60 after the start of suspension culturing, which were cultured under conditions involving preconditioning with LDN193189 and SAG in step 1 (condition 2), also contain, like condition 1, FoxG1-positive cerebral cells. The analysis of serial sections revealed that a cell aggregate containing FoxG1-positive cells contain Pax6-positive dorsal cerebral neural precursor cells at about 30% in the total cells, Tbr1-positive layer 6 neurons at about 5% in the total cells, and Ctip2-positive layer 5 neurons at about 15%.

Furthermore, it was found that the cell aggregate on day 60 after the start of suspension culturing, which were cultured under any of the four conditions: condition 1 or condition 2 in step 1, conditions with addition of SAG in step 2 (conditions (A)) or conditions without addition of SAG (conditions (B)), contains FoxG1-positive cerebral cells.

From the results, it was found that cerebral tissue, cerebral neural precursor cell, and cerebral layer specific neuron (e.g., layer 6 neuron, layer 5 neuron) can be produced from human iPS cells subjected to feeder-free culturing as a starting material by adding TGFβ family signal transduction pathway inhibiting substance and/or Shh signal transduction pathway activating substance in step 1, and TGFβ family signal transduction pathway inhibiting substance and Wnt signal transduction pathway inhibiting substance in step 3.

Example 33: Production Example of Neural Tissue by Using Human iPS Cells Subjected to Feeder-Free Culturing as a Starting Material, and TGFβ Family Signal Transduction Pathway Inhibiting Substance in Step 1

Human iPS cells one day before subconfluence (1231A3 strain), which had been subjected to feeder-free culturing, were subjected to feeder-free culturing under the following 2 conditions for one day according to the method described in Example 8.
Condition 1: SB431542 (TGFβR inhibitor, 5 μM)
Condition 2: LDN193189 (BMPR inhibitor, 100 nM)
Condition 3: Free of exogenous TGFβ family signal transduction pathway inhibiting substance and Shh signal transduction pathway activating substance (without preconditioning)

The thus-prepared human iPS cells under conditions 1-3 were treated with the cell dispersion solution by using TrypLE Select (manufactured by Life Technologies), further dispersed into single cells by pipetting operation, and. As the serum-free medium therefor, a serum-free medium which is a 1:1 mixture of F-12 medium and IMDM medium supplemented with 10% KSR, 450 μM 1-monothioglycerol, 1× Chemically defined lipid concentrate was used.

Thereafter, the cells were seeded in the following two kinds of culture dish.
  conditions (A). The above human iPS cells dispersed into single cells were suspended in 100 μl of the above serum-free medium at $1.2 \times 10^4$ cells per well of a non-cell-adhesive U-bottomed 96-well culture plate (SUMMON Spheroid U-bottom plate PrimeSurface 96U-bottom plate, SUMITOMO BAKELITE), and subjected to suspension culturing at 37° C., 5% $CO_2$.
  conditions (B). The above human iPS cells dispersed into single cells were suspended in 4 ml of the above serum-free medium at $2.4 \times 10^5$ cells per 1 culture dish of a non-cell-adhesive 60 mm F-bottomed cell culture dish (petri dish for suspension culturing, SUMITOMO BAKELITE), and subjected to suspension culturing at 37° C., 5% $CO_2$.

Under condition 3 without preconditioning, at the time of the start of suspension culturing (day 0 after the start of suspension culturing, step 2 start), Y27632 (20 μM) was added to the above serum-free medium, and the serum-free medium under conditions without addition of exogenous Shh signal transduction pathway activating substance was used.

Figure 33:
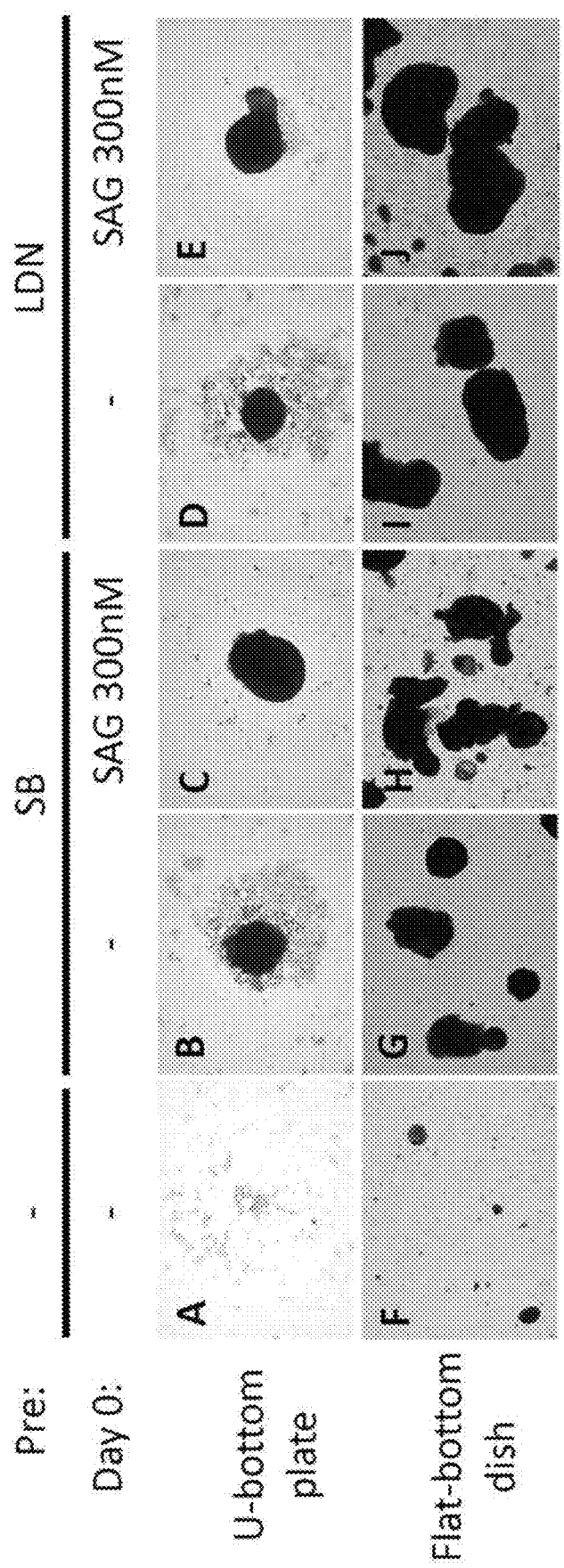
FIG. 33 shows bright field images of cells cultured under various conditions (A-J).

Under condition 1 and 2, at the time of the start of suspension culturing (day 0 after the start of suspension culturing, start of step 2), Y27632 (20 μM) was added to the above serum-free medium, and the serum-free medium under conditions with further addition of exogenous Shh signal transduction pathway activating substance, SAG (final concentration 300 nM) was used (FIG. 33). Under any of conditions 1-3, on day 2 after the start of suspension culturing, cell aggregates were formed. On day 4 after the start of suspension culturing, the above serum-free medium free of Y27632 and SAG was added. Thereafter, once every 2-4 days, a half amount of the medium was changed to the above serum-free medium free of Y27632 and SAG.

The thus-prepared cell aggregates were subjected to bright field observation under an inverted microscope (BIOREVO manufactured by KEYENCE) on day 19 after the start of suspension culturing. As a result, it was found that, without preconditioning (condition 3), a cell aggregate did not grow, and neuroepithelium was hardly formed both in a U-bottom plate (conditions A) and a F-bottom culture dish (conditions B) (FIG. 33, A, F). On the other hand, under conditions with preconditioning with TGFβR inhibitor (SB431542) or BMPR inhibitor (LDN193189) in step 1 (conditions 1 and 2), a cell aggregate grew and neuroepithelium was formed both in a U-bottom plate (conditions A) and a F-bottom culture dish (conditions B) (FIG. 33, B-E, G-J). That is, it was found that the production efficiency of neuroepithelium is improved by the preconditioning operation in step 1 both in a U-bottomed plate (conditions A) and a F-bottom culture dish (conditions B).

Example 34: Example of Formation of Retinal Tissue by Preconditioning Operation of Human iPS Cells, Cultured Using Feeder-Free Medium StemFit (AK03N), with Shh Signal Transduction Pathway Activating Substance in Step 1, Addition of Shh Signal Transduction Pathway Activating Substance in Step 2, and Addition of BMP4 in Step 3

Human iPS cells (Ff-I01 strain, obtained from Kyoto University) were subjected to feeder-free culturing according to the method described in "Scientific Reports, 4, 3594 (2014)". As a feeder-free medium, StemFit medium (AK03N, manufactured by Ajinomoto Co., Inc.) was used, and as a feeder-free scaffold, Laminin 511-E8 (manufactured by Nippi, Inc.) was used.

Feeder-free cultured human iPS cells 2 days before subconfluence were subjected to feeder-free culturing according to the method described in Example 8, in the presence of SAG (Shh signal transduction pathway activating substance, 300 nM) (step 1, preconditioning treatment) for 2 days.

The above human iPS cells were treated with the cell dispersion solution by using TrypLE Select (manufactured by Life Technologies), further dispersed into single cells by pipetting operation, after which the above human iPS cells dispersed into single cells were suspended in 100 μl of a serum-free medium to $1.0 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium therefor, a serum-free medium which is a 1:1 mixture of F-12 medium and IMDM medium supplemented with 10% KSR, 450 μM 1-monothioglycerol, 1× Chemically defined lipid concentrate was used.

At the time of the start of suspension culturing (day 0 after the start of suspension culturing, step 2 start), Y27632 (final concentration 20 μM) and SAG (Shh signal transduction pathway activating substance, 500 nM) were added to the above serum-free medium. By day 2 after the start of suspension culturing, a cell aggregate was formed (step 2 completed, step 3 start).

On day 3 after the start of suspension culturing, a medium (50 μl) free of Y27632 and SAG and containing human recombinant BMP4 (manufactured by R&D) was added such that the final concentration of exogenous human recombinant BMP4 was 1.5 nM (55 ng/ml) or 5 nM (183 ng/ml). On day 6 after the start of suspension culturing, 50 μl of the medium were discarded, and 50 μl of a medium free of Y27632 and SAG and containing human recombinant BMP4 (manufactured by R&D) was added to maintain the final concentration of exogenous human recombinant BMP4 at 1.5 nM (55 ng/ml) or 5 nM (183 ng/ml). Thereafter, once every 2-4 days, a half amount of the medium was changed to the above serum-free medium free of Y27632, SAG and human recombinant BMP4.

Figure 34:
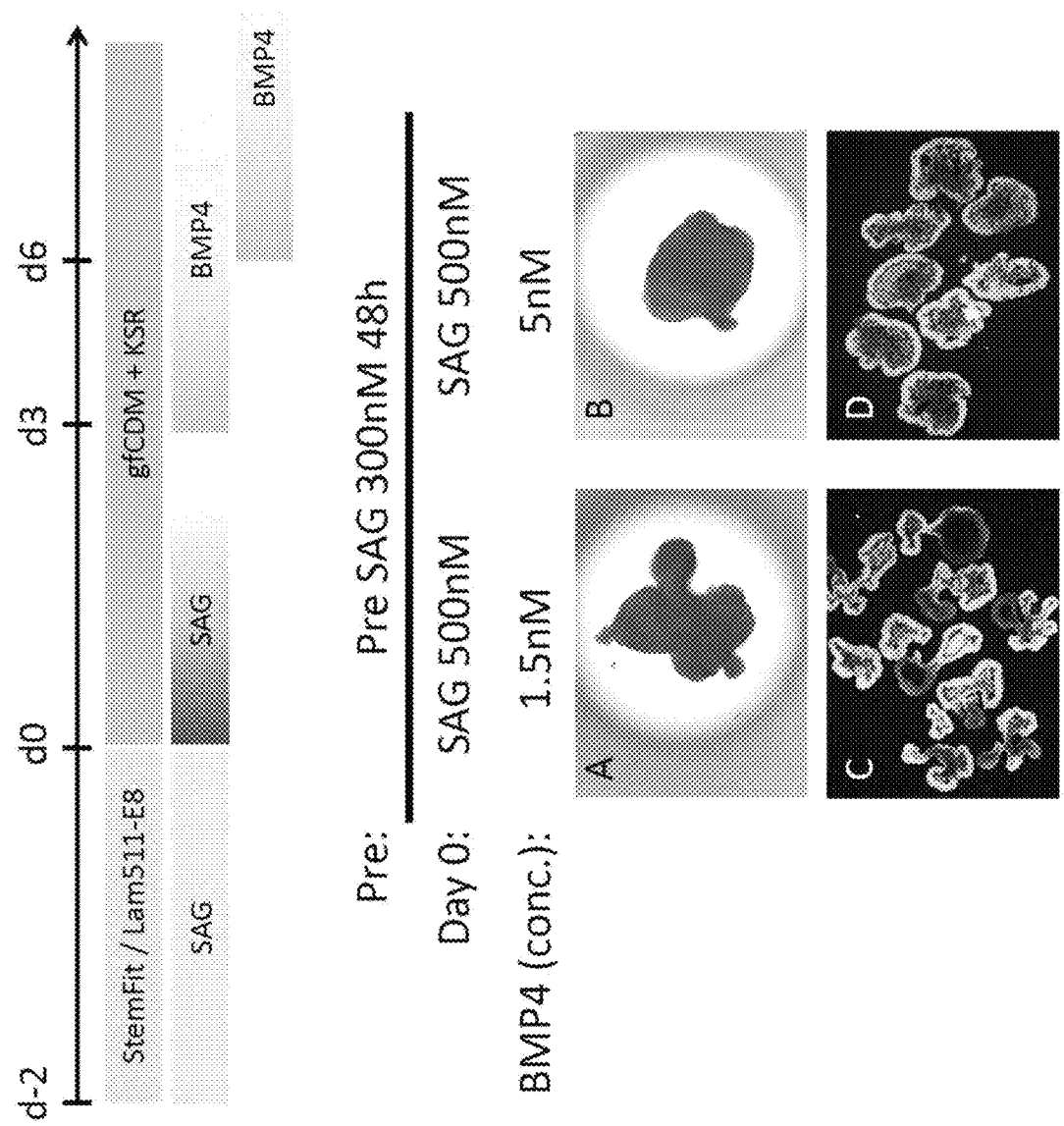
FIG. 34 shows culture conditions of Example 33, bright field images of cells after culture (A,B), and immunohistochemical staining images (C,D) of aggregates for Chx10.

The thus-prepared cells were subjected to bright field observation under an inverted microscope (KEYENCE) on day 19 after the start of suspension culturing. As a result, it was found that a cell aggregate grows and a neural tissue can be formed efficiently under conditions involving addition of BMP4 at 1.5 nM or 5 nM (FIG. 34, A-B).

From these results, it was found that a neural tissue can be produced efficiently from feeder-free cultured human iPS cells under conditions involving preconditioning with a Shh signal transduction pathway activating substance (SAG) for 2 days in step 1, addition of a Shh signal transduction pathway activating substance in step 2, and addition of BMP4 at 1.5 nM or 5 nM in step 3.

The cell aggregates on day 19 after the start of suspension culturing were fixed with 4% para-formaldehyde to prepare frozen sections. These frozen sections were immunostained for Chx10 (anti-Chx10 antibody, Exalpha, sheep), which is one of the retinal tissue markers. These immunostained sections were observed under an inverted fluorescence microscope. As a result, the proportion of Chx10-positive cells in the total cells is about 70% under conditions with the addition of BMP4 twice to maintain the final concentration of 1.5 nM (FIG. 234 C). In addition, the proportion of Chx10-positive cells in the total cells is about 90% under conditions with the addition of BMP4 twice to maintain the final concentration of 5 nM (FIG. 34, D).

From these results, it was found that a retinal tissue can be produced efficiently under conditions involving preconditioning of human iPS cells cultured in feeder-free medium StemFit (AK03N) with a Shh signal transduction pathway activating substance (SAG) for 2 days in step 1, addition of a Shh signal transduction pathway activating substance in step 2, and addition of a BMP signal transduction pathway activating substance 2 times at 5 nM in step 3 (i.e., conditions to maintain BMP signal transduction pathway activating substance concentration at 5 nM for 6 days).

Example 35: Example of Formation of Retinal Tissue from Feeder-Free Human iPS Cells by Preconditioning with Shh Signal Activating Substance for 1-4 Days in Step 1, Using Shh Signal Activating Substance in Step 2, and Adding BMP Signal Activating Substance in Step 3

Human iPS cells (Ff-I01 strain, obtained from Kyoto University) was subjected to feeder-free culturing according to the method described in "Scientific Reports, 4, 3594 (2014)". As a feeder-free medium, StemFit medium (AK03N, manufactured by Ajinomoto Co., Inc.) was used, and as a feeder-free scaffold, Laminin 511-E8 (manufactured by Nippi, Inc.) was used.

Preconditioning treatment was performed under the following 4 conditions.

Condition 1: Human iPS cells 24 hr before subconfluence were subjected to feeder-free culturing in Stem Fit medium (AK03N) supplemented with SAG (Shh signal transduction pathway activating substance, 300 nM) for 24 hr.

Condition 2: Human iPS cells 48 hr before subconfluence were subjected to feeder-free culturing in Stem Fit medium (AK03N) supplemented with SAG (Shh signal transduction pathway activating substance, 300 nM) for 48 hr.

Condition 3: Human iPS cells 72 hr before subconfluence were subjected to feeder-free culturing in Stem Fit medium (AK03N) supplemented with SAG (Shh signal transduction pathway activating substance, 300 nM) for 72 hr.

Condition 4: Human iPS cells 96 hr before subconfluence were subjected to feeder-free culturing in Stem Fit medium (AK03N) supplemented with SAG (Shh signal transduction pathway activating substance, 300 nM) for 96 hr.

The human iPS cells cultured under the above condition 4 were each treated with the cell dispersion solution by using TrypLE Select (manufactured by Life Technologies), further dispersed into single cells by pipetting operation, after which the above human iPS cells dispersed into single cells were suspended in 100 μl of a serum-free medium to $1.0 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium therefor, a serum-free medium which is a 1:1 mixture of F-12 medium and IMDM medium supplemented with 10% KSR, 450 μM 1-monothioglycerol, 1× Chemically defined lipid concentrate was used.

Figure 35:
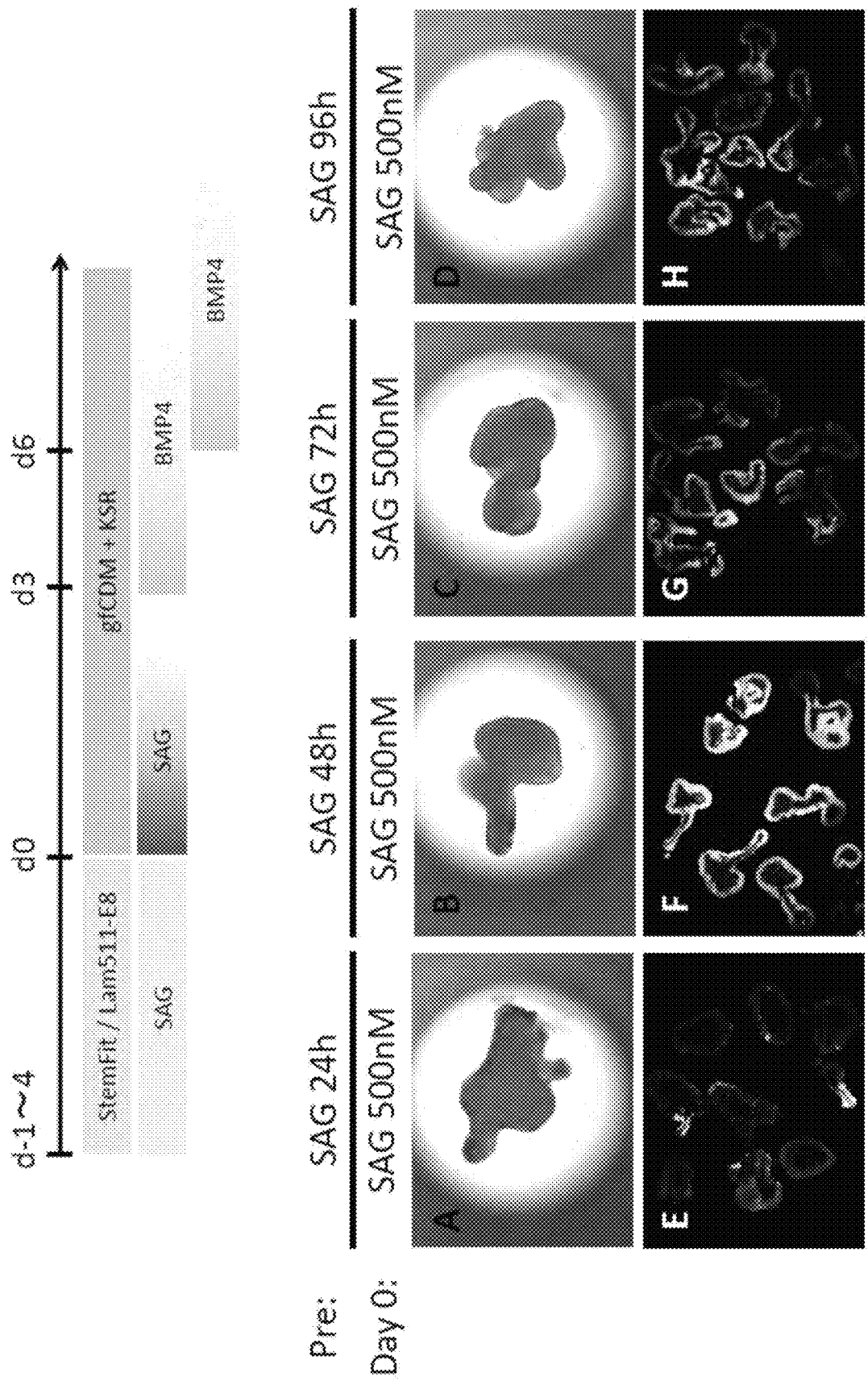
FIG. 35 shows culture conditions of Example 34, bright field images of cells after culture (A-D), and immunohistochemical staining images of aggregates for Chx10 (E-H).

At the time of the start of suspension culturing (day 0 after the start of suspension culturing, step 2 start), Y27632 (final concentration 20 μM) and SAG (Shh signal transduction pathway activating substance, 500 nM) were added to the above serum-free medium (FIG. 35). By day 2 after the start of suspension culturing, a cell aggregate was formed under any conditions (step 2 completed, step 3 start).

On day 3 after the start of suspension culturing, a medium (50 μl) free of Y27632 and SAG and containing human recombinant BMP4 (manufactured by R&D) was added such that the final concentration of exogenous human recombinant BMP4 was 1.5 nM (55 ng/ml). On day 6 after the start of suspension culturing, 50 μl of the medium was discarded, and 50 μl of a medium free of Y27632 and SAG and containing human recombinant BMP4 (manufactured by R&D) was added to maintain the final concentration of exogenous human recombinant BMP4 at 1.5 nM (55 ng/ml). Thereafter, once every 2-4 days, a half amount of the medium was changed to the above serum-free medium free of Y27632, SAG and human recombinant BMP4.

The thus-prepared cell aggregates were subjected to bright field observation under an inverted microscope (KEYENCE) on day 19 after the start of suspension culturing. As a result, it was found that a cell aggregate grows and neuroepithelium can be formed efficiently under conditions involving preconditioning of any of the above conditions 1-4 (FIG. 35, A-D).

From these results, it was found that a neural tissue can be produced efficiently from feeder-free cultured human iPS cells under conditions involving preconditioning with a Shh signal transduction pathway activating substance for 1-4 days in step 1, addition of a Shh signal transduction pathway activating substance in step 2, and addition of a BMP signal transduction pathway activating substance in step 3.

The thus-prepared cell aggregates on day 19 after the start of suspension culturing were fixed with 4% para-formaldehyde to prepare frozen sections. These frozen sections were immunostained for Chx10 (anti-Chx10 antibody, Exalpha, sheep), which is one of the retinal tissue markers, and observed under a fluorescence microscope. As a result, it was found that the proportion of Chx10-positive cells in the total cells is about 10% by conditions involving preconditioning with SAG for 24 hr (condition 1) (FIG. 35, E). On the other hand, it was found that the proportion of Chx10-positive cells in the total cells is about 80% by conditions involving preconditioning with SAG for 48, 72 or 96 hr (conditions 2, 3, 4) (FIG. 35, F-H)

From these results, it was found that a retinal tissue can be produced efficiently under any conditions involving preconditioning with a Shh signal transduction pathway activating substance (SAG) for 1-4 days in step 1, addition of a Shh signal transduction pathway activating substance in step 2, and addition of a BMP signal transduction pathway activating substance.

Example 36: Example of Formation of Retinal Tissue from Feeder-Free Human iPS Cells by Preconditioning with Shh Signal Transduction Pathway Activating Substance and BMP Signal Transduction Pathway Inhibiting Substance for 30 Min-2 Days in Step 1, and Adding BMP Signal Transduction Pathway Activating Substance in Step 3

Human iPS cells (1231A3 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

Preconditioning treatment was performed under the following 5 conditions.

Condition 1: Human iPS cells immediately before subconfluence were subjected to feeder-free culturing in Stem Fit medium (AK03) supplemented with LDN193189 (BMPR inhibitor, 100 nM) and SAG (Shh signal transduction pathway activating substance, 300 nM) for 30 min.

Condition 2: Human iPS cells immediately before subconfluence were subjected to feeder-free culturing in Stem Fit medium (AK03) supplemented with LDN193189 (BMPR inhibitor, 100 nM) and SAG (Shh signal transduction pathway activating substance, 300 nM) for 6 hr.

Condition 3: Human iPS cells one day before subconfluence were subjected to feeder-free culturing in Stem Fit medium (AK03) supplemented with LDN193189 (BMPR inhibitor, 100 nM) and SAG (Shh signal transduction pathway activating substance, 300 nM) for 24 hr.

Condition 4: Human iPS cells two days before subconfluence were subjected to feeder-free culturing in Stem Fit medium (AK03) supplemented with LDN193189 (BMPR inhibitor, 100 nM) and SAG (Shh signal transduction pathway activating substance, 300 nM) for 48 hr.

Condition 5: Subconfluent human iPS cells were subjected to feeder-free culturing under conditions free of addition of TGFβ family signal transduction pathway inhibiting substance and/or Shh signal transduction pathway activating substance.

The human iPS cells cultured under the above 5 conditions were each treated with the cell dispersion solution by using TrypLE Select (manufactured by Life Technologies), further dispersed into single cells by pipetting operation, after which the above human iPS cells dispersed into single cells were suspended in 100 µl of a serum-free medium to $1.2 \times 10^4$ cells per well of a non-cell-adhesive 96-well culture plate (PrimeSurface 96V-bottom plate, manufactured by SUMITOMO BAKELITE), and subjected to suspension culturing at 37° C., 5% $CO_2$. As the serum-free medium therefor, a serum-free medium which is a 1:1 mixture of F-12 medium and IMDM medium supplemented with 10% KSR, 450 µM 1-monothioglycerol, 1× Chemically defined lipid concentrate was used.

At the time of the start of suspension culturing (day 0 after the start of suspension culturing, step 2 start), Y27632 (final concentration 20 µM) was added to the above serum-free medium. By day 2 after the start of suspension culturing, a cell aggregate was formed under any conditions (step 2 completed, step 3 start).

On day 3 after the start of suspension culturing, a medium (50 µl) free of Y27632 and SAG and containing human recombinant BMP4 (manufactured by R&D) was added such that the final concentration of exogenous human recombinant BMP4 was 1.5 nM (55 ng/ml). Thereafter, once every 2-4 days, a half amount of the medium was changed to the above serum-free medium free of Y27632, SAG and human recombinant BMP4.

Figure 36:
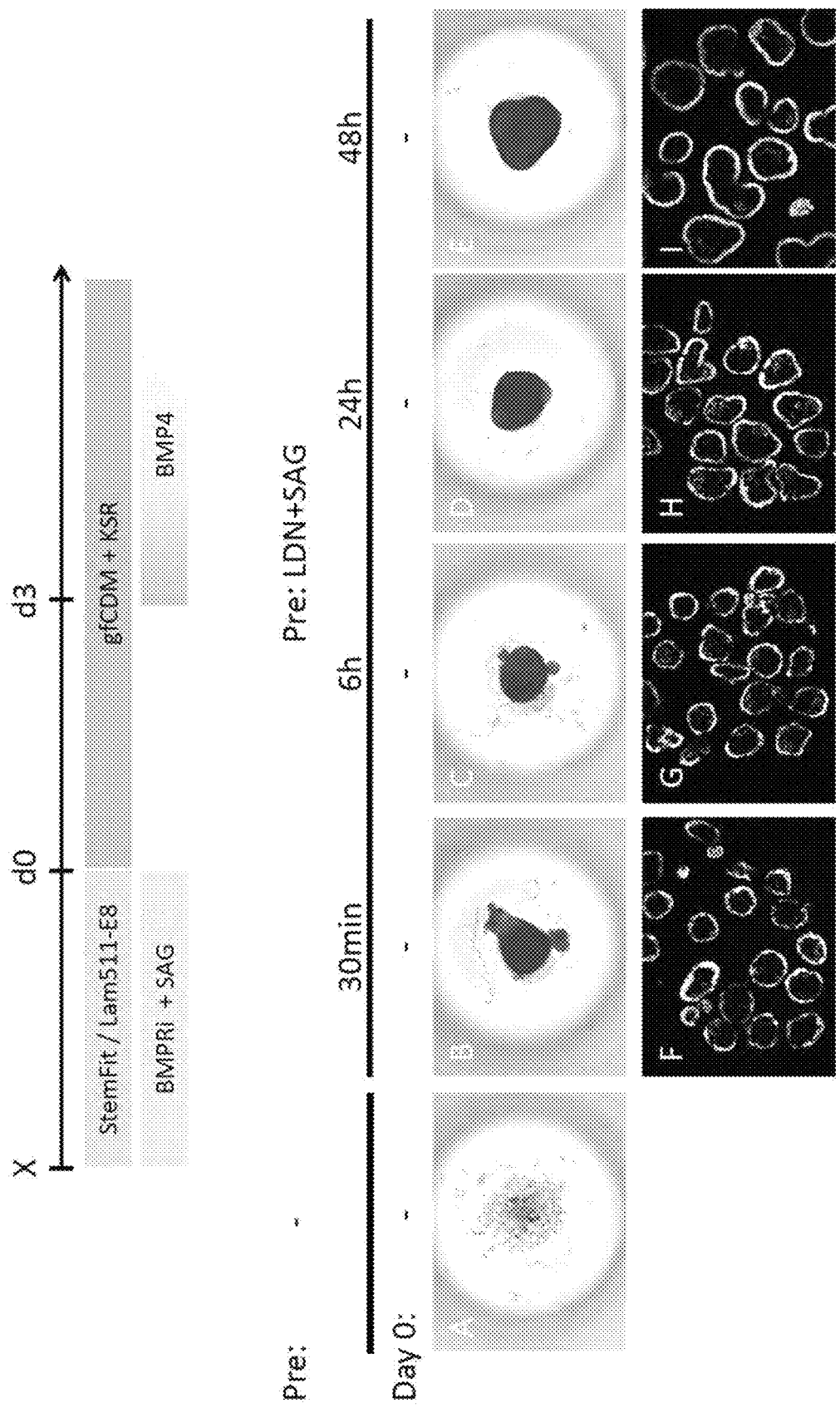
FIG. 36 shows culture conditions of Example 35, bright field images of cells after culture (A-E), and immunohistochemical staining images of aggregates for Chx10 (F-I).

The thus-prepared cells on day 19 after the start of suspension culturing were subjected to bright field observation with an inverted microscope (manufactured by KEYENCE). As a result, the aggregate was collapsed and neuroepithelium was hardly formed under conditions without a preconditioning operation (condition 5) (FIG. 36, A). On the other hand, it was found that an aggregate grows and neuroepithelium can be efficiently formed under conditions involving a preconditioning treatment with LDN193189 and SAG for any period of 30 min, 6 hr, 24 hr and 48 hr (conditions 1-4) (FIG. 36, B-E).

From these results, it was found that a neural tissue can be produced efficiently from feeder-free cultured human iPS cells under conditions involving preconditioning with a Shh signal activating substance for 30 min-2 days in step 1, and addition of a BMP signal activating substance in step 3.

The thus-prepared cell aggregates on day 22 after the start of suspension culturing were fixed with 4% para-formaldehyde to prepare frozen sections. These frozen sections were immunostained for Chx10 (anti-Chx10 antibody, Exalpha, sheep), which is one of the retinal tissue markers. These immunostained sections were observed under an inverted fluorescence microscope. As a result, it was found that the proportion of Chx10-positive cells in the total cells is about 80% by conditions involving preconditioning with LDN193189 and SAG for any period of 30 min, 6 hr, 24 hr and 48 hr (conditions 1-4) (FIG. 36, F-I).

From these results, it was found that a retinal tissue can be produced efficiently from feeder-free human iPS cells under conditions involving preconditioning with a Shh signal transduction pathway activating substance and a BMP signal transduction pathway inhibiting substance for 30 min-2 days in step 1, and addition of a BMP signal transduction pathway activating substance in step 3.

INDUSTRIAL APPLICABILITY

According to the production method of the present invention, it is possible to perform differentiation induction of pluripotent stem cells into neural cells in the absence of feeder cells and produce a neural tissue. The production method of the present invention is useful since it can produce a neural tissue to be used as a material for toxicity and efficacy evaluation of pharmaceutical product candidate compounds and other chemical substances, tests for application to transplantation material for a neural tissue transplantation treatment, or treatments.

The contents disclosed in any publication cited herein, including patents, specifications of patent applications, and scientific documents, are hereby incorporated in their entireties by reference, to the extent that they have been disclosed herein.

This application is based on a patent application No. 2014-217867 filed in Japan (filing date: Oct. 24, 2014), the contents of which are incorporated in full herein.

The invention claimed is:

1. A method for producing retinal progenitor cells, comprising the following steps (1)-(3):
   (1) a first step of culturing pluripotent stem cells in the absence of feeder cells and in a medium comprising (a) a TGFβ family signal transduction pathway inhibiting substance and/or a Sonic hedgehog signal transduction pathway activating substance, and (b) a factor for maintaining undifferentiated state, wherein at least 60% of the cells obtained in the first step are Oct3/4 positive stem cells,
   (2) a second step of dispersing the cells obtained in the first step and culturing the dispersed cells in suspension to form a cell aggregate, wherein the aggregate is formed within about 72 hours after the cells obtained in the first step are dispersed, and wherein the aggregate obtained in the second step contains of mixture of cells expressing Oct3/4 and cells expressing at least one substance selected from the group consisting of SOX1, N-cadherin, OTX2, and Nestin, and
   (3) a third step of culturing the aggregate obtained in the second step in suspension in the presence of a BMP signal transduction pathway activating substance as a differentiation inducing factor until retinal progenitor cells appear, thereby obtaining an aggregate containing retinal progenitor cells.

2. The production method according to claim 1, wherein the factor for maintaining undifferentiated state is an FGF signal transduction pathway activating substance.

3. The production method according to claim 2, wherein the FGF signal transduction pathway activating substance is bFGF.

4. The production method according to claim 1, wherein the TGFβ family signal transduction pathway inhibiting substance is a Nodal/Activin signal transduction pathway inhibiting substance, a TGFβ signal transduction pathway inhibiting substance, or a BMP signal transduction pathway inhibiting substance.

5. The production method according to claim 1, wherein the TGFβ family signal transduction pathway inhibiting substance is Lefty, SB431542, A-83-01 or LDN193189.

6. The production method according to claim 1, wherein the Sonic hedgehog signal transduction pathway activating substance is Shh, SAG or Purmorphamine.

7. The production method according to claim 1, wherein, in the second step, the cells are cultured in suspension in a serum-free medium containing a Sonic hedgehog signal transduction pathway activating substance.

8. The production method according to claim 7, wherein the pluripotent stem cells are human pluripotent stem cells, and the Sonic hedgehog signal transduction pathway activating substance in the medium in the second step has a concentration corresponding to Sonic hedgehog signal transduction activity of SAG at 10 nM 700 nM.

9. The production method according to claim 1, wherein the BMP signal transduction pathway activating substance is one or more proteins selected from the group consisting of BMP2, BMP4, BMP7 and GDF7.

10. The production method according to claim 1, wherein the BMP signal transduction pathway activating substance is BMP4.

11. The production method according to claim 1, wherein, in the third step, the BMP signal transduction pathway activating substance is added to the medium between day 1 and day 9 after the start of the second step.

12. The production method according to claim 1, wherein, in the third step, the aggregate is cultured in a medium containing a Sonic hedgehog signal transduction pathway activating substance at a concentration not more than a concentration corresponding to Sonic hedgehog signal transduction activity of SAG at 700 nM.

13. The production method according to claim 1, wherein a period for the culturing in the first step is 0.5 hr-144 hr.

14. The production method according to claim 1, wherein the first step is performed by an adhesion culturing method.

15. The production method according to claim 1, wherein, in the third step, the BMP signal transduction pathway activating substance is added to the medium between day 3 and day 6 after the start of the second step.

16. The production method according to claim 1, wherein the pluripotent stem cells are primate pluripotent stem cells.

17. The production method according to claim 1, wherein the pluripotent stem cells are human pluripotent stem cells.

18. The production method according to claim 1, wherein the pluripotent stem cells are induced pluripotent stem cells.

19. The production method according to claim 1, wherein uniformed aggregates are formed in the second step.

20. The production method according to claim 1, wherein the suspension culturing is performed in the absence of a basement membrane preparation.

21. The production method according to claim 1, wherein, in the second step, the dispersed cells are cultured in the absence of a Wnt signal transduction pathway inhibiting substance.

22. The production method according to claim 1, wherein at least 90% of the cells obtained in the first step are Oct3/4 positive stem cells.

23. The production method according to claim 1, wherein aggregate is formed within about 48 hours after the cells obtained in the first step are dispersed.

24. The production method according to claim 1, wherein aggregate is formed within about 24 hours after the cells obtained in the first step are dispersed.

25. The production method according to claim 1, wherein aggregate is formed within about 12 hours after the cells obtained in the first step are dispersed.

26. A method for producing an aggregate comprising one or more cells selected from the group consisting of neural retinal progenitor cell, photoreceptor precursor cell, photoreceptor cell, rod photoreceptor cell, cone photoreceptor cell, horizontal cell, amacrine cell, retinal interneuron, retinal ganglion cell, retinal pigment epithelial cell, and ciliary marginal zone cell retinal progenitor cell, comprising the following steps (1) and (2):
   (1) a step of producing an aggregate comprising retinal progenitor cells by the method described in claim 1, and
   (2) a step of suspension culturing of the aggregate obtained in step (1).

27. A method for producing a retinal tissue comprising the following steps (1) and (2):
   (1) a step of producing an aggregate comprising one or more cells selected from the group consisting of neural retinal progenitor cell, photoreceptor precursor cell, photoreceptor cell, rod photoreceptor cell, cone photoreceptor cell, horizontal cell, amacrine cell, retinal interneuron, retinal ganglion cell, retinal pigment epithelial cell, and ciliary marginal zone cell retinal progenitor cell by the method of claim 26; and (2) a step of cutting out a retinal tissue from the aggregate obtained in step (1).

\* \* \* \* \*